US011858999B2

(12) United States Patent
Tocker et al.

(10) Patent No.: US 11,858,999 B2
(45) Date of Patent: *Jan. 2, 2024

(54) IL-17 RECEPTOR A ANTIGEN BINDING PROTEINS

(71) Applicant: AMGEN K-A, INC., Thousand Oaks, CA (US)

(72) Inventors: Joel E. Tocker, Issaquah, WA (US); Jacques J. Peschon, Seattle, WA (US); David Fitzpatrick, Karana Downs (AU); James F. Smothers, Quincy, MA (US); Christopher Mehlin, Seattle, WA (US); Ai Ching Lim, Mercer Island, WA (US)

(73) Assignee: AMGEN K-A, INC., Thousand Oaks, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 16/985,868

(22) Filed: Aug. 5, 2020

(65) Prior Publication Data

US 2020/0362045 A1 Nov. 19, 2020

Related U.S. Application Data

(60) Continuation of application No. 16/229,716, filed on Dec. 21, 2018, now Pat. No. 11,180,564, which is a continuation of application No. 15/058,738, filed on Mar. 2, 2016, now Pat. No. 10,208,122, which is a continuation of application No. 14/304,472, filed on Jun. 13, 2014, now abandoned, which is a continuation of application No. 13/472,074, filed on May 15, 2012, now Pat. No. 8,790,648, which is a division of application No. 12/443,962, filed as application No. PCT/US2007/021174 on Oct. 1, 2007, now abandoned.

(60) Provisional application No. 60/969,895, filed on Sep. 4, 2007, provisional application No. 60/873,072, filed on Dec. 5, 2006, provisional application No. 60/827,882, filed on Oct. 2, 2006.

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC ...... *C07K 16/2866* (2013.01); *A61K 39/3955* (2013.01); *A61K 45/06* (2013.01); *A61K 2039/505* (2013.01); *A61K 2039/507* (2013.01); *C07K 2317/21* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
CPC ............ C07K 16/2866; C07K 2317/56; C07K 2317/565; C07K 2317/76; A61K 2039/505
USPC ............................................ 424/133.1, 142.1
See application file for complete search history.

(56) References Cited

U.S. PATENT DOCUMENTS

| | | |
|---|---|---|
| 4,946,778 A | 8/1990 | Ladner et al. |
| 5,116,964 A | 5/1992 | Capon et al. |
| 5,136,021 A | 8/1992 | Dembinski et al. |
| 5,530,101 A | 6/1996 | Queen et al. |
| 5,703,088 A | 12/1997 | Sharpe et al. |
| 5,716,805 A | 2/1998 | Srinivasan et al. |
| 5,869,286 A | 2/1999 | Yao et al. |
| 6,043,344 A | 3/2000 | Jacobs et al. |
| 6,072,033 A | 6/2000 | Yao et al. |
| 6,072,037 A | 6/2000 | Yao et al. |
| 6,083,906 A | 7/2000 | Troutt |
| 6,096,305 A | 8/2000 | Yao et al. |
| 6,100,235 A | 8/2000 | Yao et al. |
| 6,114,598 A | 9/2000 | Kucherlapati et al. |
| 6,162,963 A | 12/2000 | Kucherlapati et al. |
| 6,171,586 B1 | 1/2001 | Lam et al. |
| 6,191,104 B1 | 2/2001 | Spriggs et al. |
| 6,197,525 B1 | 3/2001 | Yao et al. |
| 6,406,867 B1 | 6/2002 | Yu et al. |
| 6,680,057 B1 | 1/2004 | Yao et al. |
| 6,793,919 B2 | 9/2004 | Mohler |

(Continued)

FOREIGN PATENT DOCUMENTS

| | | |
|---|---|---|
| EP | 0308378 | 3/1989 |
| EP | 0315062 | 5/1989 |

(Continued)

OTHER PUBLICATIONS

Wei et al (Front Immunol May 4, 2022;13:885609. doi: 10.3389/fimmu.2022.885609. eCollection 2022).*

(Continued)

*Primary Examiner* — Lynn A Bristol
(74) *Attorney, Agent, or Firm* — Casimir Jones SC; Lisa Mueller

(57) ABSTRACT

The present invention relates to IL-17 Receptor A (IL-17RA or IL-17R) antigen binding proteins, such as antibodies, polynucleotide sequences encoding said antigen binding proteins, and compositions and methods for diagnosing and treating diseases mediated by IL-17 Receptor A activation by one or more IL-17 ligands. The present invention relates to the identification of neutralizing determinants on IL-17 Receptor A (IL-17RA or IL-17R) and antibodies that bind thereto. Aspects of the invention also include antibodies that compete for binding with the IL-17RA neutralizing antibodies described herein.

4 Claims, 21 Drawing Sheets

Specification includes a Sequence Listing.

(56) References Cited

U.S. PATENT DOCUMENTS

| | | | |
|---|---|---|---|
| 6,833,268 B1 | 12/2004 | Green et al. | |
| 7,049,426 B2 | 5/2006 | Green et al. | |
| 7,064,244 B2 | 6/2006 | Jakobovits et al. | |
| 7,273,843 B2 | 9/2007 | Yao et al. | |
| 7,432,237 B2 | 10/2008 | Yao et al. | |
| 7,767,206 B2 | 8/2010 | Tocker | |
| 7,786,284 B2 | 8/2010 | Tocker et al. | |
| 7,833,527 B2 * | 11/2010 | Tocker | A61P 11/06 424/135.1 |
| 7,939,070 B2 | 5/2011 | Tocker | |
| 8,435,518 B2 * | 5/2013 | Tocker | A61P 21/00 530/387.3 |
| 8,545,842 B2 | 10/2013 | Tocker | |
| 8,790,648 B2 * | 7/2014 | Tocker | A61P 17/00 530/387.3 |
| 8,883,151 B2 | 11/2014 | Liu et al. | |
| 9,073,999 B2 | 7/2015 | Tocker | |
| 10,072,085 B2 * | 9/2018 | Liu | A61P 25/00 |
| 10,208,122 B2 * | 2/2019 | Tocker | A61P 1/04 |
| 2002/0136724 A1 | 9/2002 | Mohler | |
| 2003/0180255 A1 | 9/2003 | Goddard et al. | |
| 2004/0120898 A1 | 6/2004 | Yao et al. | |
| 2004/0120899 A1 | 6/2004 | Yao et al. | |
| 2005/0013814 A1 | 1/2005 | Mohler | |
| 2006/0275306 A1 | 12/2006 | Andya et al. | |
| 2007/0129302 A1 | 6/2007 | Gao et al. | |
| 2007/0134199 A1 | 6/2007 | Frevert | |
| 2008/0213282 A1 | 9/2008 | Jacob et al. | |
| 2008/0219979 A1 | 9/2008 | Tocker | |
| 2008/0220479 A1 | 9/2008 | Tocker | |
| 2008/0221307 A1 | 9/2008 | Tocker | |
| 2009/0068737 A1 | 3/2009 | Yao et al. | |
| 2009/0074758 A1 | 3/2009 | Tocker | |
| 2009/0130122 A1 | 5/2009 | Mohler | |
| 2009/0274703 A1 | 11/2009 | Mohler | |
| 2009/0291076 A1 | 11/2009 | Morichika et al. | |
| 2010/0028345 A1 | 2/2010 | Tocker et al. | |
| 2010/0233186 A1 | 9/2010 | Yao et al. | |
| 2010/0278840 A1 | 11/2010 | Mohler | |
| 2010/0292442 A1 | 11/2010 | Tocker | |
| 2011/0008356 A1 | 1/2011 | Peschon et al. | |
| 2011/0008841 A1 | 1/2011 | Tocker | |
| 2011/0052600 A1 | 3/2011 | Budelsky et al. | |
| 2011/0081339 A1 | 4/2011 | Tocker | |
| 2011/0166331 A1 | 7/2011 | Tocker | |
| 2012/0201821 A1 | 8/2012 | Gonzalez et al. | |
| 2012/0251547 A1 | 10/2012 | Tocker et al. | |
| 2012/0308566 A1 * | 12/2012 | Martin | A61P 35/00 424/174.1 |
| 2013/0004969 A1 | 1/2013 | Peschon et al. | |
| 2013/0022621 A1 | 1/2013 | Liu et al. | |
| 2013/0064788 A1 | 3/2013 | Barnes | |
| 2014/0234330 A1 * | 8/2014 | Budelsky | C07K 16/244 435/375 |
| 2014/0322238 A1 | 10/2014 | Budelsky et al. | |
| 2014/0356355 A1 | 12/2014 | Tocker | |
| 2015/0017184 A1 | 1/2015 | Liu et al. | |
| 2016/0159914 A1 | 6/2016 | Budelsky et al. | |
| 2016/0208004 A1 | 7/2016 | Budelsky et al. | |

FOREIGN PATENT DOCUMENTS

| | | |
|---|---|---|
| EP | 0393438 | 10/1990 |
| EP | 0398327 | 11/1990 |
| EP | 0412486 | 2/1991 |
| EP | 0417563 | 3/1991 |
| EP | 0418014 | 3/1991 |
| EP | 0422339 | 4/1991 |
| EP | 0433900 | 6/1991 |
| EP | 0464533 | 1/1992 |
| EP | 0512528 | 11/1992 |
| EP | 0526905 | 2/1993 |
| EP | 0568928 | 11/1993 |
| EP | 1977763 | 10/2008 |
| FR | 2910324 | 6/2008 |
| GB | 2218101 | 11/1989 |
| GB | 2243569 | 11/1991 |
| JP | 1991127800 | 5/1991 |
| WO | WO 198909622 | 10/1989 |
| WO | WO 199013575 | 11/1990 |
| WO | WO 199103553 | 3/1991 |
| WO | WO 199116437 | 10/1991 |
| WO | WO 199201002 | 1/1992 |
| WO | WO 199211018 | 7/1992 |
| WO | WO 199213095 | 8/1992 |
| WO | WO 199216221 | 10/1992 |
| WO | WO 199307863 | 4/1993 |
| WO | WO 199311161 | 6/1993 |
| WO | WO 199319777 | 10/1993 |
| WO | WO 199321946 | 11/1993 |
| WO | WO 199406476 | 3/1994 |
| WO | WO 199413804 | 6/1994 |
| WO | WO 199518826 | 7/1995 |
| WO | WO 199554326 | 12/1995 |
| WO | WO 199629408 | 9/1996 |
| WO | WO 199704097 | 2/1997 |
| WO | WO 199801555 | 1/1998 |
| WO | WO 199823284 | 6/1998 |
| WO | WO 199914240 | 3/1999 |
| WO | WO 199960127 | 11/1999 |
| WO | WO 200015759 | 3/2000 |
| WO | WO 200055204 | 9/2000 |
| WO | WO 200124814 | 4/2001 |
| WO | WO 200168705 | 9/2001 |
| WO | WO 200168859 | 9/2001 |
| WO | WO 2002058717 | 8/2002 |
| WO | WO 2003072060 | 9/2003 |
| WO | WO 2004002519 | 1/2004 |
| WO | WO 2004003019 | 1/2004 |
| WO | WO 2005016275 | 2/2005 |
| WO | WO 2005063290 | 7/2005 |
| WO | WO 2005063291 | 7/2005 |
| WO | WO 2006054059 | 5/2006 |
| WO | WO 2006/088925 | 8/2006 |
| WO | WO 2006138181 | 12/2006 |
| WO | WO 2007019232 | 2/2007 |
| WO | WO 2007027761 | 3/2007 |
| WO | WO 2007037795 | 4/2007 |
| WO | WO 2007053533 | 5/2007 |
| WO | WO 2007092772 | 8/2007 |
| WO | WO 2008049070 | 4/2008 |
| WO | WO 2008054603 | 5/2008 |
| WO | WO 2008079290 | 7/2008 |
| WO | WO 2008084237 | 7/2008 |
| WO | WO 2008118930 | 10/2008 |
| WO | WO 2008156709 | 12/2008 |
| WO | WO 2009006301 | 1/2009 |
| WO | WO 2009026122 | 2/2009 |
| WO | WO 2009136976 | 11/2009 |
| WO | WO 2011046958 | 4/2011 |
| WO | WO 2011088120 | 7/2011 |
| WO | WO 2012045848 | 4/2012 |
| WO | WO 2013016220 | 1/2013 |
| WO | WO 2015153144 | 10/2015 |
| WO | WO 2016031250 | 3/2016 |

OTHER PUBLICATIONS

Rafael-Vidal et al (Int. J. Mol. Sci. 2020, 21, 7100; doi:10.3390/ijms21197100).*

Roofeh et al. (Expert Opin Emerg Drugs. Dec. 2020 ; 25(4): 455-466. doi:10.1080/14728214.2020.1836156).*

ClinicalTrials.gov_Study of KHK4827 (AMG827); NCT03957681; May 21, 2019.*

Aarvak et al., "Analysis of IL-17 and other cytokines and surface makers of RA inflammatory T cell clones," American College of Rheumatology (ACR) meeting, Poster 1448, Nov. 1997.

Aarvak et al., "IL-17 is produced by some proinflammatory Th1/Th0 cells but not by Th2 Cells," J. Immunol. 162:1246-1251, 1999.

Aggarwal, S. and Gurney, A., "IL-17: prototype member of an emerging cytokine family," J. Leukocyte Biol, 71:1-8, 2002.

(56) References Cited

OTHER PUBLICATIONS

Albanesi et al., "IL-17 is produced by nickel-specific T lymphocytes and regulates ICAM-1 expression and chemokine production in human keratinocytes: Synergistic or antagonist effects with IFN-y and TNF-a," J. Immunol., 162:494-502, 1999.
Albrecht et al., "Primary structure of the herpesvirus saimiri genome," J. Virol., 66(8):5047-5058, 1992.
Amin, A. R. et al., "The expression and regulation of nitric oxide synthase in human osteoarthritis-affected chrondrocytes: Evidence for up-regulated neuronal nitric oxide synthase," J. Exp. Med., 182:2097-2102, Dec. 1995.
Ankarcrona, M. et al., "Interleukin-1 ß-induced nitric oxide production activates apoptosis in pancreatic RINm5F cells," Exp Cell Rsh, 213:172-177, 1994.
Anonymous: "NCT02052608 on Jan. 31, 2014 : ClinicalTrials.gov Archive", Retrieved from the Internet: URL https://clinicaltrials.gov/archive/NCT/02052609/2014-01-31.
Antonysamy, M. et al., "Evidence of a role of IL-17 in organ allograft rejection: IL-17 promotes the functional differentiation of dendritic cell progenitors," J. Immunol., 162:577-584, 1999.
Arend, W. et al., "Inhibition of the production and effects of interleukin-1 and tumor necrosis factor α in the rheumatoid arthritis & Rhem"., 38(2):151-160, 1995.
Attur, M. G. et al., "Interlcukin-17 up-regulation of nitric oxide production in human osteoarthritis cartilage," Arthritis & Rheum., 40(6):1050-1053, 1997.
Ballantyne et al., "Blocking IL-25 prevents airway hyperresponsiveness in allerigc asthma," J Allergy Clin Immunol, 2007, 120(6):1324-31.
Baragi, V. M. et al., "Transplantation of transduced chrondrocytes protects articular cartilage from interleukin 1-induced extracellular matrix degradation," J. Clin. Invest., 96(5):2454-2460, 1995.
Barker et al., "p75NTR is positively promiscuous: novel partner and new insights," Neuron, 42:529-33 (2004).
Bird et al., "Single-chain antigen-binding proteins," Science 242:423-426, 1988.
Bowie et al., "Deciphering the message in protein sequences: Tolerance to amino acid substitutions," Science, 47:1306-1310, 1990.
Brorson, K. et al., "Mutational analysis of avidity and fine specificity of anti-levan antibodies," J. Immunol., 163:6694-6701, 1999.
Brummell, DA et al., "Probing the combining site of an anti-carbohydrate antibody by saturation-mutagenesis: role of the heavy-chain CDR3 residues," Biochem., 32:1180-1187, 1993.
Burks, E. et al., "In vitro scanning saturation mutagenesis of an antibody biding pocket," Proc. Tatl. Acad. Sci. USA, 94:412-417, 1997.
Busse et al., "Randomized, Double-Blind, Placebo-controlled Study of Brodalumab, a Human Anti-IL-17 Receptor Monoclonal Antibody, in Moderate to Severe Asthma," Am J Respir Crit Care Med, 2013, 188(11):1294-1302.
Cannetti et al., "IL-18 enhances collagen-induced arthritis by recruiting neutrophils via TNF-α and leukotriene B4," J Immunol, 171:1009-1015, 2003.
Caron, J. P. et al., "Chondroprotective effect of intraarticular injections of interleukin-1 receptor antagonist in experimental osteoarthritis," Arthritis & Rheum., 39(9):1535-1544, 1996.
Casset et al., "A peptide mimetic of an anti-CD4 monoclonal antibody by rational design," BBRC 307, 2003, 198-205.
Chabaud et al., "The combination of tumor necrosis factor a blockade with interleukin-1 and interleukin-17 blockade is more effective for controlling synovial inflammation and bone resortion in an ex vivo model," Arthritis Rheum, 44(6):1293-1303 (2001).
Chabaud, M. et al., "Contribution of interleukin 17 to synovium matrix destruction in rheumatoid arthritis," Cytokine, 12(7):1092-1099, 2000.
Chabaud, M. et al., "Enhancing effect of IL-17 on IL-1-Induced IL-6 and leukemia inhibitory factor production by rheumatoid arthritis synoviocytes and its regulation by Th2 cytokines," J. Immumol., 161:409-414, 1998.
Chabaud, M. et al., "Human Interluekin-17: A T Cell-Derived Proinflammatory Cytokine Produced by the Rheumatoid Synovium," Arthritis & Rheumatism, 42(5):963-970, 1999.
Chabaud, M. et al., "Regulation of the effects of IL 17 and IL 6 and LIF production by RA synoviocytes," American College of Rheumatology (ACR) meeting, poster 1449, Nov. 1997.
Chang et al., "Interleukin-17C Promotes Th17 Cell Responses and Autoimmune Disease via Interleukin-17 Receptor E," Immunity, vol. 35, vol. 4, pp. 611-621, (2011).
Charles et al., "Regulation of cytokines, cytokine inhibitors, and acute-phase proteins following anti-TNF-α therapy in rheumatoid arthritis," J Immunol, 163:1521-1528, 1999.
Chen et al., "Selection and Analysis of an Optimized Anti-VEGF Antibody: Crystal Structure of an Affinitymature Fab in Complex with Antigen," J. Mol. Bio. 293, 1999, 865-881.
Clinical Trials of AMG 827 (Sep. 10, 2009) "Study to Evaluate the Safety, Tolerability, and Efficacy of AMG 827 in Subjects with Psoriasis," <https://clinicaltrials.gov/ct2/show/NCT00975637>.
Clinicaltrials.gov, <https://clinicaltrials.gov/archive/NCT02052609/2014_01_13> (Oct. 16, 2014, pp. 12, search for brodalumab).
Coleman, P. M., "Effects of amino acid sequence changes on atibody-antigen interactions," Res. Immunol., 145:33-36, 1994.
Crystal, R., "Transfer of genes to humans: Early lessons and obstacles to success," Sci., 270:404-410, 1995.
Cua et al., "Innate IL-17-producing cells: the sentinels of the immune system," Nat Rev Immunol., 2010, 10:479-489.
Cunnane et al., "Serum amyloid A in the assessment of early inflammatory arthritis," J. Rheumatol, 27:58-63, 2000.
Daugherty et al., Formulation and delivery issues for monoclonal antibody therapeutics, Adv. Drug Deliv. Rev., 58(5-6): 686-706 (2006).
Davies et al., "Affinity improvement of single antibody VH domains: residues in all three hypervariable regions affect antigen binding," Immunotechnology, vol. 2, No. 3, pp. 169-179, 1996.
De Graaf et al., "Expression of scFvs and scFv fusion proteins in eukaryotic cells," Methods Mol Biol. 178:379-87, 2002.
De Pascalis et al., "Grafting of "Abbreviated" Complementarity-Determining Regions Containing Specificity—Determining Residues Essential for Ligand Contact to Engineer a Less Immunogenic Humanized Monoclonal Antibody," The Journal of Immunology, 2002, 169, 3076-3084.
Deonarain, M. "Ligand-targeted receptor-mediated vectors fo gene delivery," Exp. Opin. Ther. Patents, vol. 8:53-69, 1998.
Dogra et al., "Biologic therapy in psoriasis," Indian J. Dermatol. Venereol. Leprol., 72(4):256-265, 2006.
Dudler et al., "In vivo effects of murine recombinant interleukin-17 on synovial joint in mice," American College of Rheumatology (ACR) meeting, Poster 1450, Nov. 1997.
Dufner, P. et al., "Harnessing phage and ribosome display for antibody optimization," Trends Biotechnol., 24(11):523-529, 2006.
Fanslow et al., "Regulation of alloreactivity | vivo IL-4 and the soluble IL-4 receptor," J. Immunol., 47(2):535-540, 1991.
Fanslow et al., "Regulation of alloreactivity in vivo by a soluble form of the interleukin-1 receptor," Science, 248:739-742, 1990.
Farahnik et al., "Brodalumab for the Treatment of Psoriasis: A Review of Phase III Trials." Dermatol Ther (Heidelb). Jun. 2016;6(2):111-24.
Fort et al., "IL-25 Induces IL-4, IL-5, and IL-13 and Th2-Associated Pathologies In Vivo," Immunity, 2001, 15:985-995.
Fossiez et al., "T cell interleukin-17 induces stromal cells to produce proinflammatory and hematopoietic cytokines," J. Exp. Med., 183:2593-2603, 1996.
Fouihoux et al., "Production of IL-17 and its regulation in rheumatoid synovium," American College of Rheumatology (ACR) meeting, Poster 1447, 1997.
Frömmel, C. and Holzhütter, H. G., "An estimate on the effect of point mutation and natural selection on the rate of amino acid replacement in proteins," J. Mol. Evol., 21:233-257, 1985.
Fujino et al., "Increased expression of interleukin 17 in inflammatory bowel disease," Gut, 52:65-70 (2003).
Gaffen et al., "The IL-17 cytokine family, Vitamins and Hormones," Academic Press, New York, NY, US, 255-82 (2006).

(56) References Cited

OTHER PUBLICATIONS

Gaffen, "Structure and signaling in the IL-17 receptor family," Nat. Rev. Immunol., 9(8):556-68 (2009).
GenBank Accession No. H55639 (1995).
GenBank Accession No. MMU31993 (1996).
GenBank Accession No. NM_014339 (2014).
Goodman and Gilman, "The Pharmacological Basis of Therapeutics," MacMillan 7th Edition, 1985.
Green et al., "Antigen-specific human monoclonal antibodies from mice engineered with huma Ig heavy and light chain YACS," Nat Genet, 7:13-21, 1994.
Green, "Antibody engineering via genetic engineering of the mouse: XenoMouse strains are a vehicle or the facile generation of therapeutic human monoclonal antibodies." J Immunol Methods. Dec. 10, 1999; 231 (1-2):11-23.
Harrington et al., "Interleukin 17-producing CD4+ effector T cells develop via lineage distinct from the T helper type 1 and 2 lineages," Nat. Immunol., 6(11):1123-32 (2005).
Haudenschild et al., "Soluble and transmembrane isoforms of novel interleukin-17 receptor-like protein by RNA splicing and expression in prostate cancer," Journal of Biological Chemistry, vol. 277, No. 6, pp. 4309-4316, 2002.
Hermanns-Le et al., "Ustekinumab in Psoriasis Immunopathology with Emphasis on the Th17-IL23 Axis: A Primer," J. Biomed. Biotech. 2012: 1-6, 2012.
Hoffstetter et al., "Therapeutic efficacy of IL-17 neutralization in murine experimental autoimmune encephalomyelitis." Cellecular Immunol. Oct. 1, 2005, 237(2): 123-130.
Holliger et al., "Diabodies: small bivalent and bispecific antibody fragments," Proc. Natl. Acad. Sci. U.S.A. 90:6444-6448, 1993.
Holliger et al., "Engineering bispecific antibodies," Current Opinion Biotechnol, 1993, vol. 4, Issue 4, pp. 446-449.
Holm et al., "Functional mapping and single chain construction of the anti-cytokeratin 8 monoclonal antibody TS1," Mol. Immunol. 2007, 44:1075-1084.
Holt et al., "Domain antibodies: proteins for therapy," Trends in Biotechnology, vol. 21, No. 11, pp. 484-490, (2003).
Honorati et al., "IL-17 enhances the susceptibility of U-2 OS osteosarcoma cells to NK cells lysis," Clinical and Experimental Immunology Sep. 2003, vol. 133, No. 3, pp. 344-349, 2003.
Hu et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res. 56:3055-3061, 1996.
Huston et al., "Protein engineering of antibody binding sites: Recovery of specific activity in an anti-digoxin singlechain Fv analogue produced in *Escherichia coli*," Proc. Natl. Acad. Sci. U.S.A. 85:5879-5883, 1988.
Hwang et al., "Expression of IL-17 homologs and their receptors in the synovial cells of rheumatoid arthritis patients," Mol. Cells, 19(2):180-4 (2005).
Hymowitz et al., "IL-17s adopt a cystine knot fold fold: structure and activity of a novel cytokine, IL-17F, and implications for receptor biding," EMBO J., 20:5332-41 (2001).
Infante-Duarte et al., "Microbial lipopeptides induce the production of IL-17 in the Th cells, J. Immunol.," 65:6107-15 (2000).
International Preliminary Examination Report for Application No. PCT/US2001/049504 dated Apr. 24, 2003 (7 pages).
International Preliminary Report on Patentability for Application No. PCT/US2007/021174 dated Apr. 7, 2009 (12 pages).
International Preliminary Report on Patentability for Application No. PCT/US2008/007460 dated Dec. 17, 2009 (7 pages).
International Preliminary Report on Patentability for Application No. PCT/US2011/020985 dated Jul. 17, 2012 (7 pages).
International Search Report and Written Opinion for Application No. PCT/JP2015/004306 dated Oct. 13, 2015 (10 pages).
International Search Report and Written Opinion for Application No. PCT/US2009/001085 dated Feb. 17, 2010 (10 pages).
International Search Report and Written Opinion for Application No. PCT/US2010/052366 dated Dec. 23, 2010 (22 pages).
International Search Report and Written Opinion for Application No. PCT/US2012/047677 dated Oct. 18, 2012 (20 pages).
Janeway et al., Immunology, 3rd edition, Garland Publishing Inc., p. G3 (1997).
Jang, Y. J. et al., "The structural basis for DNA biding by an anti-DNA autoantibody," Mol. Immunol., 35:1207-1217, 1998.
Jia et al., "A novel method of multiplexed competitive antibody binning for the characterization of monoclonal antibodies," J Immunol Methods, 288:91-98, 2004.
Jones, "Replacing the complementarity-determining regions in a human antibody with those from a mouse," Nature 321:522-525, 1986.
Joosten et al., "IL-1αβ Blockade Prevents Cartilage and Bone Destruction in Murine Type II Collagen-Induced Arthritis, Whereas TNF-α Blockade Only Ameliorates Joint Inflammation," J. Immunol., 163:5049-5055, 1999.
Jovanovic et al., "IL-37 stimulates the production and expression of proinflammatory cytokines, IL-13 and TNF-a, by human macrophages," J. Immunol., 160:3513-21 (1998).
Jovanovic et al., "IL-17 stimulates the secretion of proinflammatory cytokines by human macrophages," American College of Rheumatology (ACR) meeting, Poster 1446, Nov. 1997.
Jovanovic et al., "Stimulation of 92-kd gelatinase (matrix metalloproteinase 9) production by interleukin-17 in human monocyte/macrophanges," Arthritis & Rheum., 43(5):1134-44 (2000).
Kamerzell et al., "Increasing IgG Concentration Modulates the Conformational Heterogeneity and Bonding Network that Influence Solution Properties," J. Phys. Chem., 113:6109-18 (2009).
Kauffman et al., "A phase I evaluating the safety, pharmacokinetics, and clinical response of a human IL-12 p40 antibody in subjects with plaque psoriasis," J. Invest. Dermatol., 123:1037-44 (2004).
Kawaguchi et al., "IL-17 cytokine family," J. Allergy Clin. Immunol., 114:1265 (2004).
Kawaguchi M et al: "Identification of a novel cytokine, ML-1, and its expression in subjects with asthma." Journal of Immunology, 2001, vol. 167, No. 8, pp. 4430-4435.
Kerdel & Zaiac, "An Evolution in switching therapy for psoriasis patients who fail to meet treatment goals." Dermatology Therapy 2015, 28:390-403.
Kimura et al., "IL-6-dependent and independent pathways in the development of interleukin 17-producing T helper cells," Proc Natl Acad Sci, USA, 104(29):12099-12104, 2007.
Kipriyanov, "Generation and production of engineered antibodies." Mol Biotechnol. Jan. 2004; 26(1):39-60.
Kircik and Kumar, "Scalp psoriasis," J. Drugs Dermolog. 9:s101-s102, 2010.
Kobayashi, H. et al., "Tryptophan H33 plays an important role in pyrimidine (6-4) pyrimidine photoproduct binding by hign-affinity antibody," Protein Eng., 12:879-884, 1999.
Kolls et al., "Interleukin-17 family members and inflammation," Immunity, 21:467-476 (2004).
Konishi et al., "IL-18 contributes to the spontaneous development of atopic dermatitis-like inflammatory skin lesion independently of IgE/stat6 under specific pathogen-free conditions," Proc Natl Acad Sci, USA, 99(17):11340-11345, 2002.
Kortt et al., "Dimeric and trimeric antibodies: high avidity scFvs for cancer targeting," Biomel. Eng. 18:95-108, 2001.
Kortt et al., "Single-chain Fv fragments of anti-neuraminidase antibody NC10 containing five- and ten-residue linkers form dimers and with zero-residue linker a trimer," Prot. Eng. 10(4):423, 1997.
Kotake, S., "IL-17 in synovial fluids from patients with rheumatoid arthritis is a potent stimulator of osteoclastogenesis," J. Clin. Invest., 103(9):1345-1352, 1999.
Kriangkum et al., "Bispecific and bifunctional single chain recombinant antibodies," Biomol. Eng. 18(2):31-40, 2001.
Kuestner et al., "Identification of the IL-17 receptor-related molecle, IL-17RC as a receptor for IL17A and IL-17F," J Immunol. Oct. 15, 2007;179(8):5462-73.
Kumar, S. et al., "Molecular cloning and expressing of the Fabs of human autoantibodies in *Escherichia coli*," 275(45):35129-35136, 2000.
Kurasawa et al., "Increased interleukin-17 production in patients with systemic sclerosis," Arthritis & Rheum., 43(11):2455-63 (2000).

(56) References Cited

OTHER PUBLICATIONS

Langrish et al., "IL-23 drives a pathogenic T cell population that induces autoimmune inflammation," J Exp Med, 201(2):233-240 (2005).
Lee et al., "IL-18 E42A mutant is resistant to the inhibitory effects of HPV-16 E6 and E7 oncogenes on the IL-18-mediated immune response," Cancer Lett., 229:261-270, 2005.
Leonardi et al., "Anti-Interleukin-17 Monoclonal Antibody Ixekizumab in Chronic Plaque Psoriasis," New England Journal of Medicine, vol. 366, No. 13, pp. 1190-1199, 2012.
Li et al., "Cloning and characterization of IL-17B and IL-17C, two new members of the IL-17 cytokine family," Proc. Natl. Acad. Sci. USA, 97(2):773-8 (2000).
Li et al., "The expression of interleukin-17, interferon-gamma, and macrophage inflannatory protein-3 alpha Mrna in patients with psoriasis vulgaris," J. Huazhong Univ. Sci. Technolog. Med. Sci. 24(3):294-6 (2004).
Liew, "Nitric oxide in infectious and autoimmune diseases," CIBA Foundation Symposium, 195:234-244, 1995.
Linden et al., "Airway neutrophils and interleukin-17," Eur. Respir. J., 15(5):973-7 (2000).
Littman et al., "Th17 and regulatory T cells in mediating and restraining inflammation," Cell, 2010, 140(6):845-58.
Livingston et al., "Identification and Characterization of Synthetic Small Molecule Macrocycle Antagonists of Human IL17A," ACR Annual Meeting, Nov. 9-14, 2012.
Lotz et al., "IL-17 promotes cartilage degradation, Arthritis and Rheum.," 39 suppl. (9):S120 (1996).
Lu et al., "The yin and yang of neurotrophin action," Nat. Rev. Immunol., 6:603-14 (2005).
Lubberts et al., "IL-17 promotes bone erosion in murine collagen-induced arthritis through loss of the receptor activator of NF-x13 ligand/osteoprotegerin balance," J. Immunol, 170:2655-62 (2003).
Lubberts et al., "IL-1-independent role of IL-17 in synovial inflamation and joint destruction during collageninduced arthritis," J. Immunol, 167:1004-13 (2001).
Lubberts et al., "Requirement of IL-17 Receptor Signaling in Radiation-Resistant Cells in the Joint for Full Progression of Destructive Synovitis." The Journal of Immunology, 175(2): 3360-3368.
Lubberts et al., "The role of T cell interleukin-17 in conduction destructive arthritis: lessons from animal models," Arthritis Res. Ther., 7:29-37 (2005).
Lubberts et al., "Treatment with a neutralizing anti-murine interluekin-17 antibogyd after the onset of collagen-induced arthritis reduces joint inflammation, cartilage destruction, and bone erosion." Arthritis & Rheumatis, 50(2): 650-659.
MacCallum et al., "Antibody-antigen Interactions: Contact Analysis and Binding Site Topography," J. Mol. Biol., 1996, 262:732-745.
Mangan et al., "Transforming growth factor-β induces development of the TH17 lineage," Nature, 441:231-234, 2006.
Mannon et al., "Anti-interleukin-12 antibody for active Crohn's disease," N. Engl. J. Med. 351:2069-2080 (2004).
Matusevicius et al., "Interleukin-17 mRNA expression in blood and CSF mononuclear cells is augmented in multiple sclerosis," Mult. Scler., 5:101-4 (1999).
McAllister et al., "Role of IL-17A, IL-17F, and the IL-17 receptor in regulating growth-related oncogene-α and granulocyte colony-simulating factor in bronchial epithelium: Implications for airway inflammation in cystic fibrosis," J Immunol, 175:404-412, 2005.
McInnes et al., "Efficacy and safe of secukinumab, a fully human anti-interleukin-17A monoclonal antibody, in patients with moderate-to-severe psoriatric arthritis: a 24-week, randomised, double-blind, placebo-controlled, phase II proof-of-concept trial," Ann Rheum Dis, 2013, pp. 1-8.
Mease et al., "Managing patients with psoriatric disease: the diagnosis and pharmacologic treatment of psoriatic arthritis in patients with psoriasis," Drugs, 2014, vol. 74, No. 4, p. 423-441.

Mendez et al., "Functional transplant of megabase human immunoglobulin loci recapitulates human antibody response in mice," Nat Genet, 15:146-156, 1997.
Miller et al., "Targeted vectors for gene therapy," FASEB J., vol. 9:190-199, 1995.
Miossec, "Interleukin-17 in rheumatoid arthritis," Arthritis & Rheum, 48(3):594-601 (2003).
Molet et al., "IL-17 is increased in asthmatic airway and induces human bronchial fibroblasts to produce cytokines," J. Allergy Clin. Immunol., 108(3):430-8 (2001).
Monoclonal anti-human IL-17 R antibody, <http://www.rndsystems.com> R&D Systems, 2004.
Moseley et al., "Interleukin-17 family and IL-17 receptors," Cytokine & Growth Factor Reviews, 14:155-74 (2003).
Moy et al., "Immunologic Overlap of Helper T-Cell Subtypes 17 and 22 in Erythrodermic Psoriasis and Atopic Dermatitis." JAMA Dermatol. Jul. 2015;151(7):753-60.
Nakae et al., "Suppression of immune induction of collagen-induced arthritis in IL-17-deficient mice," J. Immunol., 171:6173-7 (2003).
Nakae et al., IL-17 production from activated T cells is required for the spontaneous development of destructive arthritis in mice deficient in IL-I receptor antagonist, Proc. Natl. Acad. Sci. USA, 100(10):5986-90 (2003).
Nanevicz et al., "Mechanisms of thrombin receptor agonist specificity," J Biol Chem, 270(37):21619-21625, 1995.
Neve et al., "Expression of an efficient small molecular weight tumour necrosis factor/lymphotoxin antagonist," Cytokine, 8(5):365-370, 1996.
Ngo et al., "Computational Protein Structure Prediciton, and the Levinthal Paradox," The Protein Folding Problem and Tertiary Structure Prediction, 1994, pp. 433, 491-495.
Nicholas et al., "Gene Expression in Cells Infected with Gammaherpesvirus Saimiri: Properties of Transcripts from Two Immediate-Early Genes," Virol. 179:189-200, 1990.
Nickoloff, B. and Nestle, F., "Recent insights into the immunopathogenesis of psoriasis provide new therapeutic opportunities," J. Clin. Invest. 113(12):1664-1675, 2004.
Niederau et al., "Inflammatory mediators and acute phase proteins in patients with Crohn's disease and ulcerative colitis," Hepato-Gastroenterol., 44:90-107, 1997.
Numasaki et al., "IL-17 enhances the net angiogenic activity and in vivo growth of human non-small cell lung cancer in SCID mice through promoting CXCR-2-dependent angiogenesis," Journal of Immunology, vol. 175, No. 9, pp. 6177-6189, 2005.
Numasaki et al., "Regulatory roles of IL-17 and IL-17 in G-CSF production by lung microvascular endothelial cells stimulated with IL-10 and/or INF-a," Immunol. Lett., 95:97-104 (2004).
Oda et al., "Interleukin-17F induces pulmonary neuthrophilia and amplifies antigen-induced allergic response," Am. J. Respir. Crit. Med., 171:12-18 (2005).
Ouyang et al., "The biological functions of T helper 17 cell effector cytokines in inflammation," Immunity, 2008, 28(4):454-67.
Papp et al., "Brodalumab, an Anti-Interleukin-17-Receptor Antibody for Psoriasis," NEJM 2012, 366(13):1181-9.
Park et al., "A distinct lineage of CD4 T cells regulates tissue inflammation by producing interleukin 17," Nat Immunol, 6(11):1133-1141, 2005.
Pelidou et al., "Enhancement of Acute Phase and Inhibition of Chronic Phase of Experimental Autoimmune Neuritis in Lewis Rats by Intranasal Administration of Recombinant Mouse Interleukin 17: Potential Immunoregulatory Role," Exp. Neuro, 163:165-172, 2000.
Petersen, T., "In vivo pharmacological disease models for psoriasis and atopic dermatitis in drug discovery," Basic & Clinical Pharmacology & Toxicology, 99:104-115, 2006.
Pincus, "The American College of Rheumatology (ACR) core data set and derivate "patient only" indices to assess rheumatoid arthritis," Clin. Exp. Rheumatol. 23(5) Suppl. 39:S109-13 (2005).
Pongcharoen et al., "The effect of interleukin-17 on the proliferation and invasion of JEG-3 human choriocarcinoma cells," Amercian Journal of Reproductive Immunology, vol. 55, No. 4, pp. 291-300, 2006.

(56) References Cited

OTHER PUBLICATIONS

Ramirez-Carrozzi et al., "IL-17C regulates the innate immune function of epithelial cells in an autocrine manner," Nature Immunology, vol. 12, No. 12, pp. 1159-1166 (2011).
Reiter et al., "Engineering antibody Fv fragments for cancer detection and therapy: Bisulfide-stabilized Fv fragments,"Nature Biotech. 14:1239-1245, 1996.
Rich et al., "Nail Psoriasis Severity Index: a useful tool for evaluation of nail psoriasis," J. Am. Acad. Dermatol. 49(2): 206-12, 2003.
Rickel et al., "Identification of functional roles for both IL-17RB and IL-17RA in mediating IL-25 induced activities," J. Immunol., 181:4299-4310 (2008).
Rong et al., "IL-17RD (Sef or IL-17RLM) interactis with IL-17 receptor and mediates IL-17 signaling," Cell Res., 19:208-15 (2009).
Roque et al., "Antibodies and genetically engineered related molecules: production and purification," Biotechnol. Prog. 20:639-654, 2004.
Rouvier et al., "CLTA-8, Cloned from an Activated T Cell, Bearing AU-Rich Messenger RNA Instability Sequences, and Homologous to a Herpesvirus Saimiri Gene," J. Immunol., 150:5445-5456, 1993.
Rudikoff et al., "Single amino acid substitution altering antigen-binding specificity," Proc Natl Acad Sci USA 1982, vol. 79, p. 1979.
Saenz et al., "Welcome to the neighborhood: epithelial cell-derived cytokines license innate and adaptive immune responses at mucosal sites," Immunol Rev., 2008, 226:172-190.
Sambrook et al., Molecular Cloning: A Laboratory Manual, 3rd ed., Cold Spring Harbor Laboratory Press, Cold Spring Harbor, N.Y.
Schnyder et al., "IL-17 reduces TNF-induced Rantes and VCAM-1 expression," Cytokine, 31(3):191-202 (2005).
Shen et al., "Structure-function relationships in the IL-17 receptor: Implications for signal transduction and therapy," Cytokine, Academic Press Ltd., vol. 41, No. 2, pp. 92-104 (2008).
Simon et al., "Peptoids: a modular approach to drug discovery," Proc. Natl. Acad. Sci. U.S.A. 89:9367, 1992.
Smith-Gill, S. et al., "Contributions of immunoglobulin heavy and light chains to antibody specificity for lysozyme and two haptens," J. Immunol., 139(12):4135-4144, 1987.
Song et al., "IL-17RE is the functional receptor for IL-17C and mediates mucosal immunity to infecton with instestinal pathogens," Nature Immunology, vol. 12, No. 12, pp. 1151-1158, (2011).
Song, M. et al., "Light chain of natural antibody plays a dominant role in protein antigen binding," Biochem. Biophys. Res. Comm., 268:390-394, 2000.
Spriggs, "Interleukin-17 and its receptor," J. Clin. Immunol. 17(5):366-9 (1997).
Steiner et al., "Expression and function of pro-inflammatory interleukin IL-17 and IL-17 receptor in normal, benign hyperplastic, and malignant prostate," The Prostate Aug. 1, 2003 LNKD, vol. 56, No. 3, pp. 171-182, 2003.
Stemmer et al., "Single-step assembly of a gene and entire plasmid from large numbers of oligodeoxyribonucleotides," Gene, 164:49-53, 1995.
Sykes et al., "Xenograft Tolerance," Immunological Reviews, vol. 141:245-276, 1994.
Teraki et al., "A case of generalized psoriasiform and pustular eruption induced by infliximab: evidence for skin-homing Th17 in the pathogenesis: Correspondence", British Journal of Dermatology Nov. 4, 2010, 163(6): 1347-1351.
Teunissen et al., "Interleukin-17 and interferon-7 synergize in the enhancement of proinflammatory cytokin production by human keratinocytes," J. Invest. Dermatol., 111:645-9 (1998).
Tian et al., "Evi27 encodes a novel membrane protein with homology to the IL17 receptor," Ocogene, 19:2098 (2000).
Tomlinson et al., "Methods for generating multivalent and bispecific antibody fragments. Methods Enzymol," Methods Enzymol. 326:461-479, 2000.
Toy et al., "Cutting Edge: Interleukins 17 signals through a heteromeric receptor complex," J. Immunol, 177:36-9 (2006).
Trofatter et al., "An Expression-independent Catalog of Genes from Human Chromosome 22," Genome Res. 3(6):214-224 (1995).
Umezawa, "BSD Medical Reports Clinical Study Data: brodalumab in psoriasis," Wireless News, 2014 <http:search.proquest.com/docview/210289466> retrieved from the internet on May 13, 2015.
Vajdos et al., "Comprehensive Functional Maps of the Antigen-binding Site of an Anti-ErbB2 Antibody Obtained with Shotgun Scanning Mutagenesis," J. Mol. Biol. 320, 2002, 415-428.
Van de Kerkhof, PCM, "Consistent control of psoriasis by continuos long-term therapy: the promise of biological treatments," JEADV, 1468-3083:639-650, 2006.
Verhoeyen et al., "Reshaping human antibodies: Grafting an antilysozyme activity," Science 239:1534-1536, 1988.
Verma et al., "Gene Theraphy—promises, problems and prospects," Nature, vol. 389:239-242, 1997.
Viswanathan et al., "Total skin clearance results in improvements in health-related quality of life and reduced symptom severity among patients with moderate to severe psoriasis," J Dermatolog Treat, 2015, 26(3):235-239.
Wang et al., IL-25 augments type 2 immune responses by enhancing the expansion and functions of TSLP-DC-activated Th2 memory cells, J Exp Med., 2007, 204(8):1837-1847.
Ward et al., "Binding activities of a repertoire of single immunoglobulin variable domains secreted from *Escherichia coli*," Nature, 1989, 341:544-546.
Webmd.com definition for DMARDS, pp. 1-3, Jul. 2, 2009.
Wong et al., Elevation of proinflammatory cytokine (IL-18, IL-17, IL-12) and Th2 cytokine (IL-4) concentrations in patiens with systemic lupus erythematosus, Lupu, 9:589-93 (2000).
Wozel, "Psoriasis treatment in difficult locations: scalp, nails, and intertriginous areas," Clin. Derm. 26:448-459, 2008.
Wright et al., "The Human IL-17F/IL-17A Heterodimeric Cytokine Signals through the IL-17RA/IL-17RC Receptor Complex," J Immunol, 2008, 181(4):2799-2805.
Wu et al., "Humanization of a Murine Monoclonal Antibody by Simultaneous Optimization of Framework and CDR Residues," J. Mol. Biol. 294, 1999, 151-162.
Yamasaki et al., "Efficacy and safety of brodalumab in patients with generalized pustular psoriasis and psoriatic erythroderma: results from a 52-week, open-lable study."Br J Dermatol. Mar. 2017;176(3):741-751.
Yao et al., "Complete nucleotide sequence of the mouse CTLA8 gene," Gene, 168:223-225, 1996.
Yao et al., "Herpesvirus saimiri encodes a new cytokine, IL-17, which binds to a novel cytokine receptor," Immuity, 3:811-21 (1995).
Yao et al., "Human lL-17: A novel cytokine derived from T cells," J. Immunol., 155:5483-5486 (1995).
Yao et al., "Molecular characterization of the human interleukin (IL)-17 receptor," Cytokine, 9(11):794-800 (1997).
Ye et al., "Requirement of interleukin 17 receptor signaling for lung CXC chemokine and granulocyte colonystimulating factor expression, neutrophils recruitment, and host defense," J. Exp. Med., 194(4):519-27 (2001).
Yoshimoto et al., "IL-12 up-regulates IL-18 receptor expression on T cells Th1 cell ad B cells: Synergism with IL-18 for IFN-y production," J Immunol, 161:3400-3407, 1998.
You et al., "Differential expression of IL-17RC isoforms in androgen-dependent and adrogen-independent prostate cancers," vol. 9, No. 6, pp. 464-470, (2007).
You et al., Interleukin-17 receptor-like gene is novel antiapoptotic gene highly expressed in androgenindependent prostate cancer, Cancer Res., 66(1):175-83 (2006).
Zhang et al., "Critical Role of IL-17 Receptor Signaling in Acute TNBS-Induced Colitis," Inflammatory Bowel Dise, May 1, 2006, 12(5): 382-388.
Zhou et al., "IL-17A versus IL-17F induced intracellular signal transduction pathways and modulation by IL-17RA and IL-17RC RNA interference in AGS gastric adenocarcinoma cells," Cytokine, vol. 38, No. 3, pp. 157-164, 2007.

(56) References Cited

OTHER PUBLICATIONS

Ziolkowska et al., "High levels of IL-17 in rheumatoid arthritis patients: IL-15 triggers in vitro IL-17 production via cyclosporine A-sensitive mechanism," J. Immunol., 84:2832-8 (2000).

Zupnick et al., "Mutational analysis of the p53 core domain L1 loop," J Biol Chem, 281 (29):20464-20473, 2006.

\* cited by examiner

| V_H DOMAINS | CDR1 | SYNTHETIC LINKER | CDR2 | SYNTHETIC LINKER | CDR3 |
|---|---|---|---|---|---|
| SEQ ID NO:24 | --SYYWS | GGGAAAGGGAAA | RIY...PSG.RTN...YNPSLKS | GGGAAAGGGAAA | ...E.A...Y.ELQLG...LYYYGMDV |
| SEQ ID NO:23 | --SYYWS | GGGAAAGGGAAA | RIY...PSG.RTN...YNPSLKS | GGGAAAGGGAAA | ...E.A...Y.ELQLG...LYYYGMDV |
| SEQ ID NO:5 | --SYYWS | GGGAAAGGGAAA | RIY...PSG.NTI...YNPSLKS | GGGAAAGGGAAA | ...E.N..YSE.SSG...LYYYYGMDV |
| SEQ ID NO:1 | --NYYWN | GGGAAAGGGAAA | DIY...YSG.STN...YNPSLKS | GGGAAAGGGAAA | D.GELANYY...GSGSYQFYYYYGMDV |
| SEQ ID NO:2 | --GYYWS | GGGAAAGGGAAA | EIN...HSG.RTN...YNPSLKS | GGGAAAGGGAAA | ...GP....YYFD.SSG.Y.LYYYGLDV |
| SEQ ID NO:25 | SGGYYWS | GGGAAAGGGAAA | YIY...YSG.NTY...YNPSLRS | GGGAAAGGGAAA | EAGGNSAYY...........Y..GMDV |
| SEQ ID NO:10 | SGGYYWS | GGGAAAGGGAAA | YIY...FSG.SAY...YNPSLKS | GGGAAAGGGAAA | E......YY.D.SSG.....YPDAFDI |
| SEQ ID NO:7 | --RYGIS | GGGAAAGGGAAA | ..WISAYNG.NTN....YAQKLQG | GGGAAAGGGAAA | R.......DYDILT.G......YYNGFDP |
| SEQ ID NO:9 | --RYGIS | GGGAAAGGGAAA | ..WISAYNG.NTN....YAQKLQG | GGGAAAGGGAAA | R.......DYDILT.G......YYNGFDP |
| SEQ ID NO:6 | --RYGIS | GGGAAAGGGAAA | ..WISAYNG.NTN....YAQKLQG | GGGAAAGGGAAA | R......DYDILT.G......YYNGFDP |
| SEQ ID NO:8 | --RYGIS | GGGAAAGGGAAA | ..WISAYNG.NTN....YAQNLQG | GGGAAAGGGAAA | R......DYDILT.G......YYNGFDP |
| SEQ ID NO:14 | --RYGIS | GGGAAAGGGAAA | ..WISTYSG.NTN....YAQKLQG | GGGAAAGGGAAA | R...QLYFDY------------------ |
| SEQ ID NO:22 | --RYGIS | GGGAAAGGGAAA | ..WISAYSG.NTN....YAQKLQG | GGGAAAGGGAAA | R...QLYFDY------------------ |
| SEQ ID NO:16 | --SYGIS | GGGAAAGGGAAA | ..WISAYNG.NTK....YAQKLQG | GGGAAAGGGAAA | K...QLVFDY------------------ |
| SEQ ID NO:17 | --SYGIS | GGGAAAGGGAAA | ..WISAYNG.NTK....YAQKLQG | GGGAAAGGGAAA | K...QLVFDY------------------ |
| SEQ ID NO:12 | --SYGIS | GGGAAAGGGAAA | ..WISTYKG.NTN....YAQKLQG | GGGAAAGGGAAA | K...QLVFDY------------------ |
| SEQ ID NO:19 | --SYGIS | GGGAAAGGGAAA | ..WISTYSG.NTK....YAQKFQG | GGGAAAGGGAAA | R...QLALDY------------------ |
| SEQ ID NO:13 | --SYGMQ | GGGAAAGGGAAA | VIN....YDG.NKK..YYADSVKG | GGGAAAGGGAAA | ............GRVR.D......YYGMDV |
| SEQ ID NO:15 | --SYGMQ | GGGAAAGGGAAA | VIN....YDG.NKK..YYADSVKG | GGGAAAGGGAAA | ............GRVR.D......YYYGMDV |
| SEQ ID NO:4 | --SYGMH | GGGAAAGGGAAA | VIN....YDGSN.K..HYADSVKG | GGGAAAGGGAAA | ...D.T...G.V.........Y----- |
| SEQ ID NO:3 | --SYGMH | GGGAAAGGGAAA | VIN....YDGSN.K..HYADSVKG | GGGAAAGGGAAA | ...D.T...G.V.........Y----- |
| SEQ ID NO:11 | --SYGMH | GGGAAAGGGAAA | VIN....YDGSN.K..YYADSVKG | GGGAAAGGGAAA | ...D.T...K.D.........Y----- |
| SEQ ID NO:21 | --SYSMN | GGGAAAGGGAAA | II.....SSRS.SIIHYADSVKG | GGGAAAGGGAAA | ...PKV..G..G............GMDV |
| SEQ ID NO:20 | --SYSMN | GGGAAAGGGAAA | FI.....SARS.STIYYADSVKG | GGGAAAGGGAAA | ...PKV..G..G............GMDV |
| SEQ ID NO:26 | --DYYWS | GGGAAAGGGAAA | YI.....SS.SGSTIYYADSVKG | GGGAAAGGGAAA | ...DRTYYFGS.G.S......Y.EGMDV |
| SEQ ID NO:18 | --DYYMH | GGGAAAGGGAAA | ..WMHPNSGG.TDL....AQRFQG | GGGAAAGGGAAA | .CG......Y..CST.LSCSFYFY.FDL |

Fig. 2

| V_L DOMAINS | CDR1 | SYNTHETIC LINKER | CDR2 | SYNTHETIC LINKER | CDR3 |
|---|---|---|---|---|---|
| SEQ ID NO:33 | RASQGIR.N.....D.LG | GGGAAAGGGAAA | AASSLQS | GGGAAAGGGAAA | LQH.KSY....PL.T |
| SEQ ID NO:32 | RASQGIR.N.....D.LG | GGGAAAGGGAAA | AASSLQS | GGGAAAGGGAAA | LQH.KSY....PL.T |
| SEQ ID NO:34 | RASQGIR.N.....D.LG | GGGAAAGGGAAA | AASSLQS | GGGAAAGGGAAA | LQH.KSY....PL.T |
| SEQ ID NO:35 | RASQGIR.N.....D.LG | GGGAAAGGGAAA | AASSFQS | GGGAAAGGGAAA | LQH.KSY....PL.T |
| SEQ ID NO:31 | RASQGIR.N.....D.LG | GGGAAAGGGAAA | AASSLQS | GGGAAAGGGAAA | LQH.NSY....PP.T |
| SEQ ID NO:27 | RASQGIR.N.....D.LG | GGGAAAGGGAAA | AASSLQS | GGGAAAGGGAAA | LQH.NSN....PF.T |
| SEQ ID NO:49 | RASQGII.N.....D.LG | GGGAAAGGGAAA | AASSLQS | GGGAAAGGGAAA | LQH.NSY....PP.T |
| SEQ ID NO:36 | RASQGIR.S......WLA | GGGAAAGGGAAA | AASSLQS | GGGAAAGGGAAA | .Q...Q.ANNFPR.T |
| SEQ ID NO:52 | RASQAI..S.....IYLA | GGGAAAGGGAAA | AASTLQS | GGGAAAGGGAAA | .Q...Q.YSSYPR.T |
| SEQ ID NO:46 | RASQGI..S.....NYLA | GGGAAAGGGAAA | AASTLQS | GGGAAAGGGAAA | .Q...K.YNRAPF.T |
| SEQ ID NO:47 | RASQGI..S.....NYLA | GGGAAAGGGAAA | AASTLQS | GGGAAAGGGAAA | .Q...K.YNRAPF.T |
| SEQ ID NO:29 | RASQSI..S.....SYLN | GGGAAAGGGAAA | AASSLQS | GGGAAAGGGAAA | .Q...Q.QSYS.TPF.T |
| SEQ ID NO:53 | RASQSV.YS.....N.LA | GGGAAAGGGAAA | GASTRAT | GGGAAAGGGAAA | .Q...Q.YYNWP.WT |
| SEQ ID NO:30 | RASQSV..SR....N.LA | GGGAAAGGGAAA | GASTRAT | GGGAAAGGGAAA | .Q...Q.YNNWPTWT |
| SEQ ID NO:37 | RASQSV..SS....N.LA | GGGAAAGGGAAA | GASTRAA | GGGAAAGGGAAA | .Q...H.YINWPKWT |
| SEQ ID NO:41 | RASQSV..SS....N.LA | GGGAAAGGGAAA | DASTRAA | GGGAAAGGGAAA | .Q...Q.YDNWPL.T |
| SEQ ID NO:48 | RASQSV..SS....N.LA | GGGAAAGGGAAA | DASTRAA | GGGAAAGGGAAA | .Q...Q.YDNWPL.T |
| SEQ ID NO:40 | RASQSV..SS....N.LA | GGGAAAGGGAAA | DASTRAT | GGGAAAGGGAAA | .Q...Q.YDNWPL.T |
| SEQ ID NO:43 | RASQSV..SS....N.LA | GGGAAAGGGAAA | GASTRAT | GGGAAAGGGAAA | .Q...Q.YDNWPL.T |
| SEQ ID NO:38 | RASQSI..SS....S.LA | GGGAAAGGGAAA | GASTRAT | GGGAAAGGGAAA | .Q...Q.YDNWPL.T |
| SEQ ID NO:45 | RASQSI..SS....N.LA | GGGAAAGGGAAA | GASTRAT | GGGAAAGGGAAA | .Q...Q.YDTWPL.T |
| SEQ ID NO:42 | RASQSI..ST....S.LA | GGGAAAGGGAAA | GTSTRAT | GGGAAAGGGAAA | .Q...Q.YDIWPL.T |
| SEQ ID NO:28 | RASQSV..SR....N.LV | GGGAAAGGGAAA | GASTRAN | GGGAAAGGGAAA | .Q...Q.YDNWPL.T |
| SEQ ID NO:44 | KTSQSVLYSSKNKNFLA | GGGAAAGGGAAA | WASTRES | GGGAAAGGGAAA | .Q...Q.YKSW..RT |
| SEQ ID NO:39 | KSSQSLLHS.DGKTYLY | GGGAAAGGGAAA | EVSTRFS | GGGAAAGGGAAA | .Q...Q.YYSTP.FT |
| SEQ ID NO:50 | RSSQSLVYS.DGHTCLN | GGGAAAGGGAAA | KVSNWDS | GGGAAAGGGAAA | MQSIQL....PL.T |
| SEQ ID NO:51 | RSSQSLVYS.DGHTCLN | GGGAAAGGGAAA | KVSNWDS | GGGAAAGGGAAA | MQ....GTHWPLCS |

Fig. 3

| BIN | mAb | Bead Region 33 A | 34 B | 35 P | 36 C | 37 D | 38 E | 42 H | 43 F | 72 huIgG |
|---|---|---|---|---|---|---|---|---|---|---|
| 1 | A | -220 | 1199 | 6592 | 330 | 337 | 300 | 8643 | 345 | 84 |
| 1 | B | -326 | 453 | 5020 | 150 | 213 | 182 | 6786 | 173 | 37 |
| 1 | C | -178 | 816 | 5963 | 260 | 264 | 163 | 2948 | 239 | 54 |
| 1 | D | -233 | 684 | 5645 | 217 | 207 | 192 | 3181 | 269 | 123 |
| 1 | E | -70.5 | 447 | 3527 | 173 | 168 | 130 | 2536 | 152 | 26 |
| 1 | F | 114 | 545 | 1716 | 253 | 179 | 175 | 3971 | 187 | 140 |
| 1 | G | -162 | 1305 | 4487 | 354 | 344 | 260 | 3995 | 304 | -5 |
| 2 | H | 7507 | 1643 | 3421 | 2495 | 790 | 573 | -140 | 2805 | 74 |
| 3 | I | 3482 | 853 | 2627 | 4910 | 1636 | 1360 | 211 | 2133 | 22 |
| 3 | J | 1812 | 420 | 2258 | 2775 | 875 | 807 | -109 | 1810 | 35 |
| 3 | K | 3125 | 834 | 2605 | 4553 | 1622 | 1412 | 216 | 2124 | 100 |
| 3 | L | 2356 | 571 | 2093 | 3517 | 1084 | 890 | 64 | 1589 | 34 |
| 3 | M | 1936 | 455 | 1897 | 3040 | 888 | 765 | 73 | 1410 | 32 |
| 3 | N | 2473 | 597 | 2468 | 3975 | 1202 | 999 | 68 | 1917 | 56 |
| 3 | O | 2998 | 630 | 2536 | 4511 | 1368 | 1256 | 120 | 2223 | 95 |
| 4 | P | 12079 | 3005 | 474 | 10707 | 3369 | 3424 | 6069 | 2543 | 73 |
| 5 | Q | 9527 | 1897 | 2157 | 4766 | 1383 | 1174 | 10203 | 2201 | 28 |
| 6 | R | 6796 | 1065 | 1411 | 2994 | 783 | 666 | 8296 | 1242 | 50 |
|   | huIgG | -194 | -6 | 216 | 118 | 46 | 45 | -34 | 25.5 | 65 |

*Fig. 16A*

| BIN | mAb | 45 R | 46 I | 47 J | 51 K | 52 Q | 53 L | 55 G | 56 M | 61 N | 62 O | 72 huIgG |
|---|---|---|---|---|---|---|---|---|---|---|---|---|
| 1 | A | 7064 | 5302 | 2323 | 7206 | 9649 | 3017 | 454 | 1859 | 2646 | 3800 | 84 |
| 1 | B | 5885 | 3710 | 1395 | 4970 | 8280 | 1980 | 235 | 1303 | 1948 | 2638 | 37 |
| 1 | C | 3954 | 6723 | 3591 | 8223 | 5497 | 3540 | 346 | 2882 | 3632 | 5517 | 54 |
| 1 | D | 3552 | 6652 | 3644 | 8684 | 4686 | 4257 | 318 | 2975 | 3843 | 5545 | 123 |
| 1 | E | 1655 | 4333 | 2420 | 5605 | 2394 | 2661 | 334 | 1766 | 2409 | 3313 | 26 |
| 1 | F | 1120 | 3107 | 2123 | 4107 | 1650 | 1724 | 342 | 1021 | 1511 | 2626 | 140 |
| 1 | G | 5109 | 6887 | 2901 | 8972 | 7846 | 3591 | 480 | 2377 | 3231 | 5377 | -5 |
| 2 | H | 7525 | -5 | -51 | -111 | 9606 | -41 | 3208 | -75 | 24 | 5.5 | 74 |
| 3 | I | 48 | 33 | 2 | -182 | 57 | -26 | 4909 | 13 | 56 | 16 | 22 |
| 3 | J | 53.5 | -5 | 72 | -100 | 86 | -11 | 1915 | 10 | 38 | 75 | 35 |
| 3 | K | 114 | 1 | -3 | -196 | 90 | -76 | 4492 | 85 | 66 | 28 | 100 |
| 3 | L | 52 | 63 | 61 | -25 | 105 | 39 | 3714 | 44 | 41 | 72 | 34 |
| 3 | M | 40 | 26 | 31 | -5 | 60 | 18 | 3275 | 20 | 11 | 49 | 32 |
| 3 | N | 76 | 18 | 8 | -44 | 98 | -1 | 4258 | 40 | 43 | 55 | 56 |
| 3 | O | 76 | 10 | 59 | -111 | 135 | 18 | 4492 | 73 | 83 | 139 | 95 |
| 4 | P | 2553 | 5003 | 4475 | 6271 | 3718 | 2521 | 6001 | 1645 | 2359 | 3788 | 73 |
| 5 | Q | 34 | 2.5 | 23 | -181 | 100 | -58 | 6276 | 44.5 | 39 | 175 | 28 |
| 6 | R | 25 | 58 | 26 | -29 | 60 | 15 | 4016 | 24 | 24 | 140 | 50 |
|  | huIgG | 31 | -72 | 42 | -235 | 64 | -36 | 216 | 27 | 3 | 20 | 65 |

*Fig. 16B*

MAIRRCWPRVVPGPALGWLLLLLNVLAPGRASPRLLDFPAPVCAQEGLSCR
VK                                  Domain A NSTCLDDSWIHPKNLTPSSPKNIYINLSVSSTQHGELVPVLHVEWTLQTDASI
LY                       Domain B LEGAELSVLQLNTNERLCVKFQFLSMLQHHRKRWRFSFSHFVVDPGQEYE
                        Domain C VTVHHLPKPIPDGDPNHKSKIIFVPDCEDSKMKMTTSCVSSGSLWDPNITV
                      Domain D ETLDTQHLRVDFTLWNESTPYQVLLESFSDSENHSCFDVVKQIFAPRQEEF
HQ Domain E                        Domain F

RANVTFTLSKFHWCCHHHVQVQPFFSSCLNDCLRHAVTVPCPVISNTTVP
KPVADYIPLW

SEQ ID NO:432

*Fig. 17*

|  |  |  | 1 | 50 |
|---|---|---|---|---|
| SEQ ID NO:433 | Construct A | (1) | MGAARSPPSAVPGPLLGLLLLLLGVLAPGGASLRLLDFPAPVCAQEGLSC |
| SEQ ID NO:434 | Construct B | (1) | MGAARSPPSAVPGPLLGLLLLLLGVLAPGGASLRLLDHRALVCSQPGLNC |
| SEQ ID NO:435 | Construct C | (1) | MGAARSPPSAVPGPLLGLLLLLLGVLAPGGASLRLLDHRALVCSQPGLNC |
| SEQ ID NO:436 | Construct D | (1) | MGAARSPPSAVPGPLLGLLLLLLGVLAPGGASLRLLDHRALVCSQPGLNC |
| SEQ ID NO:437 | Construct E | (1) | MGAARSPPSAVPGPLLGLLLLLLGVLAPGGASLRLLDHRALVCSQPGLNC |
| SEQ ID NO:438 | Construct F | (1) | MGAARSPPSAVPGPLLGLLLLLLGVLAPGGASLRLLDHRALVCSQPGLNC |
| SEQ ID NO:439 | Construct G | (1) | MGAARSPPSAVPGPLLGLLLLLLGVLAPGGASLRLLDFPAPVCAQEGLSC |
| SEQ ID NO:440 | Construct H | (1) | MGAARSPPSAVPGPLLGLLLLLLGVLAPGGASLRLLDHRALVCSQPGLNC |
| SEQ ID NO:441 | Construct I | (1) | MGAARSPPSAVPGPLLGLLLLLLGVLAPGGASLRLLDHRALVCSQPGLNC |
| SEQ ID NO:442 | Construct J | (1) | MGAARSPPSAVPGPLLGLLLLLLGVLAPGGASLRLLDHRALVCSQPGLNC |
| SEQ ID NO:445 | Construct M | (1) | MGAARSPPSAVPGPLLGLLLLLLGVLAPGGASLRLLDHRALVCSQPGLNC |
| SEQ ID NO:446 | Construct N | (1) | MGAARSPPSAVPGPLLGLLLLLLGVLAPGGASLRLLDHRALVCSQPGLNC |
| SEQ ID NO:443 | Construct K | (1) | MGAARSPPSAVPGPLLGLLLLLLGVLAPGGASLRLLDFPAPVCAQEGLSC |
| SEQ ID NO:444 | Construct L | (1) | MGAARSPPSAVPGPLLGLLLLLLGVLAPGGASLRLLDHRALVCSQPGLNC |
| SEQ ID NO:431 | huIL17RFpH | (1) | MGAARSPPSAVPGPLLGLLLLLLGVLAPGGASLRLLDHRALVCSQPGLNC |
| SEQ ID NO:432 | muIL-17R | (1) | MAIRRCWPRVVPGPALGWLLLLNVLAPGRASPRLLDFPAPVCAQEGLSC |

|  |  | 51 | 100 |
|---|---|---|---|
|  | Construct A | (51) | RVKNSTCLDDSWIHPRNLTPSSPKDLQIQLHFAHTQQGDLFPVAHIEWTL |
|  | Construct B | (51) | TVKNSTCLDDSWIHPRNLTPSSPKNIYINLSVSSTQHGELVPVLHVEWTL |
|  | Construct C | (51) | TVKNSTCLDDSWIHPRNLTPSSPKDLQIQLHFAHTQQGDLFPVAHIEWTL |
|  | Construct D | (51) | TVKNSTCLDDSWIHPRNLTPSSPKDLQIQLHFAHTQQGDLFPVAHIEWTL |
|  | Construct E | (51) | TVKNSTCLDDSWIHPRNLTPSSPKDLQIQLHFAHTQQGDLFPVAHIEWTL |
|  | Construct F | (51) | TVKNSTCLDDSWIHPRNLTPSSPKDLQIQLHFAHTQQGDLFPVAHIEWTL |
|  | Construct G | (51) | RVKNSTCLDDSWIHPRNLTPSSPKDLQIQLHFAHTQQGDLFPVAHIEWTL |
|  | Construct H | (51) | TVKNSTCLDDSWIHPRNLTPSSPKNIYINLSVSSTQHGELVPVLHVEWTL |
|  | Construct I | (51) | TVKNSTCLDDSWIHPRNLTPSSPKDLQIQLHFAHTQQGDLFPVAHIEWTL |
|  | Construct J | (51) | TVKNSTCLDDSWIHPRNLTPSSPKDLQIQLHFAHTQQGDLFPVAHIEWTL |
|  | Construct M | (51) | TVKNSTCLDDSWIHPRNLTPSSPKDLQIQLHFAHTQQGDLFPVAHIEWTL |
|  | Construct N | (51) | TVKNSTCLDDSWIHPRNLTPSSPKDLQIQLHFAHTQQGDLFPVAHIEWTL |
|  | Construct K | (51) | RVKNSTCLDDSWIHPRNLTPSSPKDLQIQLHFAHTQQGDLFPVAHIEWTL |
|  | Construct L | (51) | TVKNSTCLDDSWIHPRNLTPSSPKNIYINLSVSSTQHGELVPVLHVEWTL |
|  | huIL17RFpH | (51) | TVKNSTCLDDSWIHPRNLTPSSPKDLQIQLHFAHTQQGDLFPVAHIEWTL |
|  | muIL-17R | (51) | RVKNSTCLDDSWIHPKNLTPSSPKNIYINLSVSSTQHGELVPVLHVEWTL |

*Fig. 18A*

|              |       | 101                                                  150 |
|--------------|-------|------------------------------------------------------------|
| Construct A  | (101) | QTDASILYLEGAELSVLQLNTNERLCVRFEFLSKLRHHHRRWRFTFSHFV |
| Construct B  | (101) | QTDASILYLEGAELSVLQLNTNERLCVRFEFLSKLRHHHRRWRFTFSHFV |
| Construct C  | (101) | QTDASILYLEGAELSVLQLNTNERLCVKFQFLSMLQHHRKRWRFSFSHFV |
| Construct D  | (101) | QTDASILYLEGAELSVLQLNTNERLCVRFEFLSKLRHHHRRWRFTFSHFV |
| Construct E  | (101) | QTDASILYLEGAELSVLQLNTNERLCVRFEFLSKLRHHHRRWRFTFSHFV |
| Construct F  | (101) | QTDASILYLEGAELSVLQLNTNERLCVRFEFLSKLRHHHRRWRFTFSHFV |
| Construct G  | (101) | QTDASILYLEGAELSVLQLNTNERLCVRFEFLSKLRHHHRRWRFTFSHFV |
| Construct H  | (101) | QTDASILYLEGAELSVLQLNTNERLCVRFEFLSKLRHHHRRWRFTFSHFV |
| Construct I  | (101) | QTDASILYLEGAELSVLQLNTNERLCVKFQFLSMLQHHRKRWRFSFSHFV |
| Construct J  | (101) | QTDASILYLEGAELSVLQLNTNERLCVRFEFLSKLRHHHRRWRFTFSHFV |
| Construct M  | (101) | QTDASILYLEGAELSVLQLNTNERLCVKFQFLSMLQHHRKRWRFSFSHFV |
| Construct N  | (101) | QTDASILYLEGAELSVLQLNTNERLCVRFEFLSKLRHHHRRWRFTFSHFV |
| Construct K  | (101) | QTDASILYLEGAELSVLQLNTNERLCVRFEFLSKLRHHHRRWRFTFSHFV |
| Construct L  | (101) | QTDASILYLEGAELSVLQLNTNERLCVRFEFLSKLRHHHRRWRFTFSHFV |
| huIL17RFpH   | (101) | QTDASILYLEGAELSVLQLNTNERLCVRFEFLSKLRHHHRRWRFTFSHFV |
| muIL-17R     | (101) | QTDASILYLEGAELSVLQLNTNERLCVKFQFLSMLQHHRKRWRFSFSHFV |

|              |       | 151                                                  200 |
|--------------|-------|------------------------------------------------------------|
| Construct A  | (151) | VDPDQEYEVTVHHLPKPIPDGDPNHQSKNFLVPDCEHARMKVTTPCMSSG |
| Construct B  | (151) | VDPDQEYEVTVHHLPKPIPDGDPNHQSKNFLVPDCEHARMKVTTPCMSSG |
| Construct C  | (151) | VDPGQEYEVTVHHLPKPIPDGDPNHQSKNFLVPDCEHARMKVTTPCMSSG |
| Construct D  | (151) | VDPDQEYEVTVHHLPKPIPDGDPNHKSKIIFVPDCEDSKMKMTTSCVSSG |
| Construct E  | (151) | VDPDQEYEVTVHHLPKPIPDGDPNHQSKNFLVPDCEHARMKVTTPCMSSG |
| Construct F  | (151) | VDPDQEYEVTVHHLPKPIPDGDPNHQSKNFLVPDCEHARMKVTTPCMSSG |
| Construct G  | (151) | VDPDQEYEVTVHHLPKPIPDGDPNHQSKNFLVPDCEHARMKVTTPCMSSG |
| Construct H  | (151) | VDPDQEYEVTVHHLPKPIPDGDPNHQSKNFLVPDCEHARMKVTTPCMSSG |
| Construct I  | (151) | VDPGQEYEVTVHHLPKPIPDGDPNHQSKNFLVPDCEHARMKVTTPCMSSG |
| Construct J  | (151) | VDPDQEYEVTVHHLPKPIPDGDPNHKSKIIFVPDCEDSKMKMTTSCVSSG |
| Construct M  | (151) | VDPGQEYEVTVHHLPKPIPDGDPNHQSKNFLVPDCEHARMKVTTPCMSSG |
| Construct N  | (151) | VDPDQEYEVTVHHLPKPIPDGDPNHKSKIIFVPDCEDSKMKMTTSCVSSG |
| Construct K  | (151) | VDPDQEYEVTVHHLPKPIPDGDPNHQSKNFLVPDCEHARMKVTTPCMSSG |
| Construct L  | (151) | VDPDQEYEVTVHHLPKPIPDGDPNHQSKNFLVPDCEHARMKVTTPCMSSG |
| huIL17RFpH   | (151) | VDPDQEYEVTVHHLPKPIPDGDPNHQSKNFLVPDCEHARMKVTTPCMSSG |
| muIL-17R     | (151) | VDPGQEYEVTVHHLPKPIPDGDPNHKSKIIFVPDCEDSKMKMTTSCVSSG |

*Fig. 18B*

```
                    201                                               250
Construct A  (201)  SLWDPNITVETLEAHQLRVSFTLWNESTHYQILLTSFPHMENHSCFEHMH
Construct B  (201)  SLWDPNITVETLEAHQLRVSFTLWNESTHYQILLTSFPHMENHSCFEHMH
Construct C  (201)  SLWDPNITVETLEAHQLRVSFTLWNESTHYQILLTSFPHMENHSCFEHMH
Construct D  (201)  SLWDPNITVETLEAHQLRVSFTLWNESTHYQILLTSFPHMENHSCFEHMH
Construct E  (201)  SLWDPNITVETLDTQHLRVDFTLWNESTHYQILLTSFPHMENHSCFEHMH
Construct F  (201)  SLWDPNITVETLEAHQLRVSFTLWNESTPYQVLLESFSDSENHSCFDVVK
Construct G  (201)  SLWDPNITVETLDTQHLRVDFTLWNESTHYQILLTSFPHMENHSCFEHMH
Construct H  (201)  SLWDPNITVETLDTQHLRVDFTLWNESTHYQILLTSFPHMENHSCFEHMH
Construct I  (201)  SLWDPNITVETLDTQHLRVDFTLWNESTHYQILLTSFPHMENHSCFEHMH
Construct J  (201)  SLWDPNITVETLDTQHLRVDFTLWNESTHYQILLTSFPHMENHSCFEHMH
Construct M  (201)  SLWDPNITVETLEAHQLRVSFTLWNESTPYQVLLESFSDSENHSCFDVVK
Construct N  (201)  SLWDPNITVETLEAHQLRVSFTLWNESTPYQVLLESFSDSENHSCFDVVK
Construct K  (201)  SLWDPNITVETLEAHQLRVSFTLWNESTPYQVLLESFSDSENHSCFDVVK
Construct L  (201)  SLWDPNITVETLEAHQLRVSFTLWNESTPYQVLLESFSDSENHSCFDVVK
 huIL17RFpH  (201)  SLWDPNITVETLEAHQLRVSFTLWNESTHYQILLTSFPHMENHSCFEHMH
   muIL-17R  (201)  SLWDPNITVETLDTQHLRVDFTLWNESTPYQVLLESFSDSENHSCFDVVK
                    251                                               300
Construct A  (251)  HIPAPRPEEFHQRSNVTLTLRNLKGCCRHQVQIQPFFSSCLNDCLRHSAT
Construct B  (251)  HIPAPRPEEFHQRSNVTLTLRNLKGCCRHQVQIQPFFSSCLNDCLRHSAT
Construct C  (251)  HIPAPRPEEFHQRSNVTLTLRNLKGCCRHQVQIQPFFSSCLNDCLRHSAT
Construct D  (251)  HIPAPRPEEFHQRSNVTLTLRNLKGCCRHQVQIQPFFSSCLNDCLRHSAT
Construct E  (251)  HIPAPRPEEFHQRSNVTLTLRNLKGCCRHQVQIQPFFSSCLNDCLRHSAT
Construct F  (251)  QIFAPRQEEFHQRANVTFTLSKFHWCCHHHVQVQPFFSSCLNDCLRHAMT
Construct G  (251)  HIPAPRPEEFHQRSNVTLTLRNLKGCCRHQVQIQPFFSSCLNDCLRHSAT
Construct H  (251)  HIPAPRPEEFHQRSNVTLTLRNLKGCCRHQVQIQPFFSSCLNDCLRHSAT
Construct I  (251)  HIPAPRPEEFHQRSNVTLTLRNLKGCCRHQVQIQPFFSSCLNDCLRHSAT
Construct J  (251)  HIPAPRPEEFHQRSNVTLTLRNLKGCCRHQVQIQPFFSSCLNDCLRHSAT
Construct M  (251)  QIFAPRQEEFHQRANVTFTLSKFHWCCHHHVQVQPFFSSCLNDCLRHAMT
Construct N  (251)  QIFAPRQEEFHQRANVTFTLSKFHWCCHHHVQVQPFFSSCLNDCLRHAMT
Construct K  (251)  QIFAPRQEEFHQRANVTFTLSKFHWCCHHHVQVQPFFSSCLNDCLRHAMT
Construct L  (251)  QIFAPRQEEFHQRANVTFTLSKFHWCCHHHVQVQPFFSSCLNDCLRHAMT
 huIL17RFpH  (251)  HIPAPRPEEFHQRSNVTLTLRNLKGCCRHQVQIQPFFSSCLNDCLRHSAT
   muIL-17R  (251)  QIFAPRQEEFHQRANVTFTLSKFHWCCHHHVQVQPFFSSCLNDCLRHAMT
```

*Fig. 18C*

```
                         301                                              349
Construct A    (301)  VSCPEMPDT--PEPIPDYMPLWEPRSGSSDYKDDDDKGSSHHHHHH---
Construct B    (301)  VSCPEMPDT--PEPIPDYMPLWEPRSGSSDYKDDDDKGSSHHHHHH---
Construct C    (301)  VSCPEMPDT--PEPIPDYMPLWEPRSGSSDYKDDDDKGSSHHHHHH---
Construct D    (301)  VSCPEMPDT--PEPIPDYMPLWEPRSGSSDYKDDDDKGSSHHHHHH---
Construct E    (301)  VSCPEMPDT--PEPIPDYMPLWEPRSGSSDYKDDDDKGSSHHHHHH---
Construct F    (301)  VPCPVISNTTVPKPVADYIPLWEPRSGSSDYKDDDDKGSSHHHHHH---
Construct G    (301)  VSCPEMPDT--PEPIPDYMPLWEPRSGSSDYKDDDDKGSSHHHHHH---
Construct H    (301)  VSCPEMPDT--PEPIPDYMPLWEPRSGSSDYKDDDDKGSSHHHHHH---
Construct I    (301)  VSCPEMPDT--PEPIPDYMPLWEPRSGSSDYKDDDDKGSSHHHHHH---
Construct J    (301)  VSCPEMPDT--PEPIPDYMPLWEPRSGSSDYKDDDDKGSSHHHHHH---
Construct M    (301)  VPCPVISNTTVPKPVADYIPLWEPRSGSSDYKDDDDKGSSHHHHHH---
Construct N    (301)  VPCPVISNTTVPKPVADYIPLWEPRSGSSDYKDDDDKGSSHHHHHH---
Construct K    (301)  VPCPVISNTTVPKPVADYIPLWEPRSGSSDYKDDDDKGSSHHHHHH---
Construct L    (301)  VPCPVISNTTVPKPVADYIPLWEPRSGSSDYKDDDDKGSSHHHHHH---
huIL17RFpH     (301)  VSCPEMPDT--PEPIPDYMPLWEPRSGSSDYKDDDDKGSSHHHHHH---
muIL-17R       (301)  VPCPVISNTTVPKPVADYIPLW---------------------------
```

*Fig. 18D*

|  |  | aa 38-51 chimera A | 75-96 B | 128-154 C | 176-197 D | 213-220 E | 229-319 F | A+E G | B+E H | C+E I | D+E J | A+F K | B+F L | C+F M | D+F N |
|---|---|---|---|---|---|---|---|---|---|---|---|---|---|---|---|
| BIN 1 | AM_H18/AM_L18 | 0.052 | 0.063 | 0.052 | 0.059 | 0.067 | 3105.0 | 0.052 | 0.088 | 0.059 | 0.064 | 31.310 | 0.00 | 1.551 | n.d. |
| BIN 2 | AM_H1/AM_L1 | 0.228 | 0.00 | 0.049 | 0.00 | 0.172 | 0.156 | 0.219 | 0.088 | 0.074 | 159.30 | 0.235 | 277.200 | 0.078 | n.d. |
|  | AM_H22/AM_L22 | 0.042 | 0.064 | 0.160 | 0.00 | 0.057 | 0.041 | 0.054 | 0.063 | 0.190 | 150.50 | 0.033 | 0.056 | 0.125 | n.d. |
| BIN 3 | AM_H14/AM_L14 | 0.022 | 0.038 | 0.061 | 14.500 | 0.030 | 0.021 | 0.023 | 0.050 | 0.067 | 1.181 | 0.017 | 0.040 | 0.047 | n.d. |
|  | AM_H19/AM_L19 | 0.066 | 0.112 | 0.092 | 51.020 | 0.075 | 0.053 | 0.076 | 0.130 | 0.131 | 149.40 | 0.043 | 0.100 | 0.092 | n.d. |
|  | AM_H23/AM_L23 | 0.072 | 0.504 | 3.959 | 2.100 | 0.076 | 0.046 | 0.083 | 2.269 | 2.650 | 710.50 | 0.041 | 0.185 | 0.769 | n.d. |
| BIN 4 | AM_H26/AM_L26 | 0.249 | 0.201 | 0.156 | 0.145 | 0.323 | 0.00 | 0.283 | 0.410 | 0.289 | 0.234 | 0.00 | 0.006 | 0.00 | n.d. |
| BIN 5 | AM_H21/AM_L21 | 0.018 | 0.017 | 0.030 | 0.134 | 0.026 | 0.026 | 0.025 | 0.025 | 0.032 | 0.104 | 0.017 | 0.025 | 0.035 | 0.378 |
| BIN 6 | AM_H20/AM_L20 | 0.023 | 0.020 | 0.040 | 2.675 | 0.027 | 0.029 | 0.027 | 0.033 | 0.042 | 0.897 | 0.022 | 0.027 | 0.040 | 192.400 |

*Fig. 19*

```
1    MGAARSPPSA VPGPLLGLLL LLLGVLAPGG ASLRLLDHRA LVCSQPGLNC
51   TVKNSTCLDD SWIHPRNLTP SSPKDLQIQL HFAHTQQGDL FPVAHIEWTL
101  QTDASILYLE GAELSVLQLN TNERLCVRFE FLSKLRHHHR RWRFTFSHFV
151  VDPDQEYEVT VHHLPKPIPD GDPNHQSKNF LVPDCEHARM KVTTPCMSSG
201  SLWDPNITVE TLEAHQLRVS FTLWNESTHY QILLTSFPHM ENHSCFEHMH
251  HIPAPRPEEF HQRSNVTLTL RNLKGCCRHQ VQIQPFFSSC LNDCLRHSAT
301  VSCPEMPDTP EPIPDYMPLW EPRSGSSDYK DDDDKGSSHH HHHH
```

SEQ ID NO:431

*Fig. 20*

| | chimera | | arginine mutants |
|---|---|---|---|
| BIN 1 | AM$_H$18/AM$_L$18 | F: 229-319 | S220R, E226R, T228R, S236R, L270R, Q284R |
| BIN 2 | AM$_H$1/AM$_L$1 | B: 75-96<br>D: 176-197 | D152R |
| BIN 3 | AM$_H$22/AM$_L$22 | C: 128-154<br>D: 176-197 | D152R, D154R, E156R, D184R, E186R, S198R |
| | AM$_H$14/AM$_L$14 | D: 176-197 | D152R, D154R, E156R, D184R, E186R, H297R |
| | AM$_H$19/AM$_L$19 | D: 176-197 | D152R, D154R, E156R, D184R, E186R |
| | AM$_H$23/AM$_L$23 | B: 75-96<br>C: 128-154<br>D: 176-197 | E97R, D152R, D154R, E156R, Q176R, D184R, E186R, S198R, T235R, H297R |
| BIN 4 | AM$_H$26/AM$_L$26 | F: 229-319 | H138R, K166R, H215R, S220R, E226R, T228R, S236R, E241R, H243R, L270R |
| BIN 5 | AM$_H$21/AM$_L$21 | D: 176-197 | E113R, S115R, D152R, D154R, E156R, S177R, S198R |
| BIN 6 | AM$_H$20/AM$_L$20 | D: 176-197 | D152R, D154R, E156R, S177R, L270R |

*Fig. 22*

SEQUENCE LISTING

<160> NUMBER OF SEQ ID NOS: 472

<210> SEQ ID NO 1
<211> LENGTH: 131
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Asn Trp Ile Arg Gln Ser Pro Gly Lys Gly Leu Glu Trp Ile
        35                  40                  45

Gly Asp Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Asp Gly Glu Leu Ala Asn Tyr Tyr Gly Ser Gly Ser Tyr Gln Phe
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 2
<211> LENGTH: 127
<212> TYPE: PRT
<213> ORGANISM: Homo sapiens

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Tyr Tyr Phe Asp Ser Ser Gly Tyr Leu Tyr Tyr Tyr Tyr
            100                 105                 110

Gly Leu Asp Val Trp Gly Gln Gly Thr Thr Val Thr Val Ser Ser
        115                 120                 125

<210> SEQ ID NO 3
<211> LENGTH: 114
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Asn Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Val Tyr Trp Gly Gln Gly Thr Leu Val Thr Val
            100                 105                 110

Ser Ser

<210> SEQ ID NO 4
<211> LENGTH: 114
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Asn Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Val Tyr Trp Gly Gln Gly Thr Leu Val Thr Val
            100                 105                 110

Ser Ser

<210> SEQ ID NO 5
<211> LENGTH: 125
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
1               5                   10                  15

Thr Leu Pro Leu Thr Cys Thr Val Ser Gly Gly Ser Ile Arg Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Arg Ser Gly Asn Thr Ile Tyr Asn Pro Ser Leu Lys
    50                  55                  60

Ser Arg Val Thr Met Ser Ile Asp Thr Ser Lys Asn Gln Phe Ser Leu
65                  70                  75                  80

Thr Leu Ser Ser Val Thr Ala Ala Asp Thr Ala Val Tyr Tyr Cys Ala
                85                  90                  95

Arg Glu Asn Tyr Ser Glu Ser Ser Gly Leu Tyr Tyr Tyr Tyr Gly Met

```
                    100                 105                 110
Asp Val Trp Gly Gln Gly Thr Thr Val Thr Val Ser Ser
        115                 120                 125

<210> SEQ ID NO 6
<211> LENGTH: 124
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
            100                 105                 110

Pro Trp Gly Gln Gly Thr Leu Val Thr Val Ser Ser
        115                 120

<210> SEQ ID NO 7
<211> LENGTH: 124
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
            100                 105                 110

Pro Trp Gly Gln Gly Thr Leu Val Thr Val Ser Ser
        115                 120

<210> SEQ ID NO 8
<211> LENGTH: 124
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Asn Thr Phe Thr Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Asn Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
                100                 105                 110

Pro Trp Gly Gln Gly Thr Leu Val Thr Val Ser Ser
            115                 120
```

<210> SEQ ID NO 9
<211> LENGTH: 124
<212> TYPE: PRT
<213> ORGANISM: Homo sapiens

<400> SEQUENCE: 9

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
                100                 105                 110

Pro Trp Gly Gln Gly Thr Leu Val Thr Val Ser Ser
            115                 120
```

<210> SEQ ID NO 10
<211> LENGTH: 124
<212> TYPE: PRT
<213> ORGANISM: Homo sapiens

<400> SEQUENCE: 10

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Phe Ser Gly Ser Ala Tyr Tyr Asn Pro Ser
 50                  55                  60

Leu Lys Ser Arg Val Ala Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg Glu Tyr Tyr Asp Ser Ser Gly Tyr Pro Asp Ala Phe Asp
            100                 105                 110

Ile Trp Gly Gln Gly Thr Met Val Thr Val Ser Ser
        115                 120
```

<210> SEQ ID NO 11
<211> LENGTH: 114
<212> TYPE: PRT
<213> ORGANISM: Homo sapiens

<400> SEQUENCE: 11

```
Gln Val Gln Leu Val Glu Ser Gly Gly Gly Val Val Gln Pro Gly Arg
1               5                   10                  15

Ser Leu Arg Leu Ser Cys Ala Thr Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Lys Asp Tyr Trp Gly Gln Gly Thr Leu Val Thr Val
            100                 105                 110

Ser Ser
```

<210> SEQ ID NO 12
<211> LENGTH: 116
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
        115
```

<210> SEQ ID NO 13
<211> LENGTH: 121
<212> TYPE: PRT
<213> ORGANISM: Homo sapiens

<400> SEQUENCE: 13

```
Gln Val Gln Leu Val Glu Ser Gly Gly Gly Val Val Gln Pro Gly Arg
```

```
             1               5                  10                 15
            Ser Leu Arg Leu Ser Cys Ala Ala Ser Gly Phe Thr Phe Ser Ser Tyr
                        20                  25                  30

Gly Met Gln Trp Val Arg Gln Ala Pro Gly Lys Gly Leu Glu Trp Val
                        35                  40                  45

Ala Val Ile Trp Tyr Asp Gly Asn Lys Lys Tyr Tyr Ala Asp Ser Val
                        50                  55                  60

Lys Gly Arg Phe Thr Ile Ser Arg Asp Asn Ser Lys Asn Thr Leu Tyr
            65                      70                  75                  80

Leu Gln Met Asn Ser Leu Arg Ala Glu Asp Thr Ala Val Tyr Tyr Cys
                        85                  90                  95

Ala Arg Gly Arg Val Arg Asp Tyr Tyr Tyr Gly Met Asp Val Trp Gly
                        100                 105                 110

Gln Gly Thr Thr Val Thr Val Ser Ser
                        115                 120

<210> SEQ ID NO 14
<211> LENGTH: 116
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Arg Tyr
                        20                  25                  30

Gly Ile Ser Trp Val Arg Gln Ala Pro Gly Gln Gly Leu Glu Trp Met
                        35                  40                  45

Gly Trp Ile Ser Thr Tyr Ser Gly Asn Thr Asn Tyr Ala Gln Lys Leu
                        50                  55                  60

Gln Gly Arg Val Thr Met Thr Thr Asp Thr Ser Thr Ser Thr Ala Tyr
            65                      70                  75                  80

Met Glu Leu Arg Ser Leu Arg Ser Asp Asp Thr Ala Val Tyr Tyr Cys
                        85                  90                  95

Ala Arg Arg Gln Leu Tyr Phe Asp Tyr Trp Gly Gln Gly Thr Leu Val
                        100                 105                 110

Thr Val Ser Ser
                        115

<210> SEQ ID NO 15
<211> LENGTH: 121
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
            1               5                   10                  15

Ser Leu Arg Leu Ser Cys Ala Ala Ser Gly Phe Thr Phe Ser Ser Tyr
                        20                  25                  30

Gly Met Gln Trp Val Arg Gln Ala Pro Gly Lys Gly Leu Glu Trp Val
                        35                  40                  45

Ala Val Ile Trp Tyr Asp Gly Asn Lys Lys Tyr Tyr Ala Asp Ser Val
                        50                  55                  60

Lys Gly Arg Phe Thr Ile Ser Arg Asp Asn Ser Lys Asn Thr Leu Tyr
            65                      70                  75                  80

Leu Gln Met Asn Ser Leu Arg Ala Glu Asp Thr Ala Val Tyr Tyr Cys
```

```
                85                  90                  95

Ala Arg Gly Arg Val Arg Asp Tyr Tyr Tyr Gly Met Asp Val Trp Gly
            100                 105                 110

Gln Gly Thr Thr Val Thr Val Ser Ser
            115                 120

<210> SEQ ID NO 16
<211> LENGTH: 116
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Lys Tyr Ala Gln Lys Leu
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
            115

<210> SEQ ID NO 17
<211> LENGTH: 116
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ala Val Lys Val Ser Cys Lys Ala Thr Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
            115

<210> SEQ ID NO 18
<211> LENGTH: 126
<212> TYPE: PRT
<213> ORGANISM: Homo sapiens

<400> SEQUENCE: 18
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Met
        35                  40                  45

Gly Trp Met His Pro Asn Ser Gly Thr Asp Leu Ala Gln Arg Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Cys Ser Thr Leu Ser Cys Ser Phe Tyr Trp Tyr
            100                 105                 110

Phe Asp Leu Trp Gly Arg Gly Thr Leu Val Thr Val Ser Ser
        115                 120                 125

<210> SEQ ID NO 19
<211> LENGTH: 116
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Lys Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Ala Leu Asp Tyr Trp Gly Gln Gly Thr Leu Val
            100                 105                 110

Thr Val Ser Ser
    115

<210> SEQ ID NO 20
<211> LENGTH: 118
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Phe Ile Ser Ala Arg Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Asp Glu Asp Thr Ala Val Tyr Tyr Cys
                85                  90                  95

Ala Arg Pro Lys Val Gly Gly Gly Met Asp Val Trp Gly Gln Gly Thr
            100                 105                 110

Thr Val Thr Val Ser Ser
        115

<210> SEQ ID NO 21
<211> LENGTH: 118
<212> TYPE: PRT
<213> ORGANISM: Homo sapiens

<400> SEQUENCE: 21

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ile Ile Ser Ser Arg Ser Ser Ile Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Pro Lys Val Gly Gly Gly Met Asp Val Trp Gly Gln Gly Thr
            100                 105                 110

Thr Val Thr Val Ser Ser
        115

<210> SEQ ID NO 22
<211> LENGTH: 116
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 23
<211> LENGTH: 125
<212> TYPE: PRT
<213> ORGANISM: Homo sapiens
```

<400> SEQUENCE: 23

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Ala Gly Lys Arg Leu Glu Trp Ile
        35                  40                  45
Gly Arg Ile Tyr Pro Ser Gly Arg Thr Asn Tyr Asn Pro Ser Leu Lys
    50                  55                  60
Ser Arg Val Thr Met Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Ala Tyr Glu Leu Gln Leu Gly Leu Tyr Tyr Tyr Gly Met
            100                 105                 110
Asp Val Trp Gly Gln Gly Thr Pro Val Thr Val Ser Ser
            115                 120                 125
```

<210> SEQ ID NO 24
<211> LENGTH: 125
<212> TYPE: PRT
<213> ORGANISM: Homo sapiens

<400> SEQUENCE: 24

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Ala Ala Gly Lys Arg Leu Glu Trp Ile
        35                  40                  45
Gly Arg Ile Tyr Pro Ser Gly Arg Thr Asn Tyr Asn Pro Ser Leu Lys
    50                  55                  60
Ser Arg Val Thr Met Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Ala Tyr Glu Leu Gln Leu Gly Leu Tyr Tyr Tyr Gly Met
            100                 105                 110
Asp Val Trp Gly Gln Gly Thr Pro Val Thr Val Ser Ser
            115                 120                 125
```

<210> SEQ ID NO 25
<211> LENGTH: 124
<212> TYPE: PRT
<213> ORGANISM: Homo sapiens

<400> SEQUENCE: 25

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Ile Gly Tyr Ile Tyr Tyr Ser Gly Asn Thr Tyr Tyr Asn Pro Ser
    50                  55                  60
```

-continued

Leu Arg Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Glu Ala Gly Gly Asn Ser Ala Tyr Tyr Tyr Gly Met Asp
            100                 105                 110

Val Trp Gly Gln Gly Thr Thr Val Thr Val Ser Ser
            115                 120

<210> SEQ ID NO 26
<211> LENGTH: 125
<212> TYPE: PRT
<213> ORGANISM: Homo sapiens

<400> SEQUENCE: 26

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Tyr Tyr Phe Gly Ser Gly Ser Tyr Glu Gly Met
            100                 105                 110

Asp Val Trp Gly Gln Gly Thr Thr Val Thr Val Ser Ser
            115                 120                 125

<210> SEQ ID NO 27
<211> LENGTH: 107
<212> TYPE: PRT
<213> ORGANISM: Homo sapiens

<400> SEQUENCE: 27

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Phe
                85                  90                  95

Thr Phe Gly Pro Gly Thr Lys Val Asp Ile Lys
            100                 105

<210> SEQ ID NO 28
<211> LENGTH: 106
<212> TYPE: PRT
<213> ORGANISM: Homo sapiens

```
<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Val Trp Tyr Gln Gln Arg Pro Gly Gln Ala Pro Arg Leu Leu Ile
        35                  40                  45

Tyr Gly Ala Ser Thr Arg Ala Asn Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Trp Arg Thr
                85                  90                  95

Phe Gly Gln Gly Ser Lys Val Glu Ile Lys
            100                 105

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 30
<211> LENGTH: 108
<212> TYPE: PRT
<213> ORGANISM: Homo sapiens

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Trp Thr Phe Gly Gln Gly Thr Lys Val Glu Ile Lys
```

<210> SEQ ID NO 31
<211> LENGTH: 107
<212> TYPE: PRT
<213> ORGANISM: Homo sapiens

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Phe Gln Ser Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 33
<211> LENGTH: 107
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

-continued

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 35
<211> LENGTH: 107
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Val Ser Ala Ser Val Gly
1               5                   10                  15

```
Asp Arg Val Thr Ile Thr Cys Arg Ala Ser Gln Gly Ile Arg Ser Trp
                 20                  25                  30

Leu Ala Trp Tyr Gln Gln Lys Pro Gly Lys Ala Pro Lys Leu Leu Ile
         35                  40                  45

Phe Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Arg
                 85                  90                  95

Thr Phe Gly Gln Gly Thr Lys Val Glu Ile Lys
            100                 105
```

<210> SEQ ID NO 37
<211> LENGTH: 108
<212> TYPE: PRT
<213> ORGANISM: Homo sapiens

<400> SEQUENCE: 37

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Ala Gly Ile Pro Ala Arg Phe Ser Gly
    50                  55                  60

Gly Gly Ser Gly Thr Ala Phe Thr Leu Thr Ile Ser Asn Leu Gln Ser
65                  70                  75                  80

Glu Asp Phe Ala Val Tyr Tyr Cys Gln His Tyr Ile Asn Trp Pro Lys
                 85                  90                  95

Trp Thr Phe Gly Gln Gly Thr Lys Val Asp Ile Lys
            100                 105
```

<210> SEQ ID NO 38
<211> LENGTH: 107
<212> TYPE: PRT
<213> ORGANISM: Homo sapiens

<400> SEQUENCE: 38

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Ser
                 20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asn Phe Ala Val Tyr Tyr Cys Gln Gln Tyr Asp Asn Trp Pro Leu
                 85                  90                  95

Thr Phe Gly Gly Gly Thr Lys Val Glu Ile Lys
            100                 105
```

<210> SEQ ID NO 39
<211> LENGTH: 112

```
<212> TYPE: PRT
<213> ORGANISM: Homo sapiens

<400> SEQUENCE: 39

Asp Ile Val Met Thr Gln Thr Pro Leu Ser Leu Ser Val Thr Pro Gly
1               5                   10                  15

Gln Pro Ala Ser Ile Ala Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ser
                85                  90                  95

Ile Gln Leu Pro Leu Thr Phe Gly Gly Gly Thr Lys Val Glu Ile Lys
            100                 105                 110

<210> SEQ ID NO 40
<211> LENGTH: 107
<212> TYPE: PRT
<213> ORGANISM: Homo sapiens

<400> SEQUENCE: 40

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 41
<211> LENGTH: 107
<212> TYPE: PRT
<213> ORGANISM: Homo sapiens

<400> SEQUENCE: 41

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Ala Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
```

```
                85                  90                  95
Thr Phe Gly Gly Gly Thr Lys Val Glu Ile Lys
            100                 105
```

<210> SEQ ID NO 42
<211> LENGTH: 107
<212> TYPE: PRT
<213> ORGANISM: Homo sapiens

<400> SEQUENCE: 42

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Thr Ser
            20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asp Ile Trp Pro Leu
                85                  90                  95

Thr Phe Gly Gly Gly Thr Lys Val Glu Ile Lys
            100                 105
```

<210> SEQ ID NO 43
<211> LENGTH: 107
<212> TYPE: PRT
<213> ORGANISM: Homo sapiens

<400> SEQUENCE: 43

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Asp Asn Trp Pro Leu
                85                  90                  95

Thr Phe Gly Gly Gly Thr Lys Val Glu Ile Lys
            100                 105
```

<210> SEQ ID NO 44
<211> LENGTH: 113
<212> TYPE: PRT
<213> ORGANISM: Homo sapiens

<400> SEQUENCE: 44

```
Asp Ile Val Met Thr Gln Ser Pro Asp Ser Leu Ala Val Ser Leu Gly
1               5                   10                  15

Glu Arg Ala Thr Ile Asn Cys Lys Thr Ser Gln Ser Val Leu Tyr Ser
            20                  25                  30

Ser Lys Asn Lys Asn Phe Leu Ala Trp Tyr Gln Gln Lys Pro Gly Gln
        35                  40                  45
```

-continued

Pro Leu Asn Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Phe Thr Phe Gly Pro Gly Thr Lys Val Asp Ile
            100                 105                 110

Lys

<210> SEQ ID NO 45
<211> LENGTH: 107
<212> TYPE: PRT
<213> ORGANISM: Homo sapiens

<400> SEQUENCE: 45

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Asp
         50                  55                  60

Asn Gly Ser Gly Thr Glu Phe Thr Leu Thr Ile Ser Ser Leu Gln Ser
 65                  70                  75                  80

Glu Asp Phe Ala Val Tyr Phe Cys Gln Gln Tyr Asp Thr Trp Pro Leu
                 85                  90                  95

Thr Phe Gly Gly Gly Thr Lys Val Glu Ile Lys
            100                 105

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Phe Pro Glu Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Arg Ala Pro Phe
                 85                  90                  95

Thr Phe Gly Pro Gly Thr Lys Val Asp Ile Lys
            100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Phe Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Arg Ala Pro Phe
                85                  90                  95

Thr Phe Gly Pro Gly Thr Lys Val Asp Ile Lys
            100                 105

<210> SEQ ID NO 48
<211> LENGTH: 107
<212> TYPE: PRT
<213> ORGANISM: Homo sapiens

<400> SEQUENCE: 48

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Ala Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Gly Ile Ile Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys

-continued

```
                100                 105
```

<210> SEQ ID NO 50
<211> LENGTH: 113
<212> TYPE: PRT
<213> ORGANISM: Homo sapiens

<400> SEQUENCE: 50

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly His Thr Cys Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Leu Cys Ser Phe Gly Gln Gly Thr Lys Leu Glu Ile
            100                 105                 110

Lys
```

<210> SEQ ID NO 51
<211> LENGTH: 113
<212> TYPE: PRT
<213> ORGANISM: Homo sapiens

<400> SEQUENCE: 51

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly His Thr Cys Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Leu Cys Ser Phe Gly Gln Gly Thr Lys Leu Glu Ile
            100                 105                 110

Lys
```

<210> SEQ ID NO 52
<211> LENGTH: 107
<212> TYPE: PRT
<213> ORGANISM: Homo sapiens

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Ile Tyr
            20                  25                  30

Leu Ala Trp Phe Gln Gln Lys Pro Gly Lys Ala Pro Lys Ser Leu Ile
```

```
             35                  40                  45
Tyr Ala Ala Ser Ser Leu Gln Ser Gly Val Pro Ser Lys Phe Ser Gly
         50                  55                  60
Ser Val Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Ser Tyr Pro Arg
                 85                  90                  95
Thr Phe Gly Gln Gly Thr Lys Val Glu Ile Lys
            100                 105
```

<210> SEQ ID NO 53
<211> LENGTH: 107
<212> TYPE: PRT
<213> ORGANISM: Homo sapiens

<400> SEQUENCE: 53

```
Glu Ile Leu Met Thr Gln Ser Pro Ala Thr Leu Ser Val Ser Pro Gly
1               5                   10                  15
Glu Arg Ala Thr Leu Ser Cys Arg Ala Ser Gln Ser Val Tyr Ser Asn
            20                  25                  30
Leu Ala Trp Tyr Gln Gln Lys Pro Gly Gln Ala Pro Arg Leu Leu Ile
         35                  40                  45
Ser Gly Ala Ser Thr Arg Ala Thr Gly Ile Pro Ala Arg Phe Ser Gly
         50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Tyr Asn Trp Pro Trp
                 85                  90                  95
Thr Phe Gly Gln Gly Thr Lys Val Glu Ile Lys
            100                 105
```

<210> SEQ ID NO 54
<211> LENGTH: 393
<212> TYPE: DNA
<213> ORGANISM: Homo sapiens

<400> SEQUENCE: 54

```
caggtgcagc tgcaggagtc gggcccagga ctggtgaagc cttcggagac cctgtccctc    60
acctgcactg tctcaggtgg ctccatcagt aattactact ggaactggat ccggcagtcc   120
ccagggaagg gactggagtg gattggggat atctattaca gtgggagcac caactacaac   180
ccctccctca gagtcgagt caccatatca gtagacacgt ccaagaacca gttctccctg   240
aagctgagct ctgtgaccac tgcggacacg gccgtgtatt actgtgcgag agatggggaa   300
ctcgccaatt actatggttc ggggagttat cagttctact actacggg tatggacgtc   360
tggggccaag ggaccacggt caccgtctcc tca                               393
```

<210> SEQ ID NO 55
<211> LENGTH: 381
<212> TYPE: DNA
<213> ORGANISM: Homo sapiens

<400> SEQUENCE: 55

```
caggtgcagc tacagcagtg gggcgcagga ctgttgaagc cttcggagac cctgtccctc    60
acctgcgctg tctctggtgg gtccttcagt ggttactact ggagctggat ccgccagccc   120
ccagggaagg ggctggaatg gattggggaa atcaatcata gtggacgcac caattacaac   180
```

| | |
|---|---|
| ccgtccctca agagtcgagt caccatatca gtagacacgt ccaagaacca gttctccctg | 240 |
| aagctgagct ctgtgaccgc cgcggacacg gctgtttatt actgtgcgag aggcccttat | 300 |
| tactttgata gtagtggtta cctttactac tactacggtt tggacgtctg gggccaaggg | 360 |
| accacggtca ccgtctcctc a | 381 |

<210> SEQ ID NO 56
<211> LENGTH: 342
<212> TYPE: DNA
<213> ORGANISM: Homo sapiens

<400> SEQUENCE: 56

| | |
|---|---|
| caggtgcagc tggtggagtc tgggggaggc gtggtccagc ctgggaggtc cctgagactc | 60 |
| tcctgtgcag cgtctggaat caacttcagt agctatggca tgcactgggt ccgccaggct | 120 |
| ccaggcaagg ggctggagtg ggtggcagtt atatggtatg atggaagtaa taaacactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagatact | 300 |
| ggggtctact ggggccaggg aaccctggtc accgtctcct ca | 342 |

<210> SEQ ID NO 57
<211> LENGTH: 342
<212> TYPE: DNA
<213> ORGANISM: Homo sapiens

<400> SEQUENCE: 57

| | |
|---|---|
| caggtgcagc tggtggagtc tgggggaggc gtggtccagc ctgggaggtc cctgagactc | 60 |
| tcctgtgcag cgtctggaat caacttcagt agctatggca tgcactgggt ccgccaggct | 120 |
| ccaggcaagg ggctggagtg ggtggcagtt atatggtatg atggaagtaa taaacactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagatact | 300 |
| ggggtctact ggggccaggg aaccctggtc accgtctcct ca | 342 |

<210> SEQ ID NO 58
<211> LENGTH: 375
<212> TYPE: DNA
<213> ORGANISM: Homo sapiens

<400> SEQUENCE: 58

| | |
|---|---|
| caggtgcagc tgcaggagtc gggcccagga ctggtgaagc cttcggagac cctgcccctc | 60 |
| acctgcactg tctctggtgg ctccatcaga agttactact ggagctggat ccggcagccc | 120 |
| gccgggaagg gactggagtg gattggcgt atctatcgca gtgggaacac catctacaac | 180 |
| ccctccctca agagtcgagt caccatgtca atagacacgt ccaagaacca gttctccctg | 240 |
| acgctgagtt ctgtgaccgc cgcggacacg gccgtgtatt actgtgcgag agagaattac | 300 |
| tctgagagta gtggtctcta ctactactac ggtatggacg tctggggcca agggaccacg | 360 |
| gtcaccgtct cctca | 375 |

<210> SEQ ID NO 59
<211> LENGTH: 372
<212> TYPE: DNA
<213> ORGANISM: Homo sapiens

<400> SEQUENCE: 59

| | |
|---|---|
| caggttcagc tggtgcagtc tggagctgag gtgaagaagc ctggggcctc agtgaaggtc | 60 |

```
tcctgcaagg cttctggtta caccttaacc agatatggta tcagctgggt gcgacaggcc      120
cctggacaag ggcttgagtg gatgggttgg atcagcgctt acaatggtaa cacaaactat      180
gcacagaagc tccagggcag agtcaccatg accacagaca cgtccacgag cacagcctac      240
atggagctga ggagcctgag atctgacgac acggccgtgt attactgtgc gagaagggat      300
tacgatattt tgactggtta ttataacggg ttcgaccect ggggccaggg aaccctggtc      360
accgtctcct ca                                                          372
```

<210> SEQ ID NO 60
<211> LENGTH: 372
<212> TYPE: DNA
<213> ORGANISM: Homo sapiens

<400> SEQUENCE: 60

```
caggttcagc tggtgcagtc tggagctgag gtgaagaagc ctggggcctc agtgaaggtc       60
tcctgcaagg cttctggtta caccttaacc agatatggta tcagctgggt gcgacaggcc      120
cctggacaag ggcttgagtg gatgggttgg atcagcgctt acaatggtaa cacaaactat      180
gcacagaagc tccagggcag agtcaccatg accacagaca cgtccacgag cacagcctac      240
atggagctga ggagcctgag atctgacgac acggccgtgt attactgtgc gagaagggat      300
tacgatattt tgactggtta ttataacggg ttcgaccect ggggccaggg aaccctggtc      360
accgtctcct ca                                                          372
```

<210> SEQ ID NO 61
<211> LENGTH: 372
<212> TYPE: DNA
<213> ORGANISM: Homo sapiens

<400> SEQUENCE: 61

```
caggttcagc tggtgcagtc tggagctgag gtgaagaagc ctggggcctc agtgaaggtc       60
tcctgcaagg cttctggtaa caccttacc ggctatggta tcagctgggt gcgacaggcc      120
cctggacaag ggcttgagtg gatgggatgg atcagcgctt acaatggtaa cacaaactat      180
gcacagaacc tccagggcag agtcaccatg accacagaca catccacgag cacagcctac      240
atggagctga ggagcctgag atctgacgac acggccgtgt attactgtgc gagaagggat      300
tacgatattt tgactggtta ttataacggg ttcgaccect ggggccaggg aaccctggtc      360
accgtctcct ca                                                          372
```

<210> SEQ ID NO 62
<211> LENGTH: 372
<212> TYPE: DNA
<213> ORGANISM: Homo sapiens

<400> SEQUENCE: 62

```
caggttcagc tggtgcagtc tggagttgag gtgaagaagc ctggggcctc agtgaaggtc       60
tcctgcaagg cttctggtta caccttaacc agatatggta tcagctgggt gcgacaggcc      120
cctggacaag ggcttgagtg gatgggttgg atcagcgctt acaatggtaa cacaaactat      180
gcacagaagc tccagggcag agtcaccatg accacagaca catccacgag cacagcctac      240
atggagctga ggagcctgag atctgacgac acggccgtgt attactgtgc gagaagggat      300
tacgatattt tgactggtta ttataacggg ttcgaccect ggggccaggg aaccctggtc      360
accgtctcct ca                                                          372
```

<210> SEQ ID NO 63
<211> LENGTH: 372
<212> TYPE: DNA
<213> ORGANISM: Homo sapiens

<400> SEQUENCE: 63
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcaccccg ggaagggcct ggagtggatt gggtacatct atttcagtgg gagcgcctac     180
tacaacccgt ccctcaagag tcgagtcgcc atatcagtgg acacgtctaa gaaccagttc     240
tccctgaagc tgagctctgt gactgccgcg gacacggccg tatattactg tgcgagagaa     300
tactatgata gtagtggtta ccccgatgct tttgatatct ggggccaagg gacaatggtc     360
accgtctcct ca                                                         372

<210> SEQ ID NO 64
<211> LENGTH: 342
<212> TYPE: DNA
<213> ORGANISM: Homo sapiens

<400> SEQUENCE: 64
caggtgcaac tggtggagtc tgggggaggc gtggtccagc ctgggaggtc cctgagactc      60
tcctgtgcaa cgtccggaat caccttcagt agctatggca tgcactgggt ccgccaggct     120
ccaggcaagg ggctggagtg ggtggcagtt atatggtatg atggaagtaa taaatattat     180
gcagactccg tgaagggccg attcaccatc tccagagaca attccaagaa cacgctgtat     240
ctgcaaatga acagcctgag agccgaggac acggctgtgt attactgtgc gagagatacg     300
aaggactact ggggccaggg aaccctggtc accgtctcct ca                        342

<210> SEQ ID NO 65
<211> LENGTH: 348
<212> TYPE: DNA
<213> ORGANISM: Homo sapiens

<400> SEQUENCE: 65
caggttcagc tggtgcagtc tggagctgag gtgaagaagc ctggggcctc agtgaaggtc      60
tcctgcaagg cttctggtta caccctcacc agctatggta tcagctgggt gcgacaggcc     120
cctggacaag gacttgagtg gatgggatgg atcagcactt acaaaggtaa cacaaactat     180
gcacagaagc tccagggcag agtcaccatg accacagaca catccacgag cacagcctac     240
atggaactga ggagcctgag atctgacgac acggccgtgt attactgtgc gagaaagcag     300
ctcgtctttg actactgggg tcagggaacc ctggtcaccg tctcctca                  348

<210> SEQ ID NO 66
<211> LENGTH: 363
<212> TYPE: DNA
<213> ORGANISM: Homo sapiens

<400> SEQUENCE: 66
caggtgcagc tggtggagtc tgggggaggc gtggtccagc ctgggaggtc cctgagactc      60
tcctgtgcag cgtctggatt caccttcagt agctatggca tgcagtgggt ccgccaggct     120
ccaggcaagg ggctggagtg ggtggcagtt atatggtatg atggaaataa gaaatactat     180
gcagactccg tgaagggccg attcaccatc tccagagaca attccaagaa cacgctgtat     240
ctgcaaatga acagcctgag agccgaggac acggctgtgt attactgtgc gagaggacgt     300

```
gttagggact actactacgg tatggacgtc tggggccaag ggaccacggt caccgtctcc    360
tca                                                                 363

<210> SEQ ID NO 67
<211> LENGTH: 350
<212> TYPE: DNA
<213> ORGANISM: Homo sapiens

<400> SEQUENCE: 67
caggttcagc tggtgcagtc tggagctgag gtgaagaagc ctggggcctc agtgaaggtc     60
tcctgcaagg cttctggtta cacctttacc agatatggta tcagctgggt gcgacaggcc    120
cctggacaag gcttgagtg atgggatgg atcagcactt acagtggtaa cacaaactat     180
gcacagaagc tccagggcag agtcaccatg accacagaca catccacgag cacagcctac    240
atggagctga ggagcctgag atctgacgac acggccgtgt attactgtgc gagacggcag    300
ctttactttg actactgggg ccagggaacc ctggtcaccg tctcctcagc                350

<210> SEQ ID NO 68
<211> LENGTH: 363
<212> TYPE: DNA
<213> ORGANISM: Homo sapiens

<400> SEQUENCE: 68
caggtgcagc tggtggagtc tggggaggc gtggtccagc ctgggaggtc cctgagactc     60
tcctgtgcag cgtctggatt cacctcagt agctatggca tgcagtgggt ccgccaggct    120
ccaggcaagg gctggagtg gtgcagtt atatggtatg atggaaataa gaaatactat      180
gcagactccg tgaagggccg attcaccatc tccagagaca attccaagaa cacgctgtat    240
ctgcaaatga acagcctgag agccgaggac acggctgtgt attactgtgc gagaggacgt    300
gttagggact actactacgg tatggacgtc tggggccaag ggaccacggt caccgtctcc    360
tca                                                                 363

<210> SEQ ID NO 69
<211> LENGTH: 348
<212> TYPE: DNA
<213> ORGANISM: Homo sapiens

<400> SEQUENCE: 69
caggttcagc tggtgcagtc tggagctgag gtgaagaagc ctggggcctc agtgaaggtc     60
tcctgcaagg cttctggtta cacctttacc agctatggta tcagctgggt gcgacaggcc    120
cctggacaag gcttgagtg atgggatgg atcagcgctt acaatggtaa cacaaagtat     180
gcacagaagc tccagggcag agtcaccatg accacagaca catccacgag cacagtctac    240
atggagctga ggagcctgag atctgacgac acggccgtgt attactgtgc gagaaagcag    300
ctcgtctttg actactgggg ccagggaacc ctggtcaccg tctcctca                 348

<210> SEQ ID NO 70
<211> LENGTH: 348
<212> TYPE: DNA
<213> ORGANISM: Homo sapiens

<400> SEQUENCE: 70
caggttcagc tggtgcagtc tggagctgag gtgaagaagc ctggggccgc agtgaaggtc     60
tcctgcaagg ctactggtta cacccttgacc agctatggta tcagctgggt gcgacaggcc    120
```

| | |
|---|---|
| cctggacaag ggcttgagtg gatgggatgg atcagcgctt acagtggtaa tacaaagtat | 180 |
| gcacagaagc tccagggcag agtcaccatg accacagaca catccacgag cacagcctac | 240 |
| atggagctga ggagcctgag atctgacgac acggccgtgt attactgtgc gagaaagcag | 300 |
| ctcgtctttg actactgggg ccagggaacc ctggtcaccg tctcctca | 348 |

<210> SEQ ID NO 71
<211> LENGTH: 378
<212> TYPE: DNA
<213> ORGANISM: Homo sapiens

<400> SEQUENCE: 71

| | |
|---|---|
| caggtgcagc tggtgcagtc tggggctgag gtgaagaagc ctggggcctc agtgaaggtc | 60 |
| tcctgcaagg cttctggata ctccttcacc gactactaca tgcactgggt gcgacaggcc | 120 |
| cctggacaag gacttgagtg gatgggatgg atgcacccta acagtggtgg cacagactta | 180 |
| gcacagaggt ttcagggcag ggtcaccatg accaggggaca cgtccatcag cacagcctac | 240 |
| atggagctga gcaggctgag atctgacgac acggccgtgt attactgtgc gagagggggga | 300 |
| tattgtagta ctttgagctg ctccttctac tggtacttcg atctctgggg ccgtggcacc | 360 |
| ctggtcactg tctcctca | 378 |

<210> SEQ ID NO 72
<211> LENGTH: 348
<212> TYPE: DNA
<213> ORGANISM: Homo sapiens

<400> SEQUENCE: 72

| | |
|---|---|
| caggttcagc tggtgcagtc tggagctgag gtgaagaagc ctggggcctc agtgaaggtc | 60 |
| tcctgcaagg cttctggtta caccttgacc agctatggaa tcagttgggt gcgacaggcc | 120 |
| cctggacaag ggcttgagtg gatgggatgg atcagcgctt acagtggtaa cacaaagtat | 180 |
| gcacagaagt tccagggcag agtcaccatg accacagaca catccacgag cacagcctac | 240 |
| atggagctga ggagcctgag atctgacgac acggccgtgt attactgtgc gagaaggcag | 300 |
| ctcgcgttgg actactgggg ccagggaacc ctggtcaccg tctcctca | 348 |

<210> SEQ ID NO 73
<211> LENGTH: 354
<212> TYPE: DNA
<213> ORGANISM: Homo sapiens

<400> SEQUENCE: 73

| | |
|---|---|
| gaggtgcagc tggtggagtc tgggggaggc ttggtacagc ctggggggtc cctgagactc | 60 |
| tcctgtgcag cctctggatt cacccttcagc agctatagca tgaactgggt ccgccaggct | 120 |
| ccagggaagg ggctggagtg ggtttcattc attagtgcta gaagtagtac catatactac | 180 |
| gcagactctg tgaagggccg attcaccatc tccagagaca atgccaagaa ctcactgtat | 240 |
| ctgcaaatga acagcctgag agacgaggac acggctgtgt attactgtgc gagacctaaa | 300 |
| gtgggggggcg gtatggacgt ctggggccaa ggaaccacgg tcaccgtctc ctca | 354 |

<210> SEQ ID NO 74
<211> LENGTH: 354
<212> TYPE: DNA
<213> ORGANISM: Homo sapiens

<400> SEQUENCE: 74

| | |
|---|---|
| gaggtgcagt tggtggagtc tgggggaggc tcggtacagc ctggggggtc cctgagactc | 60 |

```
tcctgtgcag cctctggatt caccttcagt agctatagca tgaactgggt ccgccaggct    120
ccagggaagg ggctggagtg ggtttcaatc attagtagta gaagtagtat catacactac    180
gcagactctg tgaagggccg attcaccatc tccagagaca atgccaagaa ctcactgtat    240
ctgcaaatga acagcctgag agacgaggac acggctgtgt attactgtgc gagacctaaa    300 gtgggggggcg gtatggacgt ctggggccaa gggaccacgg tcaccgtctc ctca         354

<210> SEQ ID NO 75
<211> LENGTH: 348
<212> TYPE: DNA
<213> ORGANISM: Homo sapiens

<400> SEQUENCE: 75
caggttcagc tggtgcagtc tggagctgag gtgaagaagc ctggggcctc agtgaaggtc     60
tcctgcaagg cttctggtta cacctttacc agatatggta tcagctgggt gcgacaggcc    120
cctggacaag gcttgagtg gatgggatgg atcagcgctt acagtggtaa cacaaactat    180
gcacagaagc tccagggcag agtcaccatg accacagaca catccacgag cacagcctac    240
atggagctga ggagcctgag atctgacgac acggccgtgt attactgtgc gagacggcag    300
ctttactttg actactgggg ccagggaacc ctggtcaccg tctcctca                 348

<210> SEQ ID NO 76
<211> LENGTH: 375
<212> TYPE: DNA
<213> ORGANISM: Homo sapiens

<400> SEQUENCE: 76
caggtgcagc tgcaggagtc gggcccagga ctggtgaagc cttcggagac cctgtccctc     60
acctgcactg tcactggtgg ctccatcagg agttactact ggagctggat ccggcagccc    120
gccgggaaga gactggagtg gattgggcgt atctatccca gtgggagaac caactacaac    180
ccctccctca agagtcgagt caccatgtca gtagacacgt ccaagaacca gttctccctg    240
aagctgagct ctgtgaccgc cgcggacacg gccgtgtatt actgtgcgag agaggcatat    300
gagctgcaac tgggcctcta ctactactac ggtatggacg tctggggcca agggaccccg    360
gtcaccgtct cctca                                                     375

<210> SEQ ID NO 77
<211> LENGTH: 375
<212> TYPE: DNA
<213> ORGANISM: Homo sapiens

<400> SEQUENCE: 77
caggtgcagc tgcaggagtc gggcccagga ctggtgaagc cttcggagac cctgtccctc     60
acctgcactg tcactggtgg ctccatcagg agttactact ggagctggat ccggcaggcc    120
gccgggaaga gactggagtg gattgggcgt atctatccca gtgggagaac caactacaac    180
ccctccctca agagtcgagt caccatgtca gtagacacgt ccaagaacca gttctccctg    240
aagctgagct ctgtgaccgc cgcggacacg gccgtgtatt actgtgcgag agaggcatat    300
gagctgcaac tgggcctcta ctactactac ggtatggacg tctggggcca agggaccccg    360
gtcaccgtct cctca                                                     375

<210> SEQ ID NO 78
<211> LENGTH: 372
<212> TYPE: DNA
```

<213> ORGANISM: Homo sapiens

<400> SEQUENCE: 78

| | | | | | |
|---|---|---|---|---|---|
| caggtgcagc | tgcaggagtc | gggcccagga | ctggtgaagc | cttcacagac | cctgtccctc | 60
| acctgcactg | tctctggtgg | ctccatcagc | agtggtggtt | actactggag | ctggatccgc | 120
| cagcacccag | ggaagggcct | ggagtggatt | gggtacatct | attacagtgg | gaacacctac | 180
| tacaacccgt | ccctcaggag | tcgagttacc | atatcagttg | acacgtctaa | gaaccagttc | 240
| tccctgaagc | tgaactctgt | gactgccgcg | gacacggccg | tgtattactg | tgcgagagag | 300
| gccggtggta | actccgccta | ctactacggt | atggacgtct | ggggccaagg | gaccacggtc | 360
| accgtctcct | ca | | | | | 372

<210> SEQ ID NO 79
<211> LENGTH: 375
<212> TYPE: DNA
<213> ORGANISM: Homo sapiens

<400> SEQUENCE: 79

| | | | | | |
|---|---|---|---|---|---|
| caggtgcagc | tggtggagtc | tgggggaggc | ttggtcaagc | ctggagggtc | cctgagactc | 60
| tcctgtgcag | cctctggatt | caccttcagt | gactactaca | tgagctggat | ccgccaggct | 120
| ccagggaagg | ggctggagtg | ggtttcatac | attagtagta | gtggtagtac | catatactac | 180
| gcagactctg | tgaagggccg | attcaccatc | tccagggaca | acgccaagaa | ctcactgtat | 240
| ctgcaaatga | acagcctgag | agccgaggac | acggccgtgt | attactgtgc | gagagatcgc | 300
| acgtattact | ttggttcggg | gagttatgaa | gggatggacg | tctggggcca | agggaccacg | 360
| gtcaccgtct | cctca | | | | | 375

<210> SEQ ID NO 80
<211> LENGTH: 321
<212> TYPE: DNA
<213> ORGANISM: Homo sapiens

<400> SEQUENCE: 80

| | | | | | |
|---|---|---|---|---|---|
| gacatcctga | tgacccagtc | tccatcctcc | ctgtctgcat | ctgtcggaga | cagagtcacc | 60
| atcacttgcc | gggcaagtca | gggcattaga | aatgatttag | gctggtatca | gcagaaacca | 120
| gggaaagccc | ctaagcgcct | gatctatgct | gcatccagtt | tgcaaagtgg | ggtcccatcc | 180
| aggttcagcg | gcagtggctc | tgggacagaa | ttcactctca | caatcagcag | cctgcagcct | 240
| gaagattttg | caacttatta | ctgtctacag | cataatagta | acccattcac | tttcggccct | 300
| gggaccaaag | tggatatcaa | a | | | | 321

<210> SEQ ID NO 81
<211> LENGTH: 318
<212> TYPE: DNA
<213> ORGANISM: Homo sapiens

<400> SEQUENCE: 81

| | | | | | |
|---|---|---|---|---|---|
| gaaatagtga | tgacgcagtc | tccagccacc | ctgtctgtgt | ctccagggga | aagagccacc | 60
| ctctcctgca | gggccagtca | gagtgttagc | agaaacttag | tctggtacca | gcagagacct | 120
| ggccaggctc | ccaggctcct | catctatggg | gcatccacta | gggccaatgg | tatcccagcc | 180
| aggttcagtg | gcagtgggtc | agggacagaa | ttcactctca | ccatcagcag | cctgcagtct | 240
| gaagattttg | cagtttatta | ctgtcagcag | tataaaagct | ggcggacgtt | cggccaaggg | 300
| tccaaggtgg | aaatcaaa | | | | | 318

<210> SEQ ID NO 82
<211> LENGTH: 321
<212> TYPE: DNA
<213> ORGANISM: Homo sapiens

<400> SEQUENCE: 82

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccattcac tttcggccct   300
gggaccaaag tggatatcaa a                                             321
```

<210> SEQ ID NO 83
<211> LENGTH: 324
<212> TYPE: DNA
<213> ORGANISM: Homo sapiens

<400> SEQUENCE: 83

```
gaaatagtga tgacgcagtc tccagccacc ctgtctgtgt ctccagggga aagagccacc    60
ctctcctgca gggccagtca gagtgttagt aggaatttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcccacgtg gacgttcggc   300
caagggacca aggtggaaat caaa                                          324
```

<210> SEQ ID NO 84
<211> LENGTH: 321
<212> TYPE: DNA
<213> ORGANISM: Homo sapiens

<400> SEQUENCE: 84

```
gacatccaga tgacccagtc tccatcctcc ctgtctgcat ctgtaggaga cagagtcacc    60
atcacttgcc gggcaagtca gggcattaga aatgatttag ctggtatca gcagaagcca   120
gggaaagccc ctaaacgcct gatctatgct gcatccagtt tccaaagtgg ggtcccatca   180
aggttcagcg gcagtggatc tgggacagga ttcactctca caatcagcag cctgcagcct   240
gaagattttg caacttatta ctgtctacag cataatagtt accctccgac gttcggccaa   300
gggaccaagg tggaaatcaa a                                             321
```

<210> SEQ ID NO 85
<211> LENGTH: 321
<212> TYPE: DNA
<213> ORGANISM: Homo sapiens

<400> SEQUENCE: 85

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataaaagtt acccgctcac tttcggcgga   300
```

```
gggaccaagg tggagatcaa a                                               321
```

<210> SEQ ID NO 86
<211> LENGTH: 321
<212> TYPE: DNA
<213> ORGANISM: Homo sapiens

<400> SEQUENCE: 86

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataaaagtt acccgctcac tttcggcgga    300
gggaccaagg tggagatcaa a                                              321
```

<210> SEQ ID NO 87
<211> LENGTH: 321
<212> TYPE: DNA
<213> ORGANISM: Homo sapiens

<400> SEQUENCE: 87

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataagagtt acccgctcac tttcggcgga    300
gggaccaagg tggagatcaa a                                              321
```

<210> SEQ ID NO 88
<211> LENGTH: 321
<212> TYPE: DNA
<213> ORGANISM: Homo sapiens

<400> SEQUENCE: 88

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctacgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataaaagtt acccgctcac tttcggcgga    300
gggaccaagg tggagatcaa a                                              321
```

<210> SEQ ID NO 89
<211> LENGTH: 321
<212> TYPE: DNA
<213> ORGANISM: Homo sapiens

<400> SEQUENCE: 89

```
gacatccaga tgacccagtc tccatcttcc gtgtctgcat ctgtaggaga cagagtcacc     60
atcacttgtc gggcgagtca gggtattagg agctggttag cctggtatca gcagaaacca    120
gggaaagccc ctaagctcct gatctttgct gcatccagtt tgcaaagtgg ggtcccatca    180
aggttcagcg gcagtggatc tgggacagaa ttcactctca ccatcagcag cctgcagcct    240
gaagattttg caacttacta ttgtcaacag gctaacaatt tccctcggac gttcggccaa    300
```

-continued

```
gggaccaagg tggaaatcaa a                                              321

<210> SEQ ID NO 90
<211> LENGTH: 324
<212> TYPE: DNA
<213> ORGANISM: Homo sapiens

<400> SEQUENCE: 90
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccgctgg tatcccagcc    180
aggttcagtg gcggtgggtc tgggacagcg ttcactctca ccatcagcaa cctacagtct    240
gaagattttg cagtttatta ctgtcagcac tatataaact ggcctaagtg gacgttcggc    300
caagggacca aggtggacat caaa                                           324

<210> SEQ ID NO 91
<211> LENGTH: 321
<212> TYPE: DNA
<213> ORGANISM: Homo sapiens

<400> SEQUENCE: 91
gaaatagtaa tgacgcagtc tccagccacc ctgtctgtgt ctccagggga aagagccacc     60
ctctcctgca gggccagtca gagtattagc agcagcttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaaaattttg cagtttatta ctgtcagcaa tatgataact ggccgctcac tttcggcgga    300
gggaccaagg tggagatcaa a                                              321

<210> SEQ ID NO 92
<211> LENGTH: 336
<212> TYPE: DNA
<213> ORGANISM: Homo sapiens

<400> SEQUENCE: 92
gatattgtga tgacccagac tccactctct ctgtccgtca cccctggaca gccggcctcc     60
atcgcctgca gtctagtca gagcctcctg catagtgatg aaagaccta tttgtattgg     120 tacctgcaga agccaggcca gcctccacag ctcctgatct atgaagtttc cacccggttc    180
tctggagtgc cagataggtt cagtggcagc gggtcaggga cagatttcac actgaaaatc    240
agccgggtgg aggctgagga tgttggggtt ttttactgca tgcaaagtat acagcttccg    300
ctcactttcg gcggagggac caaggtggag atcaaa                              336

<210> SEQ ID NO 93
<211> LENGTH: 321
<212> TYPE: DNA
<213> ORGANISM: Homo sapiens

<400> SEQUENCE: 93
gaaatagtga tgacgcagtc tccagccacc ctgtctgtgt ctcctgggga aagagccacc     60
ctctcctgca gggccagtca gagtgttagc agcaacttag cctggttcca gcagaaacct    120
ggccaggctc ccaggcccct catctatgat gcatccacca gggccactgg tgtcccagcc    180
aggttcagtg gcagtgggtc tgggacagac ttcactctca ccatcagcag cctgcagtct    240
```

```
gaagattttg cagtttatta ctgtcagcag tatgataact ggccgctcac tttcggcgga    300
gggaccaagg tggagatcaa a                                              321
```

<210> SEQ ID NO 94
<211> LENGTH: 321
<212> TYPE: DNA
<213> ORGANISM: Homo sapiens

<400> SEQUENCE: 94

```
gaaatagtga tgacgcagtc tccagccacc ctgtctgtgt ctccagggga aagagtcacc    60
ctctcctgca gggccagtca gagtgttagc agcaacttag cctggttcca gcagaaacct    120
ggccaggctc ccaggcccct catctatgat gcatccacca gggccgctgg tatcccagcc    180
aggttcagtg gcagtgggtc tgggacagac ttcactctca ccatcagcag cctgcagtct    240
gaagattttg cagtttatta ctgtcagcag tatgataact ggccgctcac tttcggcgga    300
gggaccaagg tggagatcaa a                                              321
```

<210> SEQ ID NO 95
<211> LENGTH: 324
<212> TYPE: DNA
<213> ORGANISM: Homo sapiens

<400> SEQUENCE: 95

```
gaaatagtga tgacgcagtc tccagccacc ctgtctgtgt ctccagggga aagagccacc    60
ctctcctgca gggccagtca gagtattagc accagcttag cctggtacca gcagaaacct    120
ggccaggctc ccaggctcct catctatggt acatccacca gggccactgg tatcccagcc    180
aggttcagtg gcagtgggtc tgggacagag ttcactctca ccatcagcag cctgcagtct    240
gaagattttg cagtttattt ctgtcaacag tatgatatct ggccgctcac tttcggcgga    300
gggaccaagg tggagatcaa acga                                           324
```

<210> SEQ ID NO 96
<211> LENGTH: 321
<212> TYPE: DNA
<213> ORGANISM: Homo sapiens

<400> SEQUENCE: 96

```
gaaatagtga tgacgcagtc tccagccacc ctgtctgtgt ctccagggga aagagccacc    60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttattc ctgtcagcag tatgataact ggccgctcac tttcggcgga    300
gggaccaagg tggagatcaa a                                              321
```

<210> SEQ ID NO 97
<211> LENGTH: 339
<212> TYPE: DNA
<213> ORGANISM: Homo sapiens

<400> SEQUENCE: 97

```
gacatcgtga tgacccagtc tccagactcc ctggctgtgt ctctgggcga gagggccacc    60
atcaactgca agaccagcca gagtgtttta tacagctcca aaaacaagaa cttcttagct    120
tggtatcagc agaaaccagg acagcctctt aacctgctca tttactgggc atctacccgg    180
gaatccgggg tccctgaccg attcagtggc agcgggtctg ggacagattt cactctcacc    240
```

```
atcagcagcc tgcaggctga agatgtggca gtttattact gtcagcaata ttatagtact    300
ccattcactt tcggccctgg gaccaaagtg gatatcaaa                            339

<210> SEQ ID NO 98
<211> LENGTH: 321
<212> TYPE: DNA
<213> ORGANISM: Homo sapiens

<400> SEQUENCE: 98
gaaatagtga tgacgcagtc tccagccacc ctgtctgtgt ctccagggga aagagccacc     60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg acaatgggtc tgggacagag ttcactctca ccatcagcag cctgcagtct   240
gaagattttg cagtttattt ctgtcagcag tatgataccc tggcctctca ctttggcggc   300
gggaccaagg tggagatcaa a                                              321

<210> SEQ ID NO 99
<211> LENGTH: 321
<212> TYPE: DNA
<213> ORGANISM: Homo sapiens

<400> SEQUENCE: 99
gacatccaga tgacccagtc tccatcctcc ctgtctgcat ctgtaggaga cagagtcacc     60
atcacttgcc gggcgagtca gggcattagc aattatttag cctggtatca gcagaaacca   120
gggaaatttc ctgagctcct gatctatgct gcatccactt tacaatcagg ggtcccatct   180
cggttcagtg gcagtggatc tgggacagat ttcactctca ccatcagcag cctgcagcct   240
gaagatgttg caacttatta ctgtcaaaag tataaccgtg ccccattcac tttcggccct   300
gggaccaaag tggatatcaa a                                              321

<210> SEQ ID NO 100
<211> LENGTH: 321
<212> TYPE: DNA
<213> ORGANISM: Homo sapiens

<400> SEQUENCE: 100
gacatccaga tgacccagtc tccatcctcc ctgtctgcat ctgtaggaga cagagtcacc     60
atcacttgcc gggcgagtca gggcattagc aattatttag cctggtatca gcagaaacca   120
gggaaatttc ctgagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataaccgtg ccccattcac tttcggccct   300
gggaccaaag tggatatcaa a                                              321

<210> SEQ ID NO 101
<211> LENGTH: 321
<212> TYPE: DNA
<213> ORGANISM: Homo sapiens

<400> SEQUENCE: 101
gaaatagtga tgacgcagtc tccagccacc ctgtctgtgt ctccagggga aagagtcacc     60
ctctcctgca gggccagtca gagtgttagc agcaacttag cctggttcca gcagaaacct   120
ggccaggctc ccaggcccct catctatgat gcatccacca gggccgctgg tatcccagcc   180
```

```
aggttcagtg gcagtgggtc tgggacagac ttcactctca ccatcagcag cctgcagtct      240
gaagattttg cagtttatta ctgtcagcag tatgataact ggccgctcac tttcggcgga      300
gggaccaagg tggagatcaa a                                                321

<210> SEQ ID NO 102
<211> LENGTH: 321
<212> TYPE: DNA
<213> ORGANISM: Homo sapiens

<400> SEQUENCE: 102
gacatccaga tgacccagtc tccatcctcc ctgtctgcat ctgttggaga cagagtcacc       60
atctcttgcc gggcaagtca gggcattata aatgatttag gctggtatca gcagaaacca      120
gggaaagccc ctaagcgcct gatctatgct gcatccagtt tgcaaagtgg ggtcccatca      180
aggttcagcg gcagtggatc tgggacagaa ttcacttttca caatcagcag cctgcagcct      240
gaagattttg caacttatta ctgtctacag cataatagtt accctccgac gttcggccaa      300
gggaccaagg tggaaatcaa a                                                321

<210> SEQ ID NO 103
<211> LENGTH: 339
<212> TYPE: DNA
<213> ORGANISM: Homo sapiens

<400> SEQUENCE: 103
gatattgtga tgactcagtc tccactctcc ctgcccgtca cccttggaca gccggcctcc       60
atctcctgca ggtctagtca aagcctcgta tatagtgatg gacacacctg cttgaattgg      120
tttcagcaga ggccaggcca atctccaagg cgcctaattt ataaggtttc taactgggac      180
tctggggtcc cagacagatt cagcggcagt gggtcaggca ctgatttcac actgaaaatc      240
agcagggtgg aggctgacga tgttggggtt tattactgca tgcaaggtac acactggcct      300
ctgtgcagtt ttggccaggg gaccaagctg gagatcaaa                             339

<210> SEQ ID NO 104
<211> LENGTH: 339
<212> TYPE: DNA
<213> ORGANISM: Homo sapiens

<400> SEQUENCE: 104
gatattgtga tgactcagtc tccactctcc ctgcccgtca cccttggaca gccggcctcc       60
atctcctgca ggtctagtca aagcctcgta tatagtgatg gacacacctg cttgaattgg      120
tttcagcaga ggccaggcca atctccaagg cgcctaattt ataaggtttc taactgggac      180
tctggggtcc cagacagatt cagcggcagt gggtcaggca ctgatttcac actgaaaatc      240
agcagggtgg aggctgacga tgttggggtt tattactgca tgcaaggtac acactggcct      300
ctgtgcagtt ttggccaggg gaccaagctg gagatcaaa                             339

<210> SEQ ID NO 105
<211> LENGTH: 321
<212> TYPE: DNA
<213> ORGANISM: Homo sapiens

<400> SEQUENCE: 105
gacatccaga tgacccagtc tccatcctca ctgtctgcat ctgtaggaga cagagtcacc       60
atcacttgtc gggcgagtca ggccattagc atttatttag cctggtttca gcagaaacca      120
gggaaagccc ctaagtccct gatctatgct gcatccagtt tgcaaagtgg ggtcccatca      180
```

```
aagttcagcg gcagtgtatc tgggacagat ttcactctca ccatcagcag cctgcagcct    240
gaagattttg caacttatta ctgccaacag tatagtagtt accctcggac gttcggccaa    300
gggaccaagg tggaaatcaa a                                              321
```

<210> SEQ ID NO 106
<211> LENGTH: 321
<212> TYPE: DNA
<213> ORGANISM: Homo sapiens

<400> SEQUENCE: 106

```
gaaatattga tgacgcagtc tccagccacc ctgtctgtgt ctccagggga aagagccacc     60
ctctcctgca gggccagtca gagtgtttac agcaacttag cctggtacca gcagaaacct    120
ggccaggctc ccagactcct catctctggt gcttccacca gggccactgg tatcccagcc    180
aggttcagtg gcagtgggtc tgggacagag ttcactctca ccatcagcag cctgcagtct    240
gaagattttg cagtttatta ctgtcagcag tattataact ggccgtggac gttcggccaa    300
gggaccaagg tggaaatcaa a                                              321
```

<210> SEQ ID NO 107
<211> LENGTH: 5
<212> TYPE: PRT
<213> ORGANISM: Homo sapiens

<400> SEQUENCE: 107

Asn Tyr Tyr Trp Asn
1               5

<210> SEQ ID NO 108
<211> LENGTH: 16
<212> TYPE: PRT
<213> ORGANISM: Homo sapiens

<400> SEQUENCE: 108

Asp Ile Tyr Tyr Ser Gly Ser Thr Asn Tyr Asn Pro Ser Leu Lys Ser
1               5                   10                  15

<210> SEQ ID NO 109
<211> LENGTH: 23
<212> TYPE: PRT
<213> ORGANISM: Homo sapiens

<400> SEQUENCE: 109

Asp Gly Glu Leu Ala Asn Tyr Tyr Gly Ser Gly Ser Tyr Gln Phe Tyr
1               5                   10                  15

Tyr Tyr Tyr Gly Met Asp Val
            20

<210> SEQ ID NO 110
<211> LENGTH: 5
<212> TYPE: PRT
<213> ORGANISM: Homo sapiens

<400> SEQUENCE: 110

Gly Tyr Tyr Trp Ser
1               5

<210> SEQ ID NO 111
<211> LENGTH: 16
<212> TYPE: PRT
<213> ORGANISM: Homo sapiens

<400> SEQUENCE: 111

Glu Ile Asn His Ser Gly Arg Thr Asn Tyr Asn Pro Ser Leu Lys Ser
1               5                   10                  15

<210> SEQ ID NO 112
<211> LENGTH: 19
<212> TYPE: PRT
<213> ORGANISM: Homo sapiens

<400> SEQUENCE: 112

Gly Pro Tyr Tyr Phe Asp Ser Ser Gly Tyr Leu Tyr Tyr Tyr Tyr Gly
1               5                   10                  15

Leu Asp Val

<210> SEQ ID NO 113
<211> LENGTH: 5
<212> TYPE: PRT
<213> ORGANISM: Homo sapiens

<400> SEQUENCE: 113

Ser Tyr Gly Met His
1               5

<210> SEQ ID NO 114
<211> LENGTH: 17
<212> TYPE: PRT
<213> ORGANISM: Homo sapiens

<400> SEQUENCE: 114

Val Ile Trp Tyr Asp Gly Ser Asn Lys His Tyr Ala Asp Ser Val Lys
1               5                   10                  15

Gly

<210> SEQ ID NO 115
<211> LENGTH: 5
<212> TYPE: PRT
<213> ORGANISM: Homo sapiens

<400> SEQUENCE: 115

Asp Thr Gly Val Tyr
1               5

<210> SEQ ID NO 116
<211> LENGTH: 5
<212> TYPE: PRT
<213> ORGANISM: Homo sapiens

<400> SEQUENCE: 116

Ser Tyr Gly Met His
1               5

<210> SEQ ID NO 117
<211> LENGTH: 17
<212> TYPE: PRT
<213> ORGANISM: Homo sapiens

<400> SEQUENCE: 117

Val Ile Trp Tyr Asp Gly Ser Asn Lys His Tyr Ala Asp Ser Val Lys
1               5                   10                  15

Gly

```
<210> SEQ ID NO 118
<211> LENGTH: 5
<212> TYPE: PRT
<213> ORGANISM: Homo sapiens

<400> SEQUENCE: 118

Asp Thr Gly Val Tyr
1               5

<210> SEQ ID NO 119
<211> LENGTH: 5
<212> TYPE: PRT
<213> ORGANISM: Homo sapiens

<400> SEQUENCE: 119

Ser Tyr Tyr Trp Ser
1               5

<210> SEQ ID NO 120
<211> LENGTH: 16
<212> TYPE: PRT
<213> ORGANISM: Homo sapiens

<400> SEQUENCE: 120

Arg Ile Tyr Arg Ser Gly Asn Thr Ile Tyr Asn Pro Ser Leu Lys Ser
1               5                   10                  15

<210> SEQ ID NO 121
<211> LENGTH: 17
<212> TYPE: PRT
<213> ORGANISM: Homo sapiens

<400> SEQUENCE: 121

Glu Asn Tyr Ser Glu Ser Ser Gly Leu Tyr Tyr Tyr Tyr Gly Met Asp
1               5                   10                  15

Val

<210> SEQ ID NO 122
<211> LENGTH: 5
<212> TYPE: PRT
<213> ORGANISM: Homo sapiens

<400> SEQUENCE: 122

Arg Tyr Gly Ile Ser
1               5

<210> SEQ ID NO 123
<211> LENGTH: 17
<212> TYPE: PRT
<213> ORGANISM: Homo sapiens

<400> SEQUENCE: 123

Trp Ile Ser Ala Tyr Asn Gly Asn Thr Asn Tyr Ala Gln Lys Leu Gln
1               5                   10                  15

Gly

<210> SEQ ID NO 124
<211> LENGTH: 15
<212> TYPE: PRT
<213> ORGANISM: Homo sapiens

<400> SEQUENCE: 124

Arg Asp Tyr Asp Ile Leu Thr Gly Tyr Tyr Asn Gly Phe Asp Pro
1               5                   10                  15
```

<210> SEQ ID NO 125
<211> LENGTH: 5
<212> TYPE: PRT
<213> ORGANISM: Homo sapiens

<400> SEQUENCE: 125

Arg Tyr Gly Ile Ser
1               5

<210> SEQ ID NO 126
<211> LENGTH: 17
<212> TYPE: PRT
<213> ORGANISM: Homo sapiens

<400> SEQUENCE: 126

Trp Ile Ser Ala Tyr Asn Gly Asn Thr Asn Tyr Ala Gln Lys Leu Gln
1               5                   10                  15

Gly

<210> SEQ ID NO 127
<211> LENGTH: 15
<212> TYPE: PRT
<213> ORGANISM: Homo sapiens

<400> SEQUENCE: 127

Arg Asp Tyr Asp Ile Leu Thr Gly Tyr Tyr Asn Gly Phe Asp Pro
1               5                   10                  15

<210> SEQ ID NO 128
<211> LENGTH: 5
<212> TYPE: PRT
<213> ORGANISM: Homo sapiens

<400> SEQUENCE: 128

Gly Tyr Gly Ile Ser
1               5

<210> SEQ ID NO 129
<211> LENGTH: 17
<212> TYPE: PRT
<213> ORGANISM: Homo sapiens

<400> SEQUENCE: 129

Trp Ile Ser Ala Tyr Asn Gly Asn Thr Asn Tyr Ala Gln Asn Leu Gln
1               5                   10                  15

Gly

<210> SEQ ID NO 130
<211> LENGTH: 15
<212> TYPE: PRT
<213> ORGANISM: Homo sapiens

<400> SEQUENCE: 130

Arg Asp Tyr Asp Ile Leu Thr Gly Tyr Tyr Asn Gly Phe Asp Pro
1               5                   10                  15

<210> SEQ ID NO 131
<211> LENGTH: 5
<212> TYPE: PRT
<213> ORGANISM: Homo sapiens

<400> SEQUENCE: 131

```
Arg Tyr Gly Ile Ser
1               5
```

<210> SEQ ID NO 132
<211> LENGTH: 17
<212> TYPE: PRT
<213> ORGANISM: Homo sapiens

<400> SEQUENCE: 132

```
Trp Ile Ser Ala Tyr Asn Gly Asn Thr Asn Tyr Ala Gln Lys Leu Gln
1               5                   10                  15

Gly
```

<210> SEQ ID NO 133
<211> LENGTH: 15
<212> TYPE: PRT
<213> ORGANISM: Homo sapiens

<400> SEQUENCE: 133

```
Arg Asp Tyr Asp Ile Leu Thr Gly Tyr Tyr Asn Gly Phe Asp Pro
1               5                   10                  15
```

<210> SEQ ID NO 134
<211> LENGTH: 7
<212> TYPE: PRT
<213> ORGANISM: Homo sapiens

<400> SEQUENCE: 134

```
Ser Gly Gly Tyr Tyr Trp Ser
1               5
```

<210> SEQ ID NO 135
<211> LENGTH: 16
<212> TYPE: PRT
<213> ORGANISM: Homo sapiens

<400> SEQUENCE: 135

```
Tyr Ile Tyr Phe Ser Gly Ser Ala Tyr Tyr Asn Pro Ser Leu Lys Ser
1               5                   10                  15
```

<210> SEQ ID NO 136
<211> LENGTH: 14
<212> TYPE: PRT
<213> ORGANISM: Homo sapiens

<400> SEQUENCE: 136

```
Glu Tyr Tyr Asp Ser Ser Gly Tyr Pro Asp Ala Phe Asp Ile
1               5                   10
```

<210> SEQ ID NO 137
<211> LENGTH: 5
<212> TYPE: PRT
<213> ORGANISM: Homo sapiens

<400> SEQUENCE: 137

```
Ser Tyr Gly Met His
1               5
```

<210> SEQ ID NO 138
<211> LENGTH: 17
<212> TYPE: PRT
<213> ORGANISM: Homo sapiens

<400> SEQUENCE: 138

```
Val Ile Trp Tyr Asp Gly Ser Asn Lys Tyr Tyr Ala Asp Ser Val Lys
1               5                   10                  15

Gly

<210> SEQ ID NO 139
<211> LENGTH: 5
<212> TYPE: PRT
<213> ORGANISM: Homo sapiens

<400> SEQUENCE: 139

Asp Thr Lys Asp Tyr
1               5

<210> SEQ ID NO 140
<211> LENGTH: 5
<212> TYPE: PRT
<213> ORGANISM: Homo sapiens

<400> SEQUENCE: 140

Ser Tyr Gly Ile Ser
1               5

<210> SEQ ID NO 141
<211> LENGTH: 17
<212> TYPE: PRT
<213> ORGANISM: Homo sapiens

<400> SEQUENCE: 141

Trp Ile Ser Thr Tyr Lys Gly Asn Thr Asn Tyr Ala Gln Lys Leu Gln
1               5                   10                  15

Gly

<210> SEQ ID NO 142
<211> LENGTH: 7
<212> TYPE: PRT
<213> ORGANISM: Homo sapiens

<400> SEQUENCE: 142

Lys Gln Leu Val Phe Asp Tyr
1               5

<210> SEQ ID NO 143
<211> LENGTH: 5
<212> TYPE: PRT
<213> ORGANISM: Homo sapiens

<400> SEQUENCE: 143

Ser Tyr Gly Met Gln
1               5

<210> SEQ ID NO 144
<211> LENGTH: 17
<212> TYPE: PRT
<213> ORGANISM: Homo sapiens

<400> SEQUENCE: 144

Val Ile Trp Tyr Asp Gly Asn Lys Lys Tyr Tyr Ala Asp Ser Val Lys
1               5                   10                  15

Gly

<210> SEQ ID NO 145
<211> LENGTH: 12
<212> TYPE: PRT
```

<213> ORGANISM: Homo sapiens

<400> SEQUENCE: 145

Gly Arg Val Arg Asp Tyr Tyr Tyr Gly Met Asp Val
1               5                   10

<210> SEQ ID NO 146
<211> LENGTH: 5
<212> TYPE: PRT
<213> ORGANISM: Homo sapiens

<400> SEQUENCE: 146

Arg Tyr Gly Ile Ser
1               5

<210> SEQ ID NO 147
<211> LENGTH: 17
<212> TYPE: PRT
<213> ORGANISM: Homo sapiens

<400> SEQUENCE: 147

Trp Ile Ser Thr Tyr Ser Gly Asn Thr Asn Tyr Ala Gln Lys Leu Gln
1               5                   10                  15

Gly

<210> SEQ ID NO 148
<211> LENGTH: 7
<212> TYPE: PRT
<213> ORGANISM: Homo sapiens

<400> SEQUENCE: 148

Arg Gln Leu Tyr Phe Asp Tyr
1               5

<210> SEQ ID NO 149
<211> LENGTH: 5
<212> TYPE: PRT
<213> ORGANISM: Homo sapiens

<400> SEQUENCE: 149

Ser Tyr Gly Met Gln
1               5

<210> SEQ ID NO 150
<211> LENGTH: 17
<212> TYPE: PRT
<213> ORGANISM: Homo sapiens

<400> SEQUENCE: 150

Val Ile Trp Tyr Asp Gly Asn Lys Lys Tyr Tyr Ala Asp Ser Val Lys
1               5                   10                  15

Gly

<210> SEQ ID NO 151
<211> LENGTH: 12
<212> TYPE: PRT
<213> ORGANISM: Homo sapiens

<400> SEQUENCE: 151

Gly Arg Val Arg Asp Tyr Tyr Tyr Gly Met Asp Val
1               5                   10

<210> SEQ ID NO 152

```
<211> LENGTH: 5
<212> TYPE: PRT
<213> ORGANISM: Homo sapiens

<400> SEQUENCE: 152

Ser Tyr Gly Ile Ser
1               5

<210> SEQ ID NO 153
<211> LENGTH: 17
<212> TYPE: PRT
<213> ORGANISM: Homo sapiens

<400> SEQUENCE: 153

Trp Ile Ser Ala Tyr Asn Gly Asn Thr Lys Tyr Ala Gln Lys Leu Gln
1               5                   10                  15

Gly

<210> SEQ ID NO 154
<211> LENGTH: 7
<212> TYPE: PRT
<213> ORGANISM: Homo sapiens

<400> SEQUENCE: 154

Lys Gln Leu Val Phe Asp Tyr
1               5

<210> SEQ ID NO 155
<211> LENGTH: 5
<212> TYPE: PRT
<213> ORGANISM: Homo sapiens

<400> SEQUENCE: 155

Ser Tyr Gly Ile Ser
1               5

<210> SEQ ID NO 156
<211> LENGTH: 17
<212> TYPE: PRT
<213> ORGANISM: Homo sapiens

<400> SEQUENCE: 156

Trp Ile Ser Ala Tyr Ser Gly Asn Thr Lys Tyr Ala Gln Lys Leu Gln
1               5                   10                  15

Gly

<210> SEQ ID NO 157
<211> LENGTH: 7
<212> TYPE: PRT
<213> ORGANISM: Homo sapiens

<400> SEQUENCE: 157

Lys Gln Leu Val Phe Asp Tyr
1               5

<210> SEQ ID NO 158
<211> LENGTH: 5
<212> TYPE: PRT
<213> ORGANISM: Homo sapiens

<400> SEQUENCE: 158

Asp Tyr Tyr Met His
1               5
```

<210> SEQ ID NO 159
<211> LENGTH: 17
<212> TYPE: PRT
<213> ORGANISM: Homo sapiens

<400> SEQUENCE: 159

Trp Met His Pro Asn Ser Gly Gly Thr Asp Leu Ala Gln Arg Phe Gln
1               5                   10                  15
Gly

<210> SEQ ID NO 160
<211> LENGTH: 17
<212> TYPE: PRT
<213> ORGANISM: Homo sapiens

<400> SEQUENCE: 160

Gly Gly Tyr Cys Ser Thr Leu Ser Cys Ser Phe Tyr Trp Tyr Phe Asp
1               5                   10                  15
Leu

<210> SEQ ID NO 161
<211> LENGTH: 5
<212> TYPE: PRT
<213> ORGANISM: Homo sapiens

<400> SEQUENCE: 161

Ser Tyr Gly Ile Ser
1               5

<210> SEQ ID NO 162
<211> LENGTH: 17
<212> TYPE: PRT
<213> ORGANISM: Homo sapiens

<400> SEQUENCE: 162

Trp Ile Ser Ala Tyr Ser Gly Asn Thr Lys Tyr Ala Gln Lys Phe Gln
1               5                   10                  15
Gly

<210> SEQ ID NO 163
<211> LENGTH: 7
<212> TYPE: PRT
<213> ORGANISM: Homo sapiens

<400> SEQUENCE: 163

Arg Gln Leu Ala Leu Asp Tyr
1               5

<210> SEQ ID NO 164
<211> LENGTH: 5
<212> TYPE: PRT
<213> ORGANISM: Homo sapiens

<400> SEQUENCE: 164

Ser Tyr Ser Met Asn
1               5

<210> SEQ ID NO 165
<211> LENGTH: 17
<212> TYPE: PRT
<213> ORGANISM: Homo sapiens

<400> SEQUENCE: 165

Phe Ile Ser Ala Arg Ser Ser Thr Ile Tyr Tyr Ala Asp Ser Val Lys
1               5                   10                  15

Gly

<210> SEQ ID NO 166
<211> LENGTH: 9
<212> TYPE: PRT
<213> ORGANISM: Homo sapiens

<400> SEQUENCE: 166

Pro Lys Val Gly Gly Gly Met Asp Val
1               5

<210> SEQ ID NO 167
<211> LENGTH: 5
<212> TYPE: PRT
<213> ORGANISM: Homo sapiens

<400> SEQUENCE: 167

Ser Tyr Ser Met Asn
1               5

<210> SEQ ID NO 168
<211> LENGTH: 17
<212> TYPE: PRT
<213> ORGANISM: Homo sapiens

<400> SEQUENCE: 168

Ile Ile Ser Ser Arg Ser Ser Ile Ile His Tyr Ala Asp Ser Val Lys
1               5                   10                  15

Gly

<210> SEQ ID NO 169
<211> LENGTH: 9
<212> TYPE: PRT
<213> ORGANISM: Homo sapiens

<400> SEQUENCE: 169

Pro Lys Val Gly Gly Gly Met Asp Val
1               5

<210> SEQ ID NO 170
<211> LENGTH: 5
<212> TYPE: PRT
<213> ORGANISM: Homo sapiens

<400> SEQUENCE: 170

Arg Tyr Gly Ile Ser
1               5

<210> SEQ ID NO 171
<211> LENGTH: 17
<212> TYPE: PRT
<213> ORGANISM: Homo sapiens

<400> SEQUENCE: 171

Trp Ile Ser Ala Tyr Ser Gly Asn Thr Asn Tyr Ala Gln Lys Leu Gln
1               5                   10                  15

Gly

<210> SEQ ID NO 172
<211> LENGTH: 7

-continued

```
<212> TYPE: PRT
<213> ORGANISM: Homo sapiens

<400> SEQUENCE: 172

Arg Gln Leu Tyr Phe Asp Tyr
1               5

<210> SEQ ID NO 173
<211> LENGTH: 5
<212> TYPE: PRT
<213> ORGANISM: Homo sapiens

<400> SEQUENCE: 173

Ser Tyr Tyr Trp Ser
1               5

<210> SEQ ID NO 174
<211> LENGTH: 16
<212> TYPE: PRT
<213> ORGANISM: Homo sapiens

<400> SEQUENCE: 174

Arg Ile Tyr Pro Ser Gly Arg Thr Asn Tyr Asn Pro Ser Leu Lys Ser
1               5                   10                  15

<210> SEQ ID NO 175
<211> LENGTH: 17
<212> TYPE: PRT
<213> ORGANISM: Homo sapiens

<400> SEQUENCE: 175

Glu Ala Tyr Glu Leu Gln Leu Gly Leu Tyr Tyr Tyr Gly Met Asp
1               5                   10                  15
Val

<210> SEQ ID NO 176
<211> LENGTH: 5
<212> TYPE: PRT
<213> ORGANISM: Homo sapiens

<400> SEQUENCE: 176

Ser Tyr Tyr Trp Ser
1               5

<210> SEQ ID NO 177
<211> LENGTH: 16
<212> TYPE: PRT
<213> ORGANISM: Homo sapiens

<400> SEQUENCE: 177

Arg Ile Tyr Pro Ser Gly Arg Thr Asn Tyr Asn Pro Ser Leu Lys Ser
1               5                   10                  15

<210> SEQ ID NO 178
<211> LENGTH: 17
<212> TYPE: PRT
<213> ORGANISM: Homo sapiens

<400> SEQUENCE: 178

Glu Ala Tyr Glu Leu Gln Leu Gly Leu Tyr Tyr Tyr Gly Met Asp
1               5                   10                  15
Val
```

```
<210> SEQ ID NO 179
<211> LENGTH: 7
<212> TYPE: PRT
<213> ORGANISM: Homo sapiens

<400> SEQUENCE: 179

Ser Gly Gly Tyr Tyr Trp Ser
1               5

<210> SEQ ID NO 180
<211> LENGTH: 13
<212> TYPE: PRT
<213> ORGANISM: Homo sapiens

<400> SEQUENCE: 180

Tyr Ser Gly Asn Thr Tyr Tyr Asn Pro Ser Leu Arg Ser
1               5                   10

<210> SEQ ID NO 181
<211> LENGTH: 14
<212> TYPE: PRT
<213> ORGANISM: Homo sapiens

<400> SEQUENCE: 181

Glu Ala Gly Gly Asn Ser Ala Tyr Tyr Tyr Gly Met Asp Val
1               5                   10

<210> SEQ ID NO 182
<211> LENGTH: 5
<212> TYPE: PRT
<213> ORGANISM: Homo sapiens

<400> SEQUENCE: 182

Asp Tyr Tyr Met Ser
1               5

<210> SEQ ID NO 183
<211> LENGTH: 17
<212> TYPE: PRT
<213> ORGANISM: Homo sapiens

<400> SEQUENCE: 183

Tyr Ile Ser Ser Ser Gly Ser Thr Ile Tyr Tyr Ala Asp Ser Val Lys
1               5                   10                  15
Gly

<210> SEQ ID NO 184
<211> LENGTH: 16
<212> TYPE: PRT
<213> ORGANISM: Homo sapiens

<400> SEQUENCE: 184

Asp Arg Thr Tyr Tyr Phe Gly Ser Gly Ser Tyr Glu Gly Met Asp Val
1               5                   10                  15

<210> SEQ ID NO 185
<211> LENGTH: 11
<212> TYPE: PRT
<213> ORGANISM: Homo sapiens

<400> SEQUENCE: 185

Arg Ala Ser Gln Gly Ile Arg Asn Asp Leu Gly
1               5                   10
```

```
<210> SEQ ID NO 186
<211> LENGTH: 7
<212> TYPE: PRT
<213> ORGANISM: Homo sapiens

<400> SEQUENCE: 186

Ala Ala Ser Ser Leu Gln Ser
1               5

<210> SEQ ID NO 187
<211> LENGTH: 9
<212> TYPE: PRT
<213> ORGANISM: Homo sapiens

<400> SEQUENCE: 187

Leu Gln His Asn Ser Asn Pro Phe Thr
1               5

<210> SEQ ID NO 188
<211> LENGTH: 11
<212> TYPE: PRT
<213> ORGANISM: Homo sapiens

<400> SEQUENCE: 188

Arg Ala Ser Gln Ser Val Ser Arg Asn Leu Val
1               5                   10

<210> SEQ ID NO 189
<211> LENGTH: 7
<212> TYPE: PRT
<213> ORGANISM: Homo sapiens

<400> SEQUENCE: 189

Gly Ala Ser Thr Arg Ala Asn
1               5

<210> SEQ ID NO 190
<211> LENGTH: 8
<212> TYPE: PRT
<213> ORGANISM: Homo sapiens

<400> SEQUENCE: 190

Gln Gln Tyr Lys Ser Trp Arg Thr
1               5

<210> SEQ ID NO 191
<211> LENGTH: 11
<212> TYPE: PRT
<213> ORGANISM: Homo sapiens

<400> SEQUENCE: 191

Arg Ala Ser Gln Ser Ile Ser Ser Tyr Leu Asn
1               5                   10

<210> SEQ ID NO 192
<211> LENGTH: 7
<212> TYPE: PRT
<213> ORGANISM: Homo sapiens

<400> SEQUENCE: 192

Ala Ala Ser Ser Leu Gln Ser
1               5

<210> SEQ ID NO 193
<211> LENGTH: 9
```

```
<212> TYPE: PRT
<213> ORGANISM: Homo sapiens

<400> SEQUENCE: 193

Gln Gln Ser Tyr Ser Thr Pro Phe Thr
1               5

<210> SEQ ID NO 194
<211> LENGTH: 11
<212> TYPE: PRT
<213> ORGANISM: Homo sapiens

<400> SEQUENCE: 194

Arg Ala Ser Gln Ser Val Ser Arg Asn Leu Ala
1               5                   10

<210> SEQ ID NO 195
<211> LENGTH: 7
<212> TYPE: PRT
<213> ORGANISM: Homo sapiens

<400> SEQUENCE: 195

Gly Ala Ser Thr Arg Ala Thr
1               5

<210> SEQ ID NO 196
<211> LENGTH: 10
<212> TYPE: PRT
<213> ORGANISM: Homo sapiens

<400> SEQUENCE: 196

Gln Gln Tyr Asn Asn Trp Pro Thr Trp Thr
1               5                   10

<210> SEQ ID NO 197
<211> LENGTH: 11
<212> TYPE: PRT
<213> ORGANISM: Homo sapiens

<400> SEQUENCE: 197

Arg Ala Ser Gln Gly Ile Arg Asn Asp Leu Gly
1               5                   10

<210> SEQ ID NO 198
<211> LENGTH: 7
<212> TYPE: PRT
<213> ORGANISM: Homo sapiens

<400> SEQUENCE: 198

Ala Ala Ser Ser Phe Gln Ser
1               5

<210> SEQ ID NO 199
<211> LENGTH: 9
<212> TYPE: PRT
<213> ORGANISM: Homo sapiens

<400> SEQUENCE: 199

Leu Gln His Asn Ser Tyr Pro Pro Thr
1               5

<210> SEQ ID NO 200
<211> LENGTH: 11
<212> TYPE: PRT
<213> ORGANISM: Homo sapiens
```

<400> SEQUENCE: 200

Arg Ala Ser Gln Gly Ile Arg Asn Asp Leu Gly
1               5                   10

<210> SEQ ID NO 201
<211> LENGTH: 7
<212> TYPE: PRT
<213> ORGANISM: Homo sapiens

<400> SEQUENCE: 201

Ala Ala Ser Ser Leu Gln Ser
1               5

<210> SEQ ID NO 202
<211> LENGTH: 9
<212> TYPE: PRT
<213> ORGANISM: Homo sapiens

<400> SEQUENCE: 202

Leu Gln His Lys Ser Tyr Pro Leu Thr
1               5

<210> SEQ ID NO 203
<211> LENGTH: 11
<212> TYPE: PRT
<213> ORGANISM: Homo sapiens

<400> SEQUENCE: 203

Arg Ala Ser Gln Gly Ile Arg Asn Asp Leu Gly
1               5                   10

<210> SEQ ID NO 204
<211> LENGTH: 7
<212> TYPE: PRT
<213> ORGANISM: Homo sapiens

<400> SEQUENCE: 204

Ala Ala Ser Ser Leu Gln Ser
1               5

<210> SEQ ID NO 205
<211> LENGTH: 9
<212> TYPE: PRT
<213> ORGANISM: Homo sapiens

<400> SEQUENCE: 205

Leu Gln His Lys Ser Tyr Pro Leu Thr
1               5

<210> SEQ ID NO 206
<211> LENGTH: 11
<212> TYPE: PRT
<213> ORGANISM: Homo sapiens

<400> SEQUENCE: 206

Arg Ala Ser Gln Gly Ile Arg Asn Asp Leu Gly
1               5                   10

<210> SEQ ID NO 207
<211> LENGTH: 7
<212> TYPE: PRT
<213> ORGANISM: Homo sapiens

<400> SEQUENCE: 207

Ala Ala Ser Ser Leu Gln Ser
1               5

<210> SEQ ID NO 208
<211> LENGTH: 9
<212> TYPE: PRT
<213> ORGANISM: Homo sapiens

<400> SEQUENCE: 208

Leu Gln His Lys Ser Tyr Pro Leu Thr
1               5

<210> SEQ ID NO 209
<211> LENGTH: 11
<212> TYPE: PRT
<213> ORGANISM: Homo sapiens

<400> SEQUENCE: 209

Arg Ala Ser Gln Gly Ile Arg Asn Asp Leu Gly
1               5                   10

<210> SEQ ID NO 210
<211> LENGTH: 7
<212> TYPE: PRT
<213> ORGANISM: Homo sapiens

<400> SEQUENCE: 210

Ala Ala Ser Ser Leu Gln Ser
1               5

<210> SEQ ID NO 211
<211> LENGTH: 9
<212> TYPE: PRT
<213> ORGANISM: Homo sapiens

<400> SEQUENCE: 211

Leu Gln His Lys Ser Tyr Pro Leu Thr
1               5

<210> SEQ ID NO 212
<211> LENGTH: 11
<212> TYPE: PRT
<213> ORGANISM: Homo sapiens

<400> SEQUENCE: 212

Arg Ala Ser Gln Gly Ile Arg Ser Trp Leu Ala
1               5                   10

<210> SEQ ID NO 213
<211> LENGTH: 7
<212> TYPE: PRT
<213> ORGANISM: Homo sapiens

<400> SEQUENCE: 213

Ala Ala Ser Ser Leu Gln Ser
1               5

<210> SEQ ID NO 214
<211> LENGTH: 9
<212> TYPE: PRT
<213> ORGANISM: Homo sapiens

<400> SEQUENCE: 214

Gln Gln Ala Asn Asn Phe Pro Arg Thr

<210> SEQ ID NO 215
<211> LENGTH: 11
<212> TYPE: PRT
<213> ORGANISM: Homo sapiens

<400> SEQUENCE: 215

Arg Ala Ser Gln Ser Val Ser Ser Asn Leu Ala
1               5                   10

<210> SEQ ID NO 216
<211> LENGTH: 7
<212> TYPE: PRT
<213> ORGANISM: Homo sapiens

<400> SEQUENCE: 216

Gly Ala Ser Thr Arg Ala Ala
1               5

<210> SEQ ID NO 217
<211> LENGTH: 10
<212> TYPE: PRT
<213> ORGANISM: Homo sapiens

<400> SEQUENCE: 217

Gln His Tyr Ile Asn Trp Pro Lys Trp Thr
1               5                   10

<210> SEQ ID NO 218
<211> LENGTH: 11
<212> TYPE: PRT
<213> ORGANISM: Homo sapiens

<400> SEQUENCE: 218

Arg Ala Ser Gln Ser Ile Ser Ser Ser Leu Ala
1               5                   10

<210> SEQ ID NO 219
<211> LENGTH: 7
<212> TYPE: PRT
<213> ORGANISM: Homo sapiens

<400> SEQUENCE: 219

Gly Ala Ser Thr Arg Ala Thr
1               5

<210> SEQ ID NO 220
<211> LENGTH: 9
<212> TYPE: PRT
<213> ORGANISM: Homo sapiens

<400> SEQUENCE: 220

Gln Gln Tyr Asp Asn Trp Pro Leu Thr
1               5

<210> SEQ ID NO 221
<211> LENGTH: 16
<212> TYPE: PRT
<213> ORGANISM: Homo sapiens

<400> SEQUENCE: 221

Lys Ser Ser Gln Ser Leu Leu His Ser Asp Gly Lys Thr Tyr Leu Tyr
1               5                   10                  15

```
<210> SEQ ID NO 222
<211> LENGTH: 7
<212> TYPE: PRT
<213> ORGANISM: Homo sapiens

<400> SEQUENCE: 222

Glu Val Ser Thr Arg Phe Ser
1               5

<210> SEQ ID NO 223
<211> LENGTH: 9
<212> TYPE: PRT
<213> ORGANISM: Homo sapiens

<400> SEQUENCE: 223

Met Gln Ser Ile Gln Leu Pro Leu Thr
1               5

<210> SEQ ID NO 224
<211> LENGTH: 11
<212> TYPE: PRT
<213> ORGANISM: Homo sapiens

<400> SEQUENCE: 224

Arg Ala Ser Gln Ser Val Ser Ser Asn Leu Ala
1               5                   10

<210> SEQ ID NO 225
<211> LENGTH: 7
<212> TYPE: PRT
<213> ORGANISM: Homo sapiens

<400> SEQUENCE: 225

Asp Ala Ser Thr Arg Ala Thr
1               5

<210> SEQ ID NO 226
<211> LENGTH: 9
<212> TYPE: PRT
<213> ORGANISM: Homo sapiens

<400> SEQUENCE: 226

Gln Gln Tyr Asp Asn Trp Pro Leu Thr
1               5

<210> SEQ ID NO 227
<211> LENGTH: 11
<212> TYPE: PRT
<213> ORGANISM: Homo sapiens

<400> SEQUENCE: 227

Arg Ala Ser Gln Ser Val Ser Ser Asn Leu Ala
1               5                   10

<210> SEQ ID NO 228
<211> LENGTH: 7
<212> TYPE: PRT
<213> ORGANISM: Homo sapiens

<400> SEQUENCE: 228

Asp Ala Ser Thr Arg Ala Ala
1               5

<210> SEQ ID NO 229
```

```
<211> LENGTH: 9
<212> TYPE: PRT
<213> ORGANISM: Homo sapiens

<400> SEQUENCE: 229

Gln Gln Tyr Asp Asn Trp Pro Leu Thr
1               5

<210> SEQ ID NO 230
<211> LENGTH: 11
<212> TYPE: PRT
<213> ORGANISM: Homo sapiens

<400> SEQUENCE: 230

Arg Ala Ser Gln Ser Ile Ser Thr Ser Leu Ala
1               5                   10

<210> SEQ ID NO 231
<211> LENGTH: 7
<212> TYPE: PRT
<213> ORGANISM: Homo sapiens

<400> SEQUENCE: 231

Gly Thr Ser Thr Arg Ala Thr
1               5

<210> SEQ ID NO 232
<211> LENGTH: 9
<212> TYPE: PRT
<213> ORGANISM: Homo sapiens

<400> SEQUENCE: 232

Gln Gln Tyr Asp Ile Trp Pro Leu Thr
1               5

<210> SEQ ID NO 233
<211> LENGTH: 11
<212> TYPE: PRT
<213> ORGANISM: Homo sapiens

<400> SEQUENCE: 233

Arg Ala Ser Gln Ser Val Ser Ser Asn Leu Ala
1               5                   10

<210> SEQ ID NO 234
<211> LENGTH: 7
<212> TYPE: PRT
<213> ORGANISM: Homo sapiens

<400> SEQUENCE: 234

Gly Ala Ser Thr Arg Ala Thr
1               5

<210> SEQ ID NO 235
<211> LENGTH: 9
<212> TYPE: PRT
<213> ORGANISM: Homo sapiens

<400> SEQUENCE: 235

Gln Gln Tyr Asp Asn Trp Pro Leu Thr
1               5

<210> SEQ ID NO 236
<211> LENGTH: 17
<212> TYPE: PRT
```

<213> ORGANISM: Homo sapiens

<400> SEQUENCE: 236

Lys Thr Ser Gln Ser Val Leu Tyr Ser Ser Asn Lys Asn Phe Leu
1               5                   10                  15
Ala

<210> SEQ ID NO 237
<211> LENGTH: 7
<212> TYPE: PRT
<213> ORGANISM: Homo sapiens

<400> SEQUENCE: 237

Trp Ala Ser Thr Arg Glu Ser
1               5

<210> SEQ ID NO 238
<211> LENGTH: 9
<212> TYPE: PRT
<213> ORGANISM: Homo sapiens

<400> SEQUENCE: 238

Gln Gln Tyr Tyr Ser Thr Pro Phe Thr
1               5

<210> SEQ ID NO 239
<211> LENGTH: 11
<212> TYPE: PRT
<213> ORGANISM: Homo sapiens

<400> SEQUENCE: 239

Arg Ala Ser Gln Ser Ile Ser Ser Asn Leu Ala
1               5                   10

<210> SEQ ID NO 240
<211> LENGTH: 7
<212> TYPE: PRT
<213> ORGANISM: Homo sapiens

<400> SEQUENCE: 240

Gly Ala Ser Thr Arg Ala Thr
1               5

<210> SEQ ID NO 241
<211> LENGTH: 9
<212> TYPE: PRT
<213> ORGANISM: Homo sapiens

<400> SEQUENCE: 241

Gln Gln Tyr Asp Thr Trp Pro Leu Thr
1               5

<210> SEQ ID NO 242
<211> LENGTH: 11
<212> TYPE: PRT
<213> ORGANISM: Homo sapiens

<400> SEQUENCE: 242

Arg Ala Ser Gln Gly Ile Ser Asn Tyr Leu Ala
1               5                   10

<210> SEQ ID NO 243
<211> LENGTH: 7
<212> TYPE: PRT

<213> ORGANISM: Homo sapiens

<400> SEQUENCE: 243

Ala Ala Ser Thr Leu Gln Ser
1               5

<210> SEQ ID NO 244
<211> LENGTH: 9
<212> TYPE: PRT
<213> ORGANISM: Homo sapiens

<400> SEQUENCE: 244

Gln Lys Tyr Asn Arg Ala Pro Phe Thr
1               5

<210> SEQ ID NO 245
<211> LENGTH: 11
<212> TYPE: PRT
<213> ORGANISM: Homo sapiens

<400> SEQUENCE: 245

Arg Ala Ser Gln Gly Ile Ser Asn Tyr Leu Ala
1               5                   10

<210> SEQ ID NO 246
<211> LENGTH: 7
<212> TYPE: PRT
<213> ORGANISM: Homo sapiens

<400> SEQUENCE: 246

Ala Ala Ser Thr Leu Gln Ser
1               5

<210> SEQ ID NO 247
<211> LENGTH: 9
<212> TYPE: PRT
<213> ORGANISM: Homo sapiens

<400> SEQUENCE: 247

Gln Lys Tyr Asn Arg Ala Pro Phe Thr
1               5

<210> SEQ ID NO 248
<211> LENGTH: 11
<212> TYPE: PRT
<213> ORGANISM: Homo sapiens

<400> SEQUENCE: 248

Arg Ala Ser Gln Ser Val Ser Ser Asn Leu Ala
1               5                   10

<210> SEQ ID NO 249
<211> LENGTH: 7
<212> TYPE: PRT
<213> ORGANISM: Homo sapiens

<400> SEQUENCE: 249

Asp Ala Ser Thr Arg Ala Ala
1               5

<210> SEQ ID NO 250
<211> LENGTH: 9
<212> TYPE: PRT
<213> ORGANISM: Homo sapiens

```
<400> SEQUENCE: 250

Gln Gln Tyr Asp Asn Trp Pro Leu Thr
1               5

<210> SEQ ID NO 251
<211> LENGTH: 11
<212> TYPE: PRT
<213> ORGANISM: Homo sapiens

<400> SEQUENCE: 251

Arg Ala Ser Gln Gly Ile Ile Asn Asp Leu Gly
1               5                   10

<210> SEQ ID NO 252
<211> LENGTH: 7
<212> TYPE: PRT
<213> ORGANISM: Homo sapiens

<400> SEQUENCE: 252

Ala Ala Ser Ser Leu Gln Ser
1               5

<210> SEQ ID NO 253
<211> LENGTH: 9
<212> TYPE: PRT
<213> ORGANISM: Homo sapiens

<400> SEQUENCE: 253

Leu Gln His Asn Ser Tyr Pro Pro Thr
1               5

<210> SEQ ID NO 254
<211> LENGTH: 16
<212> TYPE: PRT
<213> ORGANISM: Homo sapiens

<400> SEQUENCE: 254

Arg Ser Ser Gln Ser Leu Val Tyr Ser Asp Gly His Thr Cys Leu Asn
1               5                   10                  15

<210> SEQ ID NO 255
<211> LENGTH: 7
<212> TYPE: PRT
<213> ORGANISM: Homo sapiens

<400> SEQUENCE: 255

Lys Val Ser Asn Trp Asp Ser
1               5

<210> SEQ ID NO 256
<211> LENGTH: 10
<212> TYPE: PRT
<213> ORGANISM: Homo sapiens

<400> SEQUENCE: 256

Met Gln Gly Thr His Trp Pro Leu Cys Ser
1               5                   10

<210> SEQ ID NO 257
<211> LENGTH: 16
<212> TYPE: PRT
<213> ORGANISM: Homo sapiens

<400> SEQUENCE: 257
```

```
Arg Ser Ser Gln Ser Leu Val Tyr Ser Asp Gly His Thr Cys Leu Asn
1               5                   10                  15
```

<210> SEQ ID NO 258
<211> LENGTH: 7
<212> TYPE: PRT
<213> ORGANISM: Homo sapiens

<400> SEQUENCE: 258

```
Lys Val Ser Asn Trp Asp Ser
1               5
```

<210> SEQ ID NO 259
<211> LENGTH: 10
<212> TYPE: PRT
<213> ORGANISM: Homo sapiens

<400> SEQUENCE: 259

```
Met Gln Gly Thr His Trp Pro Leu Cys Ser
1               5                   10
```

<210> SEQ ID NO 260
<211> LENGTH: 11
<212> TYPE: PRT
<213> ORGANISM: Homo sapiens

<400> SEQUENCE: 260

```
Arg Ala Ser Gln Ala Ile Ser Ile Tyr Leu Ala
1               5                   10
```

<210> SEQ ID NO 261
<211> LENGTH: 7
<212> TYPE: PRT
<213> ORGANISM: Homo sapiens

<400> SEQUENCE: 261

```
Ala Ala Ser Ser Leu Gln Ser
1               5
```

<210> SEQ ID NO 262
<211> LENGTH: 9
<212> TYPE: PRT
<213> ORGANISM: Homo sapiens

<400> SEQUENCE: 262

```
Gln Gln Tyr Ser Ser Tyr Pro Arg Thr
1               5
```

<210> SEQ ID NO 263
<211> LENGTH: 11
<212> TYPE: PRT
<213> ORGANISM: Homo sapiens

<400> SEQUENCE: 263

```
Arg Ala Ser Gln Ser Val Tyr Ser Asn Leu Ala
1               5                   10
```

<210> SEQ ID NO 264
<211> LENGTH: 7
<212> TYPE: PRT
<213> ORGANISM: Homo sapiens

<400> SEQUENCE: 264

```
Gly Ala Ser Thr Arg Ala Thr
1               5
```

<210> SEQ ID NO 265
<211> LENGTH: 9
<212> TYPE: PRT
<213> ORGANISM: Homo sapiens

<400> SEQUENCE: 265

Gln Gln Tyr Tyr Asn Trp Pro Trp Thr
1               5

<210> SEQ ID NO 266
<211> LENGTH: 15
<212> TYPE: DNA
<213> ORGANISM: Homo sapiens

<400> SEQUENCE: 266
aattactact ggaac                                                  15

<210> SEQ ID NO 267
<211> LENGTH: 75
<212> TYPE: DNA
<213> ORGANISM: Homo sapiens

<400> SEQUENCE: 267
ccagggaagg gactggagtg gattggggat atctattaca gtgggagcac caactacaac   60
ccctccctca agagt                                                  75

<210> SEQ ID NO 268
<211> LENGTH: 69
<212> TYPE: DNA
<213> ORGANISM: Homo sapiens

<400> SEQUENCE: 268
gatggggaac tcgccaatta ctatggttcg gggagttatc agttctacta ctactacggt   60
atggacgtc                                                         69

<210> SEQ ID NO 269
<211> LENGTH: 15
<212> TYPE: DNA
<213> ORGANISM: Homo sapiens

<400> SEQUENCE: 269
ggttactact ggagc                                                  15

<210> SEQ ID NO 270
<211> LENGTH: 48
<212> TYPE: DNA
<213> ORGANISM: Homo sapiens

<400> SEQUENCE: 270
gaaatcaatc atagtggacg caccaattac aacccgtccc tcaagagt               48

<210> SEQ ID NO 271
<211> LENGTH: 57
<212> TYPE: DNA
<213> ORGANISM: Homo sapiens

<400> SEQUENCE: 271
ggcccttatt actttgatag tagtggttac ctttactact actacggttt ggacgtc     57

<210> SEQ ID NO 272
<211> LENGTH: 15

```
<212> TYPE: DNA
<213> ORGANISM: Homo sapiens

<400> SEQUENCE: 272
agctatggca tgcac                                                    15

<210> SEQ ID NO 273
<211> LENGTH: 51
<212> TYPE: DNA
<213> ORGANISM: Homo sapiens

<400> SEQUENCE: 273
gttatatggt atgatggaag taataaacac tatgcagact ccgtgaaggg c             51

<210> SEQ ID NO 274
<211> LENGTH: 15
<212> TYPE: DNA
<213> ORGANISM: Homo sapiens

<400> SEQUENCE: 274
gatactgggg tctac                                                    15

<210> SEQ ID NO 275
<211> LENGTH: 15
<212> TYPE: DNA
<213> ORGANISM: Homo sapiens

<400> SEQUENCE: 275
agctatggca tgcac                                                    15

<210> SEQ ID NO 276
<211> LENGTH: 51
<212> TYPE: DNA
<213> ORGANISM: Homo sapiens

<400> SEQUENCE: 276
gttatatggt atgatggaag taataaacac tatgcagact ccgtgaaggg c             51

<210> SEQ ID NO 277
<211> LENGTH: 15
<212> TYPE: DNA
<213> ORGANISM: Homo sapiens

<400> SEQUENCE: 277
gatactgggg tctac                                                    15

<210> SEQ ID NO 278
<211> LENGTH: 15
<212> TYPE: DNA
<213> ORGANISM: Homo sapiens

<400> SEQUENCE: 278
agttactact ggagc                                                    15

<210> SEQ ID NO 279
<211> LENGTH: 48
<212> TYPE: DNA
<213> ORGANISM: Homo sapiens

<400> SEQUENCE: 279
cgtatctatc gcagtgggaa caccatctac aacccctccc tcaagagt                 48

<210> SEQ ID NO 280
```

```
<211> LENGTH: 51
<212> TYPE: DNA
<213> ORGANISM: Homo sapiens

<400> SEQUENCE: 280
gagaattact ctgagagtag tggtctctac tactactacg gtatggacgt c          51

<210> SEQ ID NO 281
<211> LENGTH: 15
<212> TYPE: DNA
<213> ORGANISM: Homo sapiens

<400> SEQUENCE: 281
agatatggta tcagc                                                  15

<210> SEQ ID NO 282
<211> LENGTH: 51
<212> TYPE: DNA
<213> ORGANISM: Homo sapiens

<400> SEQUENCE: 282
tggatcagcg cttacaatgg taacacaaac tatgcacaga agctccaggg c          51

<210> SEQ ID NO 283
<211> LENGTH: 45
<212> TYPE: DNA
<213> ORGANISM: Homo sapiens

<400> SEQUENCE: 283
agggattacg atattttgac tggttattat aacgggttcg acccc                 45

<210> SEQ ID NO 284
<211> LENGTH: 15
<212> TYPE: DNA
<213> ORGANISM: Homo sapiens

<400> SEQUENCE: 284
agatatggta tcagc                                                  15

<210> SEQ ID NO 285
<211> LENGTH: 51
<212> TYPE: DNA
<213> ORGANISM: Homo sapiens

<400> SEQUENCE: 285
tggatcagcg cttacaatgg taacacaaac tatgcacaga agctccaggg c          51

<210> SEQ ID NO 286
<211> LENGTH: 45
<212> TYPE: DNA
<213> ORGANISM: Homo sapiens

<400> SEQUENCE: 286
agggattacg atattttgac tggttattat aacgggttcg acccc                 45

<210> SEQ ID NO 287
<211> LENGTH: 15
<212> TYPE: DNA
<213> ORGANISM: Homo sapiens

<400> SEQUENCE: 287
ggctatggta tcagc                                                  15
```

```
<210> SEQ ID NO 288
<211> LENGTH: 51
<212> TYPE: DNA
<213> ORGANISM: Homo sapiens

<400> SEQUENCE: 288
tggatcagcg cttacaatgg taacacaaac tatgcacaga acctccaggg c          51

<210> SEQ ID NO 289
<211> LENGTH: 45
<212> TYPE: DNA
<213> ORGANISM: Homo sapiens

<400> SEQUENCE: 289
agggattacg atattttgac tggttattat aacgggttcg acccc                 45

<210> SEQ ID NO 290
<211> LENGTH: 15
<212> TYPE: DNA
<213> ORGANISM: Homo sapiens

<400> SEQUENCE: 290
agatatggta tcagc                                                  15

<210> SEQ ID NO 291
<211> LENGTH: 50
<212> TYPE: DNA
<213> ORGANISM: Homo sapiens

<400> SEQUENCE: 291
tggatcagcg cttacaatgg taacacaaac tatgcacaga agctccaggg            50

<210> SEQ ID NO 292
<211> LENGTH: 45
<212> TYPE: DNA
<213> ORGANISM: Homo sapiens

<400> SEQUENCE: 292
agggattacg atattttgac tggttattat aacgggttcg acccc                 45

<210> SEQ ID NO 293
<211> LENGTH: 21
<212> TYPE: DNA
<213> ORGANISM: Homo sapiens

<400> SEQUENCE: 293
agtggtggtt actactggag c                                           21

<210> SEQ ID NO 294
<211> LENGTH: 48
<212> TYPE: DNA
<213> ORGANISM: Homo sapiens

<400> SEQUENCE: 294
tacatctatt tcagtgggag cgcctactac aacccgtccc tcaagagt              48

<210> SEQ ID NO 295
<211> LENGTH: 42
<212> TYPE: DNA
<213> ORGANISM: Homo sapiens

<400> SEQUENCE: 295
gaatactatg atagtagtgg ttaccccgat gcttttgata tc                    42
```

```
<210> SEQ ID NO 296
<211> LENGTH: 15
<212> TYPE: DNA
<213> ORGANISM: Homo sapiens

<400> SEQUENCE: 296
agctatggca tgcac                                                    15

<210> SEQ ID NO 297
<211> LENGTH: 51
<212> TYPE: DNA
<213> ORGANISM: Homo sapiens

<400> SEQUENCE: 297
gttatatggt atgatggaag taataaatat tatgcagact ccgtgaaggg c            51

<210> SEQ ID NO 298
<211> LENGTH: 15
<212> TYPE: DNA
<213> ORGANISM: Homo sapiens

<400> SEQUENCE: 298
gatacgaagg actac                                                    15

<210> SEQ ID NO 299
<211> LENGTH: 15
<212> TYPE: DNA
<213> ORGANISM: Homo sapiens

<400> SEQUENCE: 299
agctatggta tcagc                                                    15

<210> SEQ ID NO 300
<211> LENGTH: 51
<212> TYPE: DNA
<213> ORGANISM: Homo sapiens

<400> SEQUENCE: 300
tggatcagca cttacaaagg taacacaaac tatgcacaga agctccaggg c            51

<210> SEQ ID NO 301
<211> LENGTH: 21
<212> TYPE: DNA
<213> ORGANISM: Homo sapiens

<400> SEQUENCE: 301
aagcagctcg tctttgacta c                                             21

<210> SEQ ID NO 302
<211> LENGTH: 15
<212> TYPE: DNA
<213> ORGANISM: Homo sapiens

<400> SEQUENCE: 302
agctatggca tgcag                                                    15

<210> SEQ ID NO 303
<211> LENGTH: 51
<212> TYPE: DNA
<213> ORGANISM: Homo sapiens

<400> SEQUENCE: 303
gttatatggt atgatggaaa taagaaatac tatgcagact ccgtgaaggg c            51
```

<210> SEQ ID NO 304
<211> LENGTH: 36
<212> TYPE: DNA
<213> ORGANISM: Homo sapiens

<400> SEQUENCE: 304
ggacgtgtta gggactacta ctacggtatg gacgtc                                    36

<210> SEQ ID NO 305
<211> LENGTH: 15
<212> TYPE: DNA
<213> ORGANISM: Homo sapiens

<400> SEQUENCE: 305
agatatggta tcagc                                                           15

<210> SEQ ID NO 306
<211> LENGTH: 51
<212> TYPE: DNA
<213> ORGANISM: Homo sapiens

<400> SEQUENCE: 306
tggatcagca cttacagtgg taacacaaac tatgcacaga agctccaggg c                   51

<210> SEQ ID NO 307
<211> LENGTH: 21
<212> TYPE: DNA
<213> ORGANISM: Homo sapiens

<400> SEQUENCE: 307
cggcagcttt actttgacta c                                                    21

<210> SEQ ID NO 308
<211> LENGTH: 15
<212> TYPE: DNA
<213> ORGANISM: Homo sapiens

<400> SEQUENCE: 308
agctatggca tgcag                                                           15

<210> SEQ ID NO 309
<211> LENGTH: 51
<212> TYPE: DNA
<213> ORGANISM: Homo sapiens

<400> SEQUENCE: 309
gttatatggt atgatggaaa taagaaatac tatgcagact ccgtgaaggg c                   51

<210> SEQ ID NO 310
<211> LENGTH: 36
<212> TYPE: DNA
<213> ORGANISM: Homo sapiens

<400> SEQUENCE: 310
ggacgtgtta gggactacta ctacggtatg gacgtc                                    36

<210> SEQ ID NO 311
<211> LENGTH: 15
<212> TYPE: DNA
<213> ORGANISM: Homo sapiens

<400> SEQUENCE: 311

```
agctatggta tcagc                                                    15

<210> SEQ ID NO 312
<211> LENGTH: 51
<212> TYPE: DNA
<213> ORGANISM: Homo sapiens

<400> SEQUENCE: 312
tggatcagcg cttacaatgg taacacaaag tatgcacaga agctccaggg c             51

<210> SEQ ID NO 313
<211> LENGTH: 21
<212> TYPE: DNA
<213> ORGANISM: Homo sapiens

<400> SEQUENCE: 313
aagcagctcg tctttgacta c                                             21

<210> SEQ ID NO 314
<211> LENGTH: 15
<212> TYPE: DNA
<213> ORGANISM: Homo sapiens

<400> SEQUENCE: 314
agctatggta tcagc                                                    15

<210> SEQ ID NO 315
<211> LENGTH: 51
<212> TYPE: DNA
<213> ORGANISM: Homo sapiens

<400> SEQUENCE: 315
tggatcagcg cttacagtgg taatacaaag tatgcacaga agctccaggg c             51

<210> SEQ ID NO 316
<211> LENGTH: 21
<212> TYPE: DNA
<213> ORGANISM: Homo sapiens

<400> SEQUENCE: 316
aagcagctcg tctttgacta c                                             21

<210> SEQ ID NO 317
<211> LENGTH: 15
<212> TYPE: DNA
<213> ORGANISM: Homo sapiens

<400> SEQUENCE: 317
gactactaca tgcac                                                    15

<210> SEQ ID NO 318
<211> LENGTH: 51
<212> TYPE: DNA
<213> ORGANISM: Homo sapiens

<400> SEQUENCE: 318
tggatgcacc ctaacagtgg tgcacagac ttagcacaga ggtttcaggg c              51

<210> SEQ ID NO 319
<211> LENGTH: 51
<212> TYPE: DNA
<213> ORGANISM: Homo sapiens

<400> SEQUENCE: 319
```

```
gggggatatt gtagtacttt gagctgctcc ttctactggt acttcgatct c        51
```

<210> SEQ ID NO 320
<211> LENGTH: 15
<212> TYPE: DNA
<213> ORGANISM: Homo sapiens

<400> SEQUENCE: 320

```
agctatggaa tcagt                                                15
```

<210> SEQ ID NO 321
<211> LENGTH: 51
<212> TYPE: DNA
<213> ORGANISM: Homo sapiens

<400> SEQUENCE: 321

```
tggatcagcg cttacagtgg taacacaaag tatgcacaga agttccaggg c        51
```

<210> SEQ ID NO 322
<211> LENGTH: 21
<212> TYPE: DNA
<213> ORGANISM: Homo sapiens

<400> SEQUENCE: 322

```
aggcagctcg cgttggacta c                                         21
```

<210> SEQ ID NO 323
<211> LENGTH: 15
<212> TYPE: DNA
<213> ORGANISM: Homo sapiens

<400> SEQUENCE: 323

```
agctatagca tgaac                                                15
```

<210> SEQ ID NO 324
<211> LENGTH: 51
<212> TYPE: DNA
<213> ORGANISM: Homo sapiens

<400> SEQUENCE: 324

```
ttcattagtg ctagaagtag taccatatac tacgcagact ctgtgaaggg c        51
```

<210> SEQ ID NO 325
<211> LENGTH: 27
<212> TYPE: DNA
<213> ORGANISM: Homo sapiens

<400> SEQUENCE: 325

```
cctaaagtgg ggggcggtat ggacgtc                                   27
```

<210> SEQ ID NO 326
<211> LENGTH: 15
<212> TYPE: DNA
<213> ORGANISM: Homo sapiens

<400> SEQUENCE: 326

```
agctatagca tgaac                                                15
```

<210> SEQ ID NO 327
<211> LENGTH: 51
<212> TYPE: DNA
<213> ORGANISM: Homo sapiens

```
<400> SEQUENCE: 327
atcattagta gtagaagtag tatcatacac tacgcagact ctgtgaaggg c        51

<210> SEQ ID NO 328
<211> LENGTH: 27
<212> TYPE: DNA
<213> ORGANISM: Homo sapiens

<400> SEQUENCE: 328
cctaaagtgg ggggcggtat ggacgtc                                   27

<210> SEQ ID NO 329
<211> LENGTH: 15
<212> TYPE: DNA
<213> ORGANISM: Homo sapiens

<400> SEQUENCE: 329
agatatggta tcagc                                                15

<210> SEQ ID NO 330
<211> LENGTH: 51
<212> TYPE: DNA
<213> ORGANISM: Homo sapiens

<400> SEQUENCE: 330
tggatcagcg cttacagtgg taacacaaac tatgcacaga agctccaggg c         51

<210> SEQ ID NO 331
<211> LENGTH: 21
<212> TYPE: DNA
<213> ORGANISM: Homo sapiens

<400> SEQUENCE: 331
cggcagcttt actttgacta c                                         21

<210> SEQ ID NO 332
<211> LENGTH: 15
<212> TYPE: DNA
<213> ORGANISM: Homo sapiens

<400> SEQUENCE: 332
agttactact ggagc                                                15

<210> SEQ ID NO 333
<211> LENGTH: 48
<212> TYPE: DNA
<213> ORGANISM: Homo sapiens

<400> SEQUENCE: 333
cgtatctatc ccagtgggag aaccaactac aacccctccc tcaagagt            48

<210> SEQ ID NO 334
<211> LENGTH: 51
<212> TYPE: DNA
<213> ORGANISM: Homo sapiens

<400> SEQUENCE: 334
gaggcatatg agctgcaact gggcctctac tactactacg gtatggacgt c         51

<210> SEQ ID NO 335
<211> LENGTH: 15
<212> TYPE: DNA
<213> ORGANISM: Homo sapiens
```

```
<400> SEQUENCE: 335
agttactact ggagc                                                          15

<210> SEQ ID NO 336
<211> LENGTH: 48
<212> TYPE: DNA
<213> ORGANISM: Homo sapiens

<400> SEQUENCE: 336
cgtatctatc ccagtgggag aaccaactac aaccccctccc tcaagagt                     48

<210> SEQ ID NO 337
<211> LENGTH: 51
<212> TYPE: DNA
<213> ORGANISM: Homo sapiens

<400> SEQUENCE: 337
gaggcatatg agctgcaact gggcctctac tactactacg gtatggacgt c                  51

<210> SEQ ID NO 338
<211> LENGTH: 21
<212> TYPE: DNA
<213> ORGANISM: Homo sapiens

<400> SEQUENCE: 338
agtggtggtt actactggag c                                                   21

<210> SEQ ID NO 339
<211> LENGTH: 39
<212> TYPE: DNA
<213> ORGANISM: Homo sapiens

<400> SEQUENCE: 339
tacagtggga acacctacta caacccgtcc ctcaggagt                                39

<210> SEQ ID NO 340
<211> LENGTH: 42
<212> TYPE: DNA
<213> ORGANISM: Homo sapiens

<400> SEQUENCE: 340
gaggccggtg gtaactccgc ctactactac ggtatggacg tc                            42

<210> SEQ ID NO 341
<211> LENGTH: 15
<212> TYPE: DNA
<213> ORGANISM: Homo sapiens

<400> SEQUENCE: 341
gactactaca tgagc                                                          15

<210> SEQ ID NO 342
<211> LENGTH: 51
<212> TYPE: DNA
<213> ORGANISM: Homo sapiens

<400> SEQUENCE: 342
tacattagta gtagtcgtag taccatatac tacgcagact ctgtgaaggg c                  51

<210> SEQ ID NO 343
<211> LENGTH: 48
<212> TYPE: DNA
```

<213> ORGANISM: Homo sapiens

<400> SEQUENCE: 343
gatcgcacgt attactttgg ttcggggagt tatgaaggga tggacgtc          48

<210> SEQ ID NO 344
<211> LENGTH: 88
<212> TYPE: PRT
<213> ORGANISM: Homo sapiens

<400> SEQUENCE: 344

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys
                85

<210> SEQ ID NO 345
<211> LENGTH: 33
<212> TYPE: DNA
<213> ORGANISM: Homo sapiens

<400> SEQUENCE: 345
cgggcaagtc agggcattag aaatgattta ggc                          33

<210> SEQ ID NO 346
<211> LENGTH: 21
<212> TYPE: DNA
<213> ORGANISM: Homo sapiens

<400> SEQUENCE: 346
gctgcatcca gtttgcaaag t                                       21

<210> SEQ ID NO 347
<211> LENGTH: 27
<212> TYPE: DNA
<213> ORGANISM: Homo sapiens

<400> SEQUENCE: 347
ctacagcata atagtaaccc attcact                                 27

<210> SEQ ID NO 348
<211> LENGTH: 33
<212> TYPE: DNA
<213> ORGANISM: Homo sapiens

<400> SEQUENCE: 348
agggccagtc agagtgttag cagaaactta gtc                          33

<210> SEQ ID NO 349
<211> LENGTH: 21
<212> TYPE: DNA
<213> ORGANISM: Homo sapiens

<400> SEQUENCE: 349

```
ggggcatcca ctagggccaa t                                            21

<210> SEQ ID NO 350
<211> LENGTH: 24
<212> TYPE: DNA
<213> ORGANISM: Homo sapiens

<400> SEQUENCE: 350
cagcagtata aaagctggcg gacg                                         24

<210> SEQ ID NO 351
<211> LENGTH: 33
<212> TYPE: DNA
<213> ORGANISM: Homo sapiens

<400> SEQUENCE: 351
cgggcaagtc agagcattag cagctattta aat                               33

<210> SEQ ID NO 352
<211> LENGTH: 21
<212> TYPE: DNA
<213> ORGANISM: Homo sapiens

<400> SEQUENCE: 352
gctgcatcca gtttgcaaag t                                            21

<210> SEQ ID NO 353
<211> LENGTH: 27
<212> TYPE: DNA
<213> ORGANISM: Homo sapiens

<400> SEQUENCE: 353
caacagagtt acagtacccc attcact                                      27

<210> SEQ ID NO 354
<211> LENGTH: 33
<212> TYPE: DNA
<213> ORGANISM: Homo sapiens

<400> SEQUENCE: 354
agggccagtc agagtgttag taggaattta gcc                               33

<210> SEQ ID NO 355
<211> LENGTH: 21
<212> TYPE: DNA
<213> ORGANISM: Homo sapiens

<400> SEQUENCE: 355
ggtgcatcca ccagggccac t                                            21

<210> SEQ ID NO 356
<211> LENGTH: 30
<212> TYPE: DNA
<213> ORGANISM: Homo sapiens

<400> SEQUENCE: 356
cagcagtata ataactggcc cacgtggacg                                   30

<210> SEQ ID NO 357
<211> LENGTH: 33
<212> TYPE: DNA
<213> ORGANISM: Homo sapiens
```

```
<400> SEQUENCE: 357
cgggcaagtc agggcattag aaatgattta ggc                              33

<210> SEQ ID NO 358
<211> LENGTH: 21
<212> TYPE: DNA
<213> ORGANISM: Homo sapiens

<400> SEQUENCE: 358
gctgcatcca gtttccaaag t                                          21

<210> SEQ ID NO 359
<211> LENGTH: 27
<212> TYPE: DNA
<213> ORGANISM: Homo sapiens

<400> SEQUENCE: 359
ctacagcata atagttaccc tccgacg                                     27

<210> SEQ ID NO 360
<211> LENGTH: 33
<212> TYPE: DNA
<213> ORGANISM: Homo sapiens

<400> SEQUENCE: 360
cgggcaagtc agggcattag aaatgattta ggc                              33

<210> SEQ ID NO 361
<211> LENGTH: 21
<212> TYPE: DNA
<213> ORGANISM: Homo sapiens

<400> SEQUENCE: 361
gctgcatcca gtttgcaaag t                                          21

<210> SEQ ID NO 362
<211> LENGTH: 27
<212> TYPE: DNA
<213> ORGANISM: Homo sapiens

<400> SEQUENCE: 362
ctacagcata aaagttaccc gctcact                                     27

<210> SEQ ID NO 363
<211> LENGTH: 33
<212> TYPE: DNA
<213> ORGANISM: Homo sapiens

<400> SEQUENCE: 363
cgggcaagtc agggcattag aaatgattta ggc                              33

<210> SEQ ID NO 364
<211> LENGTH: 21
<212> TYPE: DNA
<213> ORGANISM: Homo sapiens

<400> SEQUENCE: 364
gctgcatcca gtttgcaaag t                                          21

<210> SEQ ID NO 365
<211> LENGTH: 27
<212> TYPE: DNA
<213> ORGANISM: Homo sapiens
```

<400> SEQUENCE: 365
ctacagcata aaagttaccc gctcact                                        27

<210> SEQ ID NO 366
<211> LENGTH: 33
<212> TYPE: DNA
<213> ORGANISM: Homo sapiens

<400> SEQUENCE: 366
cgggcaagtc agggcattag aaatgattta ggc                                 33

<210> SEQ ID NO 367
<211> LENGTH: 21
<212> TYPE: DNA
<213> ORGANISM: Homo sapiens

<400> SEQUENCE: 367
gctgcatcca gtttgcaaag t                                              21

<210> SEQ ID NO 368
<211> LENGTH: 27
<212> TYPE: DNA
<213> ORGANISM: Homo sapiens

<400> SEQUENCE: 368
ctacagcata agagttaccc gctcact                                        27

<210> SEQ ID NO 369
<211> LENGTH: 30
<212> TYPE: DNA
<213> ORGANISM: Homo sapiens

<400> SEQUENCE: 369
cgggcaagtc agggcattag aaatgattta                                     30

<210> SEQ ID NO 370
<211> LENGTH: 21
<212> TYPE: DNA
<213> ORGANISM: Homo sapiens

<400> SEQUENCE: 370
gctgcatcca gtttgcaaag t                                              21

<210> SEQ ID NO 371
<211> LENGTH: 27
<212> TYPE: DNA
<213> ORGANISM: Homo sapiens

<400> SEQUENCE: 371
ctacagcata aaagttaccc gctcact                                        27

<210> SEQ ID NO 372
<211> LENGTH: 33
<212> TYPE: DNA
<213> ORGANISM: Homo sapiens

<400> SEQUENCE: 372
cgggcgagtc agggtattag gagctggtta gcc                                 33

<210> SEQ ID NO 373
<211> LENGTH: 21
<212> TYPE: DNA

```
<213> ORGANISM: Homo sapiens

<400> SEQUENCE: 373
gctgcatcca gtttgcaaag t                                              21

<210> SEQ ID NO 374
<211> LENGTH: 27
<212> TYPE: DNA
<213> ORGANISM: Homo sapiens

<400> SEQUENCE: 374
caacaggcta acaatttccc tcggacg                                        27

<210> SEQ ID NO 375
<211> LENGTH: 33
<212> TYPE: DNA
<213> ORGANISM: Homo sapiens

<400> SEQUENCE: 375
agggccagtc agagtgttag cagcaactta gcc                                 33

<210> SEQ ID NO 376
<211> LENGTH: 21
<212> TYPE: DNA
<213> ORGANISM: Homo sapiens

<400> SEQUENCE: 376
ggtgcatcca ccagggccgc t                                              21

<210> SEQ ID NO 377
<211> LENGTH: 30
<212> TYPE: DNA
<213> ORGANISM: Homo sapiens

<400> SEQUENCE: 377
cagcactata taaactggcc taagtggacg                                     30

<210> SEQ ID NO 378
<211> LENGTH: 33
<212> TYPE: DNA
<213> ORGANISM: Homo sapiens

<400> SEQUENCE: 378
agggccagtc agagtattag cagcagctta gcc                                 33

<210> SEQ ID NO 379
<211> LENGTH: 21
<212> TYPE: DNA
<213> ORGANISM: Homo sapiens

<400> SEQUENCE: 379
ggtgcatcca ccagggccac t                                              21

<210> SEQ ID NO 380
<211> LENGTH: 27
<212> TYPE: DNA
<213> ORGANISM: Homo sapiens

<400> SEQUENCE: 380
cagcaatatg ataactggcc gctcact                                        27

<210> SEQ ID NO 381
<211> LENGTH: 48
```

```
<212> TYPE: DNA
<213> ORGANISM: Homo sapiens

<400> SEQUENCE: 381
aagtctagtc agagcctcct gcatagtgat ggaaagacct atttgtat          48

<210> SEQ ID NO 382
<211> LENGTH: 21
<212> TYPE: DNA
<213> ORGANISM: Homo sapiens

<400> SEQUENCE: 382
gaagtttcca cccggttctc t                                       21

<210> SEQ ID NO 383
<211> LENGTH: 27
<212> TYPE: DNA
<213> ORGANISM: Homo sapiens

<400> SEQUENCE: 383
atgcaaagta tacagcttcc gctcact                                 27

<210> SEQ ID NO 384
<211> LENGTH: 33
<212> TYPE: DNA
<213> ORGANISM: Homo sapiens

<400> SEQUENCE: 384
agggccagtc agagtgttag cagcaactta gcc                          33

<210> SEQ ID NO 385
<211> LENGTH: 21
<212> TYPE: DNA
<213> ORGANISM: Homo sapiens

<400> SEQUENCE: 385
gatgcatcca ccagggccac t                                       21

<210> SEQ ID NO 386
<211> LENGTH: 27
<212> TYPE: DNA
<213> ORGANISM: Homo sapiens

<400> SEQUENCE: 386
cagcagtatg ataactggcc gctcact                                 27

<210> SEQ ID NO 387
<211> LENGTH: 33
<212> TYPE: DNA
<213> ORGANISM: Homo sapiens

<400> SEQUENCE: 387
agggccagtc agagtgttag cagcaactta gcc                          33

<210> SEQ ID NO 388
<211> LENGTH: 21
<212> TYPE: DNA
<213> ORGANISM: Homo sapiens

<400> SEQUENCE: 388
gatgcatcca ccagggccgc t                                       21

<210> SEQ ID NO 389
```

```
<211> LENGTH: 27
<212> TYPE: DNA
<213> ORGANISM: Homo sapiens

<400> SEQUENCE: 389
cagcagtatg ataactggcc gctcact                                           27

<210> SEQ ID NO 390
<211> LENGTH: 33
<212> TYPE: DNA
<213> ORGANISM: Homo sapiens

<400> SEQUENCE: 390
agggccagtc agagtattag caccagctta gcc                                    33

<210> SEQ ID NO 391
<211> LENGTH: 21
<212> TYPE: DNA
<213> ORGANISM: Homo sapiens

<400> SEQUENCE: 391
ggtacatcca ccagggccac t                                                 21

<210> SEQ ID NO 392
<211> LENGTH: 27
<212> TYPE: DNA
<213> ORGANISM: Homo sapiens

<400> SEQUENCE: 392
caacagtatg atatctggcc gctcact                                           27

<210> SEQ ID NO 393
<211> LENGTH: 33
<212> TYPE: DNA
<213> ORGANISM: Homo sapiens

<400> SEQUENCE: 393
agggccagtc agagtgttag cagcaactta gcc                                    33

<210> SEQ ID NO 394
<211> LENGTH: 21
<212> TYPE: DNA
<213> ORGANISM: Homo sapiens

<400> SEQUENCE: 394
ggtgcatcca ccagggccac t                                                 21

<210> SEQ ID NO 395
<211> LENGTH: 27
<212> TYPE: DNA
<213> ORGANISM: Homo sapiens

<400> SEQUENCE: 395
cagcagtatg ataactggcc gctcact                                           27

<210> SEQ ID NO 396
<211> LENGTH: 51
<212> TYPE: DNA
<213> ORGANISM: Homo sapiens

<400> SEQUENCE: 396
aagaccagcc agagtgtttt atacagctcc aaaaacaaga acttcttagc t                51
```

-continued

```
<210> SEQ ID NO 397
<211> LENGTH: 21
<212> TYPE: DNA
<213> ORGANISM: Homo sapiens

<400> SEQUENCE: 397
tgggcatcta cccgggaatc c                                            21

<210> SEQ ID NO 398
<211> LENGTH: 27
<212> TYPE: DNA
<213> ORGANISM: Homo sapiens

<400> SEQUENCE: 398
cagcaatatt atagtactcc attcact                                      27

<210> SEQ ID NO 399
<211> LENGTH: 33
<212> TYPE: DNA
<213> ORGANISM: Homo sapiens

<400> SEQUENCE: 399
agggccagtc agagtattag cagcaactta gcc                               33

<210> SEQ ID NO 400
<211> LENGTH: 21
<212> TYPE: DNA
<213> ORGANISM: Homo sapiens

<400> SEQUENCE: 400
ggtgcatcca ccagggccac t                                            21

<210> SEQ ID NO 401
<211> LENGTH: 27
<212> TYPE: DNA
<213> ORGANISM: Homo sapiens

<400> SEQUENCE: 401
cagcagtatg atacctggcc tctcact                                      27

<210> SEQ ID NO 402
<211> LENGTH: 33
<212> TYPE: DNA
<213> ORGANISM: Homo sapiens

<400> SEQUENCE: 402
cgggcgagtc agggcattag caattattta gcc                               33

<210> SEQ ID NO 403
<211> LENGTH: 21
<212> TYPE: DNA
<213> ORGANISM: Homo sapiens

<400> SEQUENCE: 403
gctgcatcca ctttacaatc a                                            21

<210> SEQ ID NO 404
<211> LENGTH: 27
<212> TYPE: DNA
<213> ORGANISM: Homo sapiens

<400> SEQUENCE: 404
caaaagtata accgtgcccc attcact                                      27
```

```
<210> SEQ ID NO 405
<211> LENGTH: 33
<212> TYPE: DNA
<213> ORGANISM: Homo sapiens

<400> SEQUENCE: 405
cgggcgagtc agggcattag caattattta gcc                                    33

<210> SEQ ID NO 406
<211> LENGTH: 21
<212> TYPE: DNA
<213> ORGANISM: Homo sapiens

<400> SEQUENCE: 406
gctgcatcca ctttgcaatc a                                                 21

<210> SEQ ID NO 407
<211> LENGTH: 27
<212> TYPE: DNA
<213> ORGANISM: Homo sapiens

<400> SEQUENCE: 407
caaaagtata accgtgcccc attcact                                           27

<210> SEQ ID NO 408
<211> LENGTH: 33
<212> TYPE: DNA
<213> ORGANISM: Homo sapiens

<400> SEQUENCE: 408
agggccagtc agagtgttag cagcaactta gcc                                    33

<210> SEQ ID NO 409
<211> LENGTH: 21
<212> TYPE: DNA
<213> ORGANISM: Homo sapiens

<400> SEQUENCE: 409
gatgcatcca ccagggccgc t                                                 21

<210> SEQ ID NO 410
<211> LENGTH: 27
<212> TYPE: DNA
<213> ORGANISM: Homo sapiens

<400> SEQUENCE: 410
cagcagtatg ataactggcc gctcact                                           27

<210> SEQ ID NO 411
<211> LENGTH: 33
<212> TYPE: DNA
<213> ORGANISM: Homo sapiens

<400> SEQUENCE: 411
cgggcaagtc agggcattat aaatgattta ggc                                    33

<210> SEQ ID NO 412
<211> LENGTH: 21
<212> TYPE: DNA
<213> ORGANISM: Homo sapiens

<400> SEQUENCE: 412
gctgcatcca gtttgcaaag t                                                 21
```

```
<210> SEQ ID NO 413
<211> LENGTH: 27
<212> TYPE: DNA
<213> ORGANISM: Homo sapiens

<400> SEQUENCE: 413
ctacagcata atagttaccc tccgacg                                          27

<210> SEQ ID NO 414
<211> LENGTH: 48
<212> TYPE: DNA
<213> ORGANISM: Homo sapiens

<400> SEQUENCE: 414
aggtctagtc aaagcctcgt atatagtgat ggacacacct gcttgaat                   48

<210> SEQ ID NO 415
<211> LENGTH: 21
<212> TYPE: DNA
<213> ORGANISM: Homo sapiens

<400> SEQUENCE: 415
aaggtttcta actgggactc t                                                21

<210> SEQ ID NO 416
<211> LENGTH: 30
<212> TYPE: DNA
<213> ORGANISM: Homo sapiens

<400> SEQUENCE: 416
atgcaaggta cacactggcc tctgtgcagt                                       30

<210> SEQ ID NO 417
<211> LENGTH: 48
<212> TYPE: DNA
<213> ORGANISM: Homo sapiens

<400> SEQUENCE: 417
aggtctagtc aaagcctcgt atatagtgat ggacacacct gcttgaat                   48

<210> SEQ ID NO 418
<211> LENGTH: 21
<212> TYPE: DNA
<213> ORGANISM: Homo sapiens

<400> SEQUENCE: 418
aaggtttcta actgggactc t                                                21

<210> SEQ ID NO 419
<211> LENGTH: 30
<212> TYPE: DNA
<213> ORGANISM: Homo sapiens

<400> SEQUENCE: 419
atgcaaggta cacactggcc tctgtgcagt                                       30

<210> SEQ ID NO 420
<211> LENGTH: 33
<212> TYPE: DNA
<213> ORGANISM: Homo sapiens

<400> SEQUENCE: 420
```
cgggcgagtc aggccattag catttattta gcc                            33

<210> SEQ ID NO 421
<211> LENGTH: 21
<212> TYPE: DNA
<213> ORGANISM: Homo sapiens

<400> SEQUENCE: 421
gctgcatcca gtttgcaaag t                                         21

<210> SEQ ID NO 422
<211> LENGTH: 27
<212> TYPE: DNA
<213> ORGANISM: Homo sapiens

<400> SEQUENCE: 422
caacagtata gtagttaccc tcggacg                                   27

<210> SEQ ID NO 423
<211> LENGTH: 33
<212> TYPE: DNA
<213> ORGANISM: Homo sapiens

<400> SEQUENCE: 423
agggccagtc agagtgttta cagcaactta gcc                            33

<210> SEQ ID NO 424
<211> LENGTH: 21
<212> TYPE: DNA
<213> ORGANISM: Homo sapiens

<400> SEQUENCE: 424
ggtgcttcca ccagggccac t                                         21

<210> SEQ ID NO 425
<211> LENGTH: 27
<212> TYPE: DNA
<213> ORGANISM: Homo sapiens

<400> SEQUENCE: 425
cagcagtatt ataactggcc gtggacg                                   27

<210> SEQ ID NO 426
<211> LENGTH: 1409
<212> TYPE: DNA
<213> ORGANISM: Homo sapiens
<220> FEATURE:
<221> NAME/KEY: CDS
<222> LOCATION: (16)..(1398)

<400> SEQUENCE: 426

```
gtcgacgccg ccacc atg gag tgg acc tgg agg gtc ctt ttc ttg gtg gca     51
                Met Glu Trp Thr Trp Arg Val Leu Phe Leu Val Ala
                 1               5                  10 gca aca ggt gcc cac tcc cag gtt cag ctg gtg cag tct gga gct         99
Ala Ala Thr Gly Ala His Ser Gln Val Gln Leu Val Gln Ser Gly Ala
             15                  20                  25 gag gtg aag aag cct ggg gcc tca gtg aag gtc tcc tgc aag gct tct    147
Glu Val Lys Lys Pro Gly Ala Ser Val Lys Val Ser Cys Lys Ala Ser
         30                  35                  40 ggt tac acc ttt acc aga tat ggt atc agc tgg gtg cga cag gcc cct    195
Gly Tyr Thr Phe Thr Arg Tyr Gly Ile Ser Trp Val Arg Gln Ala Pro
 45                  50                  55                  60
```

-continued

| | |
|---|---|
| gga caa ggg ctt gag tgg atg gga tgg atc agc act tac agt ggt aac<br>Gly Gln Gly Leu Glu Trp Met Gly Trp Ile Ser Thr Tyr Ser Gly Asn<br>                65                  70                  75 | 243 |
| aca aac tat gca cag aag ctc cag ggc aga gtc acc atg acc aca gac<br>Thr Asn Tyr Ala Gln Lys Leu Gln Gly Arg Val Thr Met Thr Thr Asp<br>           80                      85                      90 | 291 |
| aca tcc acg agc aca gcc tac atg gag ctg agg agc ctg aga tct gac<br>Thr Ser Thr Ser Thr Ala Tyr Met Glu Leu Arg Ser Leu Arg Ser Asp<br>             95                       100                  105 | 339 |
| gac acg gcc gtg tat tac tgt gcg aga cgg cag ctt tac ttt gac tac<br>Asp Thr Ala Val Tyr Tyr Cys Ala Arg Arg Gln Leu Tyr Phe Asp Tyr<br>110                      115                      120 | 387 |
| tgg ggc cag gga acc ctg gtc acc gtc tcc tca gct agc acc aag ggc<br>Trp Gly Gln Gly Thr Leu Val Thr Val Ser Ser Ala Ser Thr Lys Gly<br>125                      130                      135                  140 | 435 |
| cca tcg gtc ttc ccc ctg gcg ccc tgc tcc agg agc acc tcc gag agc<br>Pro Ser Val Phe Pro Leu Ala Pro Cys Ser Arg Ser Thr Ser Glu Ser<br>               145                      150                      155 | 483 |
| aca gcg gcc ctg ggc tgc ctg gtc aag gac tac ttc ccc gaa ccg gtg<br>Thr Ala Ala Leu Gly Cys Leu Val Lys Asp Tyr Phe Pro Glu Pro Val<br>160                      165                      170 | 531 |
| acg gtg tcg tgg aac tca ggc gct ctg acc agc ggc gtg cac acc ttc<br>Thr Val Ser Trp Asn Ser Gly Ala Leu Thr Ser Gly Val His Thr Phe<br>               175                      180                      185 | 579 |
| cca gct gtc cta cag tcc tca gga ctc tac tcc ctc agc agc gtg gtg<br>Pro Ala Val Leu Gln Ser Ser Gly Leu Tyr Ser Leu Ser Ser Val Val<br>190                      195                      200 | 627 |
| acc gtg ccc tcc agc aac ttc ggc acc cag acc tac acc tgc aac gta<br>Thr Val Pro Ser Ser Asn Phe Gly Thr Gln Thr Tyr Thr Cys Asn Val<br>205                      210                      215                  220 | 675 |
| gat cac aag ccc agc aac acc aag gtg gac aag aca gtt gag cgc aaa<br>Asp His Lys Pro Ser Asn Thr Lys Val Asp Lys Thr Val Glu Arg Lys<br>                      225                      230                  235 | 723 |
| tgt tgt gtc gag tgc cca ccg tgc cca gca cca cct gtg gca gga ccg<br>Cys Cys Val Glu Cys Pro Pro Cys Pro Ala Pro Pro Val Ala Gly Pro<br>240                      245                      250 | 771 |
| tca gtc ttc ctc ttc ccc cca aaa ccc aag gac acc ctc atg atc tcc<br>Ser Val Phe Leu Phe Pro Pro Lys Pro Lys Asp Thr Leu Met Ile Ser<br>               255                      260                      265 | 819 |
| cgg acc cct gag gtc acg tgc gtg gtg gtg gac gtg agc cac gaa gac<br>Arg Thr Pro Glu Val Thr Cys Val Val Val Asp Val Ser His Glu Asp<br>270                      275                      280 | 867 |
| ccc gag gtc cag ttc aac tgg tac gtg gac ggc gtg gag gtg cat aat<br>Pro Glu Val Gln Phe Asn Trp Tyr Val Asp Gly Val Glu Val His Asn<br>285                      290                      295                  300 | 915 |
| gcc aag aca aag cca cgg gag gag cag ttc aac agc acg ttc cgt gtg<br>Ala Lys Thr Lys Pro Arg Glu Glu Gln Phe Asn Ser Thr Phe Arg Val<br>                      305                      310                  315 | 963 |
| gtc agc gtc ctc acc gtt gtg cac cag gac tgg ctg aac ggc aag gag<br>Val Ser Val Leu Thr Val Val His Gln Asp Trp Leu Asn Gly Lys Glu<br>320                      325                      330 | 1011 |
| tac aag tgc aag gtc tcc aac aaa ggc ctc cca gcc ccc atc gag aaa<br>Tyr Lys Cys Lys Val Ser Asn Lys Gly Leu Pro Ala Pro Ile Glu Lys<br>               335                      340                      345 | 1059 |
| acc atc tcc aaa acc aaa ggg cag ccc cga gaa cca cag gtg tac acc<br>Thr Ile Ser Lys Thr Lys Gly Gln Pro Arg Glu Pro Gln Val Tyr Thr<br>350                      355                      360 | 1107 |
| ctg ccc cca tcc cgg gag gag atg acc aag aac cag gtc agc ctg acc<br>Leu Pro Pro Ser Arg Glu Glu Met Thr Lys Asn Gln Val Ser Leu Thr<br>365                      370                      375                  380 | 1155 |

```
tgc ctg gtc aaa ggc ttc tac ccc agc gac atc gcc gtg gag tgg gag    1203
Cys Leu Val Lys Gly Phe Tyr Pro Ser Asp Ile Ala Val Glu Trp Glu
            385                 390                 395 agc aat ggg cag ccg gag aac aac tac aag acc aca cct ccc atg ctg    1251
Ser Asn Gly Gln Pro Glu Asn Asn Tyr Lys Thr Thr Pro Pro Met Leu
        400                 405                 410 gac tcc gac ggc tcc ttc ttc ctc tac agc aag ctc acc gtg gac aag    1299
Asp Ser Asp Gly Ser Phe Phe Leu Tyr Ser Lys Leu Thr Val Asp Lys
    415                 420                 425 agc agg tgg cag cag ggg aac gtc ttc tca tgc tcc gtg atg cat gag    1347
Ser Arg Trp Gln Gln Gly Asn Val Phe Ser Cys Ser Val Met His Glu
430                 435                 440 gct ctg cac aac cac tac acg cag aag agc ctc tcc ctg tct ccg ggt    1395
Ala Leu His Asn His Tyr Thr Gln Lys Ser Leu Ser Leu Ser Pro Gly
445                 450                 455                 460 aaa tgagcggccg c                                                    1409
Lys

<210> SEQ ID NO 427
<211> LENGTH: 461
<212> TYPE: PRT
<213> ORGANISM: Homo sapiens

<400> SEQUENCE: 427

Met Glu Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Arg Tyr Gly Ile Ser Trp Val Arg Gln Ala Pro Gly Gln Gly Leu
    50                  55                  60

Glu Trp Met Gly Trp Ile Ser Thr Tyr Ser Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Gln Leu Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255
```

```
Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Gln
            275                 280                 285

Phe Asn Trp Tyr Val Asp Gly Val Glu Val His Asn Ala Lys Thr Lys
        290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460

<210> SEQ ID NO 428
<211> LENGTH: 741
<212> TYPE: DNA
<213> ORGANISM: Homo sapiens
<220> FEATURE:
<221> NAME/KEY: CDS
<222> LOCATION: (24)..(725)

<400> SEQUENCE: 428
gtcgacgttt aaacgccgcc acc atg gaa gcg ccg gcg cag ctt ctc ttc ctc      53
                         Met Glu Ala Pro Ala Gln Leu Leu Phe Leu
                           1               5                  10 ctg cta ctc tgg ctc cca gat acc act gga gaa ata gtg atg acg cag     101
Leu Leu Leu Trp Leu Pro Asp Thr Thr Gly Glu Ile Val Met Thr Gln
             15                  20                  25 tct cca gcc acc ctg tct gtg tct cct ggg gaa aga gcc acc ctc tcc     149
Ser Pro Ala Thr Leu Ser Val Ser Pro Gly Glu Arg Ala Thr Leu Ser
         30                  35                  40 tgc agg gcc agt cag agt gtt agc agc aac tta gcc tgg ttc cag cag     197
Cys Arg Ala Ser Gln Ser Val Ser Ser Asn Leu Ala Trp Phe Gln Gln
     45                  50                  55 aaa cct ggc cag gct ccc agg ccc ctc atc tat gat gca tcc acc agg     245
Lys Pro Gly Gln Ala Pro Arg Pro Leu Ile Tyr Asp Ala Ser Thr Arg
 60                  65                  70 gcc act ggt gtc cca gcc agg ttc agt ggc agt ggg tct ggg aca gac     293
Ala Thr Gly Val Pro Ala Arg Phe Ser Gly Ser Gly Ser Gly Thr Asp
 75                  80                  85                  90 ttc act ctc acc atc agc agc ctg cag tct gaa gat ttt gca gtt tat     341
Phe Thr Leu Thr Ile Ser Ser Leu Gln Ser Glu Asp Phe Ala Val Tyr
                 95                 100                 105 tac tgt cag cag tat gat aac tgg ccg ctc act ttc ggc gga ggg acc     389
```

```
            Tyr Cys Gln Gln Tyr Asp Asn Trp Pro Leu Thr Phe Gly Gly Thr
                        110                 115                 120 aag gtg gag atc aaa cgt acg gtg gct gca cca tct gtc ttc atc ttc          437
Lys Val Glu Ile Lys Arg Thr Val Ala Ala Pro Ser Val Phe Ile Phe
            125                 130                 135 ccg cca tct gat gag cag ttg aaa tct gga act gcc tct gtt gtg tgc          485
Pro Pro Ser Asp Glu Gln Leu Lys Ser Gly Thr Ala Ser Val Val Cys
140                 145                 150 ctg ctg aat aac ttc tat ccc aga gag gcc aaa gta cag tgg aag gtg          533
Leu Leu Asn Asn Phe Tyr Pro Arg Glu Ala Lys Val Gln Trp Lys Val
155                 160                 165                 170 gat aac gcc ctc caa tcg ggt aac tcc cag gag agt gtc aca gag cag          581
Asp Asn Ala Leu Gln Ser Gly Asn Ser Gln Glu Ser Val Thr Glu Gln
                175                 180                 185 gac agc aag gac agc acc tac agc ctc agc agc acc ctg acg ctg agc          629
Asp Ser Lys Asp Ser Thr Tyr Ser Leu Ser Ser Thr Leu Thr Leu Ser
                190                 195                 200 aaa gca gac tac gag aaa cac aaa gtc tac gcc tgc gaa gtc acc cat          677
Lys Ala Asp Tyr Glu Lys His Lys Val Tyr Ala Cys Glu Val Thr His
                205                 210                 215 cag ggc ctg agc tcg ccc gtc aca aag agc ttc aac agg gga gag tgt          725
Gln Gly Leu Ser Ser Pro Val Thr Lys Ser Phe Asn Arg Gly Glu Cys
220                 225                 230 taggatccgc ggccgc                                                        741
```

<210> SEQ ID NO 429
<211> LENGTH: 234
<212> TYPE: PRT
<213> ORGANISM: Homo sapiens

<400> SEQUENCE: 429

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Pro Leu Ile Tyr Asp Ala Ser Thr Arg Ala Thr Gly Val Pro Ala
65                  70                  75                  80

Arg Phe Ser Gly Ser Gly Ser Gly Thr Asp Phe Thr Leu Thr Ile Ser
                85                  90                  95

Ser Leu Gln Ser Glu Asp Phe Ala Val Tyr Tyr Cys Gln Gln Tyr Asp
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

```
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 430
<211> LENGTH: 866
<212> TYPE: PRT
<213> ORGANISM: Homo sapiens

<400> SEQUENCE: 430

```
Met Gly Ala Ala Arg Ser Pro Pro Ser Ala Val Pro Gly Pro Leu Leu
1               5                   10                  15

Gly Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350
```

```
Glu Lys Tyr Ser Asp Asp Thr Lys Tyr Thr Asp Gly Leu Pro Ala Ala
        355                 360                 365

Asp Leu Ile Pro Pro Leu Lys Pro Arg Lys Val Trp Ile Ile Tyr
        370                 375                 380

Ser Ala Asp His Pro Leu Tyr Val Asp Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
                435                 440                 445

Arg Gly Thr Arg Ala Lys Trp Gln Ala Leu Leu Gly Arg Gly Ala Pro
        450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
        500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
        530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Val Phe Glu Glu
                595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Val Glu Pro Gly Pro Leu Ala Asp
                675                 680                 685

Gly Ala Ala Val Arg Leu Ala Leu Ala Gly Glu Gly Glu Ala Cys Pro
        690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
                740                 745                 750

Leu Ser Leu Phe Glu Gln Ser Leu Ser Cys Gln Ala Gln Gly Gly Cys
        755                 760                 765
```

```
Ser Arg Pro Ala Met Val Leu Thr Asp Pro His Thr Pro Tyr Glu Glu
    770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
850                 855                 860

Ser Ala
865

<210> SEQ ID NO 431
<211> LENGTH: 344
<212> TYPE: PRT
<213> ORGANISM: Artificial Sequence
<220> FEATURE:
<223> OTHER INFORMATION: Synthetic construct

<400> SEQUENCE: 431

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255
```

```
Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
            325                 330                 335

Ser Ser His His His His His His
            340

<210> SEQ ID NO 432
<211> LENGTH: 322
<212> TYPE: PRT
<213> ORGANISM: Mus musculus

<400> SEQUENCE: 432

Met Ala Ile Arg Arg Cys Trp Pro Arg Val Val Pro Gly Pro Ala Leu
1               5                   10                  15

Gly Trp Leu Leu Leu Leu Leu Asn Val Leu Ala Pro Gly Arg Ala Ser
            20                  25                  30

Pro Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Lys Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His His Val Gln Val Gln Pro Phe Phe Ser
        275                 280                 285
```

```
Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp

<210> SEQ ID NO 433
<211> LENGTH: 344
<212> TYPE: PRT
<213> ORGANISM: Artificial Sequence
<220> FEATURE:
<223> OTHER INFORMATION: Synthetic construct

<400> SEQUENCE: 433

Met Gly Ala Ala Arg Ser Pro Pro Ser Ala Val Pro Gly Pro Leu Leu
1               5                   10                  15

Gly Leu Leu Leu Leu Leu Gly Val Leu Ala Pro Gly Gly Ala Ser
                20                  25                  30

Leu Arg Leu Leu Asp Phe Pro Ala Pro Val Cys Ala Gln Glu Gly Leu
            35                  40                  45

Ser Cys Arg Val Lys Asn Ser Thr Cys Leu Asp Asp Ser Trp Ile His
    50                  55                  60

Pro Arg Asn Leu Thr Pro Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320
```

Glu Pro Arg Ser Gly Ser Ser Asp Tyr Lys Asp Asp Asp Lys Gly
                325                 330                 335

Ser Ser His His His His His His
            340

<210> SEQ ID NO 434
<211> LENGTH: 344
<212> TYPE: PRT
<213> ORGANISM: Artificial Sequence
<220> FEATURE:
<223> OTHER INFORMATION: Synthetic construct

<400> SEQUENCE: 434

Met Gly Ala Ala Arg Ser Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His
            340

<210> SEQ ID NO 435
<211> LENGTH: 344
<212> TYPE: PRT
<213> ORGANISM: Artificial Sequence
<220> FEATURE:
<223> OTHER INFORMATION: Synthetic construct

<400> SEQUENCE: 435

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His
            340

<210> SEQ ID NO 436
<211> LENGTH: 344
<212> TYPE: PRT
<213> ORGANISM: Artificial Sequence
<220> FEATURE:
<223> OTHER INFORMATION: Synthetic construct

<400> SEQUENCE: 436

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340
```

<210> SEQ ID NO 437
<211> LENGTH: 344

<212> TYPE: PRT
<213> ORGANISM: Artificial Sequence
<220> FEATURE:
<223> OTHER INFORMATION: Synthetic construct

<400> SEQUENCE: 437

```
Met Gly Ala Ala Arg Ser Pro Pro Ser Ala Val Pro Gly Pro Leu Leu
1               5                   10                  15
Gly Leu Leu Leu Leu Leu Leu Gly Val Leu Ala Pro Gly Gly Ala Ser
            20                  25                  30
Leu Arg Leu Leu Asp His Arg Ala Leu Val Cys Ser Gln Pro Gly Leu
        35                  40                  45
Asn Cys Thr Val Lys Asn Ser Thr Cys Leu Asp Asp Ser Trp Ile His
    50                  55                  60
Pro Arg Asn Leu Thr Pro Ser Pro Lys Asp Leu Gln Ile Gln Leu
65                  70                  75                  80
His Phe Ala His Thr Gln Gln Gly Asp Leu Phe Pro Val Ala His Ile
                85                  90                  95
Glu Trp Thr Leu Gln Thr Asp Ala Ser Ile Leu Tyr Leu Glu Gly Ala
            100                 105                 110
Glu Leu Ser Val Leu Gln Leu Asn Thr Asn Glu Arg Leu Cys Val Arg
        115                 120                 125
Phe Glu Phe Leu Ser Lys Leu Arg His His His Arg Arg Trp Arg Phe
130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
            180                 185                 190
Thr Thr Pro Cys Met Ser Ser Gly Ser Leu Trp Asp Pro Asn Ile Thr
        195                 200                 205
Val Glu Thr Leu Asp Thr Gln His Leu Arg Val Asp Phe Thr Leu Trp
210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
                245                 250                 255
Pro Glu Glu Phe His Gln Arg Ser Asn Val Thr Leu Thr Leu Arg Asn
            260                 265                 270
Leu Lys Gly Cys Cys Arg His Gln Val Gln Ile Gln Pro Phe Phe Ser
        275                 280                 285
Ser Cys Leu Asn Asp Cys Leu Arg His Ser Ala Thr Val Ser Cys Pro
290                 295                 300
Glu Met Pro Asp Thr Pro Glu Pro Ile Pro Asp Tyr Met Pro Leu Trp
305                 310                 315                 320
Glu Pro Arg Ser Gly Ser Ser Asp Tyr Lys Asp Asp Asp Lys Gly
                325                 330                 335
Ser Ser His His His His His His
            340
```

<210> SEQ ID NO 438
<211> LENGTH: 346
<212> TYPE: PRT
<213> ORGANISM: Artificial Sequence
<220> FEATURE:

<223> OTHER INFORMATION: Synthetic construct

<400> SEQUENCE: 438

| | | | | | | | | | | | | | | | |
|---|---|---|---|---|---|---|---|---|---|---|---|---|---|---|---|
| Met | Gly | Ala | Ala | Arg | Ser | Pro | Pro | Ser | Ala | Val | Pro | Gly | Pro | Leu | Leu |
| 1 | | | | 5 | | | | | 10 | | | | | 15 | |
| Gly | Leu | Leu | Leu | Leu | Leu | Leu | Gly | Val | Leu | Ala | Pro | Gly | Gly | Ala | Ser |
| | | | 20 | | | | | 25 | | | | | 30 | | |
| Leu | Arg | Leu | Leu | Asp | His | Arg | Ala | Leu | Val | Cys | Ser | Gln | Pro | Gly | Leu |
| | | 35 | | | | | 40 | | | | | 45 | | | |
| Asn | Cys | Thr | Val | Lys | Asn | Ser | Thr | Cys | Leu | Asp | Asp | Ser | Trp | Ile | His |
| | 50 | | | | | 55 | | | | | 60 | | | | |
| Pro | Arg | Asn | Leu | Thr | Pro | Ser | Ser | Pro | Lys | Asp | Leu | Gln | Ile | Gln | Leu |
| 65 | | | | | 70 | | | | | 75 | | | | | 80 |
| His | Phe | Ala | His | Thr | Gln | Gln | Gly | Asp | Leu | Phe | Pro | Val | Ala | His | Ile |
| | | | | 85 | | | | | 90 | | | | | 95 | |
| Glu | Trp | Thr | Leu | Gln | Thr | Asp | Ala | Ser | Ile | Leu | Tyr | Leu | Glu | Gly | Ala |
| | | | 100 | | | | | 105 | | | | | 110 | | |
| Glu | Leu | Ser | Val | Leu | Gln | Leu | Asn | Thr | Asn | Glu | Arg | Leu | Cys | Val | Arg |
| | | | 115 | | | | | 120 | | | | | 125 | | |
| Phe | Glu | Phe | Leu | Ser | Lys | Leu | Arg | His | His | Arg | Arg | Trp | Arg | Phe |
| | 130 | | | | | 135 | | | | | 140 | | | | |
| Thr | Phe | Ser | His | Phe | Val | Val | Asp | Pro | Asp | Gln | Glu | Tyr | Glu | Val | Thr |
| 145 | | | | | 150 | | | | | 155 | | | | | 160 |
| Val | His | His | Leu | Pro | Lys | Pro | Ile | Pro | Asp | Gly | Asp | Pro | Asn | His | Gln |
| | | | | 165 | | | | | 170 | | | | | 175 | |
| Ser | Lys | Asn | Phe | Leu | Val | Pro | Asp | Cys | Glu | His | Ala | Arg | Met | Lys | Val |
| | | | 180 | | | | | 185 | | | | | 190 | | |
| Thr | Thr | Pro | Cys | Met | Ser | Ser | Gly | Ser | Leu | Trp | Asp | Pro | Asn | Ile | Thr |
| | | 195 | | | | | 200 | | | | | 205 | | | |
| Val | Glu | Thr | Leu | Glu | Ala | His | Gln | Leu | Arg | Val | Ser | Phe | Thr | Leu | Trp |
| | 210 | | | | | 215 | | | | | 220 | | | | |
| Asn | Glu | Ser | Thr | Pro | Tyr | Gln | Val | Leu | Leu | Glu | Ser | Phe | Ser | Asp | Ser |
| 225 | | | | | 230 | | | | | 235 | | | | | 240 |
| Glu | Asn | His | Ser | Cys | Phe | Asp | Val | Val | Lys | Gln | Ile | Phe | Ala | Pro | Arg |
| | | | | 245 | | | | | 250 | | | | | 255 | |
| Gln | Glu | Glu | Phe | His | Gln | Arg | Ala | Asn | Val | Thr | Phe | Thr | Leu | Ser | Lys |
| | | | 260 | | | | | 265 | | | | | 270 | | |
| Phe | His | Trp | Cys | Cys | His | His | Val | Gln | Val | Gln | Pro | Phe | Phe | Ser |
| | 275 | | | | | 280 | | | | | 285 | | | | |
| Ser | Cys | Leu | Asn | Asp | Cys | Leu | Arg | His | Ala | Val | Thr | Val | Pro | Cys | Pro |
| | 290 | | | | | 295 | | | | | 300 | | | | |
| Val | Ile | Ser | Asn | Thr | Thr | Val | Pro | Lys | Pro | Val | Ala | Asp | Tyr | Ile | Pro |
| 305 | | | | | 310 | | | | | 315 | | | | | 320 |
| Leu | Trp | Glu | Pro | Arg | Ser | Gly | Ser | Ser | Asp | Tyr | Lys | Asp | Asp | Asp | Asp |
| | | | | 325 | | | | | 330 | | | | | 335 | |
| Lys | Gly | Ser | Ser | His | His | His | His | His | His |
| | | | 340 | | | | | 345 | |

<210> SEQ ID NO 439
<211> LENGTH: 344
<212> TYPE: PRT
<213> ORGANISM: Artificial Sequence
<220> FEATURE:
<223> OTHER INFORMATION: Synthetic construct

<400> SEQUENCE: 439

Met Gly Ala Ala Arg Ser Pro Pro Ser Ala Val Pro Gly Pro Leu Leu
1               5                   10                  15

Gly Leu Leu Leu Leu Leu Gly Val Leu Ala Pro Gly Gly Ala Ser
            20                  25                  30

Leu Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
            195                 200                 205

Val Glu Thr Leu Asp Thr Gln His Leu Arg Val Asp Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340

<210> SEQ ID NO 440
<211> LENGTH: 344
<212> TYPE: PRT
<213> ORGANISM: Artificial Sequence
<220> FEATURE:
<223> OTHER INFORMATION: Synthetic construct

<400> SEQUENCE: 440

Met Gly Ala Ala Arg Ser Pro Pro Ser Ala Val Pro Gly Pro Leu Leu
1               5                   10                  15

Gly Leu Leu Leu Leu Leu Gly Val Leu Ala Pro Gly Gly Ala Ser
            20                  25                  30

Leu Arg Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
50                  55                  60

Pro Arg Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Asp Lys Gly
                325                 330                 335

Ser Ser His His His His His His
            340

<210> SEQ ID NO 441
<211> LENGTH: 344
<212> TYPE: PRT
<213> ORGANISM: Artificial Sequence
<220> FEATURE:
<223> OTHER INFORMATION: Synthetic construct

<400> SEQUENCE: 441

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
 50                  55                  60

Pro Arg Asn Leu Thr Pro Ser Ser Pro Lys Asp Leu Gln Ile Gln Leu
 65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
            115                 120                 125

Phe Gln Phe Leu Ser Met Leu Gln His His Arg Lys Arg Trp Arg Phe
        130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Asp Thr Gln His Leu Arg Val Asp Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340

<210> SEQ ID NO 442
<211> LENGTH: 344
<212> TYPE: PRT
<213> ORGANISM: Artificial Sequence
<220> FEATURE:
<223> OTHER INFORMATION: Synthetic construct

<400> SEQUENCE: 442

Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
            35                  40                  45

```
Asn Cys Thr Val Lys Asn Ser Thr Cys Leu Asp Asp Ser Trp Ile His
 50                  55                  60

Pro Arg Asn Leu Thr Pro Ser Ser Pro Lys Asp Leu Gln Ile Gln Leu
 65                  70                  75                  80

His Phe Ala His Thr Gln Gln Gly Asp Leu Phe Pro Val Ala His Ile
             85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
                180                 185                 190

Thr Thr Ser Cys Val Ser Ser Gly Ser Leu Trp Asp Pro Asn Ile Thr
                195                 200                 205

Val Glu Thr Leu Asp Thr Gln His Leu Arg Val Asp Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
                275                 280                 285

Ser Cys Leu Asn Asp Cys Leu Arg His Ser Ala Thr Val Ser Cys Pro
290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
                340
```

<210> SEQ ID NO 443
<211> LENGTH: 346
<212> TYPE: PRT
<213> ORGANISM: Artificial Sequence
<220> FEATURE:
<223> OTHER INFORMATION: Synthetic construct

<400> SEQUENCE: 443

```
Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
                 20                  25                  30

Leu Arg Leu Leu Asp Phe Pro Ala Pro Val Cys Ala Gln Glu Gly Leu
             35                  40                  45

Ser Cys Arg Val Lys Asn Ser Thr Cys Leu Asp Asp Ser Trp Ile His
 50                  55                  60
```

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His His Val Gln Val Gln Pro Phe Phe Ser
        275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 444
<211> LENGTH: 346
<212> TYPE: PRT
<213> ORGANISM: Artificial Sequence
<220> FEATURE:
<223> OTHER INFORMATION: Synthetic construct

<400> SEQUENCE: 444

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asn Ile Tyr Ile Asn Leu
65                  70                  75                  80

```
Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His Val Gln Val Gln Pro Phe Phe Ser
        275                 280                 285

Ser Cys Leu Asn Asp Cys Leu Arg His Ala Val Thr Val Pro Cys Pro
290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 445
<211> LENGTH: 346
<212> TYPE: PRT
<213> ORGANISM: Artificial Sequence
<220> FEATURE:
<223> OTHER INFORMATION: Synthetic construct

<400> SEQUENCE: 445

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95
```

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Lys
            115                 120                 125

Phe Gln Phe Leu Ser Met Leu Gln His His Arg Lys Arg Trp Arg Phe
        130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His Val Gln Val Gln Pro Phe Phe Ser
        275                 280                 285

Ser Cys Leu Asn Asp Cys Leu Arg His Ala Val Thr Val Pro Cys Pro
290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

```
<210> SEQ ID NO 446
<211> LENGTH: 346
<212> TYPE: PRT
<213> ORGANISM: Artificial Sequence
<220> FEATURE:
<223> OTHER INFORMATION: Synthetic construct

<400> SEQUENCE: 446
```

Met Gly Ala Ala Arg Ser Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

```
Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
                180                 185                 190

Thr Thr Ser Cys Val Ser Ser Gly Ser Leu Trp Asp Pro Asn Ile Thr
            195                 200                 205

Val Glu Thr Leu Glu Ala His Gln Leu Arg Val Ser Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His His Val Gln Val Gln Pro Phe Phe Ser
    275                 280                 285

Ser Cys Leu Asn Asp Cys Leu Arg His Ala Val Thr Val Pro Cys Pro
290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 447
<211> LENGTH: 8
<212> TYPE: PRT
<213> ORGANISM: Artificial Sequence
<220> FEATURE:
<223> OTHER INFORMATION: Synthetic peptide

<400> SEQUENCE: 447

Asp Tyr Lys Asp Asp Asp Asp Lys
1               5

<210> SEQ ID NO 448
<211> LENGTH: 12
<212> TYPE: PRT
<213> ORGANISM: Artificial Sequence
<220> FEATURE:
<223> OTHER INFORMATION: Synthetic peptide

<400> SEQUENCE: 448

Gly Gly Gly Ala Ala Ala Gly Gly Gly Ala Ala Ala
1               5                   10

<210> SEQ ID NO 449
<211> LENGTH: 88
<212> TYPE: PRT
<213> ORGANISM: Artificial Sequence
<220> FEATURE:
<223> OTHER INFORMATION: Synthetic construct
```

<400> SEQUENCE: 449

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys
                85

<210> SEQ ID NO 450
<211> LENGTH: 88
<212> TYPE: PRT
<213> ORGANISM: Artificial Sequence
<220> FEATURE:
<223> OTHER INFORMATION: Synthetic construct

<400> SEQUENCE: 450

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys
                85

<210> SEQ ID NO 451
<211> LENGTH: 88
<212> TYPE: PRT
<213> ORGANISM: Artificial Sequence
<220> FEATURE:
<223> OTHER INFORMATION: Synthetic construct

<400> SEQUENCE: 451

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys
                85

<210> SEQ ID NO 452

```
<211> LENGTH: 88
<212> TYPE: PRT
<213> ORGANISM: Artificial Sequence
<220> FEATURE:
<223> OTHER INFORMATION: Synthetic construct

<400> SEQUENCE: 452

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys
                85

<210> SEQ ID NO 453
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Variable amino acid

<400> SEQUENCE: 453

Xaa Tyr Gly Ile Ser
1               5

<210> SEQ ID NO 454
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid

<400> SEQUENCE: 454

Xaa Tyr Xaa Met Xaa
1               5

<210> SEQ ID NO 455
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Variable amino acid
```

<400> SEQUENCE: 455

Ser Tyr Gly Met Xaa
1               5

<210> SEQ ID NO 456
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (14)..(15)
<223> OTHER INFORMATION: Variable amino acid

<400> SEQUENCE: 456

Trp Ile Ser Xaa Tyr Xaa Gly Asn Thr Xaa Tyr Ala Gln Xaa Xaa Gln
1               5                   10                  15

Gly

<210> SEQ ID NO 457
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid

<400> SEQUENCE: 457

Xaa Xaa Ser Xaa Xaa Xaa Ser Xaa Ile Xaa Tyr Ala Asp Ser Val Lys
1               5                   10                  15

Gly

<210> SEQ ID NO 458
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(8)
<223> OTHER INFORMATION: Variable amino acid

```
<220> FEATURE:
<221> NAME/KEY: MOD_RES
<222> LOCATION: (10)..(10)
<223> OTHER INFORMATION: Variable amino acid

<400> SEQUENCE: 458

Val Ile Trp Tyr Asp Gly Xaa Xaa Lys Xaa Tyr Ala Asp Ser Val Lys
1               5                   10                  15

Gly

<210> SEQ ID NO 459
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 459

Xaa Gln Leu Xaa Xaa Asp Tyr
1               5

<210> SEQ ID NO 460
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid

<400> SEQUENCE: 460

Xaa Gln Leu Xaa Phe Asp Tyr
1               5

<210> SEQ ID NO 461
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid

<400> SEQUENCE: 461

Arg Ala Ser Gln Xaa Ile Xaa Xaa Xaa Leu Xaa
1               5                   10
```

```
<210> SEQ ID NO 462
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(9)
<223> OTHER INFORMATION: Variable amino acid

<400> SEQUENCE: 462

Arg Ala Ser Gln Ser Xaa Xaa Xaa Xaa Leu Ala
1               5                   10

<210> SEQ ID NO 463
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid

<400> SEQUENCE: 463

Arg Ala Ser Gln Ser Val Xaa Xaa Asn Leu Xaa
1               5                   10

<210> SEQ ID NO 464
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Variable amino acid

<400> SEQUENCE: 464

Ala Ala Ser Ser Xaa Gln Ser
1               5

<210> SEQ ID NO 465
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Variable amino acid

<400> SEQUENCE: 465

Ala Ala Ser Xaa Leu Gln Ser
1               5

<210> SEQ ID NO 466
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 466

Xaa Xaa Ser Thr Arg Ala Xaa
1               5

<210> SEQ ID NO 467
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid

<400> SEQUENCE: 467

Leu Gln His Xaa Ser Tyr Xaa Xaa Thr
1               5

<210> SEQ ID NO 468
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid

<400> SEQUENCE: 468

Gln Xaa Xaa Xaa Xaa Xaa Pro Xaa Thr
1               5

<210> SEQ ID NO 469
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Variable amino acid

<400> SEQUENCE: 469

Gln Gln Tyr Asp Xaa Trp Pro Leu Thr
1               5

<210> SEQ ID NO 470
<211> LENGTH: 10
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid

<400> SEQUENCE: 470

Gln Xaa Tyr Xaa Xaa Trp Xaa Xaa Xaa Thr
1               5                   10

<210> SEQ ID NO 471
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X1 is selected from the group consisting of V
      and I

<400> SEQUENCE: 471

Arg Ala Ser Gln Ser Xaa Ser Ser Asn Leu Ala
1               5                   10

<210> SEQ ID NO 472
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X1 is selected from the group consisting of G
      and D
<220> FEATURE:
<221> NAME/KEY: MISC_FEATURE
<222> LOCATION: (7)..(7)
<223> OTHER INFORMATION: X2 is selected from the group consisting of A
      and T

<400> SEQUENCE: 472

Xaa Ala Ser Thr Arg Ala Xaa
1               5
```

IL-17 RECEPTOR A ANTIGEN BINDING PROTEINS

CROSS REFERENCE TO RELATED APPLICATIONS

This application is a continuation of copending U.S. application Ser. No. 16/299,716, filed Dec. 21, 2018, which is a continuation of U.S. application Ser. No. 15/058,738, filed Mar. 2, 2016, now U.S. Pat. No. 10,208,122, which is a continuation of U.S. patent application Ser. No. 14/304,472, filed on Jun. 13, 2014, which is a continuation of U.S. patent application Ser. No. 13/472,074, filed on May 15, 2012, now U.S. Pat. No. 8,790,648, which is a divisional of U.S. application Ser. No. 12/443,962, filed Apr. 1, 2009, which is a national application under 35 U.S. C. § 371 of International Application No. PCT/US2007/021174, having an international filing date of Oct. 1, 2007, which claims the benefit under 35 U.S.C. § 119 of U.S. Provisional Application Ser. No. 60/969,895, filed Sep. 4, 2007, U.S. Provisional Application Ser. No. 60/873,072, filed Dec. 5, 2006 and U.S. Provisional Application Ser. No. 60/827,882, filed Oct. 2, 2006, which are hereby incorporated by reference.

REFERENCE TO THE SEQUENCE LISTING

Incorporated by reference in its entirety herein is a computer-readable nucleotide/amino acid sequence listing submitted concurrently herewith and identified as follows: One 220,011 Byte ASCII (Text) file named "36249-316_ST25.txt" created on Aug. 5, 2020.

FIELD OF THE INVENTION

The present invention relates to IL-17 Receptor A (IL-17RA or IL-17R) antigen binding proteins, such as antibodies, polynucleotide sequences encoding said antigen binding proteins, and compositions and methods for diagnosing and treating diseases mediated by IL-17 Receptor A activation by one or more IL-17 ligands. The present invention relates to the identification of neutralizing determinants on IL-17 Receptor A (IL-17RA or IL-17R) and antibodies that bind thereto. Aspects of the invention also include antibodies that compete for binding with the IL-17RA neutralizing antibodies described herein.

BACKGROUND

IL-17A is an inflammatory cytokine initially identified as a transcript selectively expressed by activated T cells. IL-17RA is a ubiquitously expressed and shown to bind IL-17A with an affinity of approximately 0.5 nM (Yao et al., 1995, *Immunity* 3:811-821). Five additional IL-17-like ligands (IL-17B-IL-17F) and four additional IL-17RA-like receptors (IL-17RB-IL-17RE) have been identified (Kolls and Linden, 2004, *Immunity* 21:467-476).

IL-17RC has been shown to bind IL-17A and IL-17F. The observations that IL-17RA deficiency and IL-17RA antibody neutralization ablate both IL-17A and IL-17F function suggest that IL-17RC cannot deliver an IL-7A or IL-17F signal in the absence of IL-17RA (Toy et al., 2006, *J. Immunol.* 177:36-39; McAllister et al. 2005, *J. Immunol.* 175:404-412). Additionally, forced expression of IL-17RC in IL-17RA deficient cells does not restore IL-17A or IL-17F function (Toy et al., 2006, *J. Immunol* 177:36-39).

IL-17A and IL-17F are predominantly expressed by activated CD4$^+$ memory T cells (Kolls and Linden, 2004, supra). It has been proposed that an IL-17A-producing pathogenic CD4+ T cell subset, ThIL-17, is expanded in the presence of IL-23 (Langrish et al., 2005, *J. Exp. Med.* 201:233-240). Additionally, both IL-15 and the TNF superfamily member OX40L have been shown to induce the expression of IL-17A (Nakae et al., 2003b, *Proc. Natl. Acad. Sci. U.S.A.* 100:5986-5990; Ziolkowska et al., 2000, *J. Immunol.* 164:2832-2838). IL-6 and TGF-beta also induce the expression of IL-17A.

IL-17A and IL-17F bind and activate IL-17RA. IL-17RA has been shown to be important in regulating immune responses. Activation of the IL-17RA leads to production of cytokines, chemokines, growth factors, and other proteins that contribute to the symptoms and/or pathology of numerous diseases. IL-17A is an inflammatory cytokine that induces the production of cytokines and other mediators leading to diseases and physiological effects such as inflammation, cartilage degradation, and bone resorption. IL-17A also plays a role in a number of inflammatory conditions including arthritis (rheumatoid arthritis), psoriasis, inflammatory bowel disease, multiple sclerosis, and asthma. (Li et al., 2004, *Huazhong Univ. Sci. Technolog. Med. Sci.* 24:294-296; Fujino et al., 2003, *Gut.* 52:65-70; Kauffman et al., 2004, *J. Invest. Dermatol.* 123:1037-1044; Mannon et al., 2004, *N. Engl. J Med.* 351:2069-2079; Matusevicius et al., 1999, *Mult Scler* 5, 101-104; Linden et al., *Eur Respir J.* 2000 May; 15(5):973-7; Molet et al., 2001, *J. Allergy Clin. Immunol.* 108:430-438). Recent studies have suggested that IL-17F plays a role in the induction of inflammatory responses (Oda et al., 2006, *American J. Resp. Crit. Care Medicine*, Jan. 15, 2006; Numasaki et al., 2004. *Immunol Lett.* 95:97-104).

Aspects of the invention provide antigen binding proteins that specifically bind IL-17RA and inhibit IL-17RA activation mediated by IL-17 family members, such as, but not limited to, IL-17A and/or IL-17F, as described more fully herein.

BRIEF DESCRIPTION OF THE DRAWINGS

FIG. 2 depicts an alignment of the amino acid sequences of the CDRs of the variable heavy ($V_H$) domains of various IL-17R antigen binding proteins (antibodies). The CDR1, CDR2, and CDR3 regions are highlighted.

FIG. 3 depicts an alignment of the amino acid sequences of the CDRs of the variable light ($V_L$) domains of various IL-17R antigen binding proteins (antibodies). The CDR1, CDR2, and CDR3 regions are highlighted.

FIG. 8D shows no changes in BAL fluid macrophage observed in either WT or IL-17RA knockout mice (naïve and OVA challenged).

FIGS. 16A and 16B show the results of multiplexed binning of IL-17RA antibodies. Shaded values indicate antibody pairs that can bind to IL-17RA simultaneously, suggesting that these antibodies bind to different neutralizing determinants. Boxed values indicate antibodies paired against themselves.

FIG. 17 shows mouse IL-17RA (SEQ ID NO:432) and the 5 domains, A, B, C, D, E, and F that replaced the counterpart domains in the human IL-17RA sequence.

FIGS. 18A-18D shows the amino acid sequences for human and mouse IL-17RA and human/mouse chimeric IL-17RA proteins.

FIG. 19 is a table summarizing the IL-17RA mAbs capacity to bind the various chimeric proteins. Shaded values denote where the IL-17RA mAbs lost binding to that particular chimera (n.d. means not determined).

FIG. 20 depicts the amino acid residues that were replaced with an arginine residue in SEQ ID NO:431.

FIG. 22 is a summary of the arginine scan, binning, and chimera data for various IL-17RA mAbs.

DETAILED DESCRIPTION OF THE INVENTION

Figure 1:
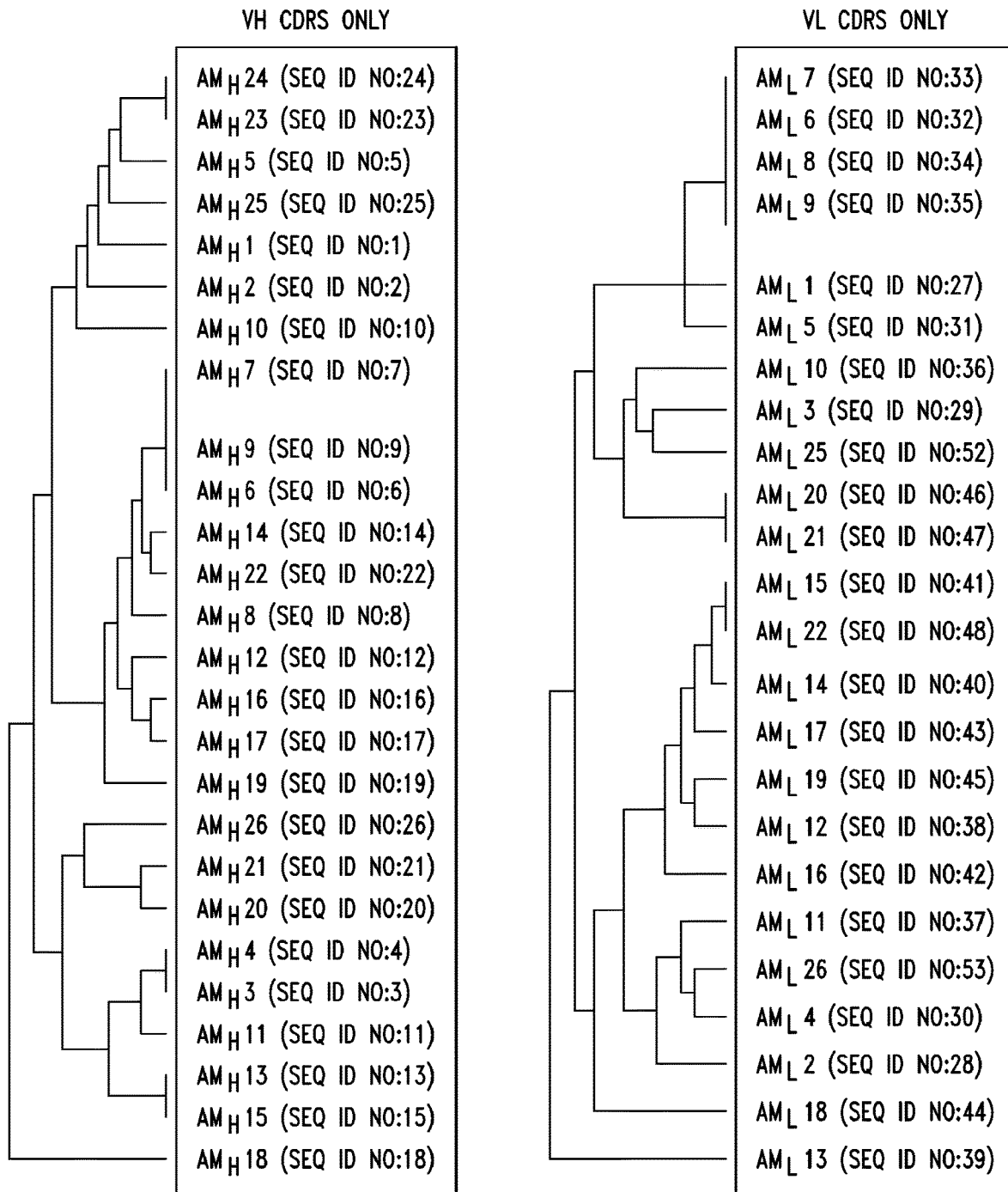
FIG. 1 shows a phylogenetic dentogram analysis of the CDRs (complementarity determining regions) of the variable heavy ($V_H$) and variable light ($V_L$) domains of various IL-17R antigen binding proteins (antibodies).

The section headings used herein are for organizational purposes only and are not to be construed as limiting the subject matter described.

Standard techniques may be used for recombinant DNA, oligonucleotide synthesis, tissue culture and transformation, protein purification etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manual*, 3$^{rd}$ ed., Cold Spring Harbor Laboratory Press, Cold Spring Harbor, N.Y., which is incorporated herein by reference for any purpose. Unless specific definitions are provided, the nomenclature used in connection with, and the laboratory procedures and techniques of, analytical chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

IL-17A, IL-17F, and IL-17RA

The biologic activities of IL-17A and IL-17F are dependent upon IL-17RA, as shown herein using both cells and mice that are genetically deficient in IL-17RA and with neutralizing mAbs (monoclonal antibodies) directed against IL-17RA (see Examples below).

"IL-17 receptor A" or "IL-17RA" (interchangeably used herein, as well as IL-17 receptor and IL-17R to refer to the same receptor) as used herein is meant the cell surface receptor and receptor complexes (such as but not limited to IL-17RA-IL-17RC complex), that bind IL-17A and IL-17F and as a result initiates a signal transduction pathway within the cell. IL-17RA proteins may also include variants. IL-17RA proteins may also include fragments, such as the extracellular domain that don't have all or part of the transmembrane and/or the intracellular domain, as well as fragments of the extracellular domain. The cloning, characterization, and preparation of IL-17RA are described, for example, in U.S. Pat. No. 6,072,033, which is incorporated herein by reference in its entirety. The amino acid sequence of the human IL-17RA is shown in SEQ ID NO:430. Soluble forms of huIL-17RA useful in the methods of the present invention include the extracellular domain or the mature form lacking the signal peptide or a fragment of the extracellular domain that retains the capacity to bind IL-17A and/or IL-17F, or a heteromeric version of IL-17A and/or IL-17F. Other forms of IL-17RA include muteins and variants that are at least between 70% and 99% homologous to the native IL-17RA of SEQ ID NO:430 and as described in U.S. Pat. No. 6,072,033, so long as the IL-17RA retains the capacity to bind IL-17A and/or IL-17F, or a heteromeric version of IL-17A and/or IL-17F. The term "IL-17RA" also includes post-translational modifications of the IL-17RA amino acid sequence. Post-translational modifications include, but is not limited to, N- and O-linked glycosylation.

IL-17RA Antigen Binding Proteins

The present invention provides antigen binding proteins that specifically bind IL-17RA. Embodiments of antigen binding proteins comprise peptides and/or polypeptides (that optionally include post-translational modifications) that specifically bind IL-17RA. Embodiments of antigen binding proteins comprise antibodies and fragments thereof, as variously defined herein, that specifically bind IL-17RA. Aspects of the invention include antibodies that specifically bind to human IL-17RA and inhibit IL-17A and/or IL-17F from binding and activating IL-17RA, or a heteromeric complex of IL-17RA and IL-17RC. Aspects of the invention include antibodies that specifically bind to human IL-17RA and inhibit an IL-17A/IL-17F heteromer from binding and activating IL-17RA, or a heteromeric complex of IL-17RA and IL-17RC. Throughout the specification, when reference is made to inhibiting IL-17A and/or IL-17F, it is understood that this also includes inhibiting heteromers of IL-17A and IL-17F. Aspects of the invention include antibodies that specifically bind to human IL-17RA and partially or fully inhibit IL-17RA from forming either a homomeric or heteromeric functional receptor complex, such as, but not limited to, an IL-17RA-IL-17RC complex. Aspects of the invention include antibodies that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex.

The antigen binding proteins of the invention specifically bind to IL-17RA. "Specifically binds" as used herein means that the antigen binding protein preferentially binds IL-17RA over other proteins. In some embodiments "specifically binds" means that the IL-17RA antigen binding proteins have a higher affinity for IL-17RA than for other proteins. For example, the equilibrium dissociation constant is $<10^{-7}$ to $10^{-11}$ M. or $<10^{-8}$ to $<10^{-10}$ M, or $<10^{-9}$ to $<10^{-10}$ M.

It is understood that when reference is made to the various embodiments of the IL-17RA antibodies described herein, that it also encompasses IL-17RA-binding fragments thereof. An IL-17RA-binding fragment comprises any of the antibody fragments or domains described herein that retains the ability to specifically bind to IL-17RA. Said IL-17RA-binding fragments may be in any of the scaffolds described herein. Said IL-17RA-binding fragments also have the capacity to inhibit activation of the IL-17RA, as described throughout the specification.

In embodiments where the IL-17RA antigen binding protein is used for therapeutic applications, one characteristic of an IL-17RA antigen binding protein is that it can inhibit binding of IL-17A and/or IL-17F to IL-17RA and one or more biological activities of, or mediated by, IL-17RA. Such antibodies are considered neutralizing antibodies because of their capacity to inhibit IL-17A and/or IL-17F from binding and causing IL-17RA signaling and/or biological activity. In this case, an antigen binding protein specifically binds IL-17RA and inhibits binding of IL-17A and/or IL-17F to IL-17RA from anywhere between 10 to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more (for example by measuring binding in an in vitro competitive binding assay as described herein). For example, IL-17RA antibodies may be tested for neutralizing ability by testing them for the production of IL-6 in human foreskin fibroblast (HFF) assay (see for example Examples 8 and 9), or any suitable assay known in the art. Examples, for illustrative purposes only, of additional biological activity of IL-17RA (e.g., assay readouts) to test for inhibition of IL-17RA signaling and/or biological activity include in vitro and/or in vivo measurement of one or more of IL-8, CXCL1, CXCL2, GM-CSF, G-CSF, M-CSF, IL-1β, TNFα, RANK-L, LIF, PGE2, IL-12, MMPs (such as but not limited to MMP3 and MMP9), GROα, NO, and/or C-telopeptide and the like.

Embodiments of antigen binding proteins comprise a scaffold structure, as variously define herein, with one or more complementarity determining regions (CDRs). Embodiments of antigen binding proteins comprise a scaffold structure with one or more variable domains, either heavy or light. Embodiments include antibodies that comprise a light chain variable region selected from the group consisting of $AM_L1$ through $AM_L26$ (SEQ ID NO:27-53, respectively, with $AM_L23$ having two versions—SEQ ID NOs:49 and 50) and/or a heavy chain variable region selected from the group consisting of $AM_H1$ through $AM_H26$ (SEQ ID NO:1-26, respectively), and fragments, derivatives, muteins, and variants thereof.

Additional examples of scaffolds that are envisioned include: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain, Src homology domain 3, PDZ domains, TEM-1 Beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ld1 receptor domains, gamma-crystallin, ubiquitin, transferring, and/or C-type lectin-like domains.

Aspects of the invention include antibodies comprising the following variable domains: $AM_L1/AM_H1$ (SEQ ID NO:27/SEQ ID NO:1), $AM_L2/AM_H2$ (SEQ ID NO:28/SEQ ID NO:2), $AM_L3/AM_H3$ (SEQ ID NO:29/SEQ ID NO:3), $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO: 10), $AM_L11/AM_H11$ (SEQ ID NO:37/SEQ ID NO:11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO:14), $AM_L15/AM_H15$ (SEQ ID NO:41/SEQ ID NO:15), $AM_L6/AM_H16$ (SEQ ID NO:42/SEQ ID NO:16), $AM_L17/AM_H17$ (SEQ ID NO:43/SEQ ID NO:17). $AM_L18/AM_H18$ (SEQ ID NO:44/SEQ ID NO:18), $AM_L19/AM_H19$ (SEQ ID NO:45/SEQ ID NO: 19), $AM_L20/AM_H20$ (SEQ ID NO:46/SEQ ID NO:20), $AM_L21/AM_H21$ (SEQ ID NO:47/SEQ ID NO:21), $AM_L22/AM_H22$ (SEQ ID NO:48/SEQ ID NO:22), $AM_L23/AM_H23$ (SEQ ID NO:49 or SEQ ID NO:50/SEQ ID NO:23), $AM_L24/AM_H24$ (SEQ ID NO:51/SEQ ID NO:24), $AM_L25/AM_H25$ (SEQ ID NO:52/SEQ ID NO:25), $AM_L26/AM_H26$ (SEQ ID NO:53/SEQ ID NO:26), and combinations thereof, as well as and fragments, derivatives, muteins, and variants thereof.

In a further embodiment, a first amino acid sequence comprises CDR3, CDR2, and CDR1, and a second amino acid sequence comprises a CDR3, CDR2, and CDR1 of TABLE 1.

In another embodiment, the antigen binding protein comprises: A) a heavy chain amino acid sequence that comprises at least one H-CDR1, H-CDR2, or H-CDR3 of a sequence selected from the group consisting of SEQ ID NO: 1-26; and/or B) a light chain amino acid sequence that comprises at least one L-CDR1, L-CDR2, or L-CDR3 of a sequence selected from the group consisting of SEQ ID NO:27-53.

In a further variation, the antigen binding protein comprises A) a heavy chain amino acid sequence that comprises a H-CDR1, a H-CDR2, and a H-CDR3 of any of SEQ ID NO:1-26, and B) a light chain amino acid sequence that comprises a L-CDR1, a L-CDR2, and a L-CDR3 of any of SEQ ID NO:27-53. In another variation, the antigen binding protein comprises an amino acid sequence that is of at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain amino acid sequence selected from the group consisting of SEQ ID NO: 1-26 or a light chain amino acid sequence selected from the group consisting of SEQ ID NO:27-53.

In certain embodiments, the CDRs include no more than one, two, three, four, five, or six amino acid additions, deletions, or substitutions from a H-CDR1 (i.e., CDR1 of the heavy chain, etc.). H-CDR2, H-CDR3, L-CDR1 (i.e., CDR1 of the light chain, etc.). L-CDR2, and L-CDR3, and fragments, derivatives, muteins, and variants thereof.

Aspects of the invention include antibodies comprising a heavy chain variable region selected from the group consisting of SEQ ID NO:1-26. Aspects of the invention include antibodies comprising a light chain variable region selected from the group consisting of SEQ ID NO:27-53. Aspects of the invention include antibodies comprising a heavy chain variable region selected from the group consisting of SEQ ID NO:1-26 having no more than one, two, three, four, five, or six amino acid additions, deletions, or substitutions. Aspects of the invention include antibodies comprising a light chain variable region selected from the group consisting of SEQ ID NO:27-53 having no more than one, two, three, four, five, or six amino acid additions, deletions, or substitutions. Aspects of the invention include antibodies comprising a heavy chain variable region selected from the group consisting of SEQ ID NO:1-26 having no more than one, two, three, four, five, or six amino acid additions, deletions, or substitutions and a light chain variable region selected from the group consisting of SEQ ID NO:27-53 having no more than one, two, three, four, five, or six amino acid additions, deletions, or substitutions.

In other embodiments, the heavy and light chain variable domains of the antigen binding proteins are defined by having a certain percent identity to a reference heavy and/or light chain variable domain. For example, the antigen binding protein comprises A) a heavy chain variable domain amino acid that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain amino acid sequence selected from the group consisting of SEQ ID NO:1-26; and B) a light chain variable domain amino acid that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain amino acid sequence selected from the group consisting of SEQ ID NOs:27-53.

Aspects of the invention include a variety of embodiments including, but not limited to, the following exemplary embodiments: Embodiment 1: an isolated antibody, comprising a monoclonal antibody or IL-17 receptor A binding fragment thereof that is not fully murine and that specifically binds IL-17 receptor A and inhibits IL-17A from binding and activating said receptor. Embodiment 2: the antibody of embodiment 1, wherein said antibody further inhibits IL-17F from binding and activating said receptor. Embodiment 3: the antibody of embodiment 1, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody.

Embodiment 4: the antibody of embodiment 3, wherein said antibody comprises an amino acid sequence selected from the group consisting of:

A. a. a light chain variable domain sequence that is at least 80% identical to a light chain variable domain sequence of $AM_L$1-26 (SEQ ID NOs:27-53, respectively);
  b. a heavy chain variable domain sequence that is at least 80% identical to a heavy chain variable domain sequence of $AM_H$1-26 (SEQ ID NOs:1-26, respectively); or
  c. the light chain variable domain of (a) and the heavy chain variable domain of (b); and B. a light chain CDR1, CDR2, CDR3 and a heavy chain CDR1, CDR2, CDR3 that differs by no more than a total of three amino acid additions, substitutions, and/or deletions in each CDR from the following sequences:
  a. a light chain CDR1 (SEQ ID NO:185), CDR2 (SEQ ID NO: 186), CDR3 (SEQ ID NO:187) and a heavy chain CDR1 (SEQ ID NO:107), CDR2 (SEQ ID NO:108), CDR3 (SEQ ID NO:109) of antibody AM-1;
  b. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO: 112) of antibody AM-2;
  c. a light chain CDR1 (SEQ ID NO:191), CDR2 (SEQ ID NO:192), CDR3 (SEQ ID NO:193) and a heavy chain CDR1 (SEQ ID NO:113), CDR2 (SEQ ID NO:114), CDR3 (SEQ ID NO: 115) of antibody AM-3;
  d. a light chain CDR1 (SEQ ID NO:194), CDR2 (SEQ ID NO:195), CDR3 (SEQ ID NO: 196) and a heavy chain CDR1 (SEQ ID NO:116), CDR2 (SEQ ID NO:117), CDR3 (SEQ ID NO: 118) of antibody AM-4;
  e. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
  f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;
  g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;

h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;

i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;

j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;

k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO:139) of antibody AM-11;

l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;

m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;

n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO: 148) of antibody AM-14;

o. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;

p. a light chain CDR1 (SEQ ID NO:230), CDR2 (SEQ ID NO:231), CDR3 (SEQ ID NO:232) and a heavy chain CDR1 (SEQ ID NO: 152), CDR2 (SEQ ID NO:153), CDR3 (SEQ ID NO:154) of antibody AM-16;

q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;

r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;

s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;

t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;

u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;

v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;

w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;

x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;

y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO:178) of antibody AM-24;

z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO: 183), CDR3 (SEQ ID NO:184) of antibody AM-26; wherein said antibody specifically binds IL-17 receptor A.

Embodiment 5: the antibody of embodiment 4, wherein said antibody comprises an amino acid sequence selected from the group consisting of:

a. a light chain variable domain and a heavy chain variable domain of $AM_L1/AM_H1$ (SEQ ID NO:27/SEQ ID NO:1);

b. a light chain variable domain and a heavy chain variable domain of $AM_L2/AM_H2$ (SEQ ID NO:28/SEQ ID NO:2);

c. a light chain variable domain and a heavy chain variable domain of $AM_L3/AM_H3$ (SEQ ID NO:29/SEQ ID NO:3);

d. a light chain variable domain and a heavy chain variable domain of $AM_L4/AM_H4$ (SEQ ID NO:30/SEQ ID NO:4);

e. a light chain variable domain and a heavy chain variable domain of $AM_L5/AM_H5$ (SEQ ID NO:31/SEQ ID NO:5);

f. a light chain variable domain and a heavy chain variable domain of $AM_L6/AM_H6$ (SEQ ID NO:32/SEQ ID NO:6)

g. a light chain variable domain and a heavy chain variable domain of $AM_L7/AM_H7$ (SEQ ID NO:33/SEQ ID NO:7);

h. a light chain variable domain and a heavy chain variable domain of $AM_L8/AM_H8$ (SEQ ID NO:34/SEQ ID NO:8);

i. a light chain variable domain and a heavy chain variable domain of $AM_L9/AM_H9$ (SEQ ID NO:35/SEQ ID NO:9);

j. a light chain variable domain and a heavy chain variable domain of $AM_L10/AM_H10$ (SEQ ID NO:36/SEQ ID NO:10);

k. a light chain variable domain and a heavy chain variable domain of AM$_L$11/AM$_H$11 (SEQ ID NO:37/SEQ ID NO: 11);
l. a light chain variable domain and a heavy chain variable domain of AM$_L$12/AM$_H$12 (SEQ ID NO:38/SEQ ID NO:12);
m. a light chain variable domain and a heavy chain variable domain of AM$_L$13/AM$_H$13 (SEQ ID NO:39/SEQ ID NO:13);
n. a light chain variable domain and a heavy chain variable domain of AM$_L$14% AM$_H$14 (SEQ ID NO:40/SEQ ID NO:14);
o. a light chain variable domain and a heavy chain variable domain of AM$_L$5/AM$_H$15 (SEQ ID NO:41/SEQ ID NO:15);
p. a light chain variable domain and a heavy chain variable domain of AM$_L$16/AM$_H$6 (SEQ ID NO:42/SEQ ID NO:16);
q. a light chain variable domain and a heavy chain variable domain of AM$_L$17/AM$_H$17 (SEQ ID NO:43/SEQ ID NO:17);
r. a light chain variable domain and a heavy chain variable domain of AM$_L$18/AM$_H$18 (SEQ ID NO:44/SEQ ID NO:18);
s. a light chain variable domain and a heavy chain variable domain of AM$_L$19/AM$_H$19 (SEQ ID NO:45/SEQ ID NO:19);
t. a light chain variable domain and a heavy chain variable domain of AM$_L$20/AM$_H$20 (SEQ ID NO:46/SEQ ID NO:20);
u. a light chain variable domain and a heavy chain variable domain of AM$_L$21/AM$_H$21 (SEQ ID NO:47/SEQ ID NO:21);
v. a light chain variable domain and a heavy chain variable domain of AM$_L$22/AM$_H$22 (SEQ ID NO:48/SEQ ID NO:22);
w. a light chain variable domain and a heavy chain variable domain of AM$_L$23/AM$_H$23 (SEQ ID NO: 49 or SEQ ID NO:50/SEQ ID NO:23);
x. a light chain variable domain and a heavy chain variable domain of AM$_L$24/AM$_H$24 (SEQ ID NO:51/SEQ ID NO:24);
y. a light chain variable domain and a heavy chain variable domain of AM$_L$25/AM$_H$25 (SEQ ID NO:52/SEQ ID NO:25); and
z. a light chain variable domain and a heavy chain variable domain of AM$_L$26/AM$_H$26 (SEQ ID NO:53/SEQ ID NO:26); wherein said antibody specifically binds IL-17 receptor A.

Embodiment 6: the antibody of embodiment 4, wherein said antibody comprises an amino acid sequence selected from the group consisting of:
a. a light chain CDR1 (SEQ ID NO:185), CDR2 (SEQ ID NO:186), CDR3 (SEQ ID NO:187) and a heavy chain CDR1 (SEQ ID NO:107), CDR2 (SEQ ID NO:108), CDR3 (SEQ ID NO:109) of antibody AM-1;
b. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO: 112) of antibody AM-2;
c. a light chain CDR1 (SEQ ID NO:191), CDR2 (SEQ ID NO:192), CDR3 (SEQ ID NO:193) and a heavy chain CDR1 (SEQ ID NO: 113), CDR2 (SEQ ID NO: 114), CDR3 (SEQ ID NO: 115) of antibody AM-3;
d. a light chain CDR1 (SEQ ID NO:194), CDR2 (SEQ ID NO:195), CDR3 (SEQ ID NO:196) and a heavy chain CDR1 (SEQ ID NO:116), CDR2 (SEQ ID NO:117), CDR3 (SEQ ID NO: 118) of antibody AM-4;
e. a light chain CDR1 (SEQ ID NO:197), CDR2 (SEQ ID NO: 198), CDR3 (SEQ ID NO:199) and a heavy chain CDR1 (SEQ ID NO:119), CDR2 (SEQ ID NO:120), CDR3 (SEQ ID NO:121) of antibody AM-5;
f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;
g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO: 127) of antibody AM-7;
h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;
i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO:139) of antibody AM-11;
l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;
n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
o. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;
p. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO: 154) of antibody AM-16;
q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
r. a light chain CDR1 (SEQ ID NO:236), CDR2 (SEQ ID NO:237), CDR3 (SEQ ID NO:238) and a heavy chain CDR1 (SEQ ID NO: 158), CDR2 (SEQ ID NO:159), CDR3 (SEQ ID NO:160) of antibody AM-18;
s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;

u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;

v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;

w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;

x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;

y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO:178) of antibody AM-24;

z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO:183), CDR3 (SEQ ID NO:184) of antibody AM-26; wherein said antibody specifically binds IL-17 receptor A.

Embodiment 7: the antibody of embodiment 2, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody.

Embodiment 8: the antibody of embodiment 7, wherein said antibody comprises an amino acid sequence selected from the group consisting of:

A. a. a light chain variable domain sequence that is at least 80% identical to a light chain variable domain sequence of $AM_L$14, 18, 19, and 22 (SEQ ID NOs: 40, 44, 45, and 48, respectively);
  b. a heavy chain variable domain sequence that is at least 80% identical to a heavy chain variable domain sequence of $AM_H$14, 18, 19, and 22 (SEQ ID NOs: 14, 18, 19, and 22, respectively); or
  c. the light chain variable domain of (a) and the heavy chain variable domain of (b);

B. a light chain CDR1, CDR2, CDR3 and a heavy chain CDR1, CDR2, CDR3 that differs by no more than a total of three amino acid additions, substitutions, and/or deletions in each CDR from the following sequences:
  a. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
  b. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
  c. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19; or
  d. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22; and C. a. a light chain variable domain and a heavy chain variable domain of $AM_L$14/$AM_H$14 (SEQ ID NO:40/SEQ ID NO: 14);
  b. a light chain variable domain and a heavy chain variable domain of $AM_L$8/$AM_H$18 (SEQ ID NO:44/SEQ ID NO:18);
  c. a light chain variable domain and a heavy chain variable domain of $AM_L$19/$AM_H$19 (SEQ ID NO:45/SEQ ID NO:19); or
  d. a light chain variable domain and a heavy chain variable domain of $AM_L$22/$AM_H$22 (SEQ ID NO:48/SEQ ID NO:22); wherein said antibody specifically binds IL-17 receptor A.

Embodiment 9: an isolated antibody, or an IL-17 receptor A binding fragment thereof, comprising
  a. a heavy chain CDR1 comprising an amino acid sequence selected from the group consisting of:
    i. $X_1$YGIS (SEQ ID NO:453), wherein $X_1$ is selected from the group consisting of R, S and G;
  b. a heavy chain CDR2 comprising an amino acid sequence selected from the group consisting of:
    i. WISX$_1$YX$_2$GNTX$_3$YAQX$_4$X$_5$QG (SEQ ID NO:456), wherein $X_1$ is selected from the group consisting of A, $X_2$ is selected from the group consisting of N, S and K, $X_3$ is selected from the group consisting of N and K, $X_4$ is selected from the group consisting of K and N, and $X_5$ is selected from the group consisting of L and F;
  c. a heavy chain CDR3 comprising an amino acid sequence selected from the group consisting of:
    i. $X_1$QLX$_2$X$_3$DY (SEQ ID NO:459), wherein $X_1$ is selected from the group consisting of R and K, $X_2$ is selected from the group consisting of Y, V, and A, and $X_3$ is selected from the group consisting of F and L;
    ii. $X_1$QLX$_2$FDY (SEQ ID NO:460), wherein $X_1$ is selected from the group consisting of R and K, and $X_2$ is selected from the group consisting of Y and V;
  d. a light chain CDR1 comprising an amino acid sequence selected from the group consisting of:
    i. RASQSX$_1$X$_2$X$_3$X$_4$LA (SEQ ID NO:462), wherein $X_1$ is selected from the group consisting of V and I, $X_2$ is selected from the group consisting of I and S, $X_3$ is selected from the group consisting of S and T, $X_4$ is selected from the group consisting of N and S, and $X_5$ is selected from the group consisting of A and N, and
    ii. RASQSX$_1$SSNLA (SEQ ID NO:471), wherein $X_1$ is selected from the group consisting of V and I;
  e. a light chain CDR2 comprising an amino acid sequence selected from the group consisting of:
    i. $X_1$X$_2$STRAX$_3$ (SEQ ID NO:466), wherein $X_1$ is selected from the group consisting of G and D, $X_2$ is selected from the group consisting of A and T, and $X_3$ is selected from the group consisting of T and A, and
    ii. $X_1$ASTRAX$_2$ (SEQ ID NO:472), wherein $X_1$ is selected from the group consisting of G and D, and $X_2$ is selected from the group consisting of A and T; and f. a light chain CDR3 comprising an amino acid sequence selected from the group consisting of:
  i. QQYDX$_1$WPLT (SEQ ID NO:469) wherein X$_1$ is selected from the group consisting of N, T, and I; wherein said antibody specifically binds IL-17 receptor A.

Embodiment 10: the antibody of embodiment 9, wherein said antibody comprises:
  a. a heavy chain CDR1 amino acid sequence comprising X$_1$YGIS, wherein X$_1$ is selected from the group consisting of R, S and G;
  b. a heavy chain CDR2 amino acid sequence comprising WISX$_1$YX$_2$GNTX$_3$YAQX$_4$X$_5$QG (SEQ ID NO:456) wherein X$_1$ is selected from the group consisting of A, X$_2$ is selected from the group consisting of N, S and K, X$_3$ is selected from the group consisting of N and K, X$_4$ is selected from the group consisting of K and N, and X$_5$ is selected from the group consisting of L and F;
  c. a heavy chain CDR3 amino acid sequence comprising X$_1$QLX$_2$FDY (SEQ ID NO:460), wherein X$_1$ is selected from the group consisting of R and K, and X$_2$ is selected from the group consisting of Y and V;
  d. a light chain CDR1 amino acid sequence comprising RASQSX$_1$SSNLA (SEQ ID NO:471), wherein X$_1$ is selected from the group consisting of V and I;
  e. a light chain CDR2 amino acid sequence comprising X$_1$ASTRAX$_2$ (SEQ ID NO:472), wherein X$_1$ is selected from the group consisting of G and D, and X$_2$ is selected from the group consisting of A and T; and
  f. a light chain CDR3 amino acid sequence comprising QQYDX$_1$WPLT (SEQ ID NO:469), wherein X$_1$ is selected from the group consisting of N, T, and I; wherein said antibody specifically binds IL-17 receptor A.

Embodiment 11: the antibody of embodiment 9, wherein said antibody comprises an amino acid sequence selected from the group consisting of:
  A. a. a light chain variable domain sequence that is at least 80% identical to a light chain variable domain sequence of AM$_L$12, 14, 16, 17, 19, and 22 (SEQ ID NOs:38, 40, 42, 43, 45, and 48 respectively);
     b. a heavy chain variable domain sequence that is at least 80% identical to a heavy chain variable domain sequence of AM$_H$12, 14, 16, 17, 19, and 22 (SEQ ID NOs:12, 14, 16, 17, 19, and 22, respectively); or
     c. the light chain variable domain of (a) and the heavy chain variable domain of (b);
  B. a light chain CDR1, CDR2, CDR3 and a heavy chain CDR1, CDR2, CDR3 that differs by no more than a total of three amino acid additions, substitutions, and/or deletions in each CDR from the following sequences:
     a. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
     b. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
     c. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
     d. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
     e. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19; or
     f. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22; and
  C. a. a light chain variable domain and a heavy chain variable domain of AM$_L$12/AM$_H$12 (SEQ ID NO:38/SEQ ID NO:12);
     b. a light chain variable domain and a heavy chain variable domain of AM$_L$14/AM$_H$14 (SEQ ID NO:40/SEQ ID NO:14);
     c. a light chain variable domain and a heavy chain variable domain of AM$_L$16/AM$_H$16 (SEQ ID NO:42/SEQ ID NO:16);
     d. a light chain variable domain and a heavy chain variable domain of AM$_L$17 AM$_H$17 (SEQ ID NO:43/SEQ ID NO:17);
     e. a light chain variable domain and a heavy chain variable domain of AM$_L$19/AM$_H$19 (SEQ ID NO:45/SEQ ID NO:19);
     c. a light chain variable domain and a heavy chain variable domain of AM$_L$22/AM$_H$22 (SEQ ID NO:48/SEQ ID NO:22); wherein said antibody specifically binds IL-17 receptor A.

Embodiment 12: a pharmaceutical composition, comprising the antibody of embodiment 4. Embodiment 14: the antibody of embodiment 4, wherein said antibody is a derivative of said antibody.

Embodiment 15: a polypeptide, comprising an amino acid sequence selected from the group consisting of:
  A. a. a light chain variable domain sequence that is at least 80% identical to a light chain variable domain sequence of AM$_L$1-26 (SEQ ID NOs:27-53, respectively);
     b. a heavy chain variable domain sequence that is at least 80% identical to a heavy chain variable domain sequence of AM$_H$1-26 (SEQ ID NOs:1-26, respectively); or
     c. the light chain variable domain of (a) and the heavy chain variable domain of (b); and
  B. a light chain CDR1, CDR2, CDR3 and a heavy chain CDR1, CDR2, CDR3 that differs by no more than a total of three amino acid additions, substitutions, and/or deletions in each CDR from the following sequences:
     a. a light chain CDR1 (SEQ ID NO:185), CDR2 (SEQ ID NO:186), CDR3 (SEQ ID NO:187) and a heavy chain CDR1 (SEQ ID NO:107), CDR2 (SEQ ID NO:108), CDR3 (SEQ ID NO:109) of antibody AM-1;
     b. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO: 112) of antibody AM-2;
     c. a light chain CDR1 (SEQ ID NO:191), CDR2 (SEQ ID NO:192), CDR3 (SEQ ID NO:193) and a heavy chain CDR1 (SEQ ID NO: 113), CDR2 (SEQ ID NO: 114), CDR3 (SEQ ID NO: 115) of antibody AM-3;
d. a light chain CDR1 (SEQ ID NO:194), CDR2 (SEQ ID NO:195), CDR3 (SEQ ID NO:196) and a heavy chain CDR1 (SEQ ID NO: 116), CDR2 (SEQ ID NO: 117), CDR3 (SEQ ID NO:118) of antibody AM-4;
e. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;
g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;
h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;
i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
k. a light chain CDR1 (SEQ ID NO:215), CDR2 (SEQ ID NO:216), CDR3 (SEQ ID NO:217) and a heavy chain CDR1 (SEQ ID NO: 137), CDR2 (SEQ ID NO:138), CDR3 (SEQ ID NO:139) of antibody AM-11;
l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;
n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
o. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;
p. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO: 169) of antibody AM-21;
v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
w. a light chain CDR1 (SEQ ID NO:251), CDR2 (SEQ ID NO:252), CDR3 (SEQ ID NO:253) and a heavy chain CDR1 (SEQ ID NO: 173), CDR2 (SEQ ID NO:174), CDR3 (SEQ ID NO:175) of antibody AM-23;
x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO:178) of antibody AM-24;
z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or
z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO:183), CDR3 (SEQ ID NO:184) of antibody AM-26; wherein said polypeptide specifically binds IL-17 receptor A.

Embodiment 16: the polypeptide of embodiment 15, wherein said polypeptide comprises an amino acid is selected from the group consisting of:
a. a light chain variable domain and a heavy chain variable domain of $AM_L1/AM_H1$ (SEQ ID NO:27/SEQ ID NO:1);

b. a light chain variable domain and a heavy chain variable domain of AM$_L$2/AM$_H$2 (SEQ ID NO:28/SEQ ID NO:2);
c. a light chain variable domain and a heavy chain variable domain of AM$_L$3/AM$_H$3 (SEQ ID NO:29/SEQ ID NO:3);
d. a light chain variable domain and a heavy chain variable domain of AM$_L$4/AM$_H$4 (SEQ ID NO:30/SEQ ID NO:4);
e. a light chain variable domain and a heavy chain variable domain of AM$_L$5/AM$_H$5 (SEQ ID NO:31/SEQ ID NO:5);
f. a light chain variable domain and a heavy chain variable domain of AM$_L$6/AM$_H$6 (SEQ ID NO:32/SEQ ID NO:6)
g. a light chain variable domain and a heavy chain variable domain of AM$_L$7/AM$_H$7 (SEQ ID NO:33/SEQ ID NO:7);
h. a light chain variable domain and a heavy chain variable domain of AM$_L$8/AM$_H$8 (SEQ ID NO:34/SEQ ID NO:8);
i. a light chain variable domain and a heavy chain variable domain of AM$_L$9/AM$_H$9 (SEQ ID NO:35/SEQ ID NO:9);
j. a light chain variable domain and a heavy chain variable domain of AM$_L$10/AM$_H$10 (SEQ ID NO:36/SEQ ID NO:10);
k. a light chain variable domain and a heavy chain variable domain of AM$_L$11/AM$_H$11 (SEQ ID NO:37/SEQ ID NO: 11);
l. a light chain variable domain and a heavy chain variable domain of AM$_L$12/AM$_H$12 (SEQ ID NO:38/SEQ ID NO:12);
m. a light chain variable domain and a heavy chain variable domain of AM$_L$13/AM$_H$3 (SEQ ID NO:39/SEQ ID NO:13);
n. a light chain variable domain and a heavy chain variable domain of AM$_L$14/AM$_H$14 (SEQ ID NO:40/SEQ ID NO:14);
o. a light chain variable domain and a heavy chain variable domain of AM$_L$15/AM$_H$15 (SEQ ID NO:41/SEQ ID NO:15);
p. a light chain variable domain and a heavy chain variable domain of AM$_L$16/AM$_H$16 (SEQ ID NO:42/SEQ ID NO:16);
q. a light chain variable domain and a heavy chain variable domain of AM$_L$17/AM$_H$17 (SEQ ID NO:43/SEQ ID NO:17);
r. a light chain variable domain and a heavy chain variable domain of AM$_L$18/AM$_H$18 (SEQ ID NO:44/SEQ ID NO: 18).
s. a light chain variable domain and a heavy chain variable domain of AM$_L$19/AM$_H$19 (SEQ ID NO:45/SEQ ID NO:19);
t. a light chain variable domain and a heavy chain variable domain of AM$_L$20/AM$_H$20 (SEQ ID NO:46/SEQ ID NO:20);
u. a light chain variable domain and a heavy chain variable domain of AM$_L$21/AM$_H$21 (SEQ ID NO:47/SEQ ID NO:21);
v. a light chain variable domain and a heavy chain variable domain of AM$_L$22/AM$_H$22 (SEQ ID NO:48/SEQ ID NO:22);
w. a light chain variable domain and a heavy chain variable domain of AM$_L$23/AM$_H$23 (SEQ ID NO: 49 or SEQ ID NO:50/SEQ ID NO:23);
x. a light chain variable domain and a heavy chain variable domain of AM$_L$24/AM$_H$24 (SEQ ID NO:51/SEQ ID NO:24);
y. a light chain variable domain and a heavy chain variable domain of AM$_L$25/AM$_H$25 (SEQ ID NO:52/SEQ ID NO:25); and
z. a light chain variable domain and a heavy chain variable domain of AM$_L$26/AM$_H$26 (SEQ ID NO:53/SEQ ID NO:26); wherein said polypeptide specifically binds IL-17 receptor A.

Embodiment 17: the polypeptide of embodiment 15, wherein said polypeptide comprises an amino acid sequence selected from the group consisting of:
a. a light chain CDR1 (SEQ ID NO:185), CDR2 (SEQ ID NO:186), CDR3 (SEQ ID NO: 187) and a heavy chain CDR1 (SEQ ID NO: 107), CDR2 (SEQ ID NO:108), CDR3 (SEQ ID NO:109) of antibody AM-1;
b. a light chain CDR1 (SEQ ID NO:188), CDR2 (SEQ ID NO:189), CDR3 (SEQ ID NO:190) and a heavy chain CDR1 (SEQ ID NO: 110), CDR2 (SEQ ID NO:111), CDR3 (SEQ ID NO:112) of antibody AM-2;
c. a light chain CDR1 (SEQ ID NO:191), CDR2 (SEQ ID NO:192), CDR3 (SEQ ID NO:193) and a heavy chain CDR1 (SEQ ID NO: 113), CDR2 (SEQ ID NO: 114), CDR3 (SEQ ID NO: 115) of antibody AM-3;
d. a light chain CDR1 (SEQ ID NO:194), CDR2 (SEQ ID NO:195), CDR3 (SEQ ID NO:196) and a heavy chain CDR1 (SEQ ID NO: 116), CDR2 (SEQ ID NO: 117), CDR3 (SEQ ID NO:118) of antibody AM-4;
e. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;
g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;
h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;
i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO: 139) of antibody AM-11;
l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
m. a light chain CDR1 (SEQ ID NO:221), CDR2 (SEQ ID NO:222), CDR3 (SEQ ID NO:223) and a heavy chain CDR1 (SEQ ID NO: 143), CDR2 (SEQ ID NO:144), CDR3 (SEQ ID NO:145) of antibody AM-13;
n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;

o. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;

p. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;

q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;

r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;

s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;

t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;

u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;

v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;

w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;

x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;

y. a light chain CDR1 (SEQ ID NO:257), CDR2 (SEQ ID NO:258), CDR3 (SEQ ID NO:259) and a heavy chain CDR1 (SEQ ID NO: 176), CDR2 (SEQ ID NO:177), CDR3 (SEQ ID NO:178) of antibody AM-24;

z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO:183), CDR3 (SEQ ID NO:184) of antibody AM-26; wherein said polypeptide specifically binds IL-17 receptor A.

Embodiment 18: the polypeptide of embodiment 15, wherein said polypeptide is a pharmaceutical composition.

Embodiment 19: an isolated antibody, selected from the group consisting of:
a) an antibody consisting of a heavy chain sequence of SEQ ID NO:427 and a light chain sequence of SEQ ID NO:429;
b) an antibody consisting essentially of a heavy chain sequence of SEQ ID NO:427 and a light chain sequence of SEQ ID NO:429;
c) an antibody comprising a heavy chain sequence of SEQ ID NO: 427;
d) an antibody comprising a light chain sequence of SEQ ID NO:429;
e) an antibody comprising a heavy chain sequence of SEQ ID NO: 427 and a light chain sequence of SEQ ID NO:429;
f) an antibody or an IL-17 receptor A binding fragment thereof comprising a heavy chain sequence of SEQ ID NO: 427;
g) an antibody or an IL-17 receptor A binding fragment thereof comprising a light chain sequence of SEQ ID NO:429;
h) an antibody or an IL-17 receptor A binding fragment thereof comprising a heavy chain sequence of SEQ ID NO:427 and a light chain sequence of SEQ ID NO:429;
i) an antibody or an IL-17 receptor A binding fragment thereof comprising a heavy chain variable region sequence of SEQ ID NO:14;
j) an antibody or an IL-17 receptor A binding fragment thereof comprising a light chain variable region sequence of SEQ ID NO:40;
k) an antibody or an IL-17 receptor A binding fragment thereof comprising a light chain variable region sequence of SEQ ID NO:40 and a heavy chain variable region sequence of SEQ ID NO:14;
l) an antibody or an IL-17 receptor A binding fragment thereof comprising a heavy chain CDR1 of SEQ ID NO: 146, a heavy chain CDR2 of SEQ ID NO:147, a heavy chain CDR3 of SEQ ID NO:148, a light chain CDR1 of SEQ ID NO:224, a light chain CDR2 of SEQ ID NO:225, and a light chain CDR3 of SEQ ID NO:226; and
m) an antibody or an IL-17 receptor A binding fragment thereof comprising a heavy chain CDR3 of SEQ ID NO: 148 and a light chain CDR3 of SEQ ID NO:226.

Embodiment 20: the antibody of embodiment 19, wherein said antibody is a pharmaceutical composition. Embodiment 21: the antibody of embodiment 19, wherein said antibody is a derivative of said antibody.

Embodiment 22: the antibody of embodiment 7, wherein said antibody comprises an amino acid sequence selected from the group consisting of:
A. a. a light chain variable domain sequence that is at least 80% identical to a light chain variable domain sequence SEQ ID NO: 40;
   b. a heavy chain variable domain sequence that is at least 80% identical to a heavy chain variable domain sequence of SEQ ID NO:14; or
   c. the light chain variable domain of (a) and the heavy chain variable domain of (b);
B. a light chain CDR1, CDR2, CDR3 and a heavy chain CDR1, CDR2, CDR3 that differs by no more than a total of three amino acid additions, substitutions, and/or deletions in each CDR from the following sequences: CDR1 (SEQ ID NO:224), CDR2 (SEQ ID NO:225), CDR3 (SEQ ID NO:226) and a heavy chain CDR1 (SEQ ID NO: 146), CDR2 (SEQ ID NO:147), CDR3 (SEQ ID NO:148); and
C. a light chain variable domain of SEQ ID NO:40 and a heavy chain variable domain SEQ ID NO:14; wherein said antibody specifically binds IL-17 receptor A.

Embodiment 23: the polypeptide of embodiment 16, wherein said polypeptide comprises a light chain variable domain of SEQ ID NO:40 and a heavy chain variable domain SEQ ID NO:14, wherein said polypeptide specifically binds IL-17 receptor A. Embodiment 24: the polypeptide of embodiment 16, wherein said polypeptide comprises SEQ ID NO:427 and SEQ ID NO:429, wherein said polypeptide specifically binds IL-17 receptor A. Embodiment 25: the polypeptide of embodiment 24, wherein said polypeptide is a pharmaceutical composition.

As a general structure, the antigen binding proteins of the invention comprise (a) a scaffold, and (b) one or a plurality of CDRs. A "complementary determining region" or "CDR," as used herein, refers to a binding protein region that constitutes the major surface contact points for antigen binding. Embodiments of the invention include one or more CDRs embedded in a scaffold structure of the antigen binding protein. The scaffold structure of the antigen binding proteins may be the framework of an antibody, or fragment or variant thereof, or may be completely synthetic in nature. Examples of various scaffold structures of the antigen binding proteins of the invention are further described hereinbelow.

The antigen binding proteins of the invention include scaffold regions and one or more CDRs. An antigen binding protein of the invention may have between one and six CDRs (as typically do naturally occurring antibodies), for example, one heavy chain CDR1 ("H-CDR1"), and/or one heavy chain CDR2 ("H-CDR2"), and/or one heavy chain CDR3 ("H-CDR3"), and/or one light chain CDR1 ("L-CDR1"), and/or one light chain CDR2 ("L-CDR2"), and/or one light chain CDR3 ("L-CDR3").

The term "naturally occurring" as used throughout the specification in connection with biological materials such as peptides, polypeptides, nucleic acids, host cells, and the like, refers to materials which are found in nature. In naturally occurring antibodies, a H-CDR1 typically comprises about five (5) to about seven (7) amino acids, H-CDR2 typically comprises about sixteen (16) to about nineteen (19) amino acids, and H-CDR3 typically comprises about three (3) to about twenty five (25) amino acids. L-CDR1 typically comprises about ten (10) to about seventeen (17) amino acids, L-CDR2 typically comprises about seven (7) amino acids, and L-CDR3 typically comprises about seven (7) to about ten (10) amino acids. Specific CDRs of the various antibodies of the invention are provided in TABLE 1 and the Sequence Listing.

TABLE 1

| | | | Corresponding Poly-nucleotide Sequence |
|---|---|---|---|
| Amino acid sequence of CDR 1 of $AM_H1$ Vh | SEQ ID NO: 107 | NYYWN | SEQ ID NO: 266 |
| Amino acid sequence of CDR 2 of $AM_H1$ Vh | SEQ ID NO: 108 | DIYYSGSTNYNP SLKS | SEQ ID NO: 267 |
| Amino acid sequence of CDR 3 of $AM_H1$ Vh | SEQ ID NO: 109 | DGELANYYGSG SYQFYYYYCIM DV | SEQ ID NO: 268 |
| Amino acid sequence of CDR 1 of $AM_H2$ Vh | SEQ ID NO: 110 | GYYWS | SEQ ID NO: 269 |

TABLE 1-continued

| | | | Corresponding Poly-nucleotide Sequence |
|---|---|---|---|
| Amino acid sequence of CDR 2 of $AM_H2$ Vh | SEQ ID NO: 111 | EINHSGRTNYNP SLKS | SEQ ID NO: 270 |
| Amino acid sequence of CDR 3 of $AM_H2$ Vh | SEQ ID NO: 112 | GPYYFDSSGYL YYYYGLDV | SEQ ID NO: 271 |
| Amino acid sequence of CDR of $AM_H3$ Vh | SEQ ID NO: 113 | SYGMH | SEQ ID NO: 272 |
| Amino acid sequence of CDR 2 of $AM_H3$ Vh | SEQ ID NO: 114 | VIWYDGSNKHY ADSVKG | SEQ ID NO: 273 |
| Amino acid sequence of CDR 3 of $AM_H3$ Vh | SEQ ID NO: 115 | DTGVY | SEQ ID NO: 274 |
| Amino acid sequence of CDR 1 of $AM_H4$ Vh | SEQ ID NO: 116 | SWATH | SEQ ID NO: 275 |
| Amino acid sequence of CDR 2 of $AM_H4$ Vh | SEQ ID NO: 117 | VIWYDGSNKHY ADSVKG | SEQ ID NO: 276 |
| Amino acid sequence of CDR 3 of $AM_H4$ Vh | SEQ ID NO: 118 | DTGVY | SEQ ID NO: 277 |
| Amino acid sequence of CDR 1 of $AM_H5$ Vh | SEQ ID NO: 119 | SYYWS | SEQ ID NO: 278 |
| Amino acid sequence of CDR 2 of $AM_H5$ Vh | SEQ ID NO: 120 | RIYRSGNTIYNP SLKS | SEQ ID NO: 279 |
| Amino acid sequence of CDR 3 of $AM_H5$ Vh | SEQ ID NO: 121 | ENYSESSGLNY YYGMDV | SEQ ID NO: 280 |
| Amino acid sequence of CDR 1 of $AM_H6$ Vh | SEQ ID NO: 122 | RYGIS | SEQ ID NO: 281 |
| Amino acid sequence of CDR 2 of $AM_H6$ Vh | SEQ ID NO: 123 | WISAYNGNTNY AQKLQG | SEQ ID NO: 282 |
| Amino acid sequence of CDR 3 of $AM_H6$ Vh | SEQ ID NO: 124 | RDYDILTGYYN GFDP | SEQ ID NO: 283 |
| Amino acid sequence of CDR 1 of $AM_H7$ Vh | SEQ ID NO: 125 | RYGIS | SEQ ID NO: 284 |

TABLE 1-continued

| | | | Corresponding Poly-nucleotide Sequence |
|---|---|---|---|
| Amino acid sequence of CDR 2 of AM$_H$7 Vh | SEQ ID NO: 126 | WISAYNGNTNYAQKLQG | SEQ ID NO: 285 |
| Amino acid sequence of CDR 3 of AM$_H$7 Vh | SEQ ID NO: 127 | RDYDILTGYYNGFDP | SEQ ID NO: 286 |
| Amino acid sequence of CDR 1 of AM$_H$8 Vh | SEQ ID NO: 128 | GYGIS | SEQ ID NO: 287 |
| Amino acid sequence of CDR 2 of AM$_H$8 Vh | SEQ ID NO: 129 | WISAYNGNTNYAQNLQG | SEQ ID NO: 288 |
| Amino acid sequence of CDR 3 of AM$_H$8 Vh | SEQ ID NO: 130 | RDYDILTGYYNGFDP | SEQ ID NO: 289 |
| Amino acid sequence of CDR 1 of AM$_H$9 Vh | SEQ ID NO: 131 | RYGIS | SEQ ID NO: 290 |
| Amino acid sequence of CDR 2 of AM$_H$9 Vh | SEQ ID NO: 132 | WISAYNGNTNYAQKLQG | SEQ ID NO: 291 |
| Amino acid sequence of CDR 3 of AM$_H$9 Vh | SEQ ID NO: 133 | RDYDILTGYYNGFDP | SEQ ID NO: 292 |
| Amino acid sequence of CDR 1 of AM$_H$10 Vh | SEQ ID NO: 134 | SGGYYWS | SEQ ID NO: 293 |
| Amino acid sequence of CDR 2 of AM$_H$10 Vh | SEQ ID NO: 135 | YIYFSGSAYYNPSLKS | SEQ ID NO: 294 |
| Amino acid sequence of CDR 3 of AM$_H$10 Vh | SEQ ID NO: 136 | EYYDSSGYPDAFDI | SEQ ID NO: 295 |
| Amino acid sequence of CDR 1 of AM$_H$11 Vh | SEQ ID NO: 137 | SYGMH | SEQ ID NO: 296 |
| Amino acid sequence of CDR 2 of AM$_H$11 Vh | SEQ ID NO: 138 | VIWYDGSNKYYADSVKG | SEQ ID NO: 297 |
| Amino acid sequence of CDR 3 of AM$_H$11 Vh | SEQ ID NO: 139 | DTKDY | SEQ ID NO: 298 |
| Amino acid sequence of CDR 1 of AM$_H$12 Vh | SEQ ID NO: 140 | SYGIS | SEQ ID NO: 299 |
| Amino acid sequence of CDR 2 of AM$_H$12 Vh | SEQ ID NO: 141 | WISTYKGNTNYAQKLQG | SEQ ID NO: 300 |
| Amino acid sequence of CDR 3 of AM$_H$12 Vh | SEQ ID NO: 142 | KQLVFDY | SEQ ID NO: 301 |
| Amino acid sequence of CDR 1 of AM$_H$13 Vh | SEQ ID NO: 143 | SYGMQ | SEQ ID NO: 302 |
| Amino acid sequence of CDR 2 of AM$_H$13 Vh | SEQ ID NO: 144 | VIWYDGNKKYYADSVKG | SEQ ID NO: 303 |
| Amino acid sequence of CDR 3 of AM$_H$13 Vh | SEQ ID NO: 145 | GRVRDYYYGMDV | SEQ ID NO: 304 |
| Amino acid sequence of CDR 1 of AM$_H$14 Vh | SEQ ID NO: 146 | RYGIS | SEQ ID NO: 305 |
| Amino acid sequence of CDR 2 of AM$_H$14 Vh | SEQ ID NO: 147 | WISTYSGNTNYAQKLQG | SEQ ID NO: 306 |
| Amino acid sequence of CDR 3 of AM$_H$14 Vh | SEQ ID NO: 148 | RQLYFDY | SEQ ID NO: 307 |
| Amino acid sequence of CDR 1 of AM$_H$15 Vh | SEQ ID NO: 149 | SYGMQ | SEQ ID NO: 308 |
| Amino acid sequence of CDR 2 of AM$_H$15 Vh | SEQ ID NO: 150 | VIWYDGNKKYYADSVKG | SEQ ID NO: 309 |
| Amino acid sequence of CDR 3 of AM$_H$15 Vh | SEQ ID NO: 151 | GRVRDYYYGMDV | SEQ ID NO: 310 |
| Amino acid sequence of CDR 1 of AM$_H$16 Vh | SEQ ID NO: 152 | SYGIS | SEQ ID NO: 311 |
| Amino acid sequence of CDR 2 of AM$_H$16 Vh | SEQ ID NO: 153 | WISAYNGNTKYAQKLQG | SEQ ID NO: 312 |
| Amino acid sequence of CDR 3 of AM$_H$16 Vh | SEQ ID NO: 154 | KQLVFDY | SEQ ID NO: 313 |
| Amino acid sequence of CDR 1 of AM$_H$17 Vh | SEQ ID NO: 155 | SYGIS | SEQ ID NO: 314 |

TABLE 1-continued

| | | | Corresponding Poly-nucleotide Sequence |
|---|---|---|---|
| Amino acid sequence of CDR 2 of AM$_H$17 Vh | SEQ ID NO: 156 | WISAYSGNTKY AQKLQG | SEQ ID NO: 315 |
| Amino acid sequence of CDR 3 of AM$_H$17 Vh | SEQ ID NO: 157 | KQLVFDY | SEQ ID NO: 316 |
| Amino acid sequence of CDR 1 of AM$_H$18 Vh | SEQ ID NO: 158 | DYYMH | SEQ ID NO: 317 |
| Amino acid sequence of CDR 2 of AM$_H$18 Vh | SEQ ID NO: 159 | WMHPNSGGTD LAQRFQG | SEQ ID NO: 318 |
| Amino acid sequence of CDR 3 of AM$_H$18 Vh | SEQ ID NO: 160 | GGYCSTLSCSFY WYFDL | SEQ ID NO: 319 |
| Amino acid sequence of CDR 1 of AM$_H$19 Vh | SEQ ID NO: 161 | SYGIS | SEQ ID NO: 320 |
| Amino acid sequence of CDR 2 of AM$_H$19 Vh | SEQ ID NO: 162 | WISAYSGNTKY AQKFQG | SEQ ID NO: 321 |
| Amino acid sequence of CDR 3 of AM$_H$19 Vh | SEQ ID NO: 163 | RQLALDY | SEQ ID NO: 322 |
| Amino acid sequence of CDR 1 of AM$_H$20 Vh | SEQ ID NO: 164 | SYSMN | SEQ ID NO: 323 |
| Amino acid sequence of CDR 2 of AM$_H$20 Vh | SEQ ID NO: 165 | FISARSSTIYYA DSVKG | SEQ ID NO: 324 |
| Amino acid sequence of CDR 3 of AM$_H$20 Vh | SEQ ID NO: 166 | PKVGGGMDV | SEQ ID NO: 325 |
| Amino acid sequence of CDR 1 of AM$_H$21 Vh | SEQ ID NO: 167 | SYSMN | SEQ ID NO: 326 |
| Amino acid sequence of CDR 2 of AM$_H$21 Vh | SEQ ID NO: 168 | IISSRSSIIHYADS VKG | SEQ ID NO: 327 |
| Amino acid sequence of CDR 3 of AM$_H$21 Vh | SEQ ID NO: 169 | PKVGGGMDV | SEQ ID NO: 328 |
| Amino acid sequence of CDR 1 of AM$_H$22 Vh | SEQ ID NO: 170 | RYGIS | SEQ ID NO: 329 |
| Amino acid sequence of CDR 2 of AM$_H$22 Vh | SEQ ID NO: 171 | WISAYSGNTNY AQKLQG | SEQ ID NO: 330 |
| Amino acid sequence of CDR 3 of AM$_H$22 Vh | SEQ ID NO: 172 | RQLYFDY | SEQ ID NO: 331 |
| Amino acid sequence of CDR 1 of AM$_H$23 Vh | SEQ ID NO: 173 | SYYWS | SEQ ID NO: 332 |
| Amino acid sequence of CDR 2 of AM$_H$23 Vh | SEQ ID NO: 174 | RIYPSGRTNYNP SLKS | SEQ ID NO: 333 |
| Amino acid sequence of CDR 3 of AM$_H$23 Vh | SEQ ID NO: 175 | EAYELQLGLYY YYGMDV | SEQ ID NO: 334 |
| Amino acid sequence of CDR 1 of AM$_H$24 Vh | SEQ ID NO: 176 | SYYWS | SEQ ID NO: 335 |
| Amino acid sequence of CDR 2 of AM$_H$24 Vh | SEQ ID NO: 177 | RIYPSGRTNYNP SLKS | SEQ ID NO: 336 |
| Amino acid sequence of CDR 3 of AM$_H$24 Vh | SEQ ID NO: 178 | EAYELQLGLYY YYGMDV | SEQ ID NO: 337 |
| Amino acid sequence of CDR 1 of AM$_H$25 Vh | SEQ ID NO: 179 | SGGYYWS | SEQ ID NO: 338 |
| Amino acid sequence of CDR 2 of AM$_H$25 Vh | SEQ ID NO: 180 | YSGNTYYNPSL RS | SEQ ID NO: 339 |
| Amino acid sequence of CDR 3 of AM$_H$25 Vh | SEQ ID NO: 181 | EAGGNSAYYYG MDV | SEQ ID NO: 340 |
| Amino acid sequence of CDR 1 of AM$_H$26 Vh | SEQ ID NO: 182 | DYYMS | SEQ ID NO: 341 |
| Amino acid sequence of CDR 2 of AM$_H$26 Vh | SEQ ID NO: 183 | YISSSGSTIYYA DSVKG | SEQ ID NO: 342 |
| Amino acid sequence of CDR 3 of AM$_H$26 Vh | SEQ ID NO: 184 | DRTYYFGSGSY EGMDV | SEQ ID NO: 343 |
| Amino acid sequence of CDR 1 of AM$_L$1 Vl | SEQ ID NO: 185 | RASQGIRNDLG | SEQ ID NO: 345 |

TABLE 1-continued

| | | | Corresponding Poly-nucleotide Sequence |
|---|---|---|---|
| Amino acid sequence of CDR 2 of AM$_L$1 Vl | SEQ ID NO: 186 | AASSLQS | SEQ ID NO: 346 |
| Amino acid sequence of CDR 3 of AM$_L$1 Vl | SEQ ID NO: 187 | LQHNSNPFT | SEQ ID NO: 347 |
| Amino acid sequence of CDR 1 of AM$_L$2 Vl | SEQ ID NO: 188 | RASQSVSRNLV | SEQ ID NO: 348 |
| Amino acid sequence of CDR 2 of AM$_L$2 Vl | SEQ ID NO: 189 | GASTRAN | SEQ ID NO: 349 |
| Amino acid sequence of CDR 3 of AM$_L$2 Vl | SEQ ID NO: 190 | QQYKSWRT | SEQ ID NO: 350 |
| Amino acid sequence of CDR 1 of AM$_L$3 Vl | SEQ ID NO: 191 | RASQSISSYLN | SEQ ID NO: 351 |
| Amino acid sequence of CDR 2 of AM$_L$3 Vl | SEQ ID NO: 192 | AASSLQS | SEQ ID NO: 352 |
| Amino acid sequence of CDR 3 of AM$_L$3 Vl | SEQ ID NO: 193 | QQSYSTPFT | SEQ ID NO: 353 |
| Amino acid sequence of CDR 1 of AM$_L$4 Vl | SEQ ID NO: 194 | RASQSVSRNLA | SEQ ID NO: 354 |
| Amino acid sequence of CDR 2 of AM$_L$4 Vl | SEQ ID NO: 195 | GASTRAT | SEQ ID NO: 355 |
| Amino acid sequence of CDR 3 of AM$_L$4 Vl | SEQ ID NO: 196 | QQYNNWPTWT | SEQ ID NO: 356 |
| Amino acid sequence of CDR 1 of AM$_L$5 Vl | SEQ ID NO: 197 | RASQGIRNDLG | SEQ ID NO: 357 |
| Amino acid sequence of CDR 2 of AM$_L$5 Vl | SEQ ID NO: 198 | AASSFQS | SEQ ID NO: 358 |
| Amino acid sequence of CDR 3 of AM$_L$5 Vl | SEQ ID NO: 199 | LQHNSYPPT | SEQ ID NO: 359 |
| Amino acid sequence of CDR 1 of AM$_L$6 Vl | SEQ ID NO: 200 | RASQGIRNDLG | SEQ ID NO: 360 |
| Amino acid sequence of CDR 2 of AM$_L$6 Vl | SEQ ID NO: 201 | AASSLQS | SEQ ID NO: 361 |
| Amino acid sequence of CDR 3 of AM$_L$6 Vl | SEQ ID NO: 202 | LQHKSYPLT | SEQ ID NO: 362 |
| Amino acid sequence of CDR 1 of AM$_L$7 Vl | SEQ ID NO: 203 | RASQGIRNDLG | SEQ ID NO: 363 |
| Amino acid sequence of CDR 2 of AM$_L$7 Vl | SEQ ID NO: 204 | AASSLQS | SEQ ID NO: 364 |
| Amino acid sequence of CDR 3 of AM$_L$7 Vl | SEQ ID NO: 205 | LQHKSYPLT | SEQ ID NO: 365 |
| Amino acid sequence of CDR 1 of AM$_L$8 Vl | SEQ ID NO: 206 | RASQGIRNDLG | SEQ ID NO: 366 |
| Amino acid sequence of CDR 2 of AM$_L$8 Vl | SEQ ID NO: 207 | AASSLQS | SEQ ID NO: 367 |
| Amino acid sequence of CDR 3 of AM$_L$8 Vl | SEQ ID NO: 208 | LQHKSYPLT | SEQ ID NO: 368 |
| Amino acid sequence of CDR 1 of AM$_L$9 Vl | SEQ ID NO: 209 | RASQGIRNDLG | SEQ ID NO: 369 |
| Amino acid sequence of CDR 2 of AM$_L$9 Vl | SEQ ID NO: 210 | AASSLQS | SEQ ID NO: 370 |
| Amino acid sequence of CDR 3 of AM$_L$9 Vl | SEQ ID NO: 211 | LQHKSYPLT | SEQ ID NO: 371 |
| Amino acid sequence of CDR 1 of AM$_L$10 Vl | SEQ ID NO: 212 | RASQGIRSWLA | SEQ ID NO: 372 |
| Amino acid sequence of CDR 2 of AM$_L$10 Vl | SEQ ID NO: 213 | AASSLQS | SEQ ID NO: 373 |
| Amino acid sequence of CDR 3 of AM$_L$10 Vl | SEQ ID NO: 214 | QQANNFPRT | SEQ ID NO: 374 |
| Amino acid sequence of CDR 4 of AM$_L$11 Vl | SEQ ID NO: 215 | RASQSVSSNLA | SEQ ID NO: 375 |

TABLE 1-continued

| | | | Corresponding Poly-nucleotide Sequence |
|---|---|---|---|
| Amino acid sequence of CDR 2 of AM$_L$11 Vl | SEQ ID NO: 216 | GASTRAA | SEQ ID NO: 376 |
| Amino acid sequence of CDR 3 of AM$_L$11 Vl | SEQ ID NO: 217 | QHYINWPKWT | SEQ ID NO: 377 |
| Amino acid sequence of CDR 1 of AM$_L$12 Vl | SEQ ID NO: 218 | RASQSISSSLA | SEQ ID NO: 378 |
| Amino acid sequence of CDR 2 of AM$_L$12 Vl | SEQ ID NO: 219 | GASTRAT | SEQ ID NO: 379 |
| Amino acid sequence of CDR 3 of AM$_L$12 Vl | SEQ ID NO: 220 | QQYDNWPLT | SEQ ID NO: 380 |
| Amino acid sequence of CDR 1 of AM$_L$13 Vl | SEQ ID NO: 221 | KSSQSLLHSDGKTYLY | SEQ ID NO: 381 |
| Amino acid sequence of CDR 2 of AM$_L$13 Vl | SEQ ID NO: 222 | EVSTRFS | SEQ ID NO: 382 |
| Amino acid sequence of CDR 3 of AM$_L$13 Vl | SEQ ID NO: 223 | MQSIQLPLT | SEQ ID NO: 383 |
| Amino acid sequence of CDR 1 of AM$_L$14 Vl | SEQ ID NO: 224 | RASQSVSSNLA | SEQ ID NO: 384 |
| Amino acid sequence of CDR 2 of AM$_L$14 Vl | SEQ ID NO: 225 | DASTRAT | SEQ ID NO: 385 |
| Amino acid sequence of CDR 3 of AM$_L$14 Vl | SEQ ID NO: 226 | QQYDNWPLT | SEQ ID NO: 386 |
| Amino acid sequence of CDR 1 of AM$_L$15 Vl | SEQ ID NO: 227 | RASQSVSSNLA | SEQ ID NO: 387 |
| Amino acid sequence of CDR 2 of AM$_L$15 Vl | SEQ ID NO: 228 | DASTRAA | SEQ ID NO: 388 |
| Amino acid sequence of CDR 3 of AM$_L$15 Vl | SEQ ID NO: 229 | QQYDNWPLT | SEQ ID NO: 389 |
| Amino acid sequence of CDR 1 of AM$_L$16 Vl | SEQ ID NO: 230 | RASQSISTSLA | SEQ ID NO: 390 |
| Amino acid sequence of CDR 2 of AM$_L$16 Vl | SEQ ID NO: 231 | GTSTRAT | SEQ ID NO: 391 |
| Amino acid sequence of CDR 3 of AM$_L$16 Vl | SEQ ID NO: 232 | QQYDIWPLT | SEQ ID NO: 392 |
| Amino acid sequence of CDR 1 of AM$_L$17 Vl | SEQ ID NO: 233 | RASQSVSSNLA | SEQ ID NO: 393 |
| Amino acid sequence of CDR 2 of AM$_L$17 Vl | SEQ ID NO: 234 | GASTRAT | SEQ ID NO: 394 |
| Amino acid sequence of CDR 3 of AM$_L$17 Vl | SEQ ID NO: 235 | QQYDNWPLT | SEQ ID NO: 395 |
| Amino acid sequence of CDR 1 of AM$_L$18 Vl | SEQ ID NO: 236 | KTSQSVLYSSKNKNFLA | SEQ ID NO: 396 |
| Amino acid sequence of CDR 2 of AM$_L$18 Vl | SEQ ID NO: 237 | WASTRES | SEQ ID NO: 397 |
| Amino acid sequence of CDR 3 of AM$_L$18 Vl | SEQ ID NO: 238 | QQYYSTPFT | SEQ ID NO: 398 |
| Amino acid sequence of CDR 1 of AM$_L$19 Vl | SEQ ID NO: 239 | RASQSISSNLA | SEQ ID NO: 399 |
| Amino acid sequence of CDR 2 of AM$_L$19 Vl | SEQ ID NO: 240 | GASTRAT | SEQ ID NO: 400 |
| Amino acid sequence of CDR 3 of AM$_L$19 Vl | SEQ ID NO: 241 | QQYDTWPLT | SEQ ID NO: 401 |
| Amino acid sequence of CDR 1 of AM$_L$20 Vl | SEQ ID NO: 242 | RASQGISNYLA | SEQ ID NO: 402 |
| Amino acid sequence of CDR 2 of AM$_L$20 Vl | SEQ ID NO: 243 | AASTLQS | SEQ ID NO: 403 |
| Amino acid sequence of CDR 3 of AM$_L$20 Vl | SEQ ID NO: 244 | QKYNRAPFT | SEQ ID NO: 404 |
| Amino acid sequence of CDR 1 of AM$_L$21 Vl | SEQ ID NO: 245 | RASQGISNYLA | SEQ ID NO: 405 |

TABLE 1-continued

| | | | Corresponding Poly-nucleotide Sequence |
|---|---|---|---|
| Amino acid sequence of CDR 2 of AM<sub>L</sub>21 Vl | SEQ ID NO: 246 | AASTLQS | SEQ ID NO: 406 |
| Amino acid sequence of CDR 3 of AM<sub>L</sub>21 Vl | SEQ ID NO: 247 | QKYNRAPFT | SEQ ID NO: 407 |
| Amino acid sequence of CDR 1 of AM<sub>L</sub>22 Vl | SEQ ID NO: 248 | RASQSVSSNLA | SEQ ID NO: 408 |
| Amino acid sequence of CDR 2 of AM<sub>L</sub>22 Vl | SEQ ID NO: 249 | DASTRAA | SEQ ID NO: 409 |
| Amino acid sequence of CDR 3 of AM<sub>L</sub>22 Vl | SEQ ID NO: 250 | QQYDNWPLT | SEQ ID NO: 410 |
| Amino acid sequence of CDR 1 of AM<sub>L</sub>23 Vl version 1 | SEQ ID NO: 251 | RASQGIINDLG | SEQ ID NO: 411 |
| Amino acid sequence of CDR 2 of AM<sub>L</sub>23 Vl version 1 | SEQ ID NO: 252 | AASSLQS | SEQ ID NO: 412 |
| Amino acid sequence of CDR 3 of AM<sub>L</sub>23 Vl version 1 | SEQ ID NO: 253 | LQHNSYPPT | SEQ ID NO: 413 |
| Amino acid sequence of CDR 1 of AM<sub>L</sub>23 Vl version 2 | SEQ ID NO: 254 | RSSQSLVYSDGHTCLN | SEQ ID NO: 414 |
| Amino acid sequence of CDR 2 of AM<sub>L</sub>23 Vl version 2 | SEQ ID NO: 255 | KVSNWDS | SEQ ID NO: 415 |
| Amino acid sequence of CDR 3 of AM<sub>L</sub>23 Vl version 2 | SEQ ID NO: 256 | MQGTHWYLCS | SEQ ID NO: 416 |
| Amino acid sequence of CDR 1 of AM<sub>L</sub>24 Vl | SEQ ID NO: 257 | RSSQSLVYSDGHTCLN | SEQ ID NO: 417 |
| Amino acid sequence of CDR 2 of AM<sub>L</sub>24 Vl | SEQ ID NO: 258 | KVSNWDS | SEQ ID NO: 418 |
| Amino acid sequence of CDR 3 of AM<sub>L</sub>24 Vl | SEQ ID NO: 259 | MQGTHWPLCS | SEQ ID NO: 419 |
| Amino acid sequence of CDR 1 of AM<sub>L</sub>25 Vl | SEQ ID NO: 260 | RASQAISIYLA | SEQ ID NO: 420 |
| Amino acid sequence of CDR 2 of AM<sub>L</sub>25 Vl | SEQ ID NO: 261 | AASSLQS | SEQ ID NO: 421 |
| Amino acid sequence of CDR 3 of AM<sub>L</sub>25 Vl | SEQ ID NO: 262 | QQYSSYPRT | SEQ ID NO: 422 |
| Amino acid sequence of CDR 1 of AM<sub>L</sub>26 Vl | SEQ ID NO: 263 | RASQSVYSNLA | SEQ ID NO: 423 |
| Amino acid sequence of CDR 2 of AM<sub>L</sub>26 Vl | SEQ ID NO: 264 | GASTRAT | SEQ ID NO: 424 |
| Amino acid sequence of CDR 3 of AM<sub>L</sub>26 Vl | SEQ ID NO: 265 | QQYYNWPWT | SEQ ID NO: 425 |

The general structure and properties of CDRs within naturally occurring antibodies have been described in the art. Briefly, in a traditional antibody scaffold, the CDRs are embedded within a framework in the heavy and light chain variable region where they constitute the regions largely responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, MD; see also Chothia and Lesk, 1987, J. Mol. Biol. 196:901-917; Chothia et al., 1989, *Nature* 342: 877-883), within a framework region (designated framework regions 1-4, FR1, FR2, FR3, and FR4, by Kabat et al. 1991, supra; see also Chothia and Lesk, 1987, supra). See, infra. The CDRs provided by the present invention, however, may not only be used to define the antigen binding domain of a traditional antibody structure, but may be embedded in a variety of other scaffold structures, as described herein.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

In another embodiment, the invention provides an antigen binding protein that specifically binds IL-17RA, wherein said antigen binding protein comprises a light chain CDR1, CDR2, CDR3 and a heavy chain CDR1, CDR2, and CDR3 that differs by no more than a total of one, two, three, four, five, or six amino acid additions, substitutions, and/or deletions from the following CDR sequences: CDR1 (SEQ ID NO:185), CDR2 (SEQ ID NO:186), CDR3 (SEQ ID NO:187) and heavy chain CDR1 (SEQ ID NO:107), CDR2 (SEQ ID NO:108), CDR3 (SEQ ID NO:109) of antibody AM-1; light chain CDR1 (SEQ ID NO:188), CDR2 (SEQ ID NO:189), CDR3 (SEQ ID NO:190) and heavy chain CDR1 (SEQ ID NO:110), CDR2 (SEQ ID NO: 111), CDR3 (SEQ ID NO:112) of antibody AM-2; light chain CDR1 (SEQ ID NO:191), CDR2 (SEQ ID NO:192), CDR3 (SEQ ID NO:193) and heavy chain CDR1 (SEQ ID NO:113), CDR2 (SEQ ID NO:114), CDR3 (SEQ ID NO: 115) of antibody AM-3; light chain CDR1 (SEQ ID NO:194), CDR2 (SEQ ID NO:195), CDR3 (SEQ ID NO:196) and heavy chain CDR1 (SEQ ID NO:116), CDR2 (SEQ ID NO: 117), CDR3 (SEQ ID NO: 118) of antibody AM-4; light chain CDR1 (SEQ ID NO:197), CDR2 (SEQ ID NO: 198), CDR3 (SEQ ID NO:199) and heavy chain CDR1 (SEQ ID NO:119), CDR2 (SEQ ID NO:120), CDR3 (SEQ ID NO:121) of antibody AM-5; light chain CDR1 (SEQ ID NO:200), CDR2 (SEQ ID NO:201), CDR3 (SEQ ID NO:202) and heavy chain CDR1 (SEQ ID NO: 122), CDR2 (SEQ ID NO:123), CDR3 (SEQ ID NO:124) of antibody AM-6; light chain CDR1 (SEQ ID NO:203), CDR2 (SEQ ID NO:204), CDR3 (SEQ ID NO:205) and heavy chain CDR1 (SEQ ID NO: 125), CDR2 (SEQ ID NO: 126), CDR3 (SEQ ID NO:127) of antibody AM-7; light chain CDR1 (SEQ ID NO:206), CDR2 (SEQ ID NO:207), CDR3 (SEQ ID NO:208) and heavy chain CDR1 (SEQ ID NO: 128), CDR2 (SEQ ID NO:129), CDR3 (SEQ ID NO:130) of antibody AM-8; light chain CDR1 (SEQ ID NO:209), CDR2 (SEQ ID NO:210), CDR3 (SEQ ID NO:211) and heavy chain CDR1 (SEQ ID NO:131), CDR2 (SEQ ID NO:132), CDR3 (SEQ ID NO:133) of antibody AM-9; light chain CDR1 (SEQ ID NO:212), CDR2 (SEQ ID NO:213), CDR3 (SEQ ID NO:214) and heavy chain CDR1 (SEQ ID NO:134), CDR2 (SEQ ID NO:135), CDR3 (SEQ ID NO: 136) of antibody AM-10; light chain CDR1 (SEQ ID NO:215), CDR2 (SEQ ID NO:216), CDR3 (SEQ ID NO:217) and heavy chain CDR1 (SEQ ID NO:137), CDR2 (SEQ ID NO:138), CDR3 (SEQ ID NO:139) of antibody AM-11; light chain CDR1 (SEQ ID NO:218), CDR2 (SEQ ID NO:219), CDR3 (SEQ ID NO:220) and heavy chain CDR1 (SEQ ID NO: 140), CDR2 (SEQ ID NO:141), CDR3 (SEQ ID NO:142) of antibody AM-12; light chain CDR1 (SEQ ID NO:221), CDR2 (SEQ ID NO:222), CDR3 (SEQ ID NO:223) and heavy chain CDR1 (SEQ ID NO:143), CDR2 (SEQ ID NO: 144), CDR3 (SEQ ID NO:145) of antibody AM-13; light chain CDR1 (SEQ ID NO:224), CDR2 (SEQ ID NO:225), CDR3 (SEQ ID NO:226) and heavy chain CDR1 (SEQ ID NO:146), CDR2 (SEQ ID NO: 147), CDR3 (SEQ ID NO:148) of antibody AM-14; light chain CDR1 (SEQ ID NO:227), CDR2 (SEQ ID NO:228), CDR3 (SEQ ID NO:229) and heavy chain CDR1 (SEQ ID NO:149), CDR2 (SEQ ID NO:150), CDR3 (SEQ ID NO:151) of antibody AM-15; light chain CDR1 (SEQ ID NO:230), CDR2 (SEQ ID NO:231), CDR3 (SEQ ID NO:232) and heavy chain CDR1 (SEQ ID NO:152), CDR2 (SEQ ID NO:153), CDR3 (SEQ ID NO:154) of antibody AM-16; light chain CDR1 (SEQ ID NO:233), CDR2 (SEQ ID NO:234), CDR3 (SEQ ID NO:235) and heavy chain CDR1 (SEQ ID NO:155), CDR2 (SEQ ID NO:156), CDR3 (SEQ ID NO:157) of antibody AM-17; light chain CDR1 (SEQ ID NO:236), CDR2 (SEQ ID NO:237), CDR3 (SEQ ID NO:238) and heavy chain CDR1 (SEQ ID NO:158), CDR2 (SEQ ID NO:159), CDR3 (SEQ ID NO:160) of antibody AM-18; light chain CDR1 (SEQ ID NO:239), CDR2 (SEQ ID NO:240), CDR3 (SEQ ID NO:241) and heavy chain CDR1 (SEQ ID NO:161), CDR2 (SEQ ID NO:162), CDR3 (SEQ ID NO:163) of antibody AM-19; light chain CDR1 (SEQ ID NO:242), CDR2 (SEQ ID NO:243), CDR3 (SEQ ID NO:244) and heavy chain CDR1 (SEQ ID NO:164), CDR2 (SEQ ID NO:165), CDR3 (SEQ ID NO:166) of antibody AM-20; light chain CDR1 (SEQ ID NO:245), CDR2 (SEQ ID NO:246), CDR3 (SEQ ID NO:247) and heavy chain CDR1 (SEQ ID NO:167), CDR2 (SEQ ID NO: 168), CDR3 (SEQ ID NO: 169) of antibody AM-21; light chain CDR1 (SEQ ID NO:248), CDR2 (SEQ ID NO:249), CDR3 (SEQ ID NO:250) and heavy chain CDR1 (SEQ ID NO:170), CDR2 (SEQ ID NO:171), CDR3 (SEQ ID NO:172) of antibody AM-22; light chain CDR1 (SEQ ID NO:251), CDR2 (SEQ ID NO:252), CDR3 (SEQ ID NO:253) and heavy chain CDR1 (SEQ ID NO:173), CDR2 (SEQ ID NO:174), CDR3 (SEQ ID NO:175) of antibody AM-23; light chain CDR1 (SEQ ID NO:254), CDR2 (SEQ ID NO:255), CDR3 (SEQ ID NO:256) and heavy chain CDR1 (SEQ ID NO: 173), CDR2 (SEQ ID NO:174), CDR3 (SEQ ID NO:175) of antibody AM-23; light chain CDR1 (SEQ ID NO:257), CDR2 (SEQ ID NO:258), CDR3 (SEQ ID NO:259) and heavy chain CDR1 (SEQ ID NO: 176), CDR2 (SEQ ID NO:177), CDR3 (SEQ ID NO:178) of antibody AM-24; light chain CDR1 (SEQ ID NO:260), CDR2 (SEQ ID NO:261), CDR3 (SEQ ID NO:262) and heavy chain CDR1 (SEQ ID NO:179), CDR2 (SEQ ID NO: 180), CDR3 (SEQ ID NO:181) of antibody AM-25; or light chain CDR1 (SEQ ID NO:263), CDR2 (SEQ ID NO:264), CDR3 (SEQ ID NO:265) and heavy chain CDR1 (SEQ ID NO:182), CDR2 (SEQ ID NO:183), CDR3 (SEQ ID NO:184) of antibody AM-26, and fragments, derivatives, muteins, and variants thereof.

The CDRs of the invention also include consensus sequences derived from groups of related monoclonal antibodies. The antibodies may be related by both sequence homology and function, as shown in the Examples. As described herein, a "consensus sequence" refers to amino acid sequences having conserved amino acids common among a number of sequences and variable amino acids that vary within given amino acid sequences. The CDR consensus sequences of the invention include CDRs corresponding to each of H-CDR1, H-CDR2, H-CDR3, L-CDR1, L-CDR2 and L-CDR3.

Consensus sequences were determined using standard phylogenic analyses of the CDRs corresponding to the VH (i.e., Variable Heavy, etc.) & VL of anti-IL-17RA antibodies. Two different approaches were employed. In a first approach, the consensus sequences were determined by keeping the CDRs contiguous within the same sequence corresponding to a VH or VL. In a second approach, the consensus sequences were determined by aligning the various types of CDRs, i.e., H-CDR1, H-CDR2, H-CDR3, L-CDR1, L-CDR2 and L-CDR3 sequences of the IL-17RA antigen binding proteins disclosed herein independently.

In the first approach, briefly, amino acid sequences corresponding to the entire variable domains of either VH or VL were convened to FASTA formatting for ease in processing comparative alignments and inferring phylogenies. Next, framework regions of these sequences were replaced with an artificial linker sequence (GGGAAAGGGAAA, SEQ ID NO:448) so that examination of the CDRs alone could be performed without introducing any amino acid position weighting bias due to coincident events (e.g., such as unrelated antibodies that serendipitously share a common germline framework heritage) whilst still keeping CDRs contiguous within the same sequence corresponding to a VH or VL. VH or VL sequences of this format were then subjected to sequence similarity alignment interrogation using a program that employs a standard ClutalW-like algorithm (see, Thompson et al., 1994, *Nucleic Acids Res.* 22:4673-4680). A gap creation penalty of 8.0 was employed along with a gap extension penalty of 2.0. This program likewise generated phylograms (phylogenic tree illustrations) based on sequence similarity alignments using either UPGMA (unweighted pair group method using arithmetic averages) or Neighbor-Joining methods (see, Saitou and Nei, 1987, *Molecular Biology and Evolution* 4:406-425) to construct & illustrate similarity and distinction of sequence groups via branch length comparison and grouping. Both methods produced similar results but UPGMA-derived trees were ultimately used as the method employs a simpler and more conservative set of assumptions. UPGMA-derived trees are shown in FIG. 1 where similar groups of sequences were defined as having fewer than 15 substitutions per 100 residues (see legend in tree illustrations for scale) amongst individual sequences within the group and were used to define consensus sequence collections. The original sequence alignments generated were employed to empirically examine and document the occurrence of amino acids tolerated at each position with a consensus group and are shown in FIGS. 2 and 3. Consensus sequences for the groups of similar sequences within each CDR were then prepared. Amino acids that varied within each group were noted with the notation $X_n$ within each consensus sequence.

The H-CDR1 consensus sequences include amino acid sequences selected from the group consisting of: a) $X_1$YGIS (SEQ ID NO:453), wherein $X_1$ is selected from the group consisting of R, S and G; b) $X_1$YX$_2$MX$_3$ (SEQ ID NO:454), wherein $X_1$ is selected from the group consisting of D and S; $X_2$ is selected from the group consisting of Y and S; and $X_3$ is selected from the group consisting of S and N; and c) SYGMX$_1$ (SEQ ID NO:455), wherein $X_1$ is selected from the group consisting of H and Q;

The H-CDR2 consensus sequences include amino acid sequence selected from the group consisting of: a) WISX$_1$YX$_2$GNTX$_3$YAQX$_4$X$_5$QG (SEQ ID NO:456), wherein $X_1$ is selected from the group consisting of A and T; $X_2$ is selected from the group consisting of N. S and K; $X_3$ is selected from the group consisting of N and K; $X_4$ is selected from the group consisting of K and N; and $X_5$ is selected from the group consisting of L and F; b) $X_1$X$_2$SX$_3$X$_4$X$_5$SX$_6$IX$_7$YADSVKG (SEQ ID NO:457), wherein $X_1$ is selected from the group consisting of Y, I and F; $X_2$ is selected from the group consisting of I and S; $X_3$ is selected from the group consisting of S and A; $X_4$ is selected from the group consisting of S and R; and $X_5$ is selected from the group consisting of G, S and no amino acid; $X_6$ is selected from the group consisting of T and I; and $X_7$ is selected from the group consisting of Y and H; and c) VIWYDGX$_1$X$_2$KX$_3$YADSVKG (SEQ ID NO:458), wherein $X_1$ is selected from the group consisting of S and N; $X_2$ is selected from the group consisting of N and K; and $X_3$ is selected from the group consisting of H and Y.

The H-CDR3 consensus sequences include amino acid sequence selected from the group consisting of: a) $X_1$QLX$_2$X$_3$DY (SEQ ID NO:459), wherein $X_1$ is selected from the group consisting of R and K, $X_2$ is selected from the group consisting of Y, V, and A, and $X_3$ is selected from the group consisting of F and L and b) $X_1$QLX$_2$FDY (SEQ ID NO:460), wherein $X_1$ is selected from the group consisting of R and K, and $X_2$ is selected from the group consisting of Y and V.

The L-CDR1 consensus sequence includes an amino acid sequence selected from the group consisting of: a) RASQX$_1$X$_2$X$_3$X$_4$LX$_5$ (SEQ ID NO:461), wherein $X_1$ is selected from the group consisting of G, S, and A; $X_2$ is selected from the group consisting of R and S; $X_3$ is selected from the group consisting of S, I and N; $X_4$ is selected from the group consisting of W and Y; and $X_5$ is selected from the group consisting of A and N; b) RASQSX$_1$X$_2$X$_3$X$_4$LA (SEQ ID NO:462), wherein $X_1$ is selected from the group consisting of V and I; $X_2$ is selected from the group consisting of I and S; $X_3$ is selected from the group consisting of S and T; $X_4$ is selected from the group consisting of N and S; and $X_5$ is selected from the group consisting of A and N; and c) RASQSVX$_1$X$_2$NLX$_3$ (SEQ ID NO:463), wherein $X_1$ is selected from the group consisting of Y and S; $X_2$ is selected from the group consisting of S and R; and $X_3$ is selected from the group consisting of A and V.

The L-CDR2 consensus sequence includes an amino acid sequence selected from the group consisting of: a) AASSX$_1$QS (SEQ ID NO:464), wherein $X_1$ is selected from the group consisting of L and F; b) AASX$_1$LQS (SEQ ID NO:465), wherein $X_1$ is selected from the group consisting of S and T; c) $X_1$X$_2$STRAX$_3$ (SEQ ID NO:466), wherein $X_1$ is selected from the group consisting of G and D; $X_2$ is selected from the group consisting of A and T; and $X_3$ is selected from the group consisting of T and A; and d) GASTRAX$_1$ (SEQ ID NO:473), wherein $X_1$ is selected from the group consisting of A, T and N.

The L-CDR3 consensus sequences include amino acid sequences selected from the group consisting of: a) LQHX$_1$SYX$_2$X$_3$T (SEQ ID NO:467), wherein $X_1$ is selected from the group consisting of K and N; $X_2$ is selected from the group consisting of P and N; and $X_3$ is selected from the group consisting of L, F and P; b) QX$_1$X$_2$X$_3$X$_4$X$_5$PX$_6$T (SEQ ID NO:468), wherein $X_1$ is selected from the group consisting of Q and K; $X_2$ is selected from the group consisting of A, S and Y; $X_3$ is selected from the group consisting of N, Y and S; $X_4$ is selected from the group consisting of N, S and R; $X_5$ is selected from the group consisting of F, T. Y and A; and $X_6$ is selected from the group consisting of R and F; c) QQYDX$_1$WPLT (SEQ ID NO:469), wherein $X_1$ is selected from the group consisting of N, T and I; and d) QX$_1$YX$_2$X$_3$WX$_4$X$_5$X$_6$T (SEQ ID NO:470), wherein $X_1$ is selected from the group consisting of H and Q; $X_2$ is selected from the group consisting of I, Y, N and K; $X_3$ is selected from the group consisting of N and S; $X_4$ is selected from the group consisting of P and R; $X_5$ is selected from the group consisting of K, no amino acid, and T; and $X_6$ is selected from the group consisting of W and no amino acid.

FIGS. 1, 2, 3, 16A, 16B, 19, and 22 show that a clear pattern in the data exists between sequence homology in the CDR domains and the antibodies function, as determined by cross-competition binning and the determination of where the antibodies bound to IL-17RA. Thus, a structure/function relation for classes of antibodies has been established for the IL-17RA antibodies provided herein.

In a second approach CDR consensus sequences were determined for each separate CDR, independently of their contiguous context within the same sequence corresponding to a VH or VL. In this approach the consensus sequences were determined by aligning each H-CDR1, H-CDR2, H-CDR3, L-CDR1, L-CDR2, and L-CDR3 in groups, i.e., by aligning the individual H-CDR1 sequences of the IL-17RA antigen binding proteins disclosed herein to determine a H-CDR1 consensus sequence, by aligning the individual H-CDR2 sequences of the IL-17RA antigen binding proteins disclosed herein to determine a H-CDR2 consensus sequence, by aligning the individual H-CDR3 sequences of the IL-17RA antigen binding proteins disclosed herein to determine a H-CDR3 consensus sequence, by aligning the individual L-CDR1 sequences of the UL-17RA antigen binding proteins disclosed herein to determine a L-CDR1 consensus sequence, by aligning the individual L-CDR2 sequences of the IL-17RA antigen binding proteins disclosed herein to determine a L-CDR2 consensus sequence, and by aligning the individual L-CDR3 sequences of the IL-17RA antigen binding proteins disclosed herein to determine a L-CDR3 consensus sequence. Similarities between sequences within each individual CDR sequences were identified. Consensus sequences for the groups of similar sequences within each CDR were then prepared. Amino acids that varied within each group were noted with the notation $X_n$ within each consensus sequence.

In another embodiment, the invention provides an antigen binding protein that specifically binds IL-17RA, wherein said antigen binding protein comprises at least one H-CDR region of any of SEQ ID NOs:107-184. Other embodiments include antigen binding proteins that specifically bind to IL-17RA, wherein said antigen binding protein comprises at least one L-CDR region of any of SEQ ID NOs:185-265. Other embodiments include antigen binding proteins that specifically binds IL-17RA, wherein said antigen binding protein comprises at least one H-CDR region of any of SEQ ID NOs:107-184 and at least one L-CDR region of any of SEQ ID NOs:185-265.

In another embodiment, the invention provides an antigen binding protein that specifically binds IL-17RA, wherein said antigen binding protein comprises at least two H-CDR regions of any of SEQ ID NOs:107-184. Other embodiments include antigen binding proteins that specifically bind to IL-17RA, wherein said antigen binding protein comprises at least two L-CDR region of any of SEQ ID NOs:185-265. Other embodiments include antigen binding proteins that specifically binds IL-17RA, wherein said antigen binding protein comprises at least two H-CDR region of any of SEQ ID NOs:107-184 and at least two L-CDR region of any of SEQ ID NOs:185-265.

In another embodiment, the invention provides an antigen binding protein that specifically binds IL-17RA, wherein said antigen binding protein comprises at least three H-CDR regions of any of SEQ ID NOs:107-184. Other embodiments include antigen binding proteins that specifically bind to IL-17RA, wherein said antigen binding protein comprises at least three L-CDR region of any of SEQ ID NOs:185-265. Other embodiments include antigen binding proteins that specifically binds IL-17RA, wherein said antigen binding protein comprises at least three H-CDR region of any of SEQ ID NOs:107-184 and at least three L-CDR region of any of SEQ ID NOs:185-265.

In another embodiment, the invention provides an antigen binding protein that specifically binds IL-17RA, wherein said antigen binding protein comprises at least one, two, or three 1H-CDR regions of any of SEQ ID NOs:107-184, wherein said H-CDR regions are at least 80%, 81%, 82%, 83%, 84%, 85%, 86%, 87%, 88%, 89%, 90%, 91%, 92%, 93%, 94%, 95%, 96%, 97%, 98%, or 99% identical to the respective H-CDR. Other embodiments include antigen binding proteins that specifically bind to IL-17RA, wherein said antigen binding protein comprises at least one, two, or three L-CDR region of any of SEQ ID NOs:185-265, wherein said L-CDR regions are at least 80%, 81%, 82%, 83%, 84%, 85%, 86%, 87%, 88%, 89%, 90%, 91%, 92%, 93%, 94%, 95%, 96%, 97%, 98%, or 99% identical to the respective L-CDR. Other embodiments include antigen binding proteins that specifically binds IL-17RA, wherein said antigen binding protein comprises at least one, two, or three H-CDR regions of any of SEQ ID NOs:107-184, wherein said H-CDR regions are at least 80%, 81%, 82%, 83%, 84%, 85%, 86%, 87%, 88%, 89%, 90%, 91%, 92%, 93%, 94%, 95%, 96%, 97%, 98%, or 99% identical to the respective H-CDR, and comprises at least one, two, or three L-CDR region of any of SEQ ID NOs:185-265, wherein said L-CDR regions are at least 80%, 81%, 82%, 83%, 84%, 85%, 86%, 87%, 88%, 89%, 90%, 91%, 92%, 93%, 94%, 95%, 96%, 97%, 98%, or 99% identical to the respective L-CDR.

In another embodiment, the invention provides an antigen binding protein that binds IL-17RA, wherein said antigen binding protein comprises at least one H-CDR region having no more than one, two, three, four, five, or six amino acid additions, deletions or substitutions of any of SEQ ID NOs:107-184 and/or at least one L-CDR region having no more than one, two, three, four, five, or six amino acid additions, deletions or substitutions of any of SEQ ID NOs:185-265.

In another embodiment, the invention provides an antigen binding protein that binds IL-17RA, wherein said antigen binding protein comprises one, two, or three H-CDR region having no more than one, two, three, four, five, or six amino acid additions, deletions or substitutions of any of SEQ ID NOs:107-184 and/or one, two, or three L-CDR region having no more than one, two, three, four, five, or six amino acid additions, deletions or substitutions of any of SEQ ID NOs:185-265.

Additional embodiments utilize antigen binding proteins comprising one CDR having no more than one, two, three, four, five, or six amino acid additions, deletions or substitutions of the sequence selected from the H-CDR regions of any of SEQ ID NOs:107-184 and a L-CDR region having no more than one, two, three, four, five, or six amino acid additions, deletions or substitutions of any of SEQ ID NOs:185-265 (e.g., the antigen binding protein has two CDR regions, one H-CDR and one L-CDH. A specific embodiment includes antigen binding proteins comprising both a H-CDR3 and a L-CDR3 region.

As will be appreciated by those in the art, for any antigen binding protein comprising more than one CDR from the sequences provided herein, any combination of CDRs independently selected from the CDR in TABLE 1 sequences is useful. Thus, antigen binding proteins comprising one, two, three, four, five, or six independently selected CDRs can be generated. However, as will be appreciated by those in the art, specific embodiments generally utilize combinations of CDRs that are non-repetitive, e.g., antigen binding proteins are generally not made with two H-CDR2 regions, etc.

In some embodiments, antigen binding proteins are generated that comprise no more than one, two, three, four, five, or six amino acid additions, deletions or substitutions of a H-CDR3 region and a L-CDR3 region, particularly with the H-CDR3 region being selected from a sequence having no more than one, two, three, four, five, or six amino acid additions, deletions or substitutions of a H-CDR3 region of any of SEQ ID NOs:107-184 and the L-CDR3 region being selected from a L-CDR3 consensus sequence having no more than one, two, three, four, five, or six amino acid additions, deletions or substitutions of a L-CDR3 region of any of SEQ ID SEQ ID NOs:185-265.

As noted herein, the antigen binding proteins of the present invention comprise a scaffold structure into which the CDR(s) of the invention may be grafted. The genus of IL-17RA antigen binding proteins comprises the subgenus of antibodies, as variously defined herein. Aspects include embodiments wherein the scaffold structure is a traditional, tetrameric antibody structure. Thus, the antigen binding protein combinations described herein include the additional components (framework, J and D regions, constant regions, etc.) that make up a heavy and/or light chain.

Embodiments include the use of human scaffold components. An exemplary embodiment of a VH variable region grafted into a traditional antibody scaffold structure is depicted in SEQ ID NO:427 and an exemplary embodiment of a VL variable region grafted into a traditional antibody scaffold structure is depicted in SEQ ID NO:429. Of course it is understood that any antibody scaffold known in the art may be employed.

In one aspect, the present invention provides antibodies that comprise a light chain variable region selected from the group consisting of $AM_L1$ through $AM_L26$ and/or a heavy chain variable region selected from the group consisting of $AM_H1$ through $AM_H26$, and fragments, derivatives, muteins, and variants thereof. Antibodies of the invention include, but are not limited to: antibodies comprising $AM_L1$/$AM_H1$ (SEQ ID NO:27/SEQ ID NO:1), $AM_L2$/$AM_H2$ (SEQ ID NO:28/SEQ ID NO:2), $AM_L3$/$AM_H3$ (SEQ ID NO:29/SEQ ID NO:3), $AM_L4$/$AM_L4$ (SEQ ID NO:30/SEQ ID NO:4), $AM_L5$/$AM_H5$ (SEQ ID NO:31/SEQ ID NO:5), $AM_L6$/$AM_H6$ (SEQ ID NO:32/SEQ ID NO:6), $AM_L7$/$AM_H7$ (SEQ ID NO:33/SEQ ID NO:7), $AM_L8$/$AM_H8$ (SEQ ID NO:34/SEQ ID NO:8), $AM_L9$/$AM_H9$ (SEQ ID NO:35/SEQ ID NO:9), $AM_L10$/$AM_H10$ (SEQ ID NO:36/SEQ ID NO:10), $AM_L11$/$AM_L11$ (SEQ ID NO:37/SEQ ID NO: 11), $AM_L12$/$AM_H12$ (SEQ ID NO:38/SEQ ID NO:12), $AM_L13$/$AM_H13$ (SEQ ID NO:39/SEQ ID NO:13), $AM_L14$/$AM_H14$ (SEQ ID NO:40/SEQ ID NO:14), $AM_L15$/$AM_H15$ (SEQ ID NO:41/SEQ ID NO: 15), $AM_L16$/$AM_H16$ (SEQ ID NO:42/SEQ ID NO:16), $AM_L17$/$AM_H17$ (SEQ ID NO:43/SEQ ID NO:17), $AM_L18$/$AM_H18$ (SEQ ID NO:44/SEQ ID NO:18), $AM_L19$/$AM_H19$ (SEQ ID NO:45/SEQ ID NO: 19), $AM_L20$/$AM_H20$ (SEQ ID NO:46/SEQ ID NO:20), $AM_L21$/$AM_H21$ (SEQ ID NO:47/SEQ ID NO:21), $AM_L22$/$AM_H22$ (SEQ ID NO:48/SEQ ID NO:22), $AM_L23$/$AM_H23$ (SEQ ID NO:49 or SEQ ID NO:50/SEQ ID NO:23), $AM_L24$/$AM_H24$ (SEQ ID NO:51/SEQ ID NO:24), $AM_L25$/$AM_H25$ (SEQ ID NO:52/SEQ ID NO:25), $AM_L26$/$AM_H26$ (SEQ ID NO:53/SEQ ID NO:26), as well as IL-17RA-binding fragments thereof and combinations thereof.

In one embodiment, the present invention provides an antibody comprising a light chain variable domain comprising a sequence of amino acids that differs from the sequence of a light chain variable domain selected from the group consisting of $AM_L1$ through $AM_L26$ only at 15, 14, 13, 12, 11, 10, 9, 8, 7, 6, 5, 4, 3, 2, or 1 residues, wherein each such sequence difference is independently either a deletion, insertion, or substitution of one amino acid residue. In another embodiment, the light-chain variable domain comprises a sequence of amino acids that is at least 70%, 75%, 800%, 810%, 82%, 83%, 84%, 85%, 86%, 87%, 88%, 89%, 90%, 91%, 92%, 93%, 94%, 95%, 96%, 97%, 98%, or 99% identical to the sequence of a light chain variable domain selected from the group consisting of $AM_L1$ through $AM_L26$. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence that encodes a light chain variable domain selected from the group consisting of $AM_L1$ through $AM_L26$. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of $AM_L1$ through $AM_L26$. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of $AM_L1$ through $AM_L26$. In another embodiment, the light chain variable domain comprises a sequence of amino acids that is encoded by a polynucleotide that hybridizes under moderately stringent conditions to a complement of a light chain polynucleotide provided in any one of $AM_L1$ through $AM_L26$ polynucleotide sequences (SEQ ID NOs:80-106).

In another embodiment, the present invention provides an antibody comprising a heavy chain variable domain comprising a sequence of amino acids that differs from the sequence of a heavy chain variable domain selected from the group consisting of $AM_H1$ through $AM_H26$ only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to the sequence of a heavy chain variable domain selected from the group consisting of $AM_H1$ through $AM_H26$. In another embodiment, the heavy chain variable domain comprises a sequence of amino acids that is encoded by a nucleotide sequence that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence that encodes a heavy chain variable domain selected from the group consisting of $AM_H1$ through $AM_H26$. In another embodiment, the heavy chain variable domain comprises a sequence of amino acids that is encoded by a polynucleotide that hybridizes under moderately stringent or stringent conditions to the complement of a polynucleotide that encodes a heavy chain variable domain selected from the group consisting of $AM_H1$ through $AM_H26$. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of $AM_H1$ through $AM_H26$. In another embodiment, the heavy chain variable domain comprises a sequence of amino acids that is encoded by a polynucleotide that hybridizes under moderately stringent or stringent conditions to a complement of a heavy chain polynucleotide provided in any one of $AM_H1$ through $AM_H26$ polynucleotide sequences (SEQ ID NOs:54-79).

Accordingly, in various embodiments, the antigen binding proteins of the invention comprise the scaffolds of traditional antibodies, including human and monoclonal antibodies, bispecific antibodies, diabodies, minibodies, domain antibodies, synthetic antibodies (sometimes referred to herein as "antibody mimetics"), chimeric antibodies, antibody fusions (sometimes referred to as "antibody conjugates"), and fragments of each, respectively. The above described CDRs and combinations of CDRs may be grafted into any of the following scaffolds.

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a) a human antibody; b) a humanized antibody; c) a chimeric antibody; d) a monoclonal antibody; e) a polyclonal antibody; f) a recombinant antibody; g) an antigen-binding antibody fragment; h) a single chain antibody; i) a diabody; j) a triabody; k) a tetrabody; l) a Fab fragment; m) a F(ab')$_2$ fragment; n) an IgD antibody; o) an IgE antibody; p) an IgM antibody; q) an IgA antibody; r) an IgG1 antibody; s) an IgG2 antibody; t) an IgG3 antibody; and u) an IgG4 antibody.

A variable region comprises at least three heavy or light chain CDRs, see, supra (Kabat et al., 1991, *Sequences of Proteins of Immunological Interest*, Public Health Service N.I.H., Bethesda, MD; see also Chothia and Lesk, 1987, *J. Mol. Biol.* 196:901-917; Chothia et al., 1989, *Nature* 342: 877-883), embedded within a framework region (designated framework regions 1-4, FR1, FR2, FR3, and FR4, by Kabat et al., 1991, supra; see also Chothia and Lesk, 1987, supra). See, infra.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the invention include all such classes of antibodies that incorporate the variable domains or the CDRs of the antigen binding proteins, as described herein.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press. N.Y. The variable regions of each light/heavy chain pair form the antibody binding site. Scaffolds of the invention include such regions.

Some naturally occurring antibodies, for example found in camels and llamas, are dimers consisting of two heavy chain and include no light chains. Muldermans et al., 2001, *J. Biotechnol.* 74:277-302; Desmyter et al., 2001, *J. Biol. Chem.* 276:26285-26290. Crystallographic studies of a camel antibody have revealed that the CDR3 regions form a surface that interacts with the antigen and thus is critical for antigen binding like in the more typical tetrameric antibodies. The invention encompasses dimeric antibodies consisting of two heavy chains, or fragments thereof, that can bind to and/or inhibit the biological activity of IL-17RA.

The variable regions of the heavy and light chains typically exhibit the same general structure of relatively conserved framework regions (FR) joined by three hypervariable regions, i.e., the complementarity determining regions or CDRs. The CDRs are the hypervariable regions of an antibody (or antigen binding protein, as outlined herein), that are responsible for antigen recognition and binding. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest. Chothia et al., 1987, *J. Mol. Biol.* 196:901-917; Chothia et al., 1989, *Nature* 342: 878-883. Scaffolds of the invention include such regions.

CDRs constitute the major surface contact points for antigen binding. See, e.g., Chothia and Lesk, 1987, *J. Mol. Biol.* 196:901-917. Further, CDR3 of the light chain and, especially, CDR3 of the heavy chain may constitute the most important determinants in antigen binding within the light and heavy chain variable regions. See, e.g., Chothia and Lesk, 1987, supra; Desiderio et al., 2001, *J. Mol. Biol.* 310:603-615; Xu and Davis, 2000, *Immunity* 13:37-45; Desmyter et al., 2001, J. Biol. Chem. 276:26285-26290; and Muyldermans, 2001, *J. Biotechnol.* 74:277-302. In some antibodies, the heavy chain CDR3 appears to constitute the major area of contact between the antigen and the antibody. Desmyter et al., 2001, supra. In vitro selection schemes in which CDR3 alone is varied can be used to vary the binding properties of an antibody. Muyldermans, 2001, supra; Desiderio et al., 2001, supra.

Naturally occurring antibodies typically include a signal sequence, which directs the antibody into the cellular pathway for protein secretion and which is not present in the mature antibody. A polynucleotide encoding an antibody of the invention may encode a naturally occurring signal sequence or a heterologous signal sequence as described below.

In one embodiment, the antigen binding protein is a monoclonal antibody, comprising from one (1) to six (6) of the depicted CDRs, as outlined herein (see TABLE 1). The antibodies of the invention may be of any type including IgM, IgG (including IgG1, IgG2, IgG3, IgG4), IgD, IgA, or IgE antibody. In specific embodiment, the antigen binding protein is an IgG type antibody. In an even more specific embodiment, the antigen binding protein is an IgG2 type antibody.

In some embodiments, for example when the antigen binding protein is an antibody with complete heavy and light chains, the CDRs are all from the same species, e.g., human. Alternatively, for example in embodiments wherein the antigen binding protein contains less than six CDRs from the sequences outlined above, additional CDRs may be either from other species (e.g., murine CDRs), or may be different human CDRs than those depicted in the sequences. For example, human H-CDR3 and L-CDR3 regions from the appropriate sequences identified herein may be used, with H-CDR1, H-CDR2, L-CDR1 and L-CDR2 being optionally selected from alternate species, or different human antibody sequences, or combinations thereof. For example, the CDRs of the invention can replace the CDR regions of commercially relevant chimeric or humanized antibodies.

Specific embodiments utilize scaffold components of the antigen binding proteins that are human components.

In some embodiments, however, the scaffold components can be a mixture from different species. As such, if the antigen binding protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. Humanized antibodies can also be generated using mice with a genetically engineered immune system. Roque et al., 2004, Biotechnol. Prog. 20:639-654. In the present invention, the identified CDRs are human, and thus both humanized and chimeric antibodies in this context include some non-human CDRs; for example, humanized antibodies may be generated that comprise the CDRH3 and CDRL3 regions, with one or more of the other CDR regions being of a different special origin.

In one embodiment, the IL-17RA antigen binding protein is a multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, Current Opinion Biotechnol. 4:446-449). e.g., prepared chemically or from hybrid hybridomas.

In one embodiment, the IL-17RA antigen binding protein is a minibody. Minibodies are minimized antibody-like proteins comprising a scFv joined to a CH3 domain. Hu et al., 1996, Cancer Res. 56:3055-3061.

In one embodiment, the IL-17RA antigen binding protein is a domain antibody; see, for example U.S. Pat. No. 6,248,516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody, dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the IL-17RA antigen binding protein is an antibody fragment, that is a fragment of any of the antibodies outlined herein that retain binding specificity to IL-17RA. In various embodiments, the antibody binding proteins comprise, but are not limited to, a F(ab). F(ab'), F(ab')2, Fv. or a single chain Fv fragments. At a minimum, an antibody, as meant herein, comprises a polypeptide that can bind specifically to IL-17RA comprising all or part of a light or heavy chain variable region, such as one or more CDRs.

Further examples of IL-17RA-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the $V_L$ and VH domains of a single antibody; (iv) the dAb fragment (Ward et al., 1989, Nature 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a $V_L$ domain are linked by a peptide linker which allows the two domains to associate to form an antigen binding site (Bird et al., 1988, Science 242:423-426. Huston et al., 1988. Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996, Nature Biotech. 14:1239-1245). Aspects of the invention include embodiments wherein the non-CDR components of these fragments are human sequences.

In one embodiment, the IL-17RA antigen binding protein is a fully human antibody. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt el al., 1997, Prot. Eng. 10:423; Kortt et al., 2001, Biomol. Eng. 18:95-108). By combining different $V_L$, and $V_H$i-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein (including but not limited to scFvs comprising the variable domain combinations of $AM_L1/AM_H$ (SEQ ID NO:27/SEQ ID NO:1), $AM_L2/AM_H2$ (SEQ ID NO:28/SEQ ID NO:2), $AM_L3/AM_H3$ (SEQ ID NO:29/SEQ ID NO:3). $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO:10), $AM_L11/AM_H11$ (SEQ ID NO:37/SEQ ID NO: 11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO: 14), $AM_L15/AM_H15$ (SEQ ID NO:41/SEQ ID NO:15), $AM_L16/AM_H16$ (SEQ ID NO:42/SEQ ID NO:16), $AM_L17/AM_H17$ (SEQ ID NO:43/SEQ ID NO:17), $AM_L18/AM_H18$ (SEQ ID NO:44/SEQ ID NO: 18), $AM_L9/AM_H19$ (SEQ ID NO:45/SEQ ID NO:19), $AM_L20/AM_H20$ (SEQ ID NO:46/SEQ ID NO:20), $AM_L21/AM_H21$ (SEQ ID NO:47/SEQ ID NO:21), AM$_L$22/AM$_H$22 (SEQ ID NO:48/SEQ ID NO:22), AM$_L$23/AM$_H$23 (SEQ ID NO:49 or SEQ ID NO:50/SEQ ID NO:23), AM$_L$24/AM$_H$24 (SEQ ID NO:51/SEQ ID NO:24), AM$_L$25/AM$_H$25 (SEQ ID NO:52/SEQ ID NO:25), AM$_L$26/AM$_H$26 (SEQ ID NO:53/SEQ ID NO:26), and combinations thereof are encompassed by the present invention.

In one embodiment, the IL-17RA antigen binding protein is an antibody fusion protein (sometimes referred to herein as an "antibody conjugate"). The conjugate partner can be proteinaceous or non-proteinaceous; the latter generally being generated using functional groups on the antigen binding protein (see the discussion on covalent modifications of the antigen binding proteins) and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

In one embodiment, the IL-17RA antigen binding protein is an antibody analog, sometimes referred to as "synthetic antibodies." For example, a variety of recent work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronection components as a scaffold.

As it is known in the art, a number of different programs can be used to identify the degree of sequence identity or similarity a protein or nucleic acid has to a known sequence.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

In certain aspects, the invention provides recombinant antigen binding proteins that bind an IL-17RA, in some embodiments a recombinant human IL-17RA or portion thereof. In this context, a "recombinant protein" is a protein made using recombinant techniques using any techniques and methods known in the art, i.e., through the expression of a recombinant nucleic acid as described herein. Methods and techniques for the production of recombinant proteins are well known in the art. Embodiments of the invention include recombinant antigen binding proteins that bind wild-type IL-17RA and variants thereof.

"Consisting essentially of" means that the amino acid sequence can vary by about 1, 2, 3, 4, 5, 6, 7, 8, 9, 10, 11, 12, 13, 14, or 15% relative to the recited SEQ ID NO: sequence and still retain biological activity, as described herein.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis. Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span-1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as IL-17RA binding.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 2.

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 2. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein. Such a modification of the IL-17RA antigen binding proteins, including antibodies, is an example of a derivative. A "derivative" of a polypeptide is a polypeptide (e.g., an antibody) that has been chemically modified. e.g., via conjugation to another chemical moiety such as, for example, polyethylene glycol, albumin (e.g., human serum albumin), phosphorylation, and glycosylation.

Other derivatives of IL-17RA antibodies within the scope of this invention include covalent or aggregative conjugates of IL-17RA antibodies, or fragments thereof, with other proteins or polypeptides, such as by expression of recombinant fusion proteins comprising heterologous polypeptides fused to the N-terminus or C-terminus of an IL-17RA antibody polypeptide. For example, the conjugated peptidic may be a heterologous signal (or leader) polypeptide, e.g., the yeast alpha-factor leader, or a peptide such as an epitope tag. IL-17RA antibody-containing fusion proteins can comprise peptides added to facilitate purification or identification of the IL-17RA antibody (e.g., poly-His). An IL-17RA antibody polypeptide also can be linked to the FLAG peptide DYKDDDDK (SEQ ID NO:447) as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, MO).

Oligomers that contain one or more IL-17RA antibody polypeptides may be employed as IL-17RA antagonists. Oligomers may be in the form of covalently-linked or non-covalently-linked dimers, trimers, or higher oligomers. Oligomers comprising two or more IL-17RA antibody polypeptides are contemplated for use, with one example being a homodimer. Other oligomers include heterodimers, homotrimers, heterotrimers, homotetramers, heterotetramers, etc.

One embodiment is directed to oligomers comprising multiple IL-17RA antibody polypeptides joined via covalent or non-covalent interactions between peptide moieties fused to the IL-17RA antibody polypeptides. Such peptides may be peptide linkers (spacers), or peptides that have the property of promoting oligomerization. Leucine zippers and certain polypeptides derived from antibodies are among the peptides that can promote oligomerization of IL-17RA antibody polypeptides attached thereto, as described in more detail below.

In particular embodiments, the oligomers comprise from two to four IL-17RA antibody polypeptides. The IL-17RA antibody moieties of the oligomer may be in any of the forms described above. e.g., variants or fragments. Preferably, the oligomers comprise IL-17RA antibody polypeptides that have IL-17RA binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing an IL-17RA binding fragment of an IL-17RA antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fe polypeptide" as used herein includes native and mutein forms of polypeptides derived from the Fc region of an antibody. Truncated forms of such polypeptides containing the hinge region that promotes dimerization also are included. Fusion proteins comprising Fe moieties (and oligomers formed therefrom) offer the advantage of facile purification by affinity chromatography over Protein A or Protein G columns.

One suitable Fe polypeptide, described in PCT application WO 93/10151 (hereby incorporated by reference), is a single chain polypeptide extending from the N-terminal hinge region to the native C-terminus of the Fc region of a human IgG antibody. Another useful Fe polypeptide is the Fe mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an IL-17RA antibody may be substituted for the variable portion of an antibody heavy and/or light chain.

Alternatively, the oligomer is a fusion protein comprising multiple IL-17RA antibody polypeptides, with or without peptidic linkers (spacer peptides). Among the suitable peptide linkers are those described in U.S. Pat. Nos. 4,751,180 and 4,935,233.

Another method for preparing oligomeric IL-17RA antibody derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an IL-17RA antibody fragment or derivative fused to a leucine zipper peptide are expressed in suitable host cells, and the soluble oligomeric IL-17RA antibody fragments or derivatives that form are recovered from the culture supernatant.

Covalent modifications are also considered derivatives of the IL-17RA antigen binding proteins and are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton. Proteins: Structure and Molecular Properties, W. H. Freeman & Co., San Francisco, 1983. pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moictics on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threoninc, or hydroxyproline, (c) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem*., pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys*. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, *Meth. Enzymol*. 138:350. Glycosylation at potential glycosylation sites may be prevented by the use of the compound tunicamycin as described by Duskin el al., 1982, *J. Biol. Chem.* 257:3105. Tunicamycin blocks the formation of protein-N-glycoside linkages.

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins of the invention comprises the addition of one or more labels.

The term "labelling group" means any detectable label. Examples of suitable labelling groups include, but are not limited to, the following: radioisotopes or radionuclides (e.g., $^3$H, $^{14}$C, $^{35}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine ripper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, s-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antigen binding protein via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, IAEDANS, EDANS, BODIPY® FL, LC® Red 640, LC® Red 705, Oregon green™, the Alexa Fluor® dyes (Alexa Fluor® 350, Alexa Fluor® 430, Alexa Fluor® 488, Alexa Fluor® 546, Alexa Fluor® 568, Alexa Fluor® 594, Alexa Fluor® 633, Alexa Fluor® 660, Alexa Fluor 680), Cascade Blue®, Cascade Yellow (5-[2-[1-[[3-(2,5-dioxopyrrolidin-1-yl)oxycarbonylphenyl]methyl]pyridin-1-ium-4-yl]-1,3-oxaaol-5-yl]-2-me y) and R-phycoerythrin (PE) (Molecular Probes, Eugene, OR), FITC, Rhodamine, and Texas Red® (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus*, or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci.* U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

Polynucleotides Encoding IL-17RA Antigen Binding Proteins

Encompassed within the invention are nucleic acids encoding IL-17RA antigen binding proteins, including antibodies, as defined herein. The polynucleotide sequences for the heavy chain variable regions $AM_H1$-26 are found in SEQ ID NOs:54-79, respectively, and the polynucleotide sequences for the light chain variable regions $AM_L1$-26 are found in SEQ ID NOs:80-106, respectively, with $AM_L23$ having two versions, as shown in SEQ ID NO:102 and 103. The SEQ ID NOs for the polynucleotide sequences encoding the H-CDR1. H-CDR2, H-CDR3, L-CDR1. L-CDR2, and L-CDR3 are provided in TABLE 1.

Aspects of the invention include polynucleotide variants (e.g., due to degeneracy) that encode the amino acid sequences described herein.

Aspects of the invention include a variety of embodiments including, but not limited to, the following exemplary embodiments: embodiment 51: an isolated polynucleotide, wherein said polynucleotide encodes a polypeptide comprising an amino acid sequence selected from the group consisting of:

A. a. a light chain variable domain sequence that is at least 80% identical to a light chain variable domain sequence of $AM_L1$-26 (SEQ ID NOs:27-53, respectively);
   b. a heavy chain variable domain sequence that is at least 80% identical to a heavy chain variable domain sequence of $AM_H1$-26 (SEQ ID NOs: 1-26, respectively); or
   c. the light chain variable domain of (a) and the heavy chain variable domain of (b); and
B. a light chain CDR1, CDR2, CDR3 and a heavy chain CDR1, CDR2, CDR3 that differs by no more than a total of three amino acid additions, substitutions, and/or deletions in each CDR from the following sequences:
   a. a light chain CDR1 (SEQ ID NO:185), CDR2 (SEQ ID NO:186), CDR3 (SEQ ID NO: 187) and a heavy chain CDR1 (SEQ ID NO: 107), CDR2 (SEQ ID NO:108), CDR3 (SEQ ID NO:109) of antibody AM-1;
   b. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO:112) of antibody AM-2;

c. a light chain CDR1 (SEQ ID NO:191), CDR2 (SEQ ID NO:192), CDR3 (SEQ ID NO:193) and a heavy chain CDR1 (SEQ ID NO: 113), CDR2 (SEQ ID NO: 114), CDR3 (SEQ ID NO:115) of antibody AM-3;
d. a light chain CDR1 (SEQ ID NO:194), CDR2 (SEQ ID NO:195), CDR3 (SEQ ID NO:196) and a heavy chain CDR1 (SEQ ID NO: 116), CDR2 (SEQ ID NO: 117), CDR3 (SEQ ID NO:118) of antibody AM-4;
e. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO: 123), CDR3 (SEQ ID NO:124) of antibody AM-6;
g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;
h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;
i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO:139) of antibody AM-11;
l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;
n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO: 148) of antibody AM-14;
o. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;
p. a light chain CDR1 (SEQ ID NO:230), CDR2 (SEQ ID NO:231), CDR3 (SEQ ID NO:232) and a heavy chain CDR1 (SEQ ID NO: 152), CDR2 (SEQ ID NO:153), CDR3 (SEQ ID NO:154) of antibody AM-16;
q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;
v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;
x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO:178) of antibody AM-24;
z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or
z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO: 183), CDR3 (SEQ ID NO:184) of antibody AM-26;
wherein said polypeptide specifically binds IL-17 receptor A.

Embodiment 52: the polynucleotide of embodiment 51, wherein said polynucleotide hybridizes under stringent conditions to the full length complement of a polynucleotide selected from the group consisting of:

a. a light chain variable domain-encoding polynucleotide and a heavy chain variable domain-encoding polynucleotide of $AM_L1/AM_H1$ (SEQ ID NO:80/SEQ ID NO:54);
b. a light chain variable domain-encoding polynucleotide and a heavy chain variable domain-encoding polynucleotide of $AM_L2/AM_H2$ (SEQ ID NO:81/SEQ ID NO:55);
c. a light chain variable domain-encoding polynucleotide and a heavy chain variable domain-encoding polynucleotide of $AM_L3/AM_H3$ (SEQ ID NO:82/SEQ ID NO:56);
d. a light chain variable domain-encoding polynucleotide and a heavy chain arabic domain-encoding polynucleotide of $AM_L4/AM_H4$ (SEQ ID NO:83/SEQ ID NO:57);
e. a light chain variable domain-encoding polynucleotide and a heavy chain variable domain-encoding polynucleotide of $AM_L5/AM_H5$ (SEQ ID NO:84/SEQ ID NO:58);
f. a light chain variable domain-encoding polynucleotide and a heavy chain variable domain-encoding polynucleotide of $AM_L6/AM_H6$ (SEQ ID NO:85/SEQ ID NO:59)
g. a light chain variable domain-encoding polynucleotide and a heavy chain variable domain-encoding polynucleotide of $AM_L7/AM_H7$ (SEQ ID NO:86/SEQ ID NO:60);
h. a light chain variable domain-encoding polynucleotide and a heavy chain variable domain-encoding polynucleotide of $AM_L8/AM_H8$ (SEQ ID NO:87/SEQ ID NO:61);
i. a light chain variable domain-encoding polynucleotide and a heavy chain variable domain-encoding polynucleotide of $AM_L9/AM_H9$ (SEQ ID NO:88/SEQ ID NO:62);
j. a light chain variable domain-encoding polynucleotide and a heavy chain variable domain-encoding polynucleotide of $AM_L10/AM_H10$ (SEQ ID NO:89/SEQ ID NO:63);
k. a light chain variable domain-encoding polynucleotide and a heavy chain variable domain-encoding polynucleotide of $AM_L11/AM_H11$ (SEQ ID NO:90/SEQ ID NO:64);
l. a light chain variable domain-encoding polynucleotide and a heavy chain variable domain-encoding polynucleotide of $AM_L12/AM_H12$ (SEQ ID NO:91/SEQ ID NO:65);
m. a light chain variable domain-encoding polynucleotide and a heavy chain variable domain-encoding polynucleotide of $AM_L13/AM_H13$ (SEQ ID NO:92/SEQ ID NO:66);
n. a light chain variable domain-encoding polynucleotide and a heavy chain variable domain-encoding polynucleotide of $AM_L14/AM_H14$ (SEQ ID NO:93/SEQ ID NO:67);
o. a light chain variable domain-encoding polynucleotide and a heavy chain variable domain-encoding polynucleotide of $AM_L15/AM_H15$ (SEQ ID NO:94/SEQ ID NO:68);
p. a light chain variable domain-encoding polynucleotide and a heavy chain variable domain-encoding polynucleotide of $AM_L16/AM_H16$ (SEQ ID NO:95/SEQ ID NO:69);
q. a light chain variable domain-encoding polynucleotide and a heavy chain variable domain-encoding polynucleotide of $AM_L17/AM_H17$ (SEQ ID NO:96/SEQ ID NO:70);
r. a light chain variable domain-encoding polynucleotide and a heavy chain variable domain-encoding polynucleotide of $AM_L18/AM_H18$ (SEQ ID NO:97/SEQ ID NO:71);
s. a light chain variable domain-encoding polynucleotide and a heavy chain variable domain-encoding polynucleotide of $AM_L19/AM_H19$ (SEQ ID NO:98/SEQ ID NO:72);
t. a light chain variable domain-encoding polynucleotide and a heavy chain variable domain-encoding polynucleotide of $AM_L20/AM_H20$ (SEQ ID NO:99/SEQ ID NO:73);
u. a light chain variable domain-encoding polynucleotide and a heavy chain variable domain-encoding polynucleotide of $AM_L21/AM_H21$ (SEQ ID NO:100/SEQ ID NO:74);
v. a light chain variable domain-encoding polynucleotide and a heavy chain variable domain-encoding polynucleotide of $AM_L22/AM_H22$ (SEQ ID NO:101/SEQ ID NO:75);
w. a light chain variable domain-encoding polynucleotide and a heavy chain variable domain-encoding polynucleotide of $AM_L23/AM_H23$ (SEQ ID NO: 102 or SEQ ID NO:103/SEQ ID NO:76);
x. a light chain variable domain-encoding polynucleotide and a heavy chain variable domain-encoding polynucleotide of $AM_L24/AM_H24$ (SEQ ID NO:104/SEQ ID NO:77);
y. a light chain variable domain-encoding polynucleotide and a heavy chain variable domain-encoding polynucleotide of $AM_L25/AM_H25$ (SEQ ID NO:105/SEQ ID NO:78); and
z. a light chain variable domain-encoding polynucleotide and a heavy chain variable domain-encoding polynucleotide of $AM_L26/AM_H26$ (SEQ ID NO:106/SEQ ID NO:79).

Embodiment 53: the polynucleotide of embodiment 51, wherein said polynucleotide hybridizes under stringent conditions to the full length complement of a polynucleotide selected from the group consisting of:
a. a light chain CDR1-encoding polynucleotide of SEQ ID NO:345, CDR2-encoding polynucleotide of SEQ ID NO:346, CDR3-encoding polynucleotide of SEQ ID NO:347 and a heavy chain CDR1-encoding polynucleotide of SEQ ID NO:266, CDR2-encoding polynucleotide of SEQ ID NO:267, and CDR3-encoding polynucleotide of SEQ ID NO:268 of antibody AM-1;
b. a light chain CDR1-encoding polynucleotide of SEQ ID NO:348, CDR2-encoding polynucleotide of SEQ ID NO:349, CDR3-encoding polynucleotide of SEQ ID NO:350 and a heavy chain CDR1-encoding polynucleotide of SEQ ID NO:269, CDR2-encoding polynucleotide of SEQ ID NO:270, CDR3-encoding polynucleotide of SEQ ID NO:271 of antibody AM-2;
c. a light chain CDR1-encoding polynucleotide of SEQ ID NO:351, CDR2-encoding polynucleotide of SEQ ID NO:352, CDR3-encoding polynucleotide of SEQ ID NO:353 and a heavy chain CDR1-encoding polynucleotide of SEQ ID NO:272, CDR2-encoding polynucleotide of SEQ ID NO:273, CDR3-encoding polynucleotide of SEQ ID NO:274 of antibody AM-3;
d. a light chain CDR1-encoding polynucleotide of SEQ ID NO:354, CDR2-encoding polynucleotide of SEQ ID NO:355, CDR3-encoding polynucleotide of SEQ ID NO:356 and a heavy chain CDR1-encoding polynucleotide of SEQ ID NO:275, CDR2-encoding polynucleotide of SEQ ID NO:276, CDR3-encoding polynucleotide of SEQ ID NO:277 of antibody AM-4;

e. a light chain CDR1-encoding polynucleotide of SEQ ID NO:357. CDR2-encoding polynucleotide of SEQ ID NO:358, CDR3-encoding polynucleotide of SEQ ID NO:359 and a heavy chain CDR1-encoding polynucleotide of SEQ ID NO:278, CDR2-encoding polynucleotide of SEQ ID NO:279, CDR3-encoding polynucleotide of SEQ ID NO:280 of antibody AM-5;

f. a light chain CDR1-encoding polynucleotide of SEQ ID NO:360, CDR2-encoding polynucleotide of SEQ ID NO:361, CDR3-encoding polynucleotide of SEQ ID NO:362 and a heavy chain CDR1-encoding polynucleotide of SEQ ID NO:281, CDR2-encoding polynucleotide of SEQ ID NO:282, CDR3-encoding polynucleotide of SEQ ID NO:283 of antibody AM-6;

g. a light chain CDR1-encoding polynucleotide of SEQ ID NO:363, CDR2-encoding polynucleotide of SEQ ID NO:364, CDR3-encoding polynucleotide of SEQ ID NO:365 and a heavy chain CDR1-encoding polynucleotide of SEQ ID NO:284, CDR2-encoding polynucleotide of SEQ ID NO:285. CDR3-encoding polynucleotide of SEQ ID NO:286 of antibody AM-7;

h. a light chain CDR1-encoding polynucleotide of SEQ ID NO:366, CDR2-encoding polynucleotide of SEQ ID NO:367, CDR3-encoding polynucleotide of SEQ ID NO:368 and a heavy chain CDR1-encoding polynucleotide of SEQ ID NO:287, CDR2-encoding polynucleotide of SEQ ID NO:288, CDR3-encoding polynucleotide of SEQ ID NO:289 of antibody AM-8;

i. a light chain CDR1-encoding polynucleotide of SEQ ID NO:369, CDR2-encoding polynucleotide of SEQ ID NO:370, CDR3-encoding polynucleotide of SEQ ID NO:371 and a heavy chain CDR1-encoding polynucleotide of SEQ ID NO:290, CDR2-encoding polynucleotide of SEQ ID NO:291, CDR3-encoding polynucleotide of SEQ ID NO:292 of antibody AM-9;

j. a light chain CDR1-encoding polynucleotide of SEQ ID NO:372, CDR2-encoding polynucleotide of SEQ ID NO:373, CDR3-encoding polynucleotide of SEQ ID NO:374 and a heavy chain CDR1-encoding polynucleotide of SEQ ID NO:293, CDR2-encoding polynucleotide of SEQ ID NO:294, CDR3-encoding polynucleotide of SEQ ID NO:295 of antibody AM-10;

k. a light chain CDR1-encoding polynucleotide of SEQ ID NO:375, CDR2-encoding polynucleotide of SEQ ID NO:376, CDR3-encoding polynucleotide of SEQ ID NO:377 and a heavy chain CDR1-encoding polynucleotide of SEQ ID NO:296, CDR2-encoding polynucleotide of SEQ ID NO:297, CDR3-encoding polynucleotide of SEQ ID NO:298 of antibody AM-11;

l. a light chain CDR1-encoding polynucleotide of SEQ ID NO:378, CDR2-encoding polynucleotide of SEQ ID NO:379, CDR3-encoding polynucleotide of SEQ ID NO:380 and a heavy chain CDR1-encoding polynucleotide of SEQ ID NO:299, CDR2-encoding polynucleotide of SEQ ID NO:300, CDR3-encoding polynucleotide of SEQ ID NO:301 of antibody AM-12;

m. a light chain CDR1-encoding polynucleotide of SEQ ID NO:381, CDR2-encoding polynucleotide of SEQ ID NO:382, CDR3-encoding polynucleotide of SEQ ID NO:383 and a heavy chain CDR1-encoding polynucleotide of SEQ ID NO:302, CDR2-encoding polynucleotide of SEQ ID NO:303, CDR3-encoding polynucleotide of SEQ ID NO:304 of antibody AM-13;

n. a light chain CDR1-encoding polynucleotide of SEQ ID NO:384, CDR2-encoding polynucleotide of SEQ ID NO:385, CDR3-encoding polynucleotide of SEQ ID NO:386 and a heavy chain CDR1-encoding polynucleotide of SEQ ID NO:305, CDR2-encoding polynucleotide of SEQ ID NO:306, CDR3-encoding polynucleotide of SEQ ID NO:307 of antibody AM-14;

o. a light chain CDR1-encoding polynucleotide of SEQ ID NO:387, CDR2-encoding polynucleotide of SEQ ID NO:388, CDR3-encoding polynucleotide of SEQ ID NO:389 and a heavy chain CDR1-encoding polynucleotide of SEQ ID NO:308, CDR2-encoding polynucleotide of SEQ ID NO:309, CDR3-encoding polynucleotide of SEQ ID NO:310 of antibody AM-15;

p. a light chain CDR1-encoding polynucleotide of SEQ ID NO:390, CDR2-encoding polynucleotide of SEQ ID NO:391, CDR3-encoding polynucleotide of SEQ ID NO:392 and a heavy chain CDR1-encoding polynucleotide of SEQ ID NO:311, CDR2-encoding polynucleotide of SEQ ID NO:312, CDR3-encoding polynucleotide of SEQ ID NO:313 of antibody AM-16;

q. a light chain CDR1-encoding polynucleotide of SEQ ID NO:393, CDR2-encoding polynucleotide of SEQ ID NO:394, CDR3-encoding polynucleotide of SEQ ID NO:395 and a heavy chain CDR1-encoding polynucleotide of SEQ ID NO:314, CDR2-encoding polynucleotide of SEQ ID NO:315, CDR3-encoding polynucleotide of SEQ ID NO:316 of antibody AM-17;

r. a light chain CDR1-encoding polynucleotide of SEQ ID NO:396, CDR2-encoding polynucleotide of SEQ ID NO:397, CDR3-encoding polynucleotide of SEQ ID NO:398 and a heavy chain CDR1-encoding polynucleotide of SEQ ID NO:317, CDR2-encoding polynucleotide of SEQ ID NO:318, CDR3-encoding polynucleotide of SEQ ID NO:319 of antibody AM-18;

s. a light chain CDR1-encoding polynucleotide of SEQ ID NO:399, CDR2-encoding polynucleotide of SEQ ID NO:400, CDR3-encoding polynucleotide of SEQ ID NO:401 and a heavy chain CDR1-encoding polynucleotide of SEQ ID NO:320, CDR2-encoding polynucleotide of SEQ ID NO:321, CDR3-encoding polynucleotide of SEQ ID NO:322 of antibody AM-19;

t. a light chain CDR1-encoding polynucleotide of SEQ ID NO:402, CDR2-encoding polynucleotide of SEQ ID NO:403, CDR3-encoding polynucleotide of SEQ ID NO:404 and a heavy chain CDR1-encoding polynucleotide of SEQ ID NO:323, CDR2-encoding polynucleotide of SEQ ID NO:324, CDR3-encoding polynucleotide of SEQ ID NO:325 of antibody AM-20;

u. a light chain CDR1-encoding polynucleotide of SEQ ID NO:405, CDR2-encoding polynucleotide of SEQ ID NO:406, CDR3-encoding polynucleotide of SEQ ID NO:407 and a heavy chain CDR1-encoding polynucleotide of SEQ ID NO:326, CDR2-encoding polynucleotide of SEQ ID NO:327, CDR3-encoding polynucleotide of SEQ ID NO:328 of antibody AM-21;

v. a light chain CDR1-encoding polynucleotide of SEQ ID NO:408, CDR2-encoding polynucleotide of SEQ ID NO:409, CDR3-encoding polynucleotide of SEQ ID NO:410 and a heavy chain CDR1 SEQ ID NO:329, CDR2-encoding polynucleotide of SEQ ID NO:330, CDR3-encoding polynucleotide of SEQ ID NO:331 of antibody AM-22;

w. a light chain CDR1-encoding polynucleotide of SEQ ID NO:411 CDR2-encoding polynucleotide of SEQ ID NO:412, CDR3-encoding polynucleotide of SEQ ID NO:413 and a heavy chain CDR1-encoding polynucleotide of SEQ ID NO:332, CDR2-encoding polynucleotide of SEQ ID NO:333, CDR3-encoding polynucleotide of SEQ ID NO:334 of antibody AM-23;

x. a light chain CDR1-encoding polynucleotide of SEQ ID NO:414, CDR2-encoding polynucleotide of SEQ ID NO:415, CDR3-encoding polynucleotide of SEQ ID NO:416 and a heavy chain CDR1-encoding polynucleotide of SEQ ID NO:332, CDR2-encoding polynucleotide of SEQ ID NO:333, CDR3-encoding polynucleotide of SEQ ID NO:334 of antibody AM-23;

y. a light chain CDR1-encoding polynucleotide of SEQ ID NO:417, CDR2-encoding polynucleotide of SEQ ID NO:418, CDR3-encoding polynucleotide of SEQ ID NO:419 and a heavy chain CDR1-encoding polynucleotide of SEQ ID NO:335, CDR2-encoding polynucleotide of SEQ ID NO:336, CDR3-encoding polynucleotide of SEQ ID NO:337 of antibody AM-24;

z. a light chain CDR1-encoding polynucleotide of SEQ ID NO:420. CDR2-encoding polynucleotide of SEQ ID NO:421, CDR3-encoding polynucleotide of SEQ ID NO:422 and a heavy chain CDR1-encoding polynucleotide of SEQ ID NO:338, CDR2-encoding polynucleotide of SEQ ID NO:339, CDR3-encoding polynucleotide of SEQ ID NO:340 of antibody AM-25; or z.2. a light chain CDR1-encoding polynucleotide of SEQ ID NO:423, CDR2-encoding polynucleotide of SEQ ID NO:424, CDR3-encoding polynucleotide of SEQ ID NO:425 and a heavy chain CDR1-encoding polynucleotide of SEQ ID NO:341, CDR2-encoding polynucleotide of SEQ ID NO:342, CDR3-encoding polynucleotide of SEQ ID NO:343 of antibody AM-26.

Embodiment 54: the polynucleotide of embodiment 51. wherein said polynucleotide encodes a polypeptide comprising an amino acid sequence selected from the group consisting of:

a. a light chain variable domain and a heavy chain variable domain of $AM_L1/AM_H1$ (SEQ ID NO:27/SEQ ID NO:1);
b. a light chain variable domain and a heavy chain variable domain of $AM_L2/AM_H2$ (SEQ ID NO:28/SEQ ID NO:2);
c. a light chain variable domain and a heavy chain variable domain of $AM_L3/AM_H3$ (SEQ ID NO:29/SEQ ID NO:3);
d. a light chain variable domain and a heavy chain variable domain of $AM_L4/AM_H4$ (SEQ ID NO:30/SEQ ID NO:4);
e. a light chain variable domain and a heavy chain variable domain of $AM_L5/AM_H5$ (SEQ ID NO:31/SEQ ID NO:5);
f. a light chain variable domain and a heavy chain variable domain of $AM_L6/AM_H6$ (SEQ ID NO:32/SEQ ID NO:6)
g. a light chain variable domain and a heavy chain variable domain of $AM_L7/AM_H7$ (SEQ ID NO:33/SEQ ID NO:7);
h. a light chain variable domain and a heavy chain variable domain of $AM_L8/AM_H8$ (SEQ ID NO:34/SEQ ID NO:8);
i. a light chain variable domain and a heavy chain variable domain of $AM_L9/AM_H9$ (SEQ ID NO:35/SEQ ID NO:9);
j. a light chain variable domain and a heavy chain variable domain of $AM_L10/AM_H10$ (SEQ ID NO:36/SEQ ID NO:10);
k. a light chain variable domain and a heavy chain variable domain of $AM_L11/AM_H11$ (SEQ ID NO:37/SEQ ID NO:11);
l. a light chain variable domain and a heavy chain variable domain of $AM_L12/AM_H12$ (SEQ ID NO:38/SEQ ID NO:12);
m. a light chain variable domain and a heavy chain variable domain of $AM_L13/AM_H13$ (SEQ ID NO:39/SEQ ID NO:13);
n. a light chain variable domain and a heavy chain variable domain of $AM_L14/AM_H14$ (SEQ ID NO:40/SEQ ID NO:14);
o. a light chain variable domain and a heavy chain variable domain of $AM_L15/AM_H15$ (SEQ ID NO:41/SEQ ID NO:15);
p. a light chain variable domain and a heavy chain variable domain of $AM_L16/AM_H16$ (SEQ ID NO:42/SEQ ID NO:16);
q. a light chain variable domain and a heavy chain variable domain of $AM_L17/AM_H17$ (SEQ ID NO:43/SEQ ID NO:17);
r. a light chain variable domain and a heavy chain variable domain of $AM_L18/AM_H18$ (SEQ ID NO:44/SEQ ID NO:18);
s. a light chain variable domain and a heavy chain variable domain of $AM_L19/AM_H19$ (SEQ ID NO:45/SEQ ID NO:19);
t. a light chain variable domain and a heavy chain variable domain of $AM_L20/AM_H20$ (SEQ ID NO:46/SEQ ID NO:20);
u. a light chain variable domain and a heavy chain variable domain of $AM_L21/AM_H21$ (SEQ ID NO:47/SEQ ID NO:21).
v. a light chain variable domain and a heavy chain variable domain of $AM_L22/AM_H22$ (SEQ ID NO:48/SEQ ID NO:22);
w. a light chain variable domain and a heavy chain variable domain of $AM_L23/AM_H23$ (SEQ ID NO: 49 or SEQ ID NO:50/SEQ ID NO:23);
x. a light chain variable domain and a heavy chain variable domain of $AM_L24/AM_H24$ (SEQ ID NO:51/SEQ ID NO:24);
y. a light chain variable domain and a heavy chain variable domain of $AM_L25/AM_H25$ (SEQ ID NO:52/SEQ ID NO:25); and
z. a light chain variable domain and a heavy chain variable domain of $AM_L26/AM_H26$ (SEQ ID NO:53/SEQ ID NO:26).

Embodiment 55. The polynucleotide of embodiment 51, wherein said polynucleotide encodes a polypeptide comprising an amino acid sequence selected from the group consisting of:

a. a light chain CDR1 (SEQ ID NO:185), CDR2 (SEQ ID NO:186), CDR3 (SEQ ID NO:187) and a heavy chain CDR1 (SEQ ID NO:107), CDR2 (SEQ ID NO:108), CDR3 (SEQ ID NO:109) of antibody AM-1;
b. a light chain CDR1 (SEQ ID NO:188), CDR2 (SEQ ID NO:189), CDR3 (SEQ ID NO:190) and a heavy chain CDR1 (SEQ ID NO: 110), CDR2 (SEQ ID NO:111), CDR3 (SEQ ID NO:112) of antibody AM-2;
c. a light chain CDR1 (SEQ ID NO:191), CDR2 (SEQ ID NO:192), CDR3 (SEQ ID NO:193) and a heavy chain CDR1 (SEQ ID NO: 113), CDR2 (SEQ ID NO: 114), CDR3 (SEQ ID NO:115) of antibody AM-3;
d. a light chain CDR1 (SEQ ID NO:194), CDR2 (SEQ ID NO:195), CDR3 (SEQ ID NO:196) and a heavy chain CDR1 (SEQ ID NO: 116), CDR2 (SEQ ID NO: 117), CDR3 (SEQ ID NO: 118) of antibody AM-4;

e. a light chain CDR1 (SEQ ID NO:197), CDR2 (SEQ ID NO:198), CDR3 (SEQ ID NO:199) and a heavy chain CDR1 (SEQ ID NO:119), CDR2 (SEQ ID NO: 120), CDR3 (SEQ ID NO:121) of antibody AM-5;

f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;

g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;

h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;

i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;

j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;

k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO:139) of antibody AM-11;

l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;

m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;

n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;

o. a light chain CDR1 (SEQ ID NO:227), CDR2 (SEQ ID NO:228), CDR3 (SEQ ID NO:229) and a heavy chain CDR1 (SEQ ID NO: 149), CDR2 (SEQ ID NO:150), CDR3 (SEQ ID NO:151) of antibody AM-15;

p. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;

q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;

r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;

s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;

t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;

u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;

v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;

w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;

x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;

y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO: 178) of antibody AM-24;

z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; or z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO: 183), CDR3 (SEQ ID NO:184) of antibody AM-26.

Embodiment 6: the polynucleotide of embodiment 2, wherein said polynucleotide is selected from the group consisting of:

a. a light chain variable domain-encoding polynucleotide and a heavy chain variable domain-encoding polynucleotide of $AM_L1/AM_H1$ (SEQ ID NO:80/SEQ ID NO:54);

b. a light chain variable domain-encoding polynucleotide and a heavy chain variable domain-encoding polynucleotide of $AM_L2/AM_H2$ (SEQ ID NO:81/SEQ ID NO:55);

c. a light chain variable domain-encoding polynucleotide and a heavy chain variable domain-encoding polynucleotide of $AM_L3/AM_H3$ (SEQ ID NO:82/SEQ ID NO:56);

d. a light chain variable domain-encoding polynucleotide and a heavy chain variable domain-encoding polynucleotide of $AM_L4/AM_H4$ (SEQ ID NO:83/SEQ ID NO:57);

e. a light chain variable domain-encoding polynucleotide and a heavy chain variable domain-encoding polynucleotide of $AM_L5/AM_H5$ (SEQ ID NO:84/SEQ ID NO:58);

f. a light chain variable domain-encoding polynucleotide and a heavy chain variable domain-encoding polynucleotide of $AM_L6/AM_H6$ (SEQ ID NO:85/SEQ ID NO:59)

g. a light chain variable domain-encoding polynucleotide and a heavy chain variable domain-encoding polynucleotide of $AM_L7/AM_H7$ (SEQ ID NO:86/SEQ ID NO:60);

h. a light chain variable domain-encoding polynucleotide and a heavy chain variable domain-encoding polynucleotide of $AM_L8/AM_H8$ (SEQ ID NO:87/SEQ ID NO:61);

i. a light chain variable domain-encoding polynucleotide and a heavy chain variable domain-encoding polynucleotide of $AM_L9/AM_H9$ (SEQ ID NO:88/SEQ ID NO:62);

j. a light chain variable domain-encoding polynucleotide and a heavy chain variable domain-encoding polynucleotide of $AM_L10/AM_H10$ (SEQ ID NO:89/SEQ ID NO:63);

k. a light chain variable domain-encoding polynucleotide and a heavy chain variable domain-encoding polynucleotide of $AM_L11/AM_H11$ (SEQ ID NO:90/SEQ ID NO:64);

l. a light chain variable domain-encoding polynucleotide and a heavy chain variable domain-encoding polynucleotide of $AM_L12/AM_H12$ (SEQ ID NO:91/SEQ ID NO:65);

m. a light chain variable domain-encoding polynucleotide and a heavy chain variable domain-encoding polynucleotide of $AM_L13/AM_H13$ (SEQ ID NO:92/SEQ ID NO:66);

n. a light chain variable domain-encoding polynucleotide and a heavy chain variable domain-encoding polynucleotide of $AM_L14/AM_H14$ (SEQ ID NO:93/SEQ ID NO:67);

o. a light chain variable domain-encoding polynucleotide and a heavy chain variable domain-encoding polynucleotide of $AM_L15/AM_H15$ (SEQ ID NO:94/SEQ ID NO:68);

p. a light chain variable domain-encoding polynucleotide and a heavy chain variable domain-encoding polynucleotide of $AM_L16/AM_H16$ (SEQ ID NO:95/SEQ ID NO:69);

q. a light chain variable domain-encoding polynucleotide and a heavy chain variable domain-encoding polynucleotide of $AM_L17/AM_H7$ (SEQ ID NO:96/SEQ ID NO:70);

r. a light chain variable domain-encoding polynucleotide and a heavy chain variable domain-encoding polynucleotide of $AM_L18/AM_H18$ (SEQ ID NO:97/SEQ ID NO:71);

s. a light chain variable domain-encoding polynucleotide and a heavy chain variable domain-encoding polynucleotide of $AM_L19/AM_H19$ (SEQ ID NO:98/SEQ ID NO:72);

t. a light chain variable domain-encoding polynucleotide and a heavy chain variable domain-encoding polynucleotide of $AM_L20/AM_H20$ (SEQ ID NO:99/SEQ ID NO:73);

u. a light chain variable domain-encoding polynucleotide and a heavy chain variable domain-encoding polynucleotide of $AM_L21/AM_H21$ (SEQ ID NO:100/SEQ ID NO:74);

v. a light chain variable domain-encoding polynucleotide and a heavy chain variable domain-encoding polynucleotide of $AM_L22/AM_H22$ (SEQ ID NO:101/SEQ ID NO:75);

w. a light chain variable domain-encoding polynucleotide and a heavy chain variable domain-encoding polynucleotide of $AM_L23/AM_H23$ (SEQ ID NO: 102 or SEQ ID NO:103/SEQ ID NO:76);

x. a light chain variable domain-encoding polynucleotide and a heavy chain variable domain-encoding polynucleotide of $AM_L24/AM_H24$ (SEQ ID NO:104/SEQ ID NO:77);

y. a light chain variable domain-encoding polynucleotide and a heavy chain variable domain-encoding polynucleotide of $AM_L25/AM_H25$ (SEQ ID NO:105/SEQ ID NO:78); and z. a light chain variable domain-encoding polynucleotide and a heavy chain variable domain-encoding polynucleotide of $AM_L26/AM_H26$ (SEQ ID NO:106/SEQ ID NO:79).

Embodiment 57: the polynucleotide of embodiment 53, wherein said polynucleotide is selected from the group consisting of:

a. a light chain CDR1-encoding polynucleoside of SEQ ID NO:345, CDR2-encoding polynucleotide of SEQ ID NO:346, CDR3-encoding polynucleotide of SEQ ID NO:347 and a heavy chain CDR1-encoding polynucleotide of SEQ ID NO:266, CDR2-encoding polynucleotide of SEQ ID NO:267, and CDR3-encoding polynucleotide of SEQ ID NO:268 of antibody AM-1;

b. a light chain CDR1-encoding polynucleotide of SEQ ID NO:348, CDR2-encoding polynucleotide of SEQ ID NO:349, CDR3-encoding polynucleotide of SEQ ID NO:350 and a heavy chain CDR1-encoding polynucleotide of SEQ ID NO:269, CDR2-encoding polynucleotide of SEQ ID NO:270, CDR3-encoding polynucleotide of SEQ ID NO:271 of antibody AM-2;

c. a light chain CDR1-encoding polynucleotide of SEQ ID NO:351, CDR2-encoding polynucleotide of SEQ ID NO:352, CDR3-encoding polynucleotide of SEQ ID NO:353 and a heavy chain CDR1-encoding polynucleotide of SEQ ID NO:272, CDR2-encoding polynucleotide of SEQ ID NO:273, CDR3-encoding polynucleotide of SEQ ID NO:274 of antibody AM-3;

d. a light chain CDR1-encoding polynucleotide of SEQ ID NO:354, CDR2-encoding polynucleotide of SEQ ID NO:355. CDR3-encoding polynucleotide of SEQ ID NO:356 and a heavy chain CDR1-encoding polynucleotide of SEQ ID NO:275, CDR2-encoding polynucleotide of SEQ ID NO:276, CDR3-encoding polynucleotide of SEQ ID NO:277 of antibody AM-4;

e. a light chain CDR1-encoding polynucleotide of SEQ ID NO:357, CDR2-encoding polynucleotide of SEQ ID NO:358, CDR3-encoding polynucleotide of SEQ ID NO:359 and a heavy chain CDR1-encoding polynucleotide of SEQ ID NO:278, CDR2-encoding polynucleotide of SEQ ID NO:279, CDR3-encoding polynucleotide of SEQ ID NO:280 of antibody AM-5;

f. a light chain CDR1-encoding polynucleotide of SEQ ID NO:360. CDR2-encoding polynucleotide of SEQ ID NO:361. CDR3-encoding polynucleotide of SEQ ID NO:362 and a heavy chain CDR1-encoding polynucleotide of SEQ ID NO:281, CDR2-encoding polynucleotide of SEQ ID NO:282, CDR3-encoding polynucleotide of SEQ ID NO:283 of antibody AM-6;

g. a light chain CDR1-encoding polynucleotide of SEQ ID NO:363, CDR2-encoding polynucleotide of SEQ ID NO:364, CDR3-encoding polynucleotide of SEQ ID NO:365 and a heavy chain CDR1-encoding polynucleotide of SEQ ID NO:284, CDR2-encoding polynucleotide of SEQ ID NO:285, CDR3-encoding polynucleotide of SEQ ID NO:286 of antibody AM-7;

h. a light chain CDR1-encoding polynucleotide of SEQ ID NO:366. CDR2-encoding polynucleotide of SEQ ID NO:367, CDR3-encoding polynucleotide of SEQ ID NO:368 and a heavy chain CDR1-encoding polynucleotide of SEQ ID NO:287, CDR2-encoding polynucleotide of SEQ ID NO:288, CDR3-encoding polynucleotide of SEQ ID NO:289 of antibody AM-8;

i. a light chain CDR1-encoding polynucleotide of SEQ ID NO:369, CDR2-encoding polynucleotide of SEQ ID NO:370, CDR3-encoding polynucleotide of SEQ ID NO:371 and a heavy chain CDR1-encoding polynucleotide of SEQ ID NO:290, CDR2-encoding polynucleotide of SEQ ID NO:291. CDR3-encoding polynucleotide of SEQ ID NO:292 of antibody AM-9;
j. a light chain CDR1-encoding polynucleotide of SEQ ID NO:372, CDR2-encoding polynucleotide of SEQ ID NO:373. CDR3-encoding polynucleotide of SEQ ID NO:374 and a heavy chain CDR1-encoding polynucleotide of SEQ ID NO:293, CDR2-encoding polynucleotide of SEQ ID NO:294, CDR3-encoding polynucleotide of SEQ ID NO:295 of antibody AM-10;
k. a light chain CDR1-encoding polynucleotide of SEQ ID NO:375, CDR2-encoding polynucleotide of SEQ ID NO:376, CDR3-encoding polynucleotide of SEQ ID NO:377 and a heavy chain CDR1-encoding polynucleotide of SEQ ID NO:296, CDR2-encoding polynucleotide of SEQ ID NO:297. CDR3-encoding polynucleotide of SEQ ID NO:298 of antibody AM-11;
l. a light chain CDR1-encoding polynucleotide of SEQ ID NO:378, CDR2-encoding polynucleotide of SEQ ID NO:379. CDR3-encoding polynucleotide of SEQ ID NO:380 and a heavy chain CDR1-encoding polynucleotide of SEQ ID NO:299. CDR2-encoding polynucleotide of SEQ ID NO:300, CDR3-encoding polynucleotide of SEQ ID NO:301 of antibody AM-12;
m. a light chain CDR1-encoding polynucleotide of SEQ ID NO:381, CDR2-encoding polynucleotide of SEQ ID NO:382, CDR3-encoding polynucleotide of SEQ ID NO:383 and a heavy chain CDR1-encoding polynucleotide of SEQ ID NO:302, CDR2-encoding polynucleotide of SEQ ID NO:303, CDR3-encoding polynucleotide of SEQ ID NO:304 of antibody AM-13;
n. a light chain CDR1-encoding polynucleotide of SEQ ID NO:384, CDR2-encoding polynucleotide of SEQ ID NO:385, CDR3-encoding polynucleotide of SEQ ID NO:386 and a heavy chain CDR1-encoding polynucleotide of SEQ ID NO:305, CDR2-encoding polynucleotide of SEQ ID NO:306. CDR3-encoding polynucleotide of SEQ ID NO:307 of antibody AM-14;
o. a light chain CDR1-encoding polynucleotide of SEQ ID NO:387, CDR2-encoding polynucleotide of SEQ ID NO:388, CDR3-encoding polynucleotide of SEQ ID NO:389 and a heavy chain CDR1-encoding polynucleotide of SEQ ID NO:308, CDR2-encoding polynucleotide of SEQ ID NO:309, CDR3-encoding polynucleotide of SEQ ID NO:310 of antibody AM-15;
p. a light chain CDR1-encoding polynucleotide of SEQ ID NO:390, CDR2-encoding polynucleotide of SEQ ID NO:391, CDR3-encoding polynucleotide of SEQ ID NO:392 and a heavy chain CDR1-encoding polynucleotide of SEQ ID NO:311, CDR2-encoding polynucleotide of SEQ ID NO:312, CDR3-encoding polynucleotide of SEQ ID NO:313 of antibody AM-16;
q. a light chain CDR1-encoding polynucleotide of SEQ ID NO:393, CDR2-encoding polynucleotide of SEQ ID NO:394, CDR3-encoding polynucleotide of SEQ ID NO:395 and a heavy chain CDR1-encoding polynucleotide of SEQ ID NO:314, CDR2-encoding polynucleotide of SEQ ID NO:315, CDR3-encoding polynucleotide of SEQ ID NO:316 of antibody AM-17;
r. a light chain CDR1-encoding polynucleotide of SEQ ID NO:396, CDR2-encoding polynucleotide of SEQ ID NO:397, CDR3-encoding polynucleotide of SEQ ID NO:398 and a heavy chain CDR1-encoding polynucleotide of SEQ ID NO:317, CDR2-encoding polynucleotide of SEQ ID NO:318, CDR3-encoding polynucleotide of SEQ ID NO:319 of antibody AM-18;
s. a light chain CDR1-encoding polynucleotide of SEQ ID NO:399, CDR2-encoding polynucleotide of SEQ ID NO:400, CDR3-encoding polynucleotide of SEQ ID NO:401 and a heavy chain CDR1-encoding polynucleotide of SEQ ID NO:320, CDR2-encoding polynucleotide of SEQ ID NO:321, CDR3-encoding polynucleotide of SEQ ID NO:322 of antibody AM-19;
t. a light chain CDR1-encoding polynucleotide of SEQ ID NO:402, CDR2-encoding polynucleotide of SEQ ID NO:403, CDR3-encoding polynucleotide of SEQ ID NO:404 and a heavy chain CDR1-encoding polynucleotide of SEQ ID NO:323, CDR2-encoding polynucleotide of SEQ ID NO:324, CDR3-encoding polynucleotide of SEQ ID NO:325 of antibody AM-20;
u. a light chain CDR1-encoding polynucleotide of SEQ ID NO:405, CDR2-encoding polynucleotide of SEQ ID NO:406, CDR3-encoding polynucleotide of SEQ ID NO:407 and a heavy chain CDR1-encoding polynucleotide of SEQ ID NO:326, CDR2-encoding polynucleotide of SEQ ID NO:327, CDR3-encoding polynucleotide of SEQ ID NO:328 of antibody AM-21;
v. a light chain CDR1-encoding polynucleotide of SEQ ID NO:408. CDR2-encoding polynucleotide of SEQ ID NO:409, CDR3-encoding polynucleotide of SEQ ID NO:410 and a heavy chain CDR1 SEQ ID NO:329, CDR2-encoding polynucleotide of SEQ ID NO:330, CDR3-encoding polynucleotide of SEQ ID NO:331 of antibody AM-22;
w. a light chain CDR1-encoding polynucleotide of SEQ ID NO:411, CDR2-encoding polynucleotide of SEQ ID NO:412, CDR3-encoding polynucleotide of SEQ ID NO:413 and a heavy chain CDR1-encoding polynucleotide of SEQ ID NO:332, CDR2-encoding polynucleotide of SEQ ID NO:333, CDR3-encoding polynucleotide of SEQ ID NO:334 of antibody AM-23;
x. a light chain CDR1-encoding polynucleotide of SEQ ID NO:414, CDR2-encoding polynucleotide of SEQ ID NO:415, CDR3-encoding polynucleotide of SEQ ID NO:416 and a heavy chain CDR1-encoding polynucleotide of SEQ ID NO:332, CDR2-encoding polynucleotide of SEQ ID NO:333, CDR3-encoding polynucleotide of SEQ ID NO:334 of antibody AM-23;
y. a light chain CDR1-encoding polynucleotide of SEQ ID NO:417, CDR2-encoding polynucleotide of SEQ ID NO:418, CDR3-encoding polynucleotide of SEQ ID NO:419 and a heavy chain CDR1-encoding polynucleotide of SEQ ID NO:335, CDR2-encoding polynucleotide of SEQ ID NO:336, CDR3-encoding polynucleotide of SEQ ID NO:337 of antibody AM-24;
z. a light chain CDR1-encoding polynucleotide of SEQ ID NO:420, CDR2-encoding polynucleotide of SEQ ID NO:421. CDR3-encoding polynucleotide of SEQ ID NO:422 and a heavy chain CDR1-encoding polynucleotide of SEQ ID NO:338, CDR2-encoding polynucleotide of SEQ ID NO:339, CDR3-encoding polynucleotide of SEQ ID NO:340 of antibody AM-25; or
z.2. a light chain CDR1-encoding polynucleotide of SEQ ID NO:423, CDR2-encoding polynucleotide of SEQ ID NO:424, CDR3-encoding polynucleotide of SEQ ID NO:425 and a heavy chain CDR1-encoding polynucleotide of SEQ ID NO:341, CDR2-encoding polynucleotide of SEQ ID NO:342, CDR3-encoding polynucleotide of SEQ ID NO:343 of antibody AM-26.

Embodiment 58: an isolated polynucleotide, wherein said polynucleotide encodes a polypeptide comprising
a. a heavy chain CDR1 comprising an amino acid sequence selected from the group consisting of:

i. X₁YGIS, wherein X₁ is selected from the group consisting of R, S and G;
b. a heavy chain CDR2 comprising an amino acid sequence selected from the group consisting of:
   i. WISX₁YX₂GNTX₃YAQX₄X₅QG, wherein X₁ is selected from the group consisting of A, X₂ is selected from the group consisting of N, S and K, X₃ is selected from the group consisting of N and K, X₄ is selected from the group consisting of K and N, and X₅ is selected from the group consisting of L and F;
c. a heavy chain CDR3 comprising an amino acid sequence selected from the group consisting of:
   i. X₁QLX₂X₃DY, wherein X₁ is selected from the group consisting of R and K, X₂ is selected from the group consisting of Y, V, and A, and X₃ is selected from the group consisting of F and L;
   ii. X₁QLX₂FDY, wherein X₁ is selected from the group consisting of R and K, and X₂ is selected from the group consisting of Y and V;
d. a light chain CDR1 comprising an amino acid sequence selected from the group consisting of:
   i. RASQSX₁X₂X₃X₄LA, wherein X₁ is selected from the group consisting of V and I, X₂ is selected from the group consisting of I and S, X₃ is selected from the group consisting of S and T, X₄ is selected from the group consisting of N and S, and X is selected from the group consisting of A and N, and
   ii. RASQSX₁SSNLA, wherein X₁ is selected from the group consisting of V and I;
e. a light chain CDR2 comprising an amino acid sequence selected from the group consisting of:
   i. X₁X₂STRAX₃, wherein X₁ is selected from the group consisting of G and D, X₂ is selected from the group consisting of A and T, and X₃ is selected from the group consisting of T and A, and
   ii. X₁ASTRAX₂, wherein X₁ is selected from the group consisting of G and D, and X₂ is selected from the group consisting of A and T; and
f. a light chain CDR3 comprising an amino acid sequence selected from the group consisting of:
   i. QQYDX₁WPLT, wherein X₁ is selected from the group consisting of N, T, and I;
wherein said polypeptide specifically binds IL-17 receptor A.

Embodiment 59. The polynucleotide of embodiment 58, wherein said polynucleotide encodes a polypeptide wherein said polypeptide comprises:
a. a heavy chain CDR1 amino acid sequence comprising X₁YGIS, wherein X₁ is selected from the group consisting of R, S and G;
b. a heavy chain CDR2 amino acid sequence comprising WISX₁YX₂GNTX₃YAQX₄X₅QG, wherein X₁ is selected from the group consisting of A, X₂ is selected from the group consisting of N, S and K, X₃ is selected from the group consisting of N and K, X₄ is selected from the group consisting of K and N, and X₅ is selected from the group consisting of L and F;
c. a heavy chain CDR3 amino acid sequence comprising X₁QLX₂FDY, wherein X₁ is selected from the group consisting of R and K, and X₂ is selected from the group consisting of Y and V;
d. a light chain CDR1 amino acid sequence comprising RASQSX₁SSNLA, wherein X₁ is selected from the group consisting of V and I;
e. a light chain CDR2 amino acid sequence comprising X₁ASTRAX₂, wherein X₁ is selected from the group consisting of G and D, and X₂ is selected from the group consisting of A and T; and
f. a light chain CDR3 amino acid sequence comprising QQYDX₁WPLT, wherein X₁ is selected from the group consisting of N, T, and I; wherein said polypeptide specifically binds IL-17 receptor A.

Embodiment 60: a plasmid, comprising said polynucleotide of embodiment 51. Embodiment 61: the plasmid of embodiment 60, wherein said plasmid is an expression vector. Embodiment 62: an isolated cell, comprising said plasmid of embodiment 60. Embodiment 63: the isolated cell of embodiment 62, wherein a chromosome of said cell comprises said polynucleotide. Embodiment 64: the isolated cell of embodiment 62, wherein said cell is a hybridoma. Embodiment 65: the isolated cell of embodiment 62, wherein said cell comprises the expression vector of embodiment 61.

Embodiment 66: the isolated cell of embodiment 65, wherein said cell is a selected from the group consisting of: a. a prokaryotic cell; b. a eukaryotic cell; c. a mammalian cell; d. an insect cell; and e. a CHO cell. Embodiment 67: a method of making a polypeptide that specifically binds IL-17 receptor A, comprising incubating said isolated cell of embodiment 65 under conditions that allow it to express said polypeptide. Embodiment 68: the polynucleotide of embodiment 51, wherein said polynucleotide encodes said polypeptide and wherein said polypeptide is an antibody that specifically binds IL-17 receptor A, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody.

Embodiment 69: the polynucleotide of embodiment 68, wherein said polynucleotide encodes said antibody and wherein said antibody is selected from the group consisting of:
a) an antibody consisting of a heavy chain sequence of SEQ ID NO:427 and a light chain sequence of SEQ ID NO:429;
b) an antibody consisting essentially of a heavy chain sequence of SEQ ID NO:427 and a light chain sequence of SEQ ID NO:429;
c) an antibody comprising a heavy chain sequence of SEQ ID NO: 427;
d) an antibody comprising a light chain sequence of SEQ ID NO:429;
e) an antibody comprising a heavy chain sequence of SEQ ID NO: 427 and a light chain sequence of SEQ ID NO:429;
f) an antibody or an IL-17 receptor A binding fragment thereof comprising a heavy chain sequence of SEQ ID NO: 427;
g) an antibody or an IL-17 receptor A binding fragment thereof comprising a light chain sequence of SEQ ID NO:429;
h) an antibody or an IL-17 receptor A binding fragment thereof comprising a heavy chain sequence of SEQ ID NO:427 and a light chain sequence of SEQ ID NO:429;
i) an antibody or an IL-17 receptor A binding fragment thereof comprising a heavy chain variable region sequence of SEQ ID NO:14;
j) an antibody or an IL-17 receptor A binding fragment thereof comprising a light chain variable region sequence of SEQ ID NO:40;

k) an antibody or an IL-17 receptor A binding fragment thereof comprising a light chain variable region sequence of SEQ ID NO:40 and a heavy chain variable region sequence of SEQ ID NO:14;

l) an antibody or an IL-17 receptor A binding fragment thereof comprising a heavy chain CDR1 of SEQ ID NO: 146, a heavy chain CDR2 of SEQ ID NO:147, a heavy chain CDR3 of SEQ ID NO:148, a light chain CDR1 of SEQ ID NO:224, a light chain CDR2 of SEQ ID NO:225, and a light chain CDR3 of SEQ ID NO:226; and m) an antibody or an IL-17 receptor A binding fragment thereof comprising a heavy chain CDR3 of SEQ ID NO: 148 and a light chain CDR3 of SEQ ID NO:226; wherein said antibody specifically binds IL-17 receptor A.

Embodiment 70: the polynucleotide of embodiment 69, wherein said antibody comprises a polynucleotide selected from the group consisting of:

a) a heavy chain-encoding polynucleotide sequence consisting of SEQ ID NO:426 and a light chain-encoding polynucleotide sequence consisting of SEQ ID NO:428;

b) a heavy chain-encoding polynucleotide sequence consisting essentially of SEQ ID NO:426 and a light chain-encoding polynucleotide sequence consisting essentially of SEQ ID NO:428;

c) a heavy chain-encoding polynucleotide sequence comprising SEQ ID NO: 426;

d) a light chain-encoding polynucleotide sequence comprising SEQ ID NO:428;

e) a heavy chain-encoding polynucleotide sequence comprising SEQ ID NO: 426 and a light chain-encoding polynucleotide sequence comprising SEQ ID NO:428;

f) a heavy chain or an IL-17 receptor A binding fragment thereof-encoding polynucleotide sequence comprising SEQ ID NO: 426;

g) a light chain or an IL-17 receptor A binding fragment thereof-encoding polynucleotide sequence comprising SEQ ID NO:428;

h) a heavy chain or an IL-17 receptor A binding fragment thereof-encoding polynucleotide sequence comprising SEQ ID NO: 426 and a light chain or an IL-17 receptor A binding fragment thereof-encoding polynucleotide sequence comprising SEQ ID NO:428;

i) a heavy chain variable region or an IL-17 receptor A binding fragment thereof-encoding polynucleotide sequence comprising SEQ ID NO:67;

j) a light chain variable region or an IL-17 receptor A binding fragment thereof-encoding polynucleotide sequence comprising SEQ ID NO:93;

k) a heavy chain variable region or an IL-17 receptor A binding fragment thereof-encoding polynucleotide sequence comprising SEQ ID NO:67 and a light chain variable region or an IL-17 receptor A binding fragment thereof-encoding polynucleotide sequence comprising SEQ ID NO:93;

l) a light chain CDR1-encoding polynucleotide comprising SEQ ID NO:384, CDR2-encoding polynucleotide comprising SEQ ID NO:385, CDR3-encoding polynucleotide comprising SEQ ID NO:386 and a heavy chain CDR1-encoding polynucleotide comprising SEQ ID NO:305, CDR2-encoding polynucleotide comprising SEQ ID NO:306, CDR3-encoding polynucleotide comprising SEQ ID NO:307; and m) a heavy chain CDR3-encoding polynucleotide comprising SEQ ID NO:307 and a light chain CDR3-encoding polynucleotide comprising SEQ ID NO:386.

Embodiment 71: the plasmid of embodiment 60, wherein the polynucleotide is the polynucleotide of embodiment 69. Embodiment 72: the isolated cell of embodiment 62, wherein the polynucleotide is the polynucleotide of embodiment 69. Embodiment 73: the isolated cell of embodiment 65, wherein said expression vector comprises the polynucleotide of embodiment 69. Embodiment 74: the isolated cell of embodiment 66, wherein the cell is a CHO cell and said CHO cell comprises the polynucleotide of embodiment 69. Embodiment 75: the method according to embodiment 67, wherein the polynucleotide is the polynucleotide of embodiment 69.

Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a IL-17RA antigen binding proteins or a desired combination of IL-17RA antigen binding protein polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular*

Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding IL-17RA antigen binding proteins as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10. degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6 (log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to IL-17RA and inhibiting signaling, although variants can also be selected which have modified characteristics as will be more fully outlined below.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, those skilled in the art could make any number of different nucleic acids, by simply modifying the sequence of one or more codons in a way which does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-17RA antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the IL-17RA antigen binding protein from the host cell. Affinity purification can be accomplished, for example, by column chromatography using antibodies against the tag as an affinity matrix. Optionally, the tag can subsequently be removed from the purified IL-17RA antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly. MA) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to IL-17RA polypeptide. As a result, increased quantities of a polypeptide such as an IL-17RA antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the IL-17RA antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an IL-17RA antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad.* U.S.A. 81:659-663); the promoter contained in the 3' long terminal repeat of Rous sarcoma virus (Yamamoto et al., 1980, *Cell* 22:787-797); herpes thymidine kinase promoter (Wagner et al., 1981. *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978. *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the clastase I gene control region that is active in pancreatic acinar cells (Swift et al., 1984, *Cell* 38:639-646; Ornitz et al., 1986, Cold Spring Harbor *Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al. 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in mycloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314: 283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising an IL-17RA antigen binding protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type 1 interleukin-1 receptor signal peptide described in U.S. Pat. No. 4,968,607; the type II interleukin-1 receptor signal peptide described in EP Patent No. 0 460 846.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an IL-17RA antigen binding sequence has been inserted into the proper site of the vector, the completed vector may be inserted into a suitable host cell for amplification and/or polypeptide expression. The transformation of an expression vector for an IL-17RA antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods ae well known to the skilled artisan, and are et forth, for example, in Sambrook et al., 2001, supra.

A host cell, when cultured under appropriate conditions, synthesizes an IL-17RA antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but ae not limited to, immortalized cell lines available from the American Type Culture Collection (ATCC®) and any cell lines used in an expression system known in the art can be used to make the recombinant polypeptides of the invention. In general, host cells ae transformed with a recombinant expression vector that comprises DNA encoding a desired anti-IL-17RA antibody polypeptide. Among the host cells that may be employed am prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC® CRL 1651) (Gluzman et al., 1981, Cell 23:175), L cells, 293 cells, C127 cells, 3T3 cells (ATCC® CCL 163), Chinese hamster ovary (CHO) cells, or their derivatives such as Veggie CHO and related cell lines which grow in serum-free media (Rasmussen et al., 1998, Cytotechnology 28: 31), HeLa cells, BHK (ATCC® CRL 10) cell lines, and the CVT/EBNA cell line derived from the African green monkey kidney cell line CV1 (ATCC® CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian col lines such as HepG2/3B, KB, NTH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyvcromyces strains, Candida,* or any yeast strain capable of expressing heterologous polypeptides. Suitable bacterial strains include *Escherichia coli, Bacillus subtilis, Salmonella typhimurium,* or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego. Calif., U.S.A. (the MaxBac® kit), and such methods are well known in the art, as described in Summers and Smith, Texas Agricultural Experiment Station Bulletin No. 1555 (1987), and Luckow and Summers, Bio/Technology 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (Cloning Vectors: A Laboratory Manual, Elsevier, New York, 1985). A host cell that comprises an isolated nucleic acid of the invention, preferably operably linked to at least one expression control sequence, is a "recombinant host cell".

In certain embodiments, cell lines may be selected through determining which cell lines have high expression levels and constitutively produce antigen binding proteins with IL-17RA binding properties. In another embodiment, a cell line from the B cell lineage that does not make its own antibody but has a capacity to make and secrete a heterologous antibody can be selected.

Identification of Domains on Human IL-17RA that Neutralizing Antibodies Bound

Examples 14-17 describe various studies elucidating domains on human IL-17RA that neutralizing IL-17RA mAbs bound. These domains are referred to as neutralizing determinants. A neutralizing determinant is a contiguous stretch of IL-17RA, that when mutated, negatively affects the binding of at least one of the neutralizing antibodies disclosed herein. A neutralizing determinant comprises at least one epitope. A neutralizing determinant may have primary, secondary, tertiary, and/or quarternary structural characteristics. A neutralizing antibody is any of the antibodies described herein that specifically binds human IL-17RA and inhibits binding of IL-17A and/or IL-17F and thereby inhibits IL-17RA signaling and/or biological activity. Examples of neutralizing antibodies include antibodies comprising $AM_L1/AM_H1$ (SEQ ID NO:27/SEQ ID NO:1). $AM_L2/AM_H2$ (SEQ ID NO:28/SEQ ID NO:2), $AM_L3/AM_H3$ (SEQ ID NO:29/SEQ ID NO:3), $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO:10), $AM_L11/AM_H11$ (SEQ ID NO:37/SEQ ID NO:11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO:14). $AM_L15/AM_H15$ (SEQ ID NO:41/SEQ ID NO:15). $AM_L16/AM_H6$ (SEQ ID NO:42/SEQ ID NO:16), $AM_L17/AM_H17$ (SEQ ID NO:43/SEQ ID NO:17), $AM_L18/AM_H18$ (SEQ ID NO:44/SEQ ID NO:18), $AM_L19/AM_H19$ (SEQ ID NO:45/SEQ ID NO:19), $AM_L20/AM_H20$ (SEQ ID NO:46/SEQ ID NO:20), $AM_L21/AM_H21$ (SEQ ID NO:47/SEQ ID NO:21), $AM_L22/AM_H22$ (SEQ ID NO:48/SEQ ID NO:22), $AM_L23/AM_H23$ (SEQ ID NO:49 or SEQ ID NO:50/SEQ ID NO:23), $AM_L24/AM_H24$ (SEQ ID NO:51/SEQ ID NO:24), $AM_L25/AM_H25$ (SEQ ID NO:52/SEQ ID NO:25), $AM_L26/AM_H26$ (SEQ ID NO:53/SEQ ID NO:26), as well as IL-17RA-binding fragments thereof and combinations thereof.

Further embodiments of neutralizing antibodies include antibodies that specifically bind to human IL-17RA and inhibit IL-17A and/or IL-17F from binding and activating IL-17RA, or a heteromeric complex of IL-17RA and IL-17RC. Further embodiments include antibodies that specifically bind to human IL-17RA and inhibit an IL-17A/IL-17F heteromer from binding and activating IL-17RA, or a heteromeric complex of IL-17RA and IL-17RC. Further embodiments include antibodies that specifically bind to human IL-17RA and partially or fully inhibit IL-17RA from forming either a homomeric or heteromeric functional receptor complex, such as, but not limited to IL-17RA-IL-17RC complex. Further embodiments include antibodies that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex.

Further examples of neutralizing antibodies include antibodies comprising at least one CDR from antibodies comprising $AM_L1/AM_H1$ (SEQ ID NO:27/SEQ ID NO:1), $AM_L2/AM_H2$ (SEQ ID NO:28/SEQ ID NO:2), $AM_L3/$ $AM_H3$ (SEQ ID NO:29/SEQ ID NO:3), $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO:10), $AM_L11/AM_H11$ (SEQ ID NO:37/SEQ ID NO:11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO:14), $AM_L15/AM_H15$ (SEQ ID NO:41/SEQ ID NO:15), $AM_L16/AM_H16$ (SEQ ID NO:42/SEQ ID NO:16), $AM_L17/AM_H17$ (SEQ ID NO:43/SEQ ID NO:17), $AM_L18/AM_H18$ (SEQ ID NO:44/SEQ ID NO:18). $AM_L19/AM_H19$ (SEQ ID NO:45/SEQ ID NO:19), $AM_L20/AM_H20$ (SEQ ID NO:46/SEQ ID NO:20), $AM_L21/AM_H21$ (SEQ ID NO:47/SEQ ID NO:21), $AM_L22/AM_H22$ (SEQ ID NO:48/SEQ ID NO:22), $AM_L0.23/AM_H23$ (SEQ ID NO:49 or SEQ ID NO:50/SEQ ID NO:23), $AM_L24/AM_H24$ (SEQ ID NO:51/SEQ ID NO:24), $AM_L25/AM_H25$ (SEQ ID NO:52/SEQ ID NO:25), $AM_L26/AM_H26$ (SEQ ID NO:53/SEQ ID NO:26), as well as IL-17RA-binding fragments thereof and combinations thereof. See Table 1.

FIGS. 16A and 16B show that antibodies A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, and G: $AM_H18/AM_L18$ competed with one another for binding to human IL-17RA and fell into a defined group (Bin 1). In general, antibodies I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$ competed with one another for binding to human IL-17RA and as a consequence fell into a different group (Bin 3). Generally speaking, the antibodies of Bin 1 did not compete with the antibodies of Bin 3. Antibody H: $AM_H1/AM_L1$ was unique in its competition pattern and formed Bin 2, but is most similar to Bin 3. Antibody P: $AM_H26/AM_L26$ formed Bin 4 and showed little cross-competition with any of the other antibodies, suggesting a neutralizing determinant unique to this antibody. Antibodies Q: $AM_H21/AM_L21$ and R: $AM_H20/AM_L20$ showed individually unique competition patterns, but with considerable similarities to Bin 3 antibodies, and formed Bins 5 and 6, respectively. This method identified groups of antibodies binding to different neutralizing determinants and provides evidence of several species within a subgenus of cross-competing antibodies.

Example 16 describes the use of human/mouse IL-17RA chimeric proteins to determine neutralizing determinants on human IL-17RA. FIG. 19 show that at least three neutralizing determinants were identified based on those regions affecting the binding of neutralizing IL-17RA antibodies, namely Domain B spanning amino acids 75-96 of human IL-17RA (SEQ ID NO:431), Domain C spanning amino acids 128-154 of human IL-17RA (SEQ ID NO:431), and Domain D spanning amino acids 176-197 of human IL-17RA (SEQ ID NO:431). Domain B spanning amino acids 75-96 of human IL-17RA (SEQ ID NO:431) negatively affected the binding of neutralizing antibodies $AM_H1/AM_L1$ and $AM_H23/AM_L23$. Domain C spanning amino acids 128-154 of human IL-17RA (SEQ ID NO:431) negatively affected the binding of neutralizing antibodies $AM_H22/AM_L22$ and $AM_H23/AM_L23$. Domain D spanning amino acids 176-197 of human IL-17RA (SEQ ID NO:431) negatively affected the binding of neutralizing antibodies $AM_H1/AM_L1$, $AM_H22/AM_L22$, $AM_H14/AM_L14$, $AM_H19/AM_L19$, $AM_H23/AM_L23$, $AM_H21/AM_L21$, and $AM_H20/AM_L20$. Thus, Domains B, C, and D are considered neutralizing determinants.

Example 17 describes the use of arginine scan techniques to further elucidate the domains on human IL-17R that the IL-17RA neutralizing antibodies bound. A summary of the arginine scan, binning, and chimera data is presented in FIG. 22. The arginine scan methodology identified several neutralizing determinants: $AM_H18/AM_L18$ bound a domain spanning amino acids 220-284 of human IL-17RA (SEQ ID NO:431); $AM_H1/AM_L1$ bound a domain focused on amino acid residue 152 of human IL-17RA (SEQ ID NO:431); $AM_H22/AM_L22$ bound a domain spanning amino acids 152-198 of human IL-17RA (SEQ ID NO:431); $AM_H14/AM_L14$ bound a domain spanning amino acids 152-297 of human IL-17RA (SEQ ID NO:431); $AM_H19/AM_L19$ bound a domain spanning amino acids 152-186 of human IL-17RA (SEQ ID NO:431); $AM_H23/AM_L23$ bound a domain spanning amino acids 97-297 of human IL-17RA (SEQ ID NO:431); $AM_H26/AM_L26$ bound a domain spanning amino acids 138-270 of human IL-17RA (SEQ ID NO:431); $AM_H21/AM_L21$ bound a domain spanning amino acids 113-198 of human IL-17RA (SEQ ID NO:431); and $AM_H20/AM_L20$ bound a domain spanning amino acids 152-270 of human IL-17RA (SEQ ID NO:431).

All of the residues shown in FIG. 22 have been shown to significantly reduce or essentially eliminate binding of a neutralizing human monoclonal antibody that specifically binds to human IL-17RA.

Embodiments include an antibody, or IL-17RA-binding fragment thereof, that specifically binds to IL-17RA and competes for binding with any one of antibodies $AM_H3/AM_L3$, $AM_H20/AM_L20$, $AM_H22/AM_L22$, $AM_H23/AM_L23$, $AM_H14/AM_L14$, $AM_H21/AM_L21$, $AM_H19/AM_L19$, $AM_H12/AM_L12$, $AM_H17/AM_L17$, or $AM_H16/AM_L16$, or any subset therein.

Embodiments include an antibody, or IL-17RA-binding fragment thereof, that specifically binds to IL-17R and competes for binding with any one of antibodies $AM_H22/AM_L22$, $AM_H23/AM_L23$, $AM_H14/AM_L14$, $AM_H19/AM_L19$, $AM_H12/AM_L12$, $AM_H17/AM_L17$, or $AM_H16/AM_L16$, or any subset therein.

Embodiments include an antibody, or IL-17RA-binding fragment thereof, that specifically binds human IL-17RA of SEQ ID NO:431 but does not specifically bind to a chimeric polypeptide consisting of SEQ ID NO:434. Embodiments include an antibody, or IL-17RA-binding fragment thereof, that specifically binds human IL-17RA of SEQ ID NO:431 but does not specifically bind to a chimeric polypeptide consisting of SEQ ID NO:435. Embodiments include an antibody, or IL-17RA-binding fragment thereof, that specifically binds human IL-17RA of SEQ ID NO:431 but does not specifically bind to a chimeric polypeptide consisting of SEQ ID NO:436.

Embodiments include an antibody, or IL-17RA-binding fragment thereof, that specifically binds a neutralizing determinant comprising amino acids 75-96 of SEQ ID NO:431 of human IL-17RA. Embodiments include an antibody, or IL-17RA-binding fragment thereof, that specifically binds a neutralizing determinant comprising amino acids 128-154 of SEQ ID NO:431 of human IL-17RA. Embodiments include an antibody, or IL-17RA-binding fragment thereof, that specifically binds a neutralizing determinant comprising amino acids 176-197 of SEQ ID NO:431 of human IL-17RA. Embodiments include an antibody, or IL-17RA-binding fragment thereof, that specifically binds a neutralizing determinant comprising amino acids 152-297 of SEQ ID NO:431 of human IL-17RA. Embodiments include an antibody, or IL-17RA-binding fragment thereof, that specifically binds a neutralizing determinant comprising amino acids 220-284 of SEQ ID NO:431 of human IL-17RA. Embodiments include an antibody, or IL-17RA-binding fragment thereof, that specifically binds a neutralizing determinant comprising amino acids 152-198 of SEQ ID NO:431 of human IL-17RA. Embodiments include an antibody, or IL-17RA-binding fragment thereof, that specifically binds a neutralizing determinant comprising amino acids 152-186 of SEQ ID NO:431 of human IL-17RA. Embodiments include an antibody, or IL-17RA-binding fragment thereof, that specifically binds a neutralizing determinant comprising amino acids 97-297 of SEQ ID NO:431 of human IL-17RA. Embodiments include an antibody, or IL-17RA-binding fragment thereof, that specifically binds a neutralizing determinant comprising amino acids 138-270 of SEQ ID NO:431 of human IL-17RA. Embodiments include an antibody, or IL-17RA-binding fragment thereof, that specifically binds a neutralizing determinant comprising amino acids 113-198 of SEQ ID NO:431 of human IL-17RA. Embodiments include an antibody, or IL-17RA-binding fragment thereof, that specifically binds a neutralizing determinant comprising amino acids 152-270 of SEQ ID NO:431 of human IL-17RA.

Further embodiments include an antibody, or IL-17RA-binding fragment thereof, that binds human IL-17RA of SEQ ID NO:431, but does not bind said IL-17RA having an amino acid substituted with arginine at any one of E97R, E113R, S115R, H138R, D152R, D154R, E156R, K166R, Q176R, S177R, D184R, E186R, S198R, H215R, S220R, T228R, T235R, E241R, H243R, L270R, Q284R, H297R of SEQ ID NO:431. Embodiments include an antibody, or IL-17RA-binding fragment thereof, that binds human IL-17RA of SEQ ID NO:431, but does not bind said IL-17RA having an amino acid substituted with arginine at any one of D152R, D154R, E156R, D184R, E186R, H297R of SEQ ID NO:431. Embodiments include an antibody, or IL-17RA-binding fragment thereof, that binds human IL-17RA of SEQ ID NO:431, but does not bind said IL-17RA having an amino acid substituted with arginine at D152R of SEQ ID NO:431.

Further embodiments include an antibody, or IL-17RA-binding fragment thereof, that specifically binds an epitope defined by any one of amino acids D152, D154, E156, D184, E186, H297 of SEQ ID NO:431. Embodiments include an antibody, or IL-17RA-binding fragment thereof, that specifically binds an epitope defined by at least two amino acids selected from the group consisting of: D152, D154, E156, D184, E186, H297 of SEQ ID NO:431. Embodiments include an antibody, or IL-17RA-binding fragment thereof, that specifically binds an epitope defined by at least three amino acids selected from the group consisting of: D152, D154, E156, D184, E186, H297 of SEQ ID NO:431. Embodiments include an antibody, or IL-17RA-binding fragment thereof, that specifically binds an epitope defined by at least four amino acids selected from the group consisting of: D152, D154, E156, D184, E186, H297 of SEQ ID NO:431. Embodiments include an antibody, or IL-17RA-binding fragment thereof, that specifically binds an epitope defined by at least five amino acids selected from the group consisting of: D152, D154, E156, D184, E186, H297 of SEQ ID NO:431. Embodiments include an antibody, or IL-17RA-binding fragment thereof, that specifically binds an epitopic defined by amino acids D152, D154, E156, D184, E186, H297 of SEQ ID NO:431.

Aspects of the invention include a variety of embodiments including, but not limited to, the following exemplary embodiments: Embodiment 101: an isolated monoclonal antibody, or IL-17RA-binding fragment thereof, that specifically binds to IL-17RA and competes for binding with an antibody selected from the group consisting of:

A. an isolated antibody, or IL-17RA-binding fragment thereof, comprising
   a. a light chain variable domain sequence that is at least 80% identical to a light chain variable domain sequence of $AM_L2$, 3, 5, 9, 10, 12, 14-17, and 19-25 (SEQ ID NOs:28, 29, 31, 35, 36, 38, 40-43, and 45-53, respectively);
   b. a heavy chain variable domain sequence that is at least 80% identical to a heavy chain variable domain sequence of $AM_H2$, 3, 5, 9, 10, 12, 14-17, and 19-25 (SEQ ID NOs:2, 3, 5, 9, 10, 12, 14-17, and 19-25, respectively);
   c. the light chain variable domain of (a) and the heavy chain variable domain of (b); wherein said antibody specifically binds to human IL-17RA;

B. an isolated antibody, or IL-17RA-binding fragment thereof, comprising
   a. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO:112) of antibody AM-2;
   b. a light chain CDR1 (SEQ ID NO:191), CDR2 (SEQ ID NO:192), CDR3 (SEQ ID NO:193) and a heavy chain CDR1 (SEQ ID NO:113), CDR2 (SEQ ID NO:114), CDR3 (SEQ ID NO: 115) of antibody AM-3;
   c. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
   d. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
   e. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
   f. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
   g. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
   h. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;
   i. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;

j. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;

k. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;

l. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;

m. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;

n. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;

o. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;

p. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;

q. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO: 178) of antibody AM-24;

r. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25; wherein said antibody specifically binds to human IL-17RA; and C. an isolated antibody, or IL-17RA-binding fragment thereof, comprising a. a light chain variable domain and a heavy chain variable domain of $AM_L2/AM_H2$ (SEQ ID NO:28/ SEQ ID NO:2);

b. a light chain variable domain and a heavy chain variable domain of $AM_L3/AM_H3$ (SEQ ID NO:29/ SEQ ID NO:3);

c. a light chain variable domain and a heavy chain variable domain of $AM_L5/AM_H5$ (SEQ ID NO:31/ SEQ ID NO:5);

d. a light chain variable domain and a heavy chain variable domain of $AM_L9/AM_H9$ (SEQ ID NO:35/ SEQ ID NO:9);

e. a light chain variable domain and a heavy chain variable domain of $AM_L10/AM_H10$ (SEQ ID NO:36/ SEQ ID NO:10);

f. a light chain variable domain and a heavy chain variable domain of $AM_L12/AM_H12$ (SEQ ID NO:38/ SEQ ID NO:12);

g. a light chain variable domain and a heavy chain variable domain of $AM_L14/AM_H14$ (SEQ ID NO:40/ SEQ ID NO:14);

h. a light chain variable domain and a heavy chain variable domain of $AM_L15/AM_H15$ (SEQ ID NO:41/ SEQ ID NO:15);

i. a light chain variable domain and a heavy chain variable domain of $AM_L16/AM_H16$ (SEQ ID NO:42/ SEQ ID NO:16);

j. a light chain variable domain and a heavy chain variable domain of $AM_L17/AM_H17$ (SEQ ID NO:43/ SEQ ID NO:17);

k. a light chain variable domain and a heavy chain variable domain of $AM_L19/AM_H19$ (SEQ ID NO:45/ SEQ ID NO:19);

l. a light chain variable domain and a heavy chain variable domain of $AM_L20/AM_H20$ (SEQ ID NO:46/ SEQ ID NO:20);

m. a light chain variable domain and a heavy chain variable domain of $AM_L21/AM_H21$ (SEQ ID NO:47/ SEQ ID NO:21);

n. a light chain variable domain and a heavy chain variable domain of $AM_L22/AM_H22$ (SEQ ID NO:48/ SEQ ID NO:22);

o. a light chain variable domain and a heavy chain variable domain of $AM_L23/AM_H23$ (SEQ ID NO:49 or SEQ ID NO:50/SEQ ID NO:23);

p. a light chain variable domain and a heavy chain variable domain of $AM_L24/AM_H24$ (SEQ ID NO:51/ SEQ ID NO:24);

q. a light chain variable domain and a heavy chain variable domain of $AM_L25/AM_H25$ (SEQ ID NO:52/ SEQ ID NO:25); wherein said antibody specifically binds to human IL-17RA.

Embodiment 102: the antibody of embodiment 101, wherein said antibody is selected from the group consisting of:

A. an isolated antibody, or IL-17RA-binding fragment thereof, comprising a. a light chain variable domain sequence that is at least 80% identical to a light chain variable domain sequence of $AM_L$9, 14, 16, 17, 19-23v2, and 26 (SEQ ID NOs:35, 40, 42, 43, 45-50, and 53, respectively);

b. a heavy chain variable domain sequence that is at least 80% identical to a heavy chain variable domain sequence of $AM_H$9, 14, 16, 17, 19-23, and 26 (SEQ ID NOs:9, 14, 16, 17, 19-23, and 26, respectively);

c. the light chain variable domain of (a) and the heavy chain variable domain of (b); wherein said antibody specifically binds to human IL-17RA;

B. an isolated antibody, or IL-17RA-binding fragment thereof, comprising a. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;

b. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;

c. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
d. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
e. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
f. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
g. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO: 169) of antibody AM-21;
h. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
i. a light chain CDR1 (SEQ ID NO:251), CDR2 (SEQ ID NO:252), CDR3 (SEQ ID NO:253) and a heavy chain CDR1 (SEQ ID NO: 173), CDR2 (SEQ ID NO:174), CDR3 (SEQ ID NO:175) of antibody AM-23;
j. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
k. a light chain variable domain and a heavy chain variable domain of $AM_L26/AM_H26$ (SEQ ID NO:53/ SEQ ID NO:26); wherein said antibody specifically binds to human IL-17RA; and
C. an isolated antibody, or IL-17RA-binding fragment thereof, comprising
a. a light chain variable domain and a heavy chain variable domain of $AM_L9/AM_H9$ (SEQ ID NO:35/ SEQ ID NO:9);
b. a light chain variable domain and a heavy chain variable domain of $AM_L14/AM_H4$ (SEQ ID NO:40/ SEQ ID NO:14);
c. a light chain variable domain and a heavy chain variable domain of $AM_L16/AM_H16$ (SEQ ID NO:42/ SEQ ID NO:16);
d. a light chain variable domain and a heavy chain variable domain of $AM_L7/AM_H17$ (SEQ ID NO:43/ SEQ ID NO: 17);
e. a light chain variable domain and a heavy chain variable domain of $AM_L19/AM_H19$ (SEQ ID NO:45/ SEQ ID NO:19);
f. a light chain variable domain and a heavy chain variable domain of $AM_L20/AM_H20$ (SEQ ID NO:46/ SEQ ID NO:20);
g. a light chain variable domain and a heavy chain variable domain of $AM_L21/AM_H21$ (SEQ ID NO:47/ SEQ ID NO:21);
h. a light chain variable domain and a heavy chain variable domain of $AM_L22/AM_H22$ (SEQ ID NO:48/ SEQ ID NO:22);
i. a light chain variable domain and a heavy chain variable domain of $AM_L0.23/AM_H23$ (SEQ ID NO:49 or SEQ ID NO:50/SEQ ID NO:23);
j. a light chain variable domain and a heavy chain variable domain of $AM_L26/AM_H26$ (SEQ ID NO:53/ SEQ ID NO:26); wherein said antibody specifically binds to human IL-17RA.

Embodiment 103: the antibody of embodiment 101, wherein said antibody selected from the group consisting of:
A. an isolated antibody, or IL-17RA-binding fragment thereof, comprising
a. a light chain variable domain sequence that is at least 80% identical to a light chain variable domain sequence of $AM_L12$, 14, 16, 17, 19, and 22 (SEQ ID NOs:38, 40, 42, 43, 45, and 48 respectively);
b. a heavy chain variable domain sequence that is at least 80% identical to a heavy chain variable domain sequence of $AM_H12$, 14, 16, 17, 19, and 22 (SEQ ID NOs:12, 14, 16, 17, 19, and 22, respectively);
c. the light chain variable domain of (a) and the heavy chain variable domain of (b); wherein said antibody specifically binds to human IL-17RA;
B. an isolated antibody, or IL-17RA-binding fragment thereof, comprising
a. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
b. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
c. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
d. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
e. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
f. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22; wherein said antibody specifically binds to human IL-17RA; and
C. an isolated antibody, or IL-17RA-binding fragment thereof, comprising
a. a light chain variable domain and a heavy chain variable domain of $AM_L12/AM_H12$ (SEQ ID NO:38/ SEQ ID NO: 12);
b. a light chain variable domain and a heavy chain variable domain of $AM_L14/AM_H14$ (SEQ ID NO:40/ SEQ ID NO:14);

c. a light chain variable domain and a heavy chain variable domain of AM$_L$16/AM$_H$16 (SEQ ID NO:42/SEQ ID NO:16);
d. a light chain variable domain and a heavy chain variable domain of AM$_L$7/AM$_H$17 (SEQ ID NO:43/SEQ ID NO:17);
e. a light chain variable domain and a heavy chain variable domain of AM$_L$19/AM$_H$19 (SEQ ID NO:45/SEQ ID NO:19);
c. a light chain variable domain and a heavy chain variable domain of AM$_L$22/AM$_H$22 (SEQ ID NO:48/SEQ ID NO:22); wherein said antibody specifically binds to human IL-17RA.

Embodiment 104: the antibody of embodiment 101, wherein said antibody is selected from the group consisting of:
A. an isolated antibody, or IL-17RA-binding fragment thereof, comprising
  a. a light chain variable domain sequence that is at least 80% identical to a light chain variable domain sequence SEQ ID NO: 40;
  b. a heavy chain variable domain sequence that is at least 80% identical to a heavy chain variable domain sequence of SEQ ID NO:14;
  c. the light chain variable domain of (a) and the heavy chain variable domain of (b); wherein said antibody specifically binds to human IL-17RA;
B. an isolated antibody, or IL-17RA-binding fragment thereof, comprising a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148); wherein said antibody specifically binds to human IL-17RA; and
C. an isolated antibody, or IL-17RA-binding fragment thereof, comprising a light chain variable domain of SEQ ID NO:40 and a heavy chain variable domain SEQ ID NO: 14; wherein said antibody specifically binds to human IL-17RA.

Embodiment 105: the antibody of embodiment 101, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody. Embodiment 106: the antibody of embodiment 105, wherein said antibody inhibits human IL-17A from binding to human IL-17RA. Embodiment 107: the antibody of embodiment 106, wherein said antibody inhibits human IL-17A and IL-17F from binding to human IL-17RA. Embodiment 108: the antibody of embodiment 106, wherein said antibody inhibits human IL-17A or IL-17F from binding to human IL-17RA.

Embodiment 109: an isolated monoclonal antibody, or IL-17RA-binding fragment thereof, selected from the group consisting of:
a) a monoclonal antibody that specifically binds human IL-17RA of SEQ ID NO:431 but does not specifically bind to a chimeric polypeptide consisting of SEQ ID NO:434;
b) a monoclonal antibody that specifically binds human IL-17RA of SEQ ID NO:431 but does not specifically bind to a chimeric polypeptide consisting of SEQ ID NO:435; and
c) a monoclonal antibody that specifically binds human IL-17RA of SEQ ID NO:431 but does not specifically bind to a chimeric polypeptide consisting of SEQ ID NO:436.

Embodiment 110: an isolated monoclonal antibody, or IL-17RA-binding fragment thereof, that specifically binds a neutralizing determinant selected from the group consisting of:
a) a polypeptide comprising amino acids 75-96 of SEQ ID NO:431 of human IL-17RA;
b) a polypeptide comprising amino acids 128-154 of SEQ ID NO:431 of human IL-17RA;
c) a polypeptide comprising amino acids 176-197 of SEQ ID NO:431 of human IL-17RA;
d) a polypeptide comprising amino acids 152-297 of SEQ ID NO:431 of human IL-17RA;
e) a polypeptide comprising amino acids 220-284 of SEQ ID NO:431 of human IL-17RA;
f) a polypeptide comprising amino acids 152-198 of SEQ ID NO:431 of human IL-17RA;
g) a polypeptide comprising amino acids 152-186 of SEQ ID NO:431 of human IL-17RA;
h) a polypeptide comprising amino acids 97-297 of SEQ ID NO:431 of human IL-17RA;
i) a polypeptide comprising amino acids 138-270 of SEQ ID NO:431 of human IL-17RA;
j) a polypeptide comprising amino acids 113-198 of SEQ ID NO:431 of human IL-17RA; and
k) a polypeptide comprising amino acids 152-270 of SEQ ID NO:431 of human IL-17RA.

Embodiment 111: an isolated monoclonal antibody, or IL-17RA-binding fragment thereof, that specifically binds human IL-17RA of SEQ ID NO:431, but does not specifically bind said IL-17RA having any one of the following amino acid substitutions E97R, E113R, S115R, H138R, D152R, D154R, E156R, K166R, Q176R, S177R, D184R, E186R, S198R, H215R, S220R, T228R, T235R, E241R, H243R, L270R, Q284R, or H297R of SEQ ID NO:431. Embodiment 112: the antibody of embodiment 111, wherein said antibody specifically binds human IL-17RA of SEQ ID NO:431, but does not specifically bind said IL-17RA having any one of the following amino acid substitutions D152R, D154R, E156R, D184R, E186R, or H297R of SEQ ID NO:431. Embodiment 113: the antibody of embodiment 111, wherein said antibody specifically binds human IL-17RA of SEQ ID NO:431, but does not specifically bind said IL-17RA having the aspartic acid residue at position 152 of SEQ ID NO:431 substituted with an arginine. Embodiment 114: the antibody of embodiment 111, wherein said antibody specifically binds an epitope defined by any one of amino acids D152, D154, E156, D184, E186, or H297 of SEQ ID NO:431. Embodiment 115: the antibody of embodiment 114, wherein said antibody specifically binds an epitope defined by at least two of the following amino acids D152, D154, E156, D184, E186, or H297 of SEQ ID NO:431. Embodiment 116: the antibody of embodiment 114, wherein said antibody specifically binds an epitope defined by at least three of the following amino acids D152, D154, E156, D184, E186, or H297 of SEQ ID NO:431. Embodiment 117: the antibody of embodiment 114, wherein said antibody specifically binds an epitope defined by at least four of the following amino acids D152, D154, E156, D184, E186, or H297 of SEQ ID NO:431. Embodiment 118: the antibody of embodiment 114, wherein said antibody specifically binds an epitope defined by at least five of the following amino acids D152, D154, E156, D184, E186, or H297 of SEQ ID NO:431. Embodiment 119: the antibody of embodiment 114, wherein said antibody specifically binds an epitope defined by amino acids D152, D154. E156, D184, E186, 11297 of SEQ ID NO:431.

Embodiment 120: an isolated monoclonal antibody, or IL-17RA-binding fragment thereof, that specifically binds to IL-17RA and competes for binding with an antibody comprising:

a. a heavy chain CDR1 comprising an amino acid sequence selected from the group consisting of:
   i. $X_1$YGIS, wherein $X_1$ is selected from the group consisting of R, S and G;
b. a heavy chain CDR2 comprising an amino acid sequence selected from the group consisting of:
   i. WIS$X_1$Y$X_2$GNT$X_3$YAQ$X_4$$X_5$QG, wherein $X_1$ is selected from the group consisting of A, $X_2$ is selected from the group consisting of N, S and K, $X_j$ is selected from the group consisting of N and K, $X_4$ is selected from the group consisting of K and N, and $X_5$ is selected from the group consisting of L and F;
c. a heavy chain CDR3 comprising an amino acid sequence selected from the group consisting of:
   i. $X_1$QL$X_2$$X_3$DY, wherein $X_1$ is selected from the group consisting of R and K, $X_2$ is selected from the group consisting of Y, V, and A, and $X_3$ is selected from the group consisting of F and L;
   ii. $X_1$QL$X_2$FDY, wherein $X_1$ is selected from the group consisting of R and K, and $X_2$ is selected from the group consisting of Y and V;
d. a light chain CDR1 comprising an amino acid sequence selected from the group consisting of:
   i. RASQS$X_1$$X_2$$X_3$$X_4$LA, wherein $X_1$ is selected from the group consisting of V and I, $X_2$ is selected from the group consisting of I and S, $X_3$ is selected from the group consisting of S and T, $X_4$ is selected from the group consisting of N and S, and $X_5$ is selected from the group consisting of A and N;
   ii. RASQS$X_1$SSNLA, wherein $X_1$ is selected from the group consisting of V and I;
e. a light chain CDR2 comprising an amino acid sequence selected from the group consisting of:
   i. $X_1$$X_2$STRA$X_3$, wherein $X_1$ is selected from the group consisting of G and D, $X_2$ is selected from the group consisting of A and T, and $X_3$ is selected from the group consisting of T and A;
   ii. $X_1$ASTRA$X_2$, wherein $X_1$ is selected from the group consisting of G and D, and $X_2$ is selected from the group consisting of A and T; and
f. a light chain CDR3 comprising an amino acid sequence selected from the group consisting of:
   i. QQYD$X_1$WPLT, wherein $X_1$ is selected from the group consisting of N. T, and I.

Embodiment 121: the antibody of embodiment 120, wherein said antibody comprises:

a. a heavy chain CDR1 amino acid sequence comprising $X_1$YGIS, wherein $X_1$ is selected from the group consisting of R, S and G;
b. a heavy chain CDR2 amino acid sequence comprising WIS$X_1$Y$X_2$GNT$X_3$YAQ$X_4$$X_5$QG, wherein $X_1$ is selected from the group consisting of A, $X_2$ is selected from the group consisting of N, S and K, $X_3$ is selected from the group consisting of N and K, $X_4$ is selected from the group consisting of K and N, and $X_5$ is selected from the group consisting of L and F;
c. a heavy chain CDR3 amino acid sequence comprising $X_1$QL$X_2$FDY, wherein $X_1$ is selected from the group consisting of R and K, and $X_2$ is selected from the group consisting of Y and V;
d. a light chain CDR1 amino acid sequence comprising RASQS$X_1$SSNLA, wherein $X_t$ is selected from the group consisting of V and I;
e. a light chain CDR2 amino acid sequence comprising $X_1$ASTRA$X_2$, wherein $X_1$ is selected from the group consisting of G and D, and $X_2$ is selected from the group consisting of A and T; and
f. a light chain CDR3 amino acid sequence comprising QQYD$X_1$WPLT, wherein $X_1$ is selected from the group consisting of N, T, and I.

Embodiment 122: the antibody of embodiment 120, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody. Embodiment 123: the antibody of embodiment 122, wherein said antibody inhibits human IL-17A from binding to human IL-17RA. Embodiment 124: the antibody of embodiment 122, wherein said antibody inhibits human IL-17A and IL-17F from binding to human IL-17RA. Embodiment 125: the antibody of embodiment 122, wherein said antibody inhibits human IL-117A or IL-17F from binding to human IL-17R A.

Use of IL-17RA Antigen Binding Proteins for Diagnostic and Therapeutic Purposes

The IL-17RA antigen binding proteins of the invention can be used in diagnostic assays, e.g., binding assays to detect and/or quantify IL-17RA expressed in a tissue or cell. The IL-17RA antigen binding proteins may be used in research to further investigate the role of IL-17RA in disease. The IL-17RA antigen binding proteins may be used to further investigate the role of IL-17RA in forming homomeric and/or heteromeric receptor complexes and the role of said complexes in disease. The IL-17RA antigen binding proteins may be used to further investigate the role of IL-17RA activation to homomeric and/or heteromeric IL-17 ligand complexes. The IL-17RA antigen binding proteins may be used to further investigate the role of IL-17RA activation to homomeric and/or heteromeric IL-17 ligand complexes and how said homomeric and/or heteromeric IL-17 ligand complexes relate to disease.

The IL-17RA antigen binding proteins of the present invention can be used for the prevention or treatment of diseases or conditions associated with the IL-17A and/or IL-17F activity. A disease or condition associated with IL-17A and/or IL-17F means any disease, condition, or pathology whose onset in a patient is caused or exacerbated by the interaction of IL-17A and/or IL-17F with IL-17RA. The severity of the disease, condition, or pathology can also be increased or decreased by the modulating the interaction of IL-17A and/or IL-17F with IL-17RA or a heterologous complex comprising IL-17RA and IL-17RC.

Antigen binding proteins of the invention that specifically bind to IL-17RA may be used in treatment of IL-17RA mediated diseases in a patient in need thereof. All aspects of the IL-17RA antigen binding proteins described throughout this specification may be used in the preparation of a medicament for the treatment of the various conditions and diseases described herein. In addition, the IL-17RA antigen binding protein of the invention can be used to inhibit IL-17RA from forming a complex with its ligand, e.g., IL-17A and/or IL-17F or any other IL-17 ligand family member that binds IL-17RA or a heterologous complex comprising IL-17RA and IL-17RC, thereby modulating the biological activity of IL-17RA in a cell or tissue. Antigen binding proteins that bind to IL-17RA thus may modulate and/or inhibit interaction with other binding compounds and as such may have therapeutic use in ameliorating IL-17RA mediated diseases. In specific embodiments, IL-17RA antigen binding proteins may inhibit IL-17A and/or IL-17F from binding IL-17RA, which may result in disruption of the IL-17RA-induced signal transduction cascade.

Increased levels of IL-17A and/or involvement of IL-17A mediated signals in disease pathogenesis have been demonstrated in a variety of conditions and diseases. Kolls and Linden, 2004, supra; Miossec, 2003, *P. Arthritis Rheum.* 48:594-601); WO2005/063290; Cannetti el al., 2003, *J. Immunol.* 171:1009-1015; Charles et al., 1999, *J. Immunol.* 163: 1521-1528; Cunnane et al., 2000, *Online J. Rheumatol.* 27:58-63; Yoshimoto, 1998, *J. Immunol.* 161: 3400-3407), (WO2005/063290), (Niederau, 1997, *Online NLM*), (WO2004/002519), (Tsutsui et al., 2000, supra), (Konishi et al., 2002, *Proc. Natl. Acad. Sci. U.S.A.* 99:11340-11345). Ziolkowska et al., 2000, supra). (Chabaud, 2001, *Arth & Rheumatism,* 44:1293). Thus, IL-17RA is said to influence the pathology of these and other diseases or conditions described herein.

As described herein, a surrogate rat anti-mouse IL-17RA antibody inhibits the course of disease and reduces bone and cartilage degradation in both a prophylactic and therapeutic rodent collagen induced arthritis model (see Examples below). As further evidence of the efficacy of interrupting the IL-17A/IL-17RA pathway. IL-17RA knockout mice are resistant to collagen-induced arthritis and IL-17RA antibody treatment is effective in arthritis induced in TNFR knockout mice, showing a TNF independent effect (see Example 6).

Inhibiting IL-17RA using the antigen binding proteins disclosed herein represents a novel and effective mechanism to inhibit the symptoms and pathology of inflammatory and autoimmune diseases, and in particular inflammation and joint degradation found in rheumatoid arthritis (RA), Preclinical data and data from RA patient tissues suggest the potential to provide efficacy in those who failed TNF inhibitor therapy and to confer added benefit in combination with TNF inhibitors, IL-6 inhibitors, and IL-1 inhibitors.

The antigen binding proteins described herein may be used in combination (pre-treatment, post-treatment, or concurrent treatment) with any of one or more TNF inhibitors for the treatment or prevention of the diseases and disorders recited herein, such as but not limited to, all forms of soluble TNF receptors including Etanercept (such as ENBREL®), as well as all forms of monomeric or multimeric p75 and/or p55 TN F receptor molecules and fragments thereof; anti-human TN F antibodies, such as but not limited to, infliximab (such as REMICADE®), and D2E7 (such as HUMIRA®), and the like. Such TNF inhibitors include compounds and proteins which block in vivo synthesis or extracellular release of TNF. In a specific embodiment, the present invention is directed to the use of an IL-17RA antigen binding protein in combination (pre-treatment, post-treatment, or concurrent treatment) with any of one or more of the following TNF inhibitors: TNF binding proteins (soluble TNF receptor type-I and soluble TNF receptor type-II ("sTNFRs"), as defined herein), anti-TNF antibodies, granulocyte colony stimulating factor; thalidomide; BN 50730; tenidap; E 5531; tiapafant PCA 4248; nimesulide; PANAVIR® (Probucol); rolipram; RP 73401; peptide T; MDL 201,449A; (1R,3S)-Cis-1-[9-(2,6-diaminopurinyl)]-3-hydroxy-4-cyclopentene hydrochloride; (1R,3R)-trans-1-(9-(2,6-diamino)purine]-3-acetoxycyclopentane; (11R,3R)-trans-1-[9-adenyl)-3-azidocyclopentane hydrochloride and (1R,3R)-trans-1-(6-hydroxy-purin-9-yl)-3-azidocyclo-pentane. TNF binding proteins are disclosed in the art (EP 308 378, EP 422 339, GB 2 218 101, EP 393 438, WO 90/13575, EP 398 327, EP 412 486, WO 91/03553. EP 418 014, JP 127,800/1991, EP 433 900, U.S. Pat. No. 5,136,021, GB 2 246 569, EP 464 533, WO 92/01002, WO 92/13095, WO 92/16221, EP 512 528. EP 526 905, WO 93/07863, EP 568 928, WO 93/21946, WO 93/19777, EP 417 563, WO 94/06476, and PCT International Application No. PCT/US97/12244).

For example, EP 393 438 and EP 422 339 teach the amino acid and nucleic acid sequences of a soluble TNF receptor type I (also known as "sTNFR-I" or "30 kDa TNF inhibitor") and a soluble TNF receptor type II (also known as "sTNFR-II" or "40 kDa TNF inhibitor"), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types and expressing the gene to produce the inhibitors. Additionally, polyvalent forms (i.e., molecules comprising more than one active moiety) of sTNFR-I and sTNFR-II have also been disclosed. In one embodiment, the polyvalent form may be constructed by chemically coupling at least one TNF inhibitor and another moiety with any clinically acceptable linker, for example polyethylene glycol (WO 92/16221 and WO 95/34326), by a peptide linker (Neve et al. (1996), *Cytokine,* 8(5):365-370, by chemically coupling to biotin and then binding to avidin (WO 91/03553) and, finally, by combining chimeric antibody molecules (U.S. Pat. No. 5,116,964, WO 89/09622, WO 91/16437 and EP 315062.

Anti-TNF antibodies include the MAK 195F Fab antibody (Holler et al. (1993), 1st International Symposium on Cytokines in Bone Marrow Transplantation, 147); CDP 571 anti-TNF monoclonal antibody (Rankin et al. (1995), *British Journal of Rheumatology,* 34:334-342); BAY X 1351 murine anti-tumor necrosis factor monoclonal antibody (Kiefl et al. (1995), 7th European Congress of Clinical Microbiology and Infectious Diseases, page 9); CenTNF cA2 anti-TNF monoclonal antibody (Elliott et al. (1994). *Lancet.* 344:1125-1127 and Elliott et al. (1994), *Lancet,* 344:1105-1110).

The antigen binding proteins described herein may be used in combination with all forms of IL-1 inhibitors, such as but not limited to, kineret (for example ANAKINRA®). Interleukin-1 receptor antagonist (IL-1ra) is a human protein that acts as a natural inhibitor of interleukin-1. Interleukin-1 receptor antagonists, as well as the methods of making and methods of using thereof, are described in U.S. Pat. No. 5,075,222; WO 91/08285; WO 91/17184; AU 9173636; WO 92/16221; WO 93/21946; WO 94/06457; WO 94/21275; FR 2706772; WO 94/21235; DE 4219626; WO 94/20517; WO 96/22793 and WO 97/28828. The proteins include glycosylated as well as non-glycosylated IL-1 receptor antagonists. Specifically, three preferred forms of IL-1ra (IL-raα, IL-1raβ and IL-1rax), each being encoded by the same DNA coding sequence and variants thereof, are disclosed and described in U.S. Pat. No. 5,075,222. Methods for producing IL-1 inhibitors, particularly IL-1ras, are also disclosed in the 5,075,222 patent. An additional class of interleukin-1 inhibitors includes compounds capable of specifically preventing activation of cellular receptors to IL-1. Such compounds include IL-1 binding proteins, such as soluble receptors and monoclonal antibodies. Such compounds also include monoclonal antibodies to the receptors. A further class of interleukin-1 inhibitors includes compounds and proteins that block in vivo synthesis and/or extracellular release of IL-1. Such compounds include agents that affect transcription of IL-1 genes or processing of IL-1 preproteins.

The antigen binding proteins described herein may be used in combination with all forms of CD28 inhibitors, such as but not limited to, abatacept (for example ORENCIA®).

The antigen binding proteins described herein may be used in combination with all forms of IL-6 and/or IL-6 receptor inhibitors, such as but not limited to, tocilizumab (for example ACTEMRA®).

The antigen binding proteins may be used in combination with one or more cytokines, lymphokines, hematopoietic factor(s), and/or an anti-inflammatory agent.

Treatment of the diseases and disorders recited herein can include the use of first line drugs for control of pain and inflammation in combination (pretreatment, post-treatment, or concurrent treatment) with treatment with one or more of the antigen binding proteins provided herein. These drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy. Sixteenth Edition, Merck, Sharp & Dohme Research Laboratories, Merck & Co., Rahway, N.J. (1992) and in Pharmaprojects, PJB Publications Ltd.

In a specific embodiment, the present invention is directed to the use of an antigen binding protein and any of one or more NSAIDs for the treatment of the diseases and disorders recited herein. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the present invention is directed to the use of an antigen binding protein in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the present invention is directed to the use of an antigen binding protein in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, fircloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present invention is directed to the use of an antigen binding protein in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present invention is directed to the use of an antigen binding protein in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present invention is directed to the use of an antigen binding protein in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present invention is directed to the use of an antigen binding protein in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present invention is directed to the use of an antigen binding protein in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the present invention is directed to the use of an antigen binding protein in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which may be used comprise: difenamizole and epirizole. Structurally related pyrazoles having similar analgesic and anti-inflammatory properties are also intended to be encompassed by this group.

In an additional specific embodiment, the present invention is directed to the use of an antigen binding protein in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazolones having similar analgesic and anti-inflammatory properties are also intended to be encompassed by this group.

In another specific embodiment, the present invention is directed to the use of an antigen binding protein in combination (pretreatment, post-treatment, or concurrent treatment) with any of one or more of the following NSAIDs: ε-acetamidocaproic acid, S-adenosyl-methionine, 3-amino-4-hydroxybutyric acid, amixetrine, anitrazafen, antrafenine, bendazac, bendazac lysinate, benzydamine, beprozin, broperamole, bucolome, bufczolac, ciproquazonc, cloximate, dazidaminc, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixim, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802. AFP860, A177B, AP504, AU8001, BPPC, BW540C, CHINOIN 127, CN100, EB382, EL508, F1044, FK-506, GV3658, ITF182, KCNTEI6090, KMFA, LA2851, MR714, MR897, MY309, ON03144, PR823, PV102, PV108, R830, RS2131, SCR152, SH440, SIR133, SPAS510, SQ27239, ST281, SY6001, TA6W, TA1-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present invention is directed to the use of an antigen binding protein in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, dcsonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydro-cortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stcaroglycolate, prednisolonc tcbutatc, prednisolone 21-trimcthylacctatc, prednisonc, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present invention is directed to the use of an antigen binding protein in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclo-phosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kcbuzone, lcvamisolc, lobcnzarit, mclittin, 6-mercaptopurinc, mcthotrcxate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present invention is directed to the use of an antigen binding protein in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group. Examples of COX-2 selective inhibitors include but not limited to etoricoxib, valdecoxib, celecoxib, licofelone, lumiracoxib, rofecoxib, and the like.

In still another specific embodiment, the present invention is directed to the use of an antigen binding protein in combination (pretreatment, post-treatment, or concurrent treatment) with any of one or more antimicrobials, prodrug esters or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, cefotadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazinc, sulfisoxazolc and co-trimoxazolc (trimcthoprimisulfamethoxazole). The lincosamides include, but are not limited to clindamycin and lincomycin. The polymyxins (polypeptides) include, but are not limited to polymyxin B and colistin.

The most cited activity of IL-17A in vitro is the induction of neutrophil mobilizing cytokines and chemokines by stromal cells (e.g. GM-CSF, IL6, IL8). These activities are potently enhanced in the presence of TNF (Ruddy et al., 2004). Similarly the biologic activities of IL-17F are also enhanced by TNF co-stimulus. Of particular note with respect to a pathogenic role for IL-17A in cartilage destruction and bone erosion associated with rheumatoid arthritis, IL-17A induces the expression of NO, MMPs, PGE2 and RANKL and plays a role in antigen specific T and B cell activation (Kolls and Linden, 2004, supra; Lubberts et al., 2005, Arthritis. Res. Ther. 7:29-37). Therefore, the antigen binding proteins may be used to inhibit the IL-17A and/or IL-17F/IL-17RA pathway and subsequent production of NO, MMPs, PGE2 and/or RANKL and treat diseases associated with the IL-17A and/or IL-17F upregulation of NO, MMPs, PGE2 and/or RANKL, as well as other proinflammatory mediators described herein.

In addition to the presence of elevated levels of IL-17A in the synovial fluid of rheumatoid arthritis patients, several lines of evidence suggest that IL-17A is a key pathogenic cytokine in arthritis. First, administration of IL-17A to the joints of mice exacerbates the symptoms of collagen-induced arthritis (Lubberts et al., 2003, J. Immunol. 170:2655-2662). Second, soluble IL-17RA. Fc inhibits collagen breakdown in human RA synovial and bone explant cultures and attenuates the symptoms in collagen induced arthritis in the mouse (Chabaud and Miossec, 2001, Arthritis Rheum. 44:1293-1303) (Lubberts et al., 2001, J. Immunol. 167: 1004-1013)). As predicted from the low affinity interaction between IL-17F and IL-17R, IL-17R-Fc does not neutralize the activity of IL-17F and so these effects are specific to IL-17A antagonism. Third, mice lacking IL-17A are resistant to IL-1-induced arthritis and have suppressed collagen-induced arthritis (Nakae et al., 2003a, J. Immunol. 171: 6173-6177; Nakae et al., 2003b, supra). These data indicate that IL-17A signaling through IL-17RA is an important mediator of inflammation and joint damage in arthritis. The antigen binding proteins may be used to inhibit IL-17A and/or IL-17F/IL-17RA activity and thereby reduce the inflammation and joint damage in arthritis.

In rheumatoid arthritis, elevated levels of mature IL-17A have been demonstrated in patient sera and synovial fluid. In some studies. IL-17A levels were shown to correlate with disease activity and response to disease modifying treatment. Extremely elevated serum levels of IL-17A have consistently been measured in systemic Juvenile Idiopathic Arthritis and the closely related Adult-Onset Still's Disease. WO2005/063290; Cannetti et al., 2003, J. Immunol. 171: 1009-1015; Charles et al., 1999, J. Immunol. 163: 1521-1528; Cunnane et al., 2000, Online J. Rheumatol. 27:58-63; Yoshimoto, 1998, J. Immunol. 161: 3400-3407. The antigen binding proteins may be used to inhibit IL-17A and/or IL-17F/IL-17RA activity and thereby treat systemic Juvenile Idiopathic Arthritis and Adult-Onset Still's Disease.

Various other autoimmune diseases have been associated with increased levels of IL-17A either in diseased tissue or in the serum. These include Systemic Lupus Erythematosus, atopic dermatitis, myasthenia gravis, type I diabetes, and sarcoidosis. IL-17A may also be involved in asthma and GvHD. The antigen binding proteins taught herein may be used to reduce the effects of the IL-17A and/or IL-17F/IL-17RA pathway in these diseases.

The antigen binding proteins may be used to reduce IL-17RA activity, comprising administering an antigen binding protein. The present invention is also directed to methods of inhibiting binding and/or signaling of IL-17A and/or IL-17F to IL-17RA comprising providing the antigen binding protein of the invention to IL-17RA. In certain embodiments, the antigen binding protein inhibits binding and/or signaling of IL-17A and IL-17F to IL-17RA. In additional embodiments, the antigen binding protein inhibits binding and/or signaling of IL-17A but not IL-17F to IL-17RA. In other embodiments, the antigen binding protein inhibits binding and/or signaling of IL-17F and not IL-17A to IL-17RA. The antigen binding proteins may be used in treating the consequences, symptoms, and/or the pathology associated with IL-17RA activity, comprising administering an antigen binding protein. The antigen binding proteins may be used to inhibit the production of one or more of an inflammatory cytokine, chemokine, matrix metalloproteinase, or other molecule associated with IL-17RA activation, comprising administering an antigen binding protein. The antigen binding proteins may be used in methods of inhibiting production of molecules such as but is not limited to:

IL-6, IL-8. CXCL1, CXCL2, GM-CSF, G-CSF, M-CSF, IL-1β, TNFα, RANK-L, LIF, PGE2, IL-12, MMPs (such as but not limited to MMP3 and MMP9), GROQ, NO, and/or C-telopeptide and the like, comprising administering an antigen binding protein. The antigen binding proteins inhibit proinflammatory and proautoimmune immune responses and may be used to treat diseases associated with activity of the IL-17A and/or IL-17F/IL-17RA pathway.

Aspects of the invention include antibodies that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex. Thus, disease states associated with IL-17RC are also associated with IL-17RA due to the fact that IL-17RC cannot signal without IL-17RA. For example, see You, Z., et al., *Cancer Res.*, 2006 Jan. 1;66(1):175-83 and You, Z., et al., *Neoplasia*, 2007 June;9(6):464-70.

The IL-17RA antigen binding proteins may be used in methods of treating IL-17RA associated disease, comprising administering an IL-17RA antigen binding protein. The IL-17RA antigen binding protein may be used to treat diseases including, but are not limited to, inflammation, autoimmune disease, cartilage inflammation, and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, systemic lupus crythematosus, vasculitis, myolitis, polymyolitis, dermatomyolitis, osteoarthritis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus, Graves' disease, Addison's disease. Raynaud's phenomenon, autoimmune hepatitis, GVHD, and the like.

Aspects of the invention include a variety of embodiments including, but not limited to, the following exemplary embodiments: embodiment 151: a method of treating a disease state associated with IL-17RA activation in a patient in need thereof, comprising administering to said patient a composition comprising an antibody that specifically binds human IL-17 Receptor A and inhibits the binding of IL-17A, wherein said antibody is selected from the group consisting of:

A. an isolated antibody, or IL-17RA-binding fragment thereof, comprising
  a. a light chain variable domain sequence that is at least 80% identical to a light chain variable domain sequence of $AM_L$1-26 (SEQ ID NOs:27-53, respectively);
  b. a heavy chain variable domain sequence that is at least 80% identical to a heavy chain variable domain sequence of $AM_H$1-26 (SEQ ID NOs:1-26, respectively);
  c. the light chain variable domain of (a) and the heavy chain variable domain of (b); wherein said antibody specifically binds to human IL-17RA;
B. an isolated antibody, or IL-17RA-binding fragment thereof, comprising
  a. a light chain CDR1 (SEQ ID NO:185), CDR2 (SEQ ID NO:186), CDR3 (SEQ ID NO:187) and a heavy chain CDR1 (SEQ ID NO:107), CDR2 (SEQ ID NO:108), CDR3 (SEQ ID NO:109) of antibody AM-1;
  b. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO: 112) of antibody AM-2;
  c. a light chain CDR1 (SEQ ID NO:191), CDR2 (SEQ ID NO: 192), CDR3 (SEQ TD NO:193) and a heavy chain CDR1 (SEQ ID NO:113), CDR2 (SEQ ID NO:114), CDR3 (SEQ ID NO: 115) of antibody AM-3;
  d. a light chain CDR1 (SEQ ID NO:194), CDR2 (SEQ ID NO:195), CDR3 (SEQ ID NO:196) and a heavy chain CDR1 (SEQ ID NO: 116), CDR2 (SEQ ID NO:117), CDR3 (SEQ ID NO:118) of antibody AM-4;
  e. a light chain CDR1 (SEQ ID NO:197), CDR2 (SEQ ID NO:198), CDR3 (SEQ ID NO:199) and a heavy chain CDR1 (SEQ ID NO: 119), CDR2 (SEQ ID NO:120), CDR3 (SEQ ID NO:121) of antibody AM-5;
  f. a light chain CDR1 (SEQ ID NO:200), CDR2 (SEQ ID NO:201), CDR3 (SEQ ID NO:202) and a heavy chain CDR1 (SEQ ID NO:122), CDR2 (SEQ ID NO:123), CDR3 (SEQ ID NO:124) of antibody AM-6;
  g. a light chain CDR1 (SEQ ID NO:203), CDR2 (SEQ ID NO:204), CDR3 (SEQ ID NO:205) and a heavy chain CDR1 (SEQ ID NO:125), CDR2 (SEQ ID NO:126), CDR3 (SEQ ID NO:127) of antibody AM-7;
  h. a light chain CDR1 (SEQ ID NO:206), CDR2 (SEQ ID NO:207), CDR3 (SEQ ID NO:208) and a heavy chain CDR1 (SEQ ID NO:128), CDR2 (SEQ ID NO:129), CDR3 (SEQ ID NO:130) of antibody AM-8;
  i. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
  j. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
  k. a light chain CDR1 (SEQ ID NO:215), CDR2 (SEQ ID NO:216), CDR3 (SEQ ID NO:217) and a heavy chain CDR1 (SEQ ID NO:137), CDR2 (SEQ ID NO:138), CDR3 (SEQ ID NO:139) of antibody AM-11;
l. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
m. a light chain CDR1 (SEQ ID NO:221), CDR2 (SEQ ID NO:222), CDR3 (SEQ ID NO:223) and a heavy chain CDR1 (SEQ ID NO:143), CDR2 (SEQ ID NO:144), CDR3 (SEQ ID NO:145) of antibody AM-13;
n. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
o. a light chain CDR1 (SEQ ID NO:227), CDR2 (SEQ ID NO:228), CDR3 (SEQ ID NO:229) and a heavy chain CDR1 (SEQ ID NO: 149), CDR2 (SEQ ID NO:150), CDR3 (SEQ ID NO:151) of antibody AM-15;
p. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
q. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
r. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
s. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
t. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
u. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;
v. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
w. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;
x. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
y. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO: 178) of antibody AM-24;
z. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25;
z.2. a light chain CDR1 (SEQ ID NO:263), CDR2 (SEQ ID NO:264), CDR3 (SEQ ID NO:265) and a heavy chain CDR1 (SEQ ID NO:182), CDR2 (SEQ ID NO: 183), CDR3 (SEQ ID NO:184) of antibody AM-26; wherein said antibody specifically binds to human IL-17RA; and C. an isolated antibody, or IL-17RA-binding fragment thereof, comprising
a. a light chain variable domain and a heavy chain variable domain of $AM_L1/AM_H1$ (SEQ ID NO:27/SEQ ID NO:1);
b. a light chain variable domain and a heavy chain variable domain of $AM_L2/AM_H2$ (SEQ ID NO:28/SEQ ID NO:2);
c. a light chain variable domain and a heavy chain variable domain of $AM_L3/AM_H3$ (SEQ ID NO:29/SEQ ID NO:3);
d. a light chain variable domain and a heavy chain variable domain of $AM_L4/AM_H4$ (SEQ ID NO:30/SEQ ID NO:4);
e. a light chain variable domain and a heavy chain variable domain of $AM_L5/AM_H5$ (SEQ ID NO:31/SEQ ID NO:5);
f. a light chain variable domain and a heavy chain variable domain of $AM_L6/AM_H6$ (SEQ ID NO:32/SEQ ID NO:6)
g. a light chain variable domain and a heavy chain variable domain of $AM_L7/AM_H7$ (SEQ ID NO:33/SEQ ID NO:7);
h. a light chain variable domain and a heavy chain variable domain of $AM_L8/AM_H8$ (SEQ ID NO:34/SEQ ID NO:8);
i. a light chain variable domain and a heavy chain variable domain of $AM_L9/AM_H9$ (SEQ ID NO:35/SEQ ID NO:9);
j. a light chain variable domain and a heavy chain variable domain of $AM_L10/AM_H10$ (SEQ ID NO:36/SEQ ID NO: 10);
k. a light chain variable domain and a heavy chain variable domain of $AM_L11/AM_H11$ (SEQ ID NO:37/SEQ ID NO: 11);
L. a light chain variable domain and a heavy chain variable domain of $AM_L12/AM_H12$ (SEQ ID NO:38/SEQ ID NO:12);
m. a light chain variable domain and a heavy chain variable domain of $AM_L13/AM_H13$ (SEQ ID NO:39/SEQ ID NO:13);
n. a light chain variable domain and a heavy chain variable domain of $AM_L14/AM_H14$ (SEQ ID NO:40/SEQ ID NO:14);
o. a light chain variable domain and a heavy chain variable domain of $AM_L15/AM_H15$ (SEQ ID NO:41/SEQ ID NO:15);

p. a light chain variable domain and a heavy chain variable domain of AM$_L$16/AM$_H$16 (SEQ ID NO:42/SEQ ID NO:16);
q. a light chain variable domain and a heavy chain variable domain of AM$_L$17/AM$_H$17 (SEQ ID NO:43/SEQ ID NO:17);
r. a light chain variable domain and a heavy chain variable domain of AM$_L$18/AM$_H$18 (SEQ ID NO:44/SEQ ID NO:18);
s. a light chain variable domain and a heavy chain variable domain of AM$_L$19/AM$_H$19 (SEQ ID NO:45/SEQ ID NO:19);
t. a light chain variable domain and a heavy chain variable domain of AM$_L$20/AM$_H$20 (SEQ ID NO:46/SEQ ID NO:20);
u. a light chain variable domain and a heavy chain variable domain of AM$_L$21/AM$_H$21 (SEQ ID NO:47/SEQ ID NO:21);
v. a light chain variable domain and a heavy chain variable domain of AM$_L$22/AM$_H$22 (SEQ ID NO:48/SEQ ID NO:22);
w. a light chain variable domain and a heavy chain variable domain of AM$_L$23/AM$_H$23 (SEQ ID NO: 49 or SEQ ID NO:50/SEQ ID NO:23);
x. a light chain variable domain and a heavy chain variable domain of AM$_L$24/AM$_H$24 (SEQ ID NO:51/SEQ ID NO:24);
y. a light chain variable domain and a heavy chain variable domain of AM$_L$25/AM$_H$25 (SEQ ID NO:52/SEQ ID NO:25);
z. a light chain variable domain and a heavy chain variable domain of AM$_L$26/AM$_H$26 (SEQ ID NO:53/SEQ ID NO:26);
wherein said antibody specifically binds to human IL-17RA.

Embodiment 152: the method of embodiment 151, wherein said disease state selected from the group consisting of: inflammation, autoimmune disease, cartilage inflammation, and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis. Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, osteoarthritis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus. Graves' disease, Addison's disease, Raynaud's phenomenon, autoimmune hepatitis, and graft versus host disease (GVHD).

Embodiment 153: the method of embodiment 151 further comprising administering to said subject a second treatment comprising a pharmaceutical composition. Embodiment 154: the method of embodiment 153, wherein said second pharmaceutical composition is selected from the group consisting of: TNF inhibitors, soluble TNF receptors, Etanercept, ENBREL®, soluble TNF receptor type-I and soluble TNF receptor type-II, monomeric or multimeric p75 and/or p55 TNF receptor molecules and fragments thereof, anti-TNF antibodies, Infliximab, REMICADE®, D2E7, or HUMIRA®, IL-1 inhibitors, IL-1 receptor inhibitors, CD28 inhibitors, non-steroidal anti-inflammatory drugs (NSAID), a slow acting antirheumatic drugs (SAARD), and disease modifying antirheumatic drugs (DMARD). Embodiment 155: a method of inhibiting the production of at least one cytokine, chemokine, matrix metalloproteinase, or other molecule associated with IL-17RA activation, comprising administering the antibody of embodiment 151 to a patient in need thereof. Embodiment 156: the method of embodiment 155, wherein said cytokine, chemokine, matrix metalloproteinase, or other molecule is selected from the group consisting of: IL-6, IL-8, CXCL1, CXCL2, GM-CSF, G-CSF, M-CSF, IL-1β, TNFα, RANK-L, LIF, PGE2, IL-12, MMP3, MMP9, GROα, NO, and C-telopeptide. Embodiment 157: a method of treating a disease state associated with IL-17RA activation in a subject in need thereof, comprising administering to said subject a composition comprising an antibody that specifically binds human IL-17 Receptor A and inhibits the binding of IL-17A and IL-17F or inhibits the binding of IL-17A or IL-17F.

Embodiment 158: the method of embodiment 157, wherein said antibody is selected from the group consisting of:
A. an isolated antibody, or IL-17RA-binding fragment thereof, comprising
  a. a light chain variable domain sequence that is at least 80% identical to a light chain variable domain sequence of AM$_L$14, 18, 19, and 22 (SEQ ID NOs: 40, 44, 45, and 48 respectively);
  b. a heavy chain variable domain sequence that is at least 80% identical to a heavy chain variable domain sequence of AM$_H$14, 18, 19, and 22 (SEQ ID NOs: 14, 18, 19, and 22 respectively);
  c. the light chain variable domain of (a) and the heavy chain variable domain of (b); wherein said antibody specifically binds to human IL-17RA;
B. an isolated antibody, or IL-17RA-binding fragment thereof, comprising
  a. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
  b. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
  c. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
  d. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22; wherein said antibody specifically binds to human IL-17RA; and
C. an isolated antibody, or IL-17RA-binding fragment thereof, comprising
   a. a light chain variable domain and a heavy chain variable domain of $AM_L14/AM_H14$ (SEQ ID NO:40/SEQ ID NO:14);
   b. a light chain variable domain and a heavy chain variable domain of $AM_L18/AM_H18$ (SEQ ID NO:44/SEQ ID NO:18);
   c. a light chain variable domain and a heavy chain variable domain of $AM_L19/AM_H19$ (SEQ ID NO:45/SEQ ID NO:19);
   d. a light chain variable domain and a heavy chain variable domain of $AM_L22/AM_H22$ (SEQ ID NO:48/SEQ ID NO:22); wherein said antibody specifically binds to human IL-17RA.

Embodiment 159: the method of embodiment 157, wherein said disease state is the disease state of claim 152. Embodiment 160: a method of inhibiting the production of at least one cytokine, chemokine, matrix metalloproteinase, or other molecule associated with IL-17RA activation, comprising administering the antibody of embodiment 157 to a patient in need thereof. Embodiment 161: the method of embodiment 160, wherein said cytokine, chemokine, matrix metalloproteinase, or other molecule is selected from the group consisting of: IL-6, IL-8, CXCL1, CXCL2, GM-CSF, G-CSF, M-CSF, IL-1β, TNFα, RANK-L, LIF, PGE2, IL-12, MMP3, MMP9, GROα, NO, and C-telopeptide.

Embodiment 162: a method of treating inflammation and autoimmune disease in a patient in need thereof comprising administering to said patient a composition comprising an antibody selected from the group consisting of:
A. an isolated antibody, or IL-17RA-binding fragment thereof, comprising
   a. a light chain variable domain sequence that is at least 80% identical to a light chain variable domain sequence of $AM_L14$, 18, 19, and 22 (SEQ ID NOs: 40, 44, 45, and 48 respectively);
   b. a heavy chain variable domain sequence that is at least 80% identical to a heavy chain variable domain sequence of $AM_H14$, 18, 19, and 22 (SEQ ID NOs: 14, 18, 19, and 22 respectively);
   c. the light chain variable domain of (a) and the heavy chain variable domain of (b); wherein said antibody specifically binds to human IL-17RA;
B. an isolated antibody, or IL-17RA-binding fragment thereof, comprising
   a. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
   b. a light chain CDR1 (SEQ ID NO:236), CDR2 (SEQ ID NO:237), CDR3 (SEQ ID NO:238) and a heavy chain CDR1 (SEQ ID NO:158), CDR2 (SEQ ID NO:159), CDR3 (SEQ ID NO:160) of antibody AM-18;
   c. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
   d. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22; wherein said antibody specifically binds to human IL-17RA; and
C. an isolated antibody, or IL-17RA-binding fragment thereof, comprising
   a. a light chain variable domain and a heavy chain variable domain of $AM_L14/AM_H14$ (SEQ ID NO:40/SEQ ID NO:14);
   b. a light chain variable domain and a heavy chain variable domain of $AM_L18/AM_H18$ (SEQ ID NO:44/SEQ ID NO:18);
   c. a light chain variable domain and a heavy chain variable domain of $AM_L19/AM_H19$ (SEQ ID NO:45/SEQ ID NO:19);
   d. a light chain variable domain and a heavy chain variable domain of $AM_L22/AM_H22$ (SEQ ID NO:48/SEQ ID NO:22); wherein said antibody specifically binds to human IL-17RA.

Embodiment 163: the method of embodiment 162, wherein said inflammation and autoimmune disease is selected from the group consisting of: arthritis, rheumatoid arthritis, ankylosing spondylitis, psoriatic arthritis, psoriasis, plaque psoriasis, dermatitis, atopic dermatitis, systemic lupus erythematosus, inflammatory bowel disease, Crohn's disease, ulcerative colitis, celiac disease, multiple sclerosis, asthma, and chronic obstructive pulmonary disease. Embodiment 164: the method of claim 151, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody. Embodiment 165: the method of embodiment 158, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody.

Embodiment 166: the method of claim 151, wherein said antibody is selected from the group consisting of:
A. an isolated antibody, or IL-17RA-binding fragment thereof, comprising
   a. a light chain variable domain sequence that is at least 80% identical to a light chain variable domain sequence SEQ ID NO: 40;
   b. a heavy chain variable domain sequence that is at least 80% identical to a heavy chain variable domain sequence of SEQ ID NO:14;
   c. the light chain variable domain of (a) and the heavy chain variable domain of (b); wherein said antibody specifically binds to human IL-17RA;
B. an isolated antibody, or IL-17RA-binding fragment thereof, comprising a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148); wherein said antibody specifically binds to human IL-17RA; and
C. an isolated antibody, or IL-17RA-binding fragment thereof, comprising a light chain variable domain of SEQ ID NO:40 and a heavy chain variable domain SEQ ID NO:14; wherein said antibody specifically binds to human IL-17RA.

Embodiment 167: the method of embodiment 166, wherein said disease state is rheumatoid arthritis. Embodiment 168: the method of embodiment 166, wherein said disease state is psoriasis. Embodiment 169: the method of embodiment 166, wherein said disease state is inflammatory bowel disease. Embodiment 170: the method of embodiment 166, wherein said disease state is asthma. Embodiment 171: the method of embodiment 166, wherein said antibody comprises a light chain variable domain of SEQ ID NO:40 and a heavy chain variable domain SEQ ID NO: 14; wherein said antibody specifically binds to human IL-17RA. Embodiment 172: the method of embodiment 166, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody. Embodiment 173: the method of claim 171, wherein said antibody is selected from the group consisting of: a. a humanized antibody; b. a chimeric antibody; c. a recombinant antibody; d. a single chain antibody; e. a diabody; f. a triabody; g. a tetrabody; h. a Fab fragment; i. a F(ab')2 fragment; j. an IgD antibody; k. an IgE antibody; l. an IgM antibody; m. an IgG1 antibody; n. an IgG2 antibody; o. an IgG3 antibody; and p. an IgG4 antibody. Embodiment 174: the method of embodiment 167, wherein said antibody comprises a light chain sequence of SEQ ID NO:429 and a heavy chain sequence of SEQ ID NO:427. Embodiment 175: the method of claim 168, wherein said antibody comprises a light chain sequence of SEQ ID NO:429 and a heavy chain sequence of SEQ ID NO:427.

It is understood that the above-described methods also encompasses comparable methods for first and second medical uses and claims thereto, as described elsewhere in this specification.

Chronic viral hepatitis affects over 500 million people worldwide, including approximately 10 million in the U.S. and Europe with chronic hepatitis C infections. A significant proportion of chronic hepatitis patients develop progressive liver fibrosis and/or hepatocellular carcinoma. While viral hepatitis vaccines are available or in development, current therapy for infected individuals relics on long courses of the combination of antiviral drugs and interferon-alpha (INF-α). INF-α is thought to be beneficial in treating viral hepatitis through its proven antiviral immunological activities and antiproliferative effects on fibroblasts, but the duration and level of its use is limited by severe side effects.

Recent data describes how INF-α may be directly apoptotic for Th17 cells (American Association for Immunologists, abstract no. 42.8, May 12-16, 2006, Boston). Th17 cells are a distinct subset of CD4+ T-cells responsible for producing IL-17A and IL-17F in response to IL-23 (Harrington, et al., *Nature Imm*, 2005 vol. 6, no. 11, 1123-1132 and Park, et al., *Nature Imm*, 2005 vol. 6, no. 11, 1133-1141). We believe this suggests a new mechanism of action for INF-α in chronic viral hepatitis that does not involve direct action of INF-α on virus or fibroblasts, but indirect actions on Th17 cells. Furthermore, it has recently been discovered that Tumor Growth Factor-Beta (TGF-β) and/or IL-6, (see for example, Kimera, A., et al., PNAS U.S.A., 2007 Jul. 17; 104(29):12099-104), both pro-fibrotic cytokine, also induces the development of TH17 cells by upregulating IL-23 receptor expression and thereby conferring responsiveness to IL-23 ((Mangan, et al., *Nature*, 2006 vol. 441 no. 11, 231-234). Responsiveness to IL-23 induces the differentiation of naïve CD4+ T-cells into TH17 cells. As mentioned above, the TH17 cells are responsible for releasing IL-17A and IL-17F, and IL-17A is known to have various stimulatory effects on fibroblasts in a number of tissues and organs. Taken together, we believe that inhibition of the IL-17RA-IL-17A/IL-17F pathway may offer a therapeutic benefit in the progressive fibrosis of chronic viral hepatitis.

An added benefit of inhibiting the IL-17RA-IL-17A/IL-17F pathway in the treatment of viral hepatitis is that one may reduce the dosage of INF-α given to the patient and consequently limit the deleterious side effects associated with INF-α therapy. A further benefit of inhibiting the IL-17RA-IL-17A/IL-17F pathway in the treatment of viral hepatitis is the possibility of achieving a synergistic therapeutic effect with INF-α therapy in combination with IL-17RA-IL-17A/IL-17F antagonist therapy, or other antagonists as described in more detail below.

Therefore, aspects of the invention are drawn to methods of treating the pathology associated with viral hepatitis by inhibiting the interaction between IL-17RA and IL-17A and/or IL-17F. Further aspects of the invention are drawn to methods of inhibiting fibrosis by inhibiting the interaction between IL-17RA and IL-17A and/or IL-17F. Further aspects of the invention are drawn to methods of treating fibrosis associated with viral hepatitis by inhibiting the interaction between IL-17RA and IL-17A and/or IL-17F. Antagonists of the IL-17RA-IL-17A/IL-17F pathway may be used to inhibit the interaction between IL-17RA and IL-17A and/or IL-17F. Antagonists of the IL-17RA-IL-17A pathway include the IL-17RA antigen binding proteins described herein, as well as IL-17RA proteins (as well as biologically active fragments and fusion proteins thereof, such as IL-17RA-Fc fusion proteins), as well as antigen binding proteins, such as antibodies and biologically active fragments thereof, that bind to IL-17A and inhibit IL-17A from activating IL-17RA, as well as antigen binding proteins, such as antibodies and biologically active fragments thereof, that bind to IL-17F and inhibit IL-17F from activating IL-17RA.

Additional aspects are drawn to methods of treating the pathology associated with viral hepatitis by antagonizing the IL-23-IL-23 receptor (IL-23R) pathway. Further aspects of the invention are drawn to methods of inhibiting fibrosis by antagonizing the IL-23-IL-23R pathway. Further aspects of the invention are drawn to methods of treating fibrosis associated with viral hepatitis by antagonizing the IL-23-IL-23R pathway. By antagonizing the IL-23-IL-23R pathway, one prevents the IL-23-induced differentiation of the TH17 cells and thereby ultimately limit the amount of circulating IL-17A and IL-17F, which may reduce the pathology associated with viral hepatitis. Antagonists to the IL-23-IL-23R pathway include antigen binding proteins, such as antibodies and biologically active fragments thereof, that bind to IL-23 and block IL-23 from activating IL-23R. Additional antagonists to IL-23-IL-23R pathway include antigen binding proteins, such as antibodies and biologically active fragments thereof, that bind to IL-23R and block IL-23 from activating IL-23R. Additional antagonists to IL-23-IL-23R pathway include IL-23R proteins, as well as biologically active fragments and fusion proteins thereof, such as IL-23R-Fc fusion proteins, that bind IL-23 and block IL-23 from activating IL-23R.

Additional aspects are drawn to methods of treating the pathology associated with viral hepatitis by antagonizing the TGF-β-TGF-βRI/TGF-βRII pathway. Further aspects of the invention are drawn to methods of inhibiting fibrosis by antagonizing the TGF-β-TGF-βRI/TGF-βRII pathway. Further aspects of the invention are drawn to methods of treating fibrosis associated with viral hepatitis by antagonizing the TGF-β-TGF-βRI/TGF-βRII pathway. By antagonizing the TGF-β-TGF-βRI/TGF-βRII pathway, one prevents the TGF-β-induced development of the TH17 cells and thereby ultimately limit the amount of circulating IL-17A and IL-17F, which may reduce the pathology associated with viral hepatitis. Antagonists to the TGF-β-TGF-βRI/TGF-βRII pathway include antigen binding proteins, such as antibodies and biologically active fragments thereof, that bind to TGF-β and block TGF-β from activating TGF-βRI and/or TGF-βRII. Additional antagonists to the TGF-β-TGF-βRI/TGF-βRII pathway include antigen binding proteins, such as antibodies and biologically active fragments thereof, that bind to TGF-βRI or TGF-βRII and block TGF-β from activating TGF-βRI or TGF-βRII.

Additional aspects are drawn to methods of treating the pathology associated with viral hepatitis by antagonizing the IL-6-IL-6R pathway. Further aspects of the invention are drawn to methods of inhibiting fibrosis by antagonizing the IL-6-IL-6R pathway. Further aspects of the invention are drawn to methods of treating fibrosis associated with viral hepatitis by antagonizing the IL-6-IL-6R pathway. By antagonizing the IL-6-IL-6R pathway, one may reduce the pathology associated with viral hepatitis. Antagonists to the IL-6-IL-6R pathway include antigen binding proteins, such as antibodies and biologically active fragments thereof, that bind to IL-6 and block IL-6 from activating IL-6R. Additional antagonists to the IL-6-IL-6R pathway include antigen binding proteins, such as antibodies and biologically active fragments thereof, that bind to IL-6R and block IL-6 from activating IL-6R.

Further aspects include combination therapy using the antagonists of the IL-17RA-IL-17A/IL-17F pathway, IL-23-IL-23R pathway, TGF-β-TGF-βRI/TGF-βRII pathway, and/or the IL-6-IL-6R pathway mentioned above in combination with each other, as well as in combination with art-recognized hepatitis therapies, such as but not limited to, interferon, and in particular INF-α. All permutations of these combinations are envisioned.

Further aspects include combination therapy using the antagonists of the IL-17RA-IL-17A/IL-17F pathway, IL-23-IL-23R pathway, TGF-β-TGF-βRI/TGF-βRII pathway, and/or the IL-6-IL-6R pathway mentioned above in combination with each other, as well as in combination with art-recognized hepatitis therapies, such as but not limited to, interferon, and in particular INF-α, as well as with antiviral agents, such as but not limited to Adefovir dipivoxil, acyclic analogues of deoxyadenosine monophosphate (Adefovir, Tenofovir disoproxil fumarate), (−) enantiomer of the deoxycytidine analogue 2'-deoxy-3'-thiacytidine (Lamivudine), carbocyclic deoxyguanosine analogues (Entecavir), L-nucleosides (β-L-2'-Deoxythymidine, β-L-2'-deoxycytidine, and β-L-2'-deoxyadenosine), [(−)-β-2',3'-dideoxy-5-fluoro-3'-thiacytidine] (Emtricitabine), 1-β-2,6-Diaminopurine dioxalane (DAPD, amdoxovir), 2'-Fluoro-5-methyl-β-L-arabinofuranosyluridine (L-FMAU, clevudine), Famciclovir, and/or Penciclovir. All permutations of these combinations are envisioned.

Diagnostic Methods

The antigen binding proteins of the invention can be used for diagnostic purposes to detect, diagnose, or monitor diseases and/or conditions associated with IL-17A and/or IL-17RA. The invention provides for the detection of the presence of IL-17RA in a sample using classical immunohistological methods known to those of skill in the art (e.g., Tijssen, 1993. *Practice and Theory of Enzyme Immunoassays*, vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of IL-17RA can be performed in vivo or in vitro.

Diagnostic applications provided herein include use of the antigen binding proteins to detect expression of IL-17RA and binding of the ligands to IL-17RA. Examples of methods useful in the detection of the presence of IL-17RA include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

One aspect of the invention provides for identifying a cell or cells that express IL-17RA. In a specific embodiment, the antigen binding protein is labeled with a labeling group and the binding of the labeled antigen binding protein to IL-17RA is detected. In a further specific embodiment, the binding of the antigen binding protein to IL-17RA detected in vivo. In a further specific embodiment, the antigen binding protein-IL-17RA is isolated and measured using techniques known in the art. See, for example, *Harlow and Lane*, 1988, *Antibodies: A Laboratory Manual*, New York: Cold Spring Harbor (ed. 1991 and periodic supplements); John E. Coligan, ed., 1993, *Current Protocols n Immunology* New York: John Wiley & Sons.

Another aspect of the invention provides for detecting the presence of a test molecule that competes for binding to IL-17RA with the antigen binding proteins of the invention. An example of one such assay would involve detecting the amount of free antigen binding protein in a solution containing an amount of IL-17RA in the presence or absence of the test molecule. An increase in the amount of free antigen binding protein (i.e., the antigen binding protein not bound to IL-17RA) would indicate that the test molecule is capable of competing for IL-17RA binding with the antigen binding protein. In one embodiment, the antigen binding protein is labeled with a labeling group. Alternatively, the test molecule is labeled and the amount of free test molecule is monitored in the presence and absence of an antigen binding protein.

Aspects of the invention include the use of the IL-17RA antigen binding proteins in in vitro assays for research purposes, such as to inhibit production of molecules such as but is not limited to: IL-6, IL-8, CXCL1, CXCL2, GM-CSF, G-CSF, M-CSF, IL-10, TNFα, RANK-L, LIF, PGE2, IL-12, MMPs (such as but not limited to MMP3 and MMP9), GROα, NO, and/or C-telopeptide and the like. Antibodies directed against an IL-17RA can be used, for example, in purifying IL-17RA proteins by immunoaffinity chromatography.

Methods of Treatment: Pharmaceutical Formulations, Routes of Administration

In some embodiments, the invention provides pharmaceutical compositions comprising a therapeutically effective amount of one or a plurality of the antigen binding proteins of the invention together with a pharmaceutically acceptable diluent, carrier, solubilizer, emulsifier, preservative, and/or adjuvant. In addition, the invention provides methods of treating a patient by administering such pharmaceutical composition. The term "patient" includes human and animal subjects.

Pharmaceutical compositions comprising one or more antigen binding proteins may be used to reduce IL-17RA activity. Pharmaceutical compositions comprising one or more antigen binding proteins may be used in treating the consequences, symptoms, and/or the pathology associated with IL-17RA activity. Pharmaceutical compositions comprising one or more antigen binding proteins may be used in methods of inhibiting binding and/or signaling of IL-17A and/or IL-17F to IL-17RA comprising providing the antigen binding protein of the invention to IL-17RA. In certain embodiments, the antigen binding protein inhibits binding and/or signaling of IL-17A and IL-17F to IL-17RA. In additional embodiments, pharmaceutical compositions comprising one or more antigen binding proteins may be used in methods of inhibiting binding and/or signaling of IL-17A but not IL-17F to IL-17RA. In other embodiments, pharmaceutical compositions comprising one or more antigen binding proteins may be used in methods of inhibiting binding and/or signaling of IL-17F and not IL-17A to IL-17RA. Aspects of the invention include antibodies that specifically bind to human IL-17RA and inhibit IL-17A and/or IL-17F from binding and activating IL-17RA, or a heteromeric complex of IL-17RA and IL-17RC. Aspects of the invention include antibodies that specifically bind to human IL-17RA and inhibit an IL-17A/IL-17F heteromer from binding and activating IL-17RA, or a heteromeric complex of IL-17RA and IL-17RC. Throughout the specification, when reference is made to inhibiting IL-17A and/or IL-17F, it is understood that this also includes inhibiting heteromers of IL-17A and IL-17F. Aspects of the invention include antibodies that specifically bind to human IL-17RA and partially or fully inhibit IL-17RA from forming either a homomeric or heteromeric functional receptor complex, such as, but not limited to IL-17RA-IL-17RC complex. Aspects of the invention include antibodies that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex.

Pharmaceutical compositions comprising one or more antigen binding proteins may be used in methods of treating the consequences, symptoms, and/or the pathology associated with IL-17RA activity. Pharmaceutical compositions comprising one or more antigen binding proteins may be used in methods of inhibiting the production of one or more of an inflammatory cytokine, chemokine, matrix metalloproteinase, or other molecule associated with IL-17RA activation, comprising administering an IL-17RA antigen binding protein. Pharmaceutical compositions comprising one or more antigen binding proteins may be used in methods of inhibiting production of IL-6, IL-8, GM-CSF, NO, MMPs, PGE2 RANKL, and/or C-telopeptide, and the like.

Pharmaceutical compositions comprising one or more antigen binding proteins may be used to treat diseases and conditions including, but are not limited to, inflammation, autoimmune disease, cartilage inflammation, and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, systemic lupus crythematosus, vasculitis, myolitis, polymyolitis, dermatomyolitis, osteoarthritis, polyarteritis nodossa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus, Graves' disease, Addison's disease, Raynaud's phenomenon, autoimmune hepatitis, GVHD, and the like Preferably, acceptable formulation materials are nontoxic to recipients at the dosages and concentrations employed. In specific embodiments, pharmaceutical compositions comprising a therapeutically effective amount of IL-17RA antigen binding proteins are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, Triton (octylphenol ethoxylate), tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18$^{th}$ Edition, (A. R. Gemmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris (Tris(hydroxymethyl) aminomethane) buffer of about pH 7.0-8.5, or acetate buffer of about pH 4.0-5.5, and may further include sorbitol or a suitable substitute therefor. In certain embodiments of the invention, IL-17RA antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the IL-17RA antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired IL-17RA antigen binding protein in a pharmaceutically acceptable vehicle. A particularly suitable vehicle for parenteral injection is sterile distilled water in which the IL-17RA antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, IL-17RA antigen binding proteins are advantageously formulated as a dry, inhalable powder. In specific embodiments, IL-17RA antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. It is also contemplated that formulations can be administered orally. IL-17RA antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the IL-17RA antigen binding protein. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of IL-17RA antigen binding proteins in a mixture with nontoxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-17RA antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.*

82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering IL-17RA antigen binding protein formulations, which can be used as pharmaceutical compositions, as described in international patent application WO 06138181A2 (PCT/US2006/022599), which is incorporated by reference in its entirety herein. One embodiment provides self-buffering IL-17RA antigen binding protein formulations comprising an IL-17RA antigen binding protein in which the total salt concentration is less than 150 mM.

One embodiment provides self-buffering IL-17RA antigen binding protein formulations that further comprise an IL-17RA antigen binding protein and one or more polyols and/or one or more surfactants. One embodiment provides self-buffering IL-17RA antigen binding protein formulations comprising an IL-17RA antigen binding protein, in which the total salt concentration is less than 150 mM, that further comprise one or more excipients, including but not limited to, pharmaceutically acceptable salts; osmotic balancing agents (tonicity agents); surfactants, polyols, anti-oxidants; antibiotics; antimycotics; bulking agents; lyoprotectants; anti-foaming agents; chelating agents; preservatives; colorants; and analgesics. One embodiment provides self-buffering IL-17RA antigen binding protein formulations comprising an IL-17RA antigen binding protein and one or more other pharmaceutically active agents.

One embodiment provides self-buffering IL-17RA antigen binding protein formulations comprising an IL-17RA antigen binding protein, wherein the IL-17RA antigen binding protein has a buffer capacity per unit volume per pH unit of at least that of approximately: 2.0 or 3.0 or 4.0 or 5.0 or 6.50 or 8.00 or 10.0 or 15.0 or 20.0 or 30.0 or 40.0 or 50.0 or 75.0 or 100 or 125 or 150 or 200 or 250 or 300 or 350 or 400 or 500 or 700 or 1,000 or 1,500 or 2,000 or 2,500 or 3,000 or 4,000 or 5,000 mM sodium acetate buffer in pure water over the range of pH 5.0 to 4.0 or pH 5.0 to 5.5, or at least 2.0 mM, or at least 3.0 mM, or at least 4.0 mM or at least 5.0 mM, or at least 7.5 mM, or at least 10 mM, or at least 20 mM.

One embodiment provides self-buffering IL-17RA antigen binding protein formulations wherein, exclusive of the buffer capacity of the protein, the buffer capacity per unit volume per pH unit of the formulation is equal to or less than that of 1.0 or 1.5 or 2.0 or 3.0 or 4.0 or 5.0 mM sodium acetate buffer in pure water over the range of pH 4.0 to 5.0 or pH 5.0 to 5.5, or optionally less than that of 1.0 mM, optionally less than that of 2.0 mM, optionally less than that of 2.5 mM, optionally less than that of 3.0 mM, and optionally less than that of 5.0 mM.

One embodiment provides self-buffering IL-17RA antigen binding protein formulations comprising an IL-17RA antigen binding protein wherein over the range of plus or minus 1 pH unit from the pH of the formulation, the buffer capacity of the IL-17RA antigen binding protein is at least approximately: 1.00 or 1.50 or 1.63 or 2.00 or 3.00 or 4.00 or 5.00 or 6.50 or 8.00 or 10.0 or 15.0 or 20.0 or 30.0 or 40.0 or 50.0 or 75.0 or 100 or 125 or 150 or 200 or 250 or 300 or 350 or 400 or 500 or 700 or 1,000 or 1,500 or 2,000 or 2,500 or 3,000 or 4,000 or 5,000 mEq per liter per pH unit, optionally at least approximately 1.00, optionally at least approximately 1.50, optionally at least approximately 1.63, optionally at least approximately 2.00, optionally at least approximately 3.00, optionally at least approximately 5.0, optionally at least approximately 10.0, and optionally at least approximately 20.0. One embodiment provides self-buffering IL-17RA antigen binding protein formulations comprising an IL-17RA antigen binding protein wherein over the range of plus or minus 1 pH unit from the pH of the formulation, exclusive of the IL-17RA antigen binding protein, the buffer capacity per unit volume per pH unit of the formulation is equal to or less than that of 0.50 or 1.00 or 1.50 or 2.00 or 3.00 or 4.00 or 5.00 or 6.50 or 8.00 or 10.0 or 20.0 or 25.0 mM sodium acetate buffer in pure water over the range pH 5.0 to 4.0 or pH 5.0 to 5.5.

One embodiment provides self-buffering IL-17RA antigen binding protein formulations comprising an IL-17RA antigen binding protein wherein over a range of plus or minus 1 pH1 unit from a desired pH, the protein provides at least approximately 55%, 60%, 65%, 70%, 75%, 80%, 85%, 90%, 95%, 97%, 98%, 99%, or 99.5% of the buffer capacity of the formulation, optionally at least approximately 75%, optionally at least approximately 85%, optionally at least approximately 90%, optionally at least approximately 95%, optionally at least approximately 99% of the buffer capacity of the formulation.

One embodiment provides self-buffering IL-17RA antigen binding protein formulations comprising an IL-17RA antigen binding protein wherein the concentration of the IL-17RA antigen binding protein is between approximately: 20 and 400, or 20 and 300, or 20 and 250, or 20 and 200, or 20 and 150 mg/ml, optionally between approximately 20 and 400 mg/ml, optionally between approximately 20 and 250, and optionally between approximately 20 and 150 mg/ml.

One embodiment provides self-buffering IL-17RA antigen binding protein formulations comprising an IL-17RA antigen binding protein wherein the pH maintained by the buffering action of the IL-17RA antigen binding protein is between approximately: 3.5 and 8.0, or 4.0 and 6.0, or 4.0 and 5.5, or 4.0 and 5.0, optionally between approximately 3.5 and 8.0, and optionally between approximately 4.0 and 5.5.

One embodiment provides self-buffering IL-17RA antigen binding protein formulations comprising an IL-17RA antigen binding protein wherein the salt concentration is less than: 150 mM or 125 mM or 100 mM or 75 mM or 50 mM or 25 mM, optionally 150 mM, optionally 125 mM, optionally 100 mM, optionally 75 mM, optionally 50 mM, and optionally 25 mM.

One embodiment provides self-buffering IL-17RA antigen binding protein formulations comprising an IL-17RA antigen binding protein and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents.

One embodiment provides self-buffering IL-17RA antigen binding protein formulations comprising an IL-17RA antigen binding protein and one or more pharmaceutically acceptable polyols in an amount that is hypotonic, isotonic, or hypertonic, preferably approximately isotonic, particularly preferably isotonic, such as but not limited to any one or more of sorbitol, mannitol, sucrose, trehalose, or glycerol, optionally approximately 5% sorbitol, 5% mannitol, 9% sucrose, 9% trehalose, or 2.5% glycerol.

One embodiment provides self-buffering IL-17RA antigen binding protein formulations comprising an IL-17RA antigen binding protein further comprising a surfactant, preferably one or more of polysorbate 20, polysorbate 80, other fatty acid esters of sorbitan, polyethoxylates, and poloxamer 188, preferably polysorbate 20 or polysorbate 80, optionally approximately 0.001 to 0.1% polysorbate 20 or polysorbate 80, optionally approximately 0.002 to 0.02% polysorbate 20 or polysorbate 80, or optionally 0.002 to 0.02% polysorbate 20 or polysorbate 80.

One embodiment provides self-buffering IL-17RA antigen binding protein formulations comprising an IL-17RA antigen binding protein wherein the formulation is sterile and suitable for treatment of a human or non-human subject.

One embodiment provides self-buffering IL-17RA antigen binding protein formulations comprising an IL-17RA antigen binding protein and a solvent, the IL-17RA antigen binding protein having a buffer capacity per unit volume per pH unit of at least that of 4.0 mM sodium acetate in water over the range of pH 4.0 to 5.0 or pH 5.0 to 5.5, wherein the buffer capacity per unit volume of the formulation exclusive of the IL-17RA antigen binding protein is equal to or less than that of 2.0 mM sodium acetate in water over the same ranges preferably determined in the same way.

One embodiment provides self-buffering IL-17RA antigen binding protein formulations comprising an IL-17RA antigen binding protein and a solvent, wherein at the pH of the formulation the buffer capacity of the protein is at least 1.63 mEq per liter for a pH change of the formulation of plus or minus 1 pH unit wherein the buffer capacity of the formulation exclusive of the protein is equal to or less than 0.81 mEq per liter at the pH of the formulation for a pH change of plus or minus 1 pH unit.

One embodiment provides self-buffering IL-17RA antigen binding protein formulations comprising an IL-17RA antigen binding protein, wherein the formulation is in the form of a lyophilate which upon reconstitution provides a formulation in accordance with any of the foregoing or following.

One embodiment provides self-buffering IL-17RA antigen binding protein formulations in a kit comprising one or more vials containing a self-buffering IL-17RA antigen binding protein formulation or a lyophilate of a self-buffering IL-17RA antigen binding protein formulation in accordance with any of the foregoing or the following, and instructions regarding use thereof.

One embodiment provides a process for preparing a self-buffering IL-17RA antigen binding protein formulation or a lyophilate thereof according to any of the foregoing or the following, comprising removing residual buffer using a counter ion.

One embodiment provides a process for preparing a self-buffering IL-17RA antigen binding protein formulation or a lyophilate thereof according to any of the foregoing or the following, comprising removing residual buffer using any one or more of the following in the presence of a counter ion: chromatography, dialysis, and/or tangential flow filtration.

One embodiment provides a process for preparing a self-buffering IL-17RA antigen binding protein formulation or a lyophilate thereof according to any of the foregoing or the following, comprising removing residual buffer using tangential flow filtration.

One embodiment provides a process for preparing a self-buffering IL-17RA antigen binding protein formulation or a lyophilate thereof according to any of the foregoing or the following comprising a step of dialysis against a solution at a pH1 below that of the preparation, and, if necessary, adjusting the pH thereafter by addition of dilute acid or dilute base.

As discussed above, certain embodiments provide self-buffering IL-17RA antigen binding proteins protein compositions, particularly pharmaceutical IL-17RA antigen binding protein compositions, that comprise, in addition to the IL-17RA antigen binding protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," *Pharm Res.* 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. *Pharmaceutical Biotechnology.* 13: 61-84 (2002), and Randolph et al., "Surfactant-protein interactions," *Pharm Biotechnol.* 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Various excipients useful in the invention are listed in TABLE 3 and further described below.

TABLE 3

Types of Excipients and Their Functions

| Type | Function | |
|---|---|---|
| | Liquids | Lyophilates |
| Tonicity Agents/ Stabilizers | Provides isotonicity to the formulation such that it is suitable for injection Examples include polyols, salts, and amino acids Help maintain the protein in a more compact state (polyols) Minimize electrostatic, solution protein-protein interactions (salts) | Stabilizers include cryo and lyoprotectants Examples include polyols, sugars and polymers Cryoprotectants protect proteins from freezing stresses Lyoprotectants stabilize proteins in the freeze-dried state |

TABLE 3-continued

Types of Excipients and Their Functions

| Type | Function | |
|---|---|---|
| | Liquids | Lyophilates |
| Bulking Agents | Not applicable | Used to enhance product elegance and to prevent blowout<br>Provides structural strength to the lyo cake<br>Examples include mannitol and glycine |
| Surfactants | Prevent/control aggregation, particle formation and surface adsorption of drug<br>Examples include polysorbate 20 and 80 | Employed if aggregation during the lyophilization process is an issue<br>May serve to reduce reconstitution times<br>Examples include polysorbate 20 and 80 |
| Anti-oxidants | Control protein oxidation | Usually not employed, molecular reactions in the lyophilized cake are greatly retarded |
| Metal Ions/ Chelating Agents | A specific metal ion is included in a liquid formulation only as a co-factor<br>Divalent cations such as zinc and magnesium are utilized in suspension formulations<br>Chelating agents are used to inhibit heavy metal ion catalyzed reactions | May be included if a specific metal ion is included only as a co-factor<br>Chelating agents are generally not needed in lyophilized formulations |
| Preservatives | Important particularly for multi-dose formulations<br>Protects against microbial growth,<br>Example: benzyl alcohol | For multi-dose formulations only<br>Provides protection against microbial growth in formulation<br>Is usually included in the reconstitution diluent (e.g. bWFI) |

Salts may be used in accordance with certain embodiments of the invention to, for example, adjust the ionic strength and/or the isotonicity of a self-buffering formulation and/or to improve the solubility and/or physical stability of a self-buffering protein or other ingredient of a self-buffering protein composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating self-buffering protein compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as chaotropic. Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

In addition to their utilities and their drawbacks (as discussed above) salts also are effective for reducing the viscosity of protein formulations and can be used in the invention for that purpose. In order to maintain isotonicity in a parenteral formulation in accordance with preferred embodiments of the invention, improve protein solubility and/or stability, improve viscosity characteristics, avoid deleterious salt effects on protein stability and aggregation, and prevent salt-mediated protein degradation, the salt concentration in self-buffering formulations in accordance with various preferred embodiments of the invention are less than 150 mM (as to monovalent ions) and 150 mEq/liter for multivalent ions. In this regard, in certain particularly preferred embodiments of the invention, the total salt concentration is from about 75 mEq/L to about 140 mEq/L.

Free amino acids can be used in self-buffering IL-17RA antigen binding protein formulations in accordance with various embodiments of the invention as bulking agents, stabilizers, and antioxidants, as well as other standard uses. However, amino acids included in self-buffering IL-17RA antigen binding protein formulations do not provide buffering action. For this reason, those with significant buffer capacity either are not employed, are not employed at any pH around which they have significant buffering activity, or are used at low concentration so that, as a result, their buffer capacity in the formulation is not significant. This is particularly the case for histidine and other amino acids that commonly are used as buffers in pharmaceutical formulations.

Subject to the foregoing consideration, lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred amino acids of the invention in this regard. PEG is useful to stabilize proteins and as a cryoprotectant and can be used in the invention in this regard, such as it is in Recombinate®.

Embodiments of the self-buffering IL-17RA antigen binding protein formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the self-buffering IL-17RA antigen binding protein formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard and can be used in the invention in much the same way it has been used in formulations of acidic fibroblast growth factor and in products such as Kineret® and Ontak®.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease (rhDNase, PulmozymeA). $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the self-buffering IL-17RA antigen binding protein formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin® (liquid, Novo Nordisk), Nutropin AQ® (liquid, Genentech) & Genotropin (lyophilized-dual chamber cartridge, Pharmacia & Upjohn) contain phenol while Somatrope® (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability. For example, three preservatives were successfully screened in the development of a liquid formulation for interleukin-1 receptor (Type I) using differential scanning calorimetry (DSC). The preservatives were rank ordered based on their impact on stability at concentrations commonly used in marketed products.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability have to be maintained over the entire product shelf-life (~18 to 24 months). An important point to note is that preservative effectiveness has to be demonstrated in the final formulation containing the active drug and all excipient components.

Self-buffering IL-17RA antigen binding protein formulations generally will be designed for specific routes and methods of administration, for specific administration dosages and frequencies of administration, for specific treatments of specific diseases, with ranges of bio-availability and persistence, among other things.

Formulations thus may be designed in accordance with the invention for delivery by any suitable route, including but not limited to orally, aurally, ophthalmically, rectally, and vaginally, and by parenteral routes, including intravenous and intraarterial injection, intramuscular injection, and subcutaneous injection.

Compositions in accordance with the invention may be produced using well-known, routine methods for making, formulating, and using proteins, particularly pharmaceutical proteins. In certain of the preferred embodiments of a number of aspects of the invention in this regard, methods for preparing the compositions comprise the use of counter ions to remove residual buffering agents. In this regard the term counter ion is any polar or charged constituent that acts to displace buffer from the composition during its preparation. Counter ions useful in this regard include, for instance, glycine, chloride, sulfate, and phosphate. The term counter ion in this regard is used to mean much the same thing as displacement ion.

Residual buffering agents can be removed using the counter ions in this regard, using a variety of well-known methods, including but not limited to, standard methods of dialysis and high performance membrane diffusion-based methods such as tangential flow diafiltration. Methods for residual buffer removal employing a counter ion in this regard can also, in some cases, be carried out using size exclusion chromatography.

In certain related preferred embodiments in this regard, compositions in accordance with the invention are prepared by a process that involves dialysis against a bufferless solution at a pH below that of the preparation containing the self-buffering protein. In particularly preferred embodiments of the invention in this regard, the bufferless solution comprises counter ions, particularly those that facilitate removal of residual buffer and do not adversely affect the self-buffering protein or the formulation thereof. In further particularly preferred embodiments of the invention in this regard, following dialysis the pH of the preparation is adjusted to the desired pH using dilute acid or dilute base.

In certain related particularly preferred embodiments in this regard, compositions in accordance with the invention are prepared by a process that involves tangential flow diafiltration against a bufferless solution at a pH below that of the preparation containing the self-buffering protein. In particularly preferred embodiments of the invention in this regard, the bufferless solution comprises counter ions, particularly those that facilitate removal of residual buffer and do not adversely affect the self-buffering protein or the formulation thereof. In further particularly preferred embodiments of the invention in this regard, following diafiltration the pH of the preparation is adjusted to the desired pH using dilute acid or dilute base.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an IL-17RA antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the IL-17RA antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 0.1 µg/kg up to about 30 mg/kg, optionally from 1 µg/kg up to about 30 mg/kg or from 10 µg/kg up to about 5 mg/kg.

Dosing frequency will depend upon the pharmacokinetic parameters of the particular IL-17RA antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antigen binding proteins of the invention can be administered to patients throughout an extended time period. Chronic administration of an antigen binding protein of the invention minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use IL-17RA antigen binding protein pharmaceutical compositions according to the invention ex vivo. In such instances, cells, tissues or organs that have been removed from the patient are exposed to IL-17RA antigen binding protein pharmaceutical compositions after which the cells, tissues and/or organs are subsequently implanted back into the patient.

In particular, IL-17RA antigen binding proteins can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

All references cited within the body of the instant specification are hereby expressly incorporated by reference in their entirety.

EXAMPLES

The following examples, including the experiments conducted and the results achieved, are provided for illustrative purposes only and are not to be construed as limiting the invention.

Example 1

IL-17RA knockout mice were generated as described in Ye et al., 2001, J. Exp. Med. 194:519-527 and tested in a standard collagen induced arthritis (CIA) model. Briefly, Genomic clones encoding murine IL-17R were isolated from a 129 derived lambda library using a murine IL-17R cDNA probe and mapped by a combination of PCR, restriction digest, and sequence analyses using deposited genomic sequences corresponding to IL-17R locus on mouse chromosome 6 (GenBank/EMBL/DDBJ accession no. AC018559). A gene targeting vector was constructed by replacing 5.7 kb of genomic sequence containing exons 4-11 (corresponding to nucleotides 445-1,172 of the murine IL-17R eDNA) with a PGKneo cassette. A thymidine kinase cassette (MC-TK) was inserted into the 5' end of the vector. 129 derived embryonic stem (ES) cells were electroporated with the targeting vector and selected in the presence of G418 and ganciclovir as described. ES clones carrying a targeted mutation in IL-17R were identified by a combination of PCR and genomic Southern blot analyses and were injected into C57BL/6 blastocysts. The resulting male chimeras were crossed to C57BL/6 females to generate mice heterozygous for the IL-17R mutation (IL-17R$^{+/-}$), which were subsequently intercrossed to generate IL-17R-deficient mice (IL-17R KO). These mice were moved to a C57BL/6 background by five successive backcrosses to C57BL/6 mice.

Figure 4:
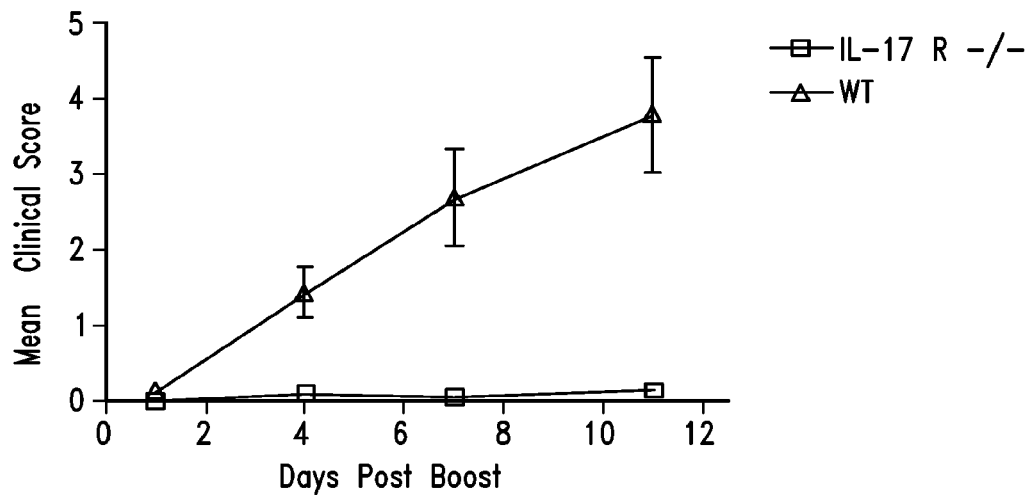
FIG. 4 shows that the mean clinical scores of IL-17RA−/− mice (knockout mice or KO mice) are much lower than that of wild-type (WT) mice in a CIA model of arthritis.

IL-17RA knockout mice showed reduced mean clinical score in the CIA model, as shown in FIG. 4 (see also Kolls et al., 2001, *J. Ex. Med.* 194:519-527; Lubberts at al., 2005, supra). In addition, the IL-17RA knockout mice showed only a 5% incidence of disease, whereas the wild-type mice showed a 71% incidence of disease.

Example 2

The histopathology of CIA-induced IL-17RA −/− mice and IL-17RA expressing mice was compared to determine the correlation between induced arthritis and the absence of IL-17RA signaling.

Mice were prepared as described in Example 1. The animals were sacrificed at fifteen to twenty weeks of age, and the histopathology of joints from the sacrificed animals were then examined. Histopathology of bone and cartilage in IL-17RA −/− knock-out mice and IL-17A/IL-17R expression mice (WT C57/BL6 (No. 2-18)) showed subchondral bone erosion of the talus and marked joint architecture disruption of tarsal-metatarsal joints (subchondral bone and articular cartilage erosion), as well as reactive periosteal bone formation (osteophytosis). Histopathology of ankle joints from mice deficient in IL-17RA −/− in an experimentally induced CIA model showed little joint inflammation and joint cartilage and bone erosion. However, the histopathologic analysis of an ankle joint of the rear paw of IL-17RA expressing mice showed marked chronic active inflammation. The significantly reduced incidence of joint inflammation and joint and bone erosion as compared to WT mice further implicates IL-17RA and IL-17RA signaling in inflammation and erosion.

Example 3

A model of MOG (Myelin Oligodendrocyte Glycoprotein)-peptide-induced EAE model mice deficient in IL-17RA showed a delay in the onset of arthritis as well as an overall reduction in clinical scores as compared to WT mice.

Figure 5:
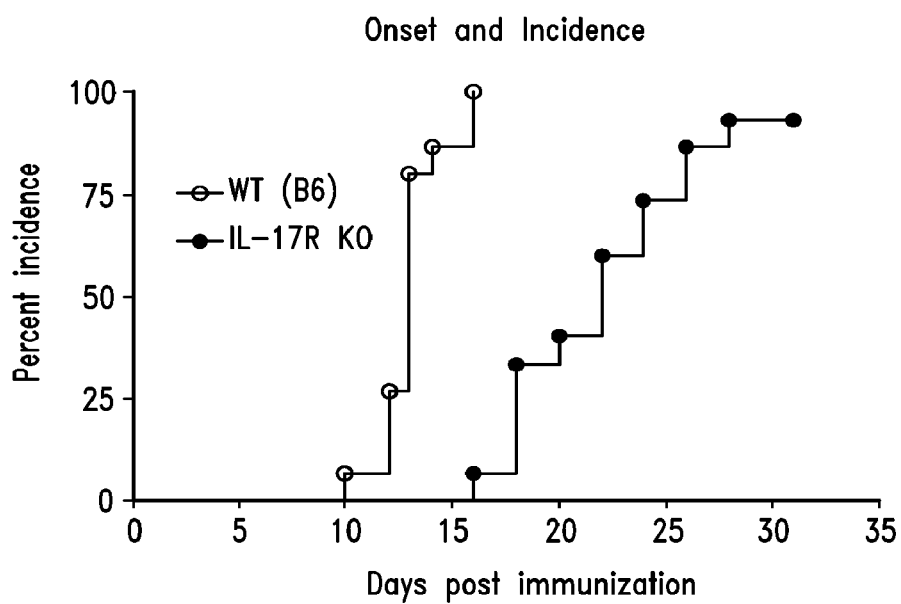
FIG. 5 shows the delay in experimental autoimmune encephalomyelitis (EAE) onset for IL-17RA knockout mice compared to wild-type mice in a myelin oligodendrocyte glycoprotein (MOG)-induced model.

IL-17RA knockout mice were prepared as described in Example 1. FIG. 5 shows the incidence and median onset of arthritis as a function of time for both IL-17RA −/− and IL-17RA wild-type mice. 15 out of 15 of the IL-17RA expressing wild-type mice exhibited arthritic symptoms, with a mean onset of 13 days. By contrast, 14 of 15 IL-17RA −/− mice exhibited arthritic symptoms, with a mean onset of 22 days (p<0.0001 versus wild-type).

Figure 6:
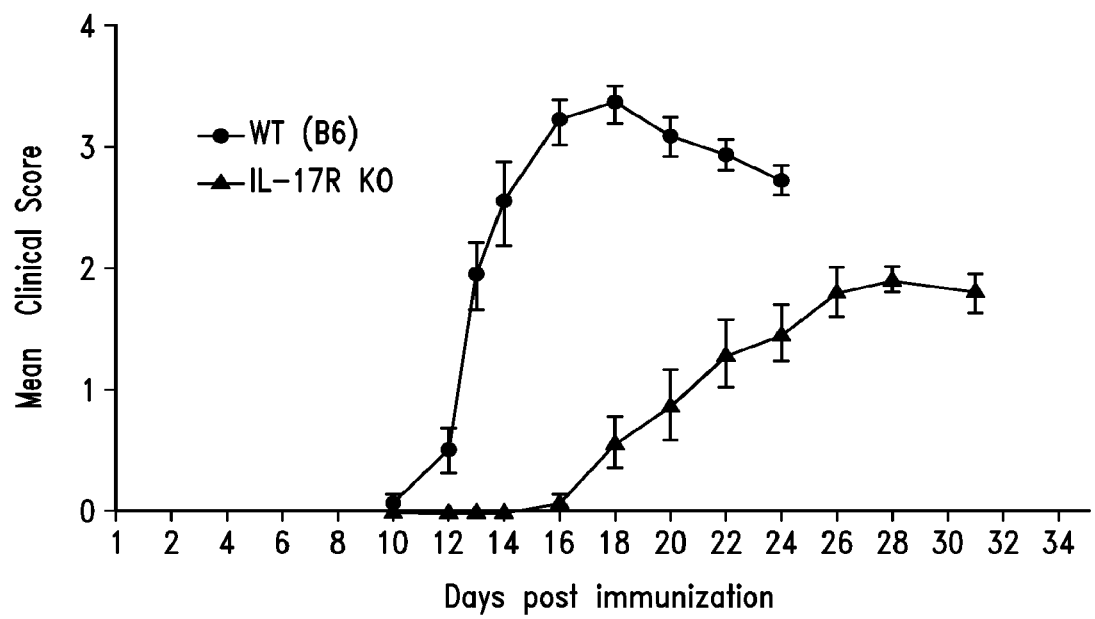
FIG. 6 shows reduced clinical scores in IL-17RA knockout mice as compared to wild-type mice in a MOG-induced model.

Clinical scores of IL-17RA −/− knockout mice show a lower mean clinical score, with a later onset, than wild-type mice. FIG. 6 shows reduced clinical scores in IL-17RA −/− knockout mice as compared to wild-type mice in a MOG-induced model. The IL-17RA −/− knockout population showed a significantly later onset of arthritis than the IL-17RA expressing wild-type population. Further, the IL-17RA −/− knockout population had a lower mean clinical score at all time points for onset of arthritis. The longer mean onset of arthritis and lower mean clinical score for arthritis observed in IL-17RA −/− mutants as compared to IL-17RA-expressing wild-type animals further implicates IL-17RA signaling in inflammation and erosion.

Example 4

Figure 7:
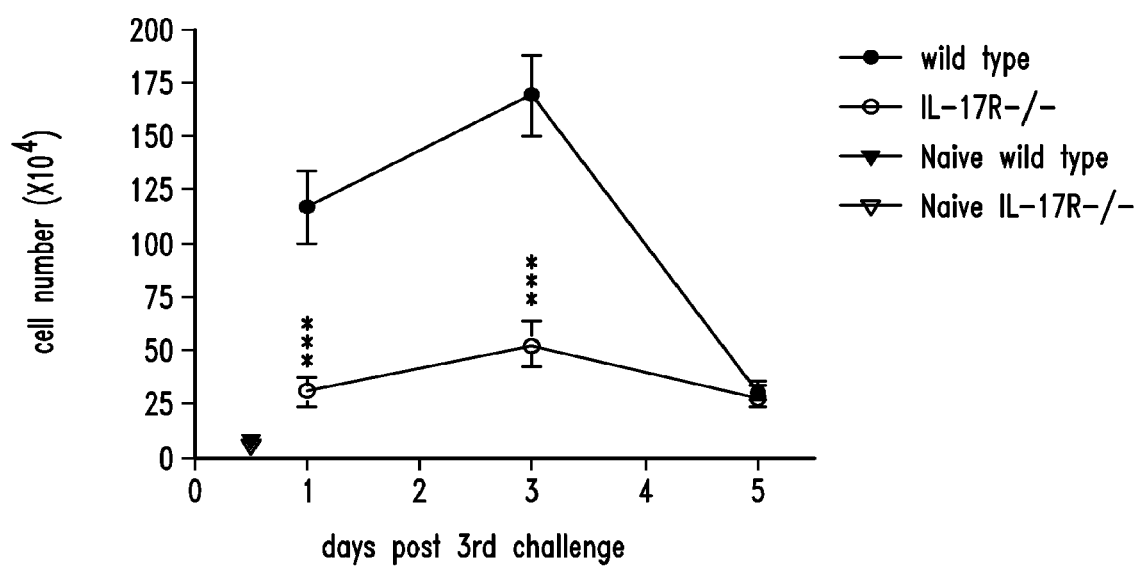
FIG. 7 shows IL-17RA knockout mice have reduced total numbers of inflammatory cells in BAL fluid compared to wild-type in an ovalbumin-induced model of asthma.
Figure 8A:
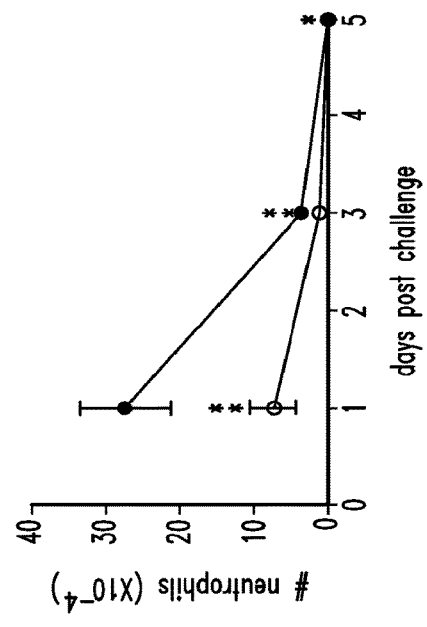
FIGS. 8A-8D show IL-17RA knockout mice have reduced numbers of esoinophils (FIG. 8A), neutrophils (FIG. 8B) and lymphocytes (FIG. 8C) in bronchoalveolar lavage (BAL) fluid as compared to wild-type mice in an ovalbumin-induced model of asthma.
Figure 8B:
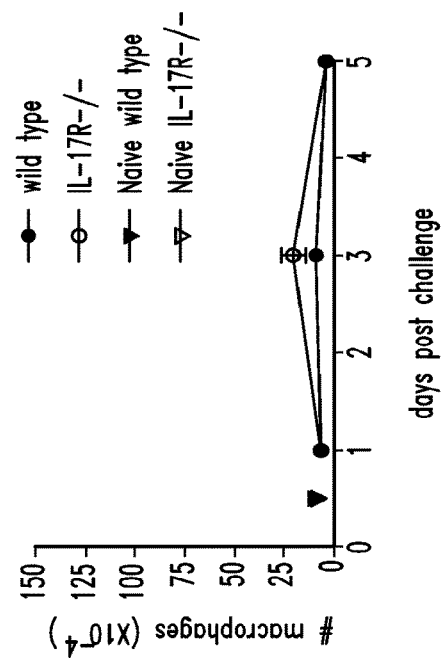
Figure 8C:
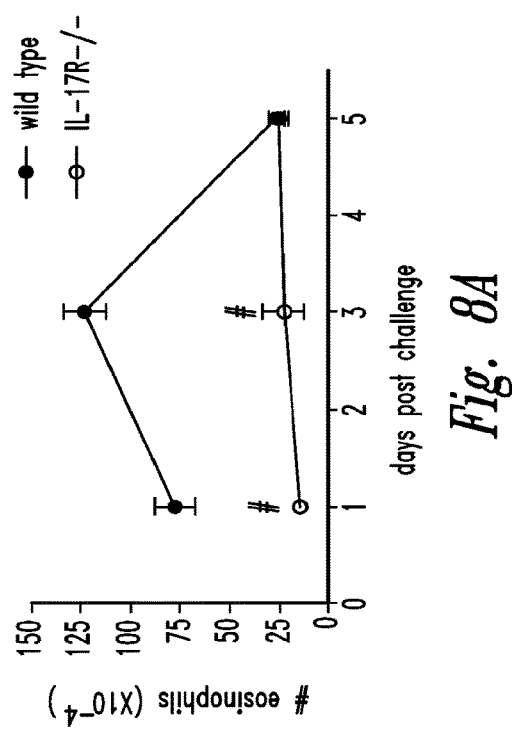
Figure 8D:
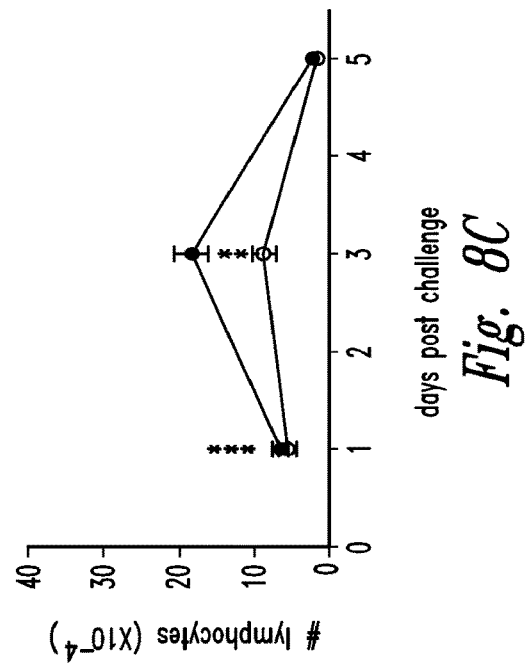

Ovalbumin sensitized and challenged IL-17RA KO mice show a significant reduction of inflammatory cells in BAL (bronchoalveolar lavage) fluid compared to wild-type mice. IL-17RA KO mice were prepared as described in Example 1, and then challenged intra-nasally with ovalbumin. The number of inflammatory cells in the IL-17RA KO population were compared to the IL-17RA expressing wild-type population. FIG. 7 shows IL-17RA KO mice have reduced total numbers of inflammatory cells in BAL fluid than IL-17RA expressing wild-type mice in an ovalbumin-induced of asthma post-third challenge.

The IL-17RA KO mouse population was compared to IL-17RA expressing wild-type mice for the incidence of esoinophils (A), neutrophils (B), lymphocytes (C) and macrophages (D) in BAL fluid in an ovalbumin-induced model of asthma. FIGS. 8A-8D show that IL-17RA KO mice have reduced numbers of esoinophils (8A), neutrophils (88) and lymphocytes (8C) in BAL fluid in the IL-17RA KO population as compared to the IL-17RA expressing wild-type population. No changes in BAL, fluid macrophage (8D) were noted in either wile-type or IL-17RA KO mice (naïve and OVA-challenged). These data suggest that IL-17RA signaling is important in regulating immune-mediated inflammatory responses.

Example 5

IL-17RA antibodies were shown to reduce incidence of arthritis in a CIA (Collagen-Induced Arthritis) mouse model when administered prophylactically and therapeutically. The IL-17RA inhibition reduced clinical arthritis in both a prophylactic and therapeutic manner for several models if CIA.

Figure 9:
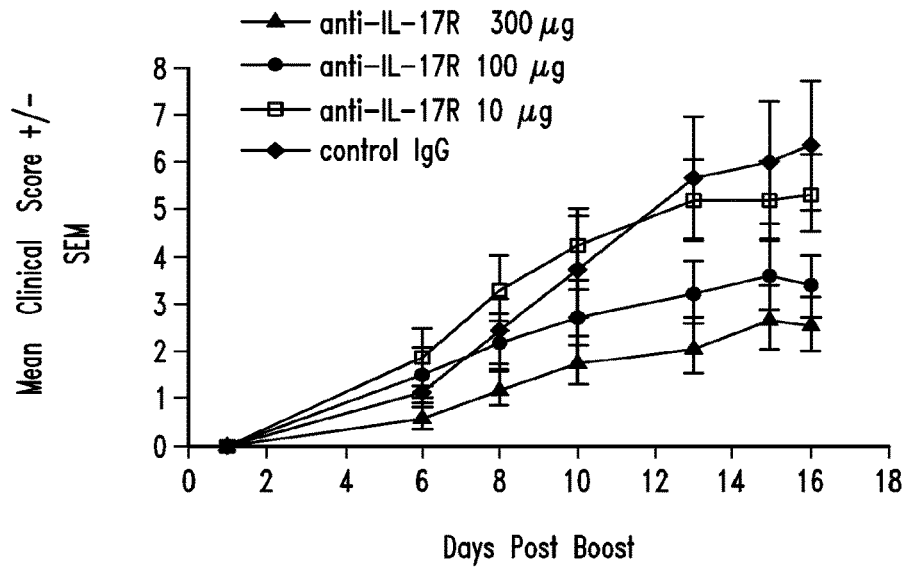
FIG. 9 shows dose-dependent inhibition by an IL-17RA mAb in a wild-type (WT) collagen-induced arthritis (CIA) model. A P<0.05 was seen when comparing IL-17RA mAb at 100 μg and 300 μg treatment groups versus control treatment group (days 13, 15 and 16).

The surrogate neutralizing mouse IL-17RA mAb administered prophylactically reduced mean clinical scores in wild-type CIA model in a dose-dependent manner. FIG. 9 shows the dose-dependent inhibition by IL-17RA mAb in wild-type CIA model. Mice were treated with either IL-17RA mAb or control Ig on a Monday, Wednesday and Friday schedule for 2.5 weeks post boost. Administration of 100 µg and 300 µg of IL-17RA antibodies resulted in a lower clinical score for 18 days post-boost than compared to isotype control Ig.

A reduction in bone loss and cartilage erosion in the joint was associated with the reduction of mean clinical scores at the 300 µg dose of the IL-17RA mAb. Histopathologic analysis and radiographic images analysis were compared to the IgG control. By both means of analysis, the ankle joint of the near paw of CBA/I male mouse treated with an IL-18R mAb (isotype control) showed marked inflammation: subchondral bone erosion of the talus, marked joint architecture disruption of tarsal-metatarsal joints (subchondrial bone and articular cartilage erosion), and reactive periosteal bone formation (ostcophytosis). In stark contrast, the ankle joint of the rear paw of a DBA/1 mouse treated with 300 µg anti-IL-17RA mAb showed well-defined joint spaces, lack of edema and lack of periosteal reactive bone or lytic lesions indicated reduced bone loss and cartilage erosion.

Example 6

Figure 10:
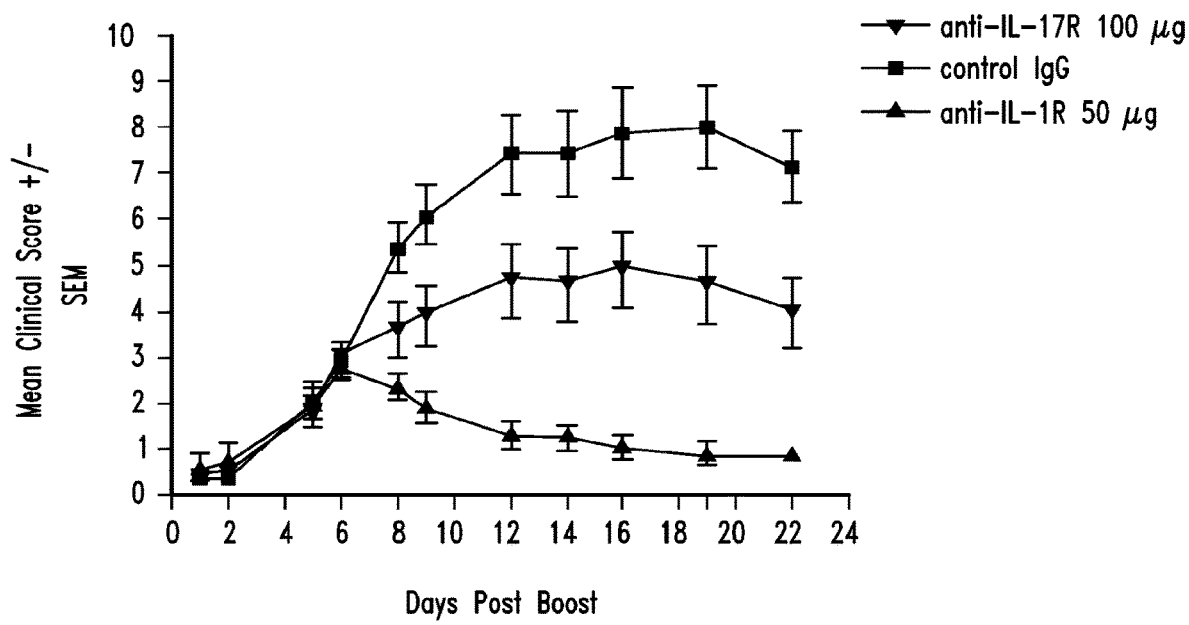
FIG. 10 shows the results of therapeutic treatment with IL-17RA mAb. The data shows stabilized mean clinical scores in wild-type mice in a standard CIA model of arthritis. These data demonstrate that IL-17RA inhibition by an IL-17RA antigen binding protein may be therapeutically useful in treating rheumatoid arthritis (RA), especially in the preservation of joint bone and cartilage.
Figure 11:
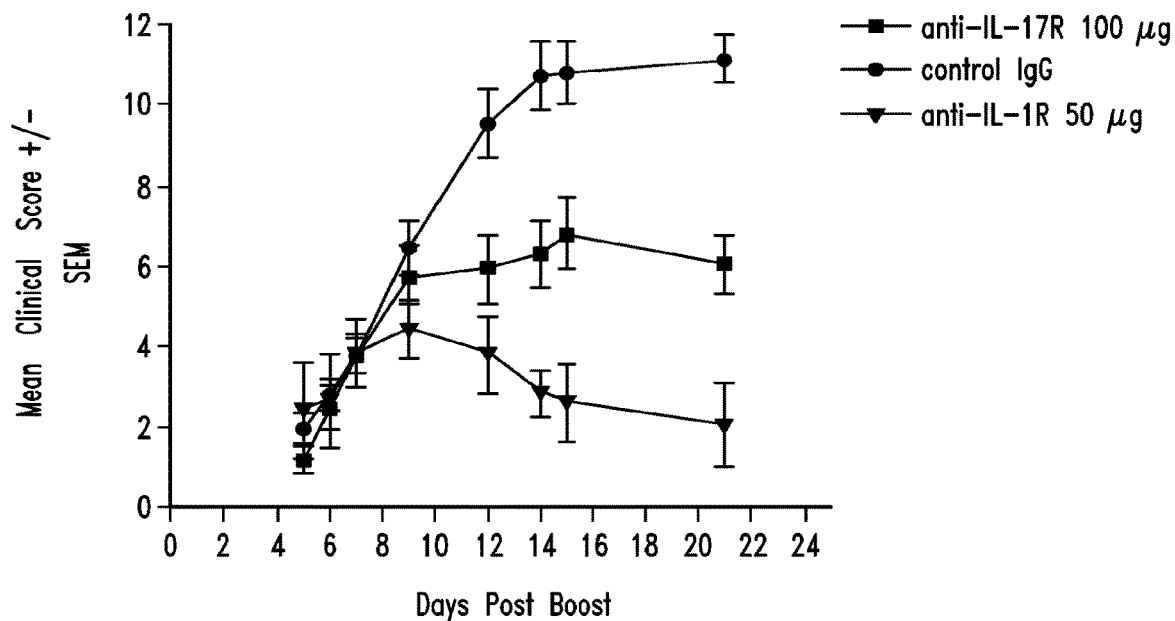
FIG. 11 shows that therapeutic treatment with anti-IL-17RA mAb stabilized mean clinical scores in TNFR p55/p75 knockout mice in a standard CIA model of arthritis. These data show that IL-17RA inhibition by an IL-17RA antigen binding protein may be therapeutically useful in treating RA, especially in the preservation of joint bone and cartilage. Notably, IL-17RA inhibition was able to stabilize disease in a model independent of TNF signaling.

IL-17RA inhibition was also shown to be effective in a CIA model when dosing was initiated after the onset of clinical signs (i.e. therapeutic dosing protocol) in a wild-type and TNFR p55/p75 KO model. Treatment was initiated approximately 6-7 days post collagen introduction in both models. FIG. 10 shows that therapeutic treatment with anti-IL-17RA mAb stabilized mean clinical scores in both wild-type mice. FIG. 11 shows that therapeutic treatment with anti-IL-17RA mAb stabilized mean clinical scores in TNFR p55/p75 KO models. Mice were treated with either an anti-IL-17RA mAb, anti-IL-1R mAb, or control Ig on a Monday, Wednesday and Friday schedule for 2 weeks post randomization into therapeutic treatment groups. These data are representative of 2 independent experiments performed in both WT and TNFR p55/p75 KO CIA models. Administering anti-IL-17RA mAbs showed a reduced clinical score as compared to control IgG in CIA induced wild-type mice. Surprisingly, the similar efficacy of anti-IL-17RA mAbs in the TNF p55/p75 KO model stabilized CIA independently of TNF signaling. This data suggests anti-IL-17RA antigen binding protein therapy may pick up non-responders to anti-TNF therapies. Combination therapy of an anti-IL-17RA antigen binding protein with anti-TNF therapies may be more beneficial than either alone.

Example 7

The development of fully human monoclonal antibodies directed against human IL-17RA was carried out using Abgenix (now Amgen Fremont Inc.) XenoMouse® technology (U.S. Pat. Nos. 6,114,598; 6,162,963; 6,833,268; 7,049,426; 7,064,244, which are incorporated herein by reference in their entirety; Green et al, 1994, *Nature Genetics* 7:13-21; Mendez et al., 1997, *Nature Genetics* 15:146-156; Green and Jakobovitis, 1998, *J. Ex. Med.* 188:483-495)). TABLE 4 shows the portions of the IL-17RA protein used as an immunogen and cell lines used to generate and screen anti-IL-17RA antibodies.

TABLE 4

| Reagent | Description |
| --- | --- |
| IL-17RA.Fc | Human IL-17RA extracellular domain with a C-terminal human Fc domain. Expressed in a stable CHO cell line. |
| IL-17RA-FLAG-polyHis (SEQ ID NO: 431) | Human IL-17RA extracellular domain with a C-terminal FLAG-polyHis tag. Expressed by transient transfection in COS PKB cells. |
| IL-17RA CHO cells | Human IL-17RA full-length expressed on the surface of CHO cells. |

IgG2 XenoMouse® mice were immunized/boosted with IL-17RA-Fc (group 1) and IL-17RA-FLAG-polyHis (group 2). Serum titers were monitored by ELISA and mice with the best titers were fused to generate hybridomas. The resulting polyclonal supernatants were screened for binding to IL-17RA by ELISA, and the positive supernatants were screened for binding to IL-17RA CHO cells by FMAT. Positive supernatants were subjected to additional screening. IgG2 XenoMouse® mice were immunized with the following immunogens: IL-17RA-Fc (group 3) and IL-17RA-FLAG-pHis (group 4) and were tested following additional immunizations.

Example 8

The anti-IL-17RA antibodies were characterized. Nonclonal hybridoma supernatants were prepared in volumes of 1-2 mls (the Ig concentrations were not determined for these supernatants). The anti-IL-17RA non-clonal hybridoma supernatants were initially screened by FACS for their ability to inhibit biotinylated human IL-17A binding to CHO cells over-expressing human IL-17RA and another CHO cell line over-expressing cynomolgus IL-17RA. Nonclonal supernatants that were able to completely or nearly completely inhibit binding of human IL-17A to CHO-huIL-17RA and CHO-cynoIL-17RA were subsequently screened at several dilutions in an IL-17A-induced cytokine/chemokine secretion assay using a human foreskin fibroblast (HFF) cell line. Anti-IL-17RA non-clonal supernatants were incubated with HFF cells (5000 cells/well in 96 well plate) for 30 minutes at 36° C. and then stimulated overnight with either IL-17A (5 ng/ml) alone or IL-17F (20 ng/ml) and TNF-alpha (5 ng/ml). Fibroblast culture supernatants were then analyzed by ELISA for the presence of either IL-6 or GRO-alpha. Anti-IL-17RA non-clonal hybridomas were selected for sub-cloning based on their performance in the CHO-IL-17RA FACS assay and HFF bioassay. An example of the selection is shown in TABLES 5, 6, and 7.

TABLE 5

| Supernatant I.D. | % positive | % positive Neg. Cntl. | MFI | HFF Bioassay | Repeat assays % inhibition of IL-6 production | | |
|---|---|---|---|---|---|---|---|
| | 1.09 | 1.57 | 10 | | | | |
| | IL-17 biot. (500 ng/ml) | | | 1:4 dil. | 1:32 | 1:4 | |
| | 8.85 | 10.22 | 77 | | | 1:32 | 1:128 |
| 1 | 1.34 | 1.78 | 9 | 56 | 14 | | |
| 2 (incl. $AM_H15/AM_L15$) | .60 | 3.77 | 6 | 80 | 72 | 98 | 91 81 |
| 3 | 1.04 | 1.60 | 8 | 46 | −5 | | |
| 4 (incl. $AM_H14/AM_L14$) | 1.72 | 0.79 | 10 | 90 | 82 | 99 | 92 84 |
| 5 | 1.59 | 1.43 | 11 | 76 | 52 | | |
| 6 | 1.45 | 1.93 | 14 | 82 | 79 | | |
| 7 | 1.00 | 1.28 | 8 | 71 | 58 | | |
| 8 | 1.43 | 1.60 | 14 | 69 | 31 | | |
| 9 | 1.34 | 2.28 | 18 | 59 | 20 | | |
| 10 | 0.79 | 1.96 | 11 | 58 | −2 | | |
| 11 | 1.93 | 1.69 | 11 | 72 | 21 | | |
| 12 | 2.23 | 1.69 | 8 | 69 | 7 | | |
| 13 (incl. $AM_{H21}/AM_{L21}$) | 1.49 | 0.49 | 6 | 82 | 53 | | |
| 14 | 1.01 | 1.25 | 8 | 63 | 23. | | |
| 15 | 1.31 | 1.45 | 9 | 74 | 45 | | |
| 16 | 1.39 | 0.72 | 8 | 58 | 4 | | |
| 17 | 0.91 | 0.94 | 7 | 73 | 38 | | |
| 18 | 1.37 | 2.85 | 13 | 49 | 6 | | |
| 19 | 1.47 | 1.15 | 8 | 74 | 61 | | |
| 20 | 1.60 | 1.20 | 7 | 42 | 46 | | |
| 21 | 1.30 | 1.65 | 8 | 47 | 4 | | |
| 22 | 0.93 | 1.02 | 8 | 54 | 16 | | |
| 23 | 1.08 | 1.12 | 7 | 72 | 59 | | |

In TABLE 5, anti-IL-17RA non-clonal hybridoma supernatants were screened for binding to IL-17RA. The first half of TABLE 5 shows the % positive and mean fluorescent intensity (MFI) in results from flow cytometry (i.e., FACS). The % positive shows inhibition of biotin-huIL-17A binding to huIL-17RA$^+$ CHO cells by the non-clonal hybridoma supernatants. The MFI column shows inhibition of biotinylated huIL-17A binding to cyno IL-17RA$^+$ CHO cells by the non-clonal hybridoma supernatants. The second half of TABLE 5 shows the HFF binding intensity for the nonclonal and mAbs as measured by the % intensity of IL-6 production. The first 2 columns show an IL-17A/HFF bioassay with non-clonal hybridoma supernatants and the last 4 columns are repeat IL-17A/HFF bioassay results with non-clonal hybridoma supernatants.

TABLE 6

FACS results on 293-Cyno IL-17R4-expressing Cells

| Supernatant I.D. | % positive | % positive Neg. Cntl. | MFI | HFF Bioassay | | | |
|---|---|---|---|---|---|---|---|
| | 1.09 | 1.57 | 1.0 | 1:4 dilution | repeat | | |
| | IL-17 biot. (500 ng/ml) | | | % inhibition of | 1:32 | 1:4 | |
| | 8.85 | 10.22 | 77 | IL-6 production | 1:32 | 1:128 | 1:512 |
| 1 (incl. $AM_H11/AM_L11$) | 1.32 | 1.4 | 9 | | | | |
| 2 | 0.87 | 2.92 | 9 | | | | |
| 3 | 1,0 | 4.47 | 16 | | | | |
| 4 | 1,03 | 5.01 | 17 | | | | |
| 5 | 0.6 | 6.53 | 18 | | | | |
| 6 (incl. $AM_{H5}/AM_L5$) | 0.73 | 4.55 | 9 | | | | |
| 7 | 0.59 | 5.18 | 8 | | | | |
| 8 | 0.45 | 7.25 | 7 | | | | |
| 9 | 2.34 | 2.36 | 6 | 61 | 36 | | |
| 10 | 6.76 | 8.35 | 64 | 37 | 12 | | |
| 11 | 0.78 | 1.16 | 6 | 61 | 24 | | |

TABLE 6-continued

| | FACS results on 293-Cyno IL-17R4-expressing Cells | | | | | | | |
|---|---|---|---|---|---|---|---|---|
| | % positive Neg. Cntl. | % positive IL-17 biot. (500 ng/ml) | MFI | HFF Bioassay 1:4 dilution % inhibition of | | repeat 1:32 | 1:4 | |
| Supernatant I.D. | 1.09 8.85 | 1.57 10.22 | 1.0 77 | IL-6 production | | | 1:32 | 1:128 1:512 |
| 12 | 0.61 | 1.64 | 6 | 74 | 56 | 71 | 67 | 45 | 35 |
| 13 | 2.98 | 5.48 | 22 | −2 | −13 | | | |
| 14 | 5.34 | 10.64 | 49 | 22 | 2 | 3 | 39 | 31 | 34 |
| 15 | 0.5 | 3.24 | 11 | 51 | −7 | | | |
| 16 (incl. AM$_H$22/AM$_L$22) | 0.54 | 2.93 | 18 | 92 | 77 | 91 | 73 | 73 | 29 |
| 17 | 1.25 | 2.2 | 17 | −8 | −76 | | | |
| 18 | 0.61 | 0.99 | 7 | 73 | 28 | | | |
| 19 (incl. AM$_H$23) | 0.69 | 1.72 | 10 | 79 | 72 | 86 | 76 | 67 | 50 |
| 20 | 1.53 | 1.94 | 31 | 5 | −31 | | | |
| 21 | 6.66 | 9.63 | 66 | −15 | 4 | | | |
| 22 | 6.33 | 10.32 | 71 | 1 | 14 | | | |
| 23 | 0.3 | 2.55 | 7 | 50 | 35 | | | |
| 24 | 0.24 | 4.11 | 6 | 34 | 15 | | | |
| 25 | 0.81 | 0.99 | 8 | −49 | 11 | | | |
| 26 | 0.43 | 1.31 | 7 | 67 | 48 | | | |
| 27 | 0.7 | 1.23 | 11 | 50 | 26 | | | |
| 28 | 0.58 | 1.32 | 9 | 56 | 47 | | | |
| 29 (incl. AM$_H$1/AM$_L$1) | 0.8 | 1.85 | 11 | 77 | 76 | 90 | 87 | 79 | 66 |
| 30 | 0.69 | 1.55 | 11 | 40 | 16 | | | |
| 31 | 0.56 | 1.96 | 12 | 12 | −11 | | | |
| 32 | 0.21 | 1.11 | 8 | 46 | 7 | | | |
| 33 | 1.24 | 1.15 | 13 | 68 | 43 | | | |
| 34 | 0.74 | 0.81 | 11 | 36 | 8 | | | |
| 35 | 0.71 | 1.37 | 9 | 65 | 21 | | | |
| 36 | 0.57 | 1.21 | 7 | 78 | 32 | | | |
| 37 | 0.59 | 1.0 | 8 | 71 | 3 | | | |
| 38 | 0.65 | 1.43 | 8 | 63 | −38 | | | |
| 39 | 0.28 | 1.23 | 7 | 43 | −21 | | | |
| 40 | 0.35 | 2.48 | 9 | 50 | −39 | | | |
| 41 | 0.64 | 1.61 | 8 | 49 | −19 | | | |
| 42 | 0.12 | 1.04 | 8 | 87 | 68 | 96 | 92 | 80 | 66 |
| 43 | 0.21 | 1.12 | 11 | 79 | 34 | | | |
| 44 | 0.32 | 1.33 | 8 | 68 | −3 | | | |
| 45 | 0.74 | 1.68 | 10 | 40 | −16 | | | |
| 46 | 0.58 | 1.74 | 10 | 64 | 7 | | | |

TABLE 6 shows IL-17RA non-clonal hybridoma supernatant screening data. The % positive and MFI columns show results from flow cytometry (FACS). The % positive columns show inhibition of biotin-huIL-17A binding to huIL-17RA$^+$ CHO cells by the non-clonal hybridoma supernatants. The MFI column shows inhibition of biotinylated huIL-17A binding to cyno IL-17RA$^+$ CHO cells by the non-clonal hybridoma supernatants. The first 2 HFF bioassay columns are IL-17A/HFF bioassay with non-clonal hybridoma supernatants and the last 4 bioassay columns are repeat EL-17A/HFF bioassay results with selected non-clonal hybridoma supernatants. A number of supernatants were selected for sub-cloning.

TABLE 7

| Supernatant ID. | % positive Neg. Cntl | | MFI | HFF bioassay | | |
|---|---|---|---|---|---|---|
| | 1.09 | 1.57 | 10 | 1:4 | 1:32 | 1:128 |
| | IL-17biot. (500 ng/ml) | | | % inhibition of IL-6 production | | |
| | 8.85 | 10.22 | 77 | | | |
| 1 | 1.85 | 1.33 | 10 | 29 | 9 | 21 |
| 2 | 1.08 | 1.46 | 16 | 90 | 61 | 50 |
| 3 | 1.29 | 1.39 | 22 | 33 | 10 | 4 |
| 4 | 1.55 | 1.33 | 18 | 53 | 66 | 58 |
| 5 | 1.69 | 0.7 | 8 | 76 | 46 | 30 |
| 6 (incl. AM$_H$13/AM$_L$13) | 1.52 | 0.89 | 6 | 73 | 78 | 75 |
| 7 | 1.54 | 0.98 | 7 | 79 | 71 | 45 |
| 8 | 1.78 | 3.44 | 34 | 73 | 63 | 30 |
| 9 | 6.34 | 8.45 | 53 | 57 | 48 | 34 |
| 10 | 1.23 | 1.58 | 10 | 82 | 71 | 31 |
| 11 | 1.62 | 2.1 | 28 | −10 | −6 | −10 |
| 12 | 1.15 | 1.04 | 16 | 71 | 63 | 37 |
| 13 | 2.43 | 1.67 | 12 | 58 | 23 | −4 |
| 14 | 1.43 | 1.03 | 13 | 42 | 17 | 18 |
| 15 | 1.62 | 1.59 | 18 | 67 | 59 | 31 |
| 16 | 1.79 | 2.2 | 25 | 61 | 57 | 45 |
| 17 | 0.91 | 1.85 | 10 | 49 | 54 | 23 |
| 18 (incl. AM$_H$12/AM$_L$12) | 1 | 1.36 | 6 | 75 | 82 | 61 |
| 19 (incl. AM$_H$17/AM$_L$17) | 1.75 | 1.23 | 3 | 90 | 81 | 73 |
| 20 | 2.31 | 0.49 | 9 | 35 | 20 | 38 |
| 21 (incl. AM$_H$16/AM$_L$16) | 1.84 | 0.76 | 6 | 86 | 90 | 71 |

TABLE 7 shows anti-IL-17RA non-clonal hybridoma supernatant screening data. The first two columns are flow cytometry data (FACS). The % positive columns show inhibition of biotin-huIL-17A binding to huIL-17RA$^+$ CHO cells by the non-clonal hybridoma supernatants. The MFI column shows inhibition of biotinylated huIL-17A binding to cynomolgus IL-17RA$^+$ CHO cells by the non-clonal hybridoma supernatants. The final three columns show IL-17A/HFF bioassay results with non-clonal hybridoma supernatants. Supernatants 6, 18, 19 and 21 were selected for subcloning.

TABLE 8

| Sub-clone ID | IL-17A/HFF bioassay IC$_{50}$ (nM) | Low resolution BIAcore K$_D$(nM) |
|---|---|---|
| 1. Subclone of (AM$_H$14/AM$_L$14) | 0.12 | 0.69 |
| 2. Subclone of (AM$_H$14/AM$_L$14)2 | 0.20 | ND |
| 3. Subclone of (AM$_H$14/AM$_L$14)3 | 0.075 | ND |
| 4. Subclone of (AM$_H$21/AM$_L$21) | 2.3 | ND |
| 5. Subclone of (AM$_H$21/AM$_L$21) | 3.1 | ND |
| 6. Subclone of (AM$_H$21/AM$_L$21) | 3.3 | 16.7 |
| 7. Subclone of (AM$_H$20/AM$_L$20) | 8.1 | ND |
| 8. Subclone of (AM$_H$20/AM$_L$20) | 6.6 | ND |
| 9. Subclone of (AM$_H$20/AM$_L$20) | 6.7 | 11.6 |
| 10. Subclone of (AM$_H$19/AM$_L$19) | 0.22 | 3.1 |
| 11. Subclone of (AM$_H$19/AM$_L$19) | 1.1 | ND |
| 12. Subclone of (AM$_H$19/AM$_L$19) | 0.50 | ND |
| 13. Subclone of (AM$_H$13/AM$_L$13) | >10 | 7.6 |
| 14. Subclone of (AM$_H$18/AM$_L$18) | 0.44 | ND |
| 15. Subclone of (AM$_H$18/AM$_L$18) | 0.40 | ND |
| 16. Subclone of (AM$_H$18/AM$_L$18) | 0.17 | 14.9 |
| 17. Subclone of (AM$_H$12/AM$_L$12) | 3.5 | ND |
| 18. Subclone of (AM$_H$12/AM$_L$12) | 3.7 | 8.2 |
| 20. Subclone of (AM$_H$12/AM$_L$12) | 5.5 | ND |
| 21. Subclone of (AM$_H$17/AM$_L$17) | 2.5 | 8.2 |
| 22. Subclone of (AM$_H$17/AM$_L$17) | 5.3 | ND |
| 23. Subclone of (AM$_H$17/AM$_L$17) | 0.57 | ND |
| 24. Subclone of (AM$_H$16/AM$_L$16) | 1.6 | ND |
| 25. Subclone of (AM$_H$16/AM$_L$16) | 2.3 | 6.2 |
| 26. Subclone of (AM$_H$16/AM$_L$16) | 1.4 | ND |
| 27. Subclone of (AM$_H$22/AM$_L$22) | 0.046 | 1.5 |
| 28. Subclone of (AM$_H$22/AM$_L$22) | 0.09 | ND |
| 29. Subclone of (AM$_H$22/AM$_L$22) | 0.07 | ND |

ND = not determined

TABLE 8 shows IL-17A/HFF bioassay IC50 values and low resolution BIAcore® K$_D$ values for subcloned hybridomas. Lower IC50 and K$_D$ values in the IL-17A/HFF IL-17RA binding assays showed that the IL-17RA mAbs inhibited binding of IL-17A to IL-17 receptor A. Antibodies were selected for further characterization based on low K$_D$ values for inhibiting IL-17A binding to human IL-17RA.

Example 9

IL-17RA human mAb clones having the heavy and light chain sequences (AM$_H$22/AM$_L$22), (AM$_H$19/AM$_L$19), (AM$_H$18/AM$_L$18) and (AM$_H$14/AM$_L$14) were selected for further bioassay characterization. TABLE 9 below shows IC50 values for the selected Abs in the HFF bioassay and a primary lung fibroblast bioassay against both IL-17A and IL-17F.

TABLE 9

| IL-17RA mAb | IL-17A/HFF IC50 (nM) | IL-17F/HFF IC50(nM) | IL-17A/lung fibroblast IC50(nM) |
|---|---|---|---|
| (AM$_H$14/AM$_L$14) | 0.13 | 0.067 | 0.04 |
| (AM$_H$22/AM$_L$22) | 0.10 | 0.033 | 0.14 |
| (AM$_H$19/AM$_L$19) | 0.20 | 0.087 | 0.22 |
| (AM$_H$18/AM$_L$18) | 0.33 | 0.073 | 0.081 |

The selected human mAbs inhibited IL-17A binding to IL-17RA. In addition to the lower IC50 values observed for IL-17A binding to IL-17RA, the selected human mAbs exhibited reduced IC50 values inhibiting the binding of IL-17F to IL-17RA (second column). Therefore, the selected human mAbs inhibit both IL-17A-IL-17RA binding and IL-17F-IL-17RA binding.

Example 10

Figure 12:
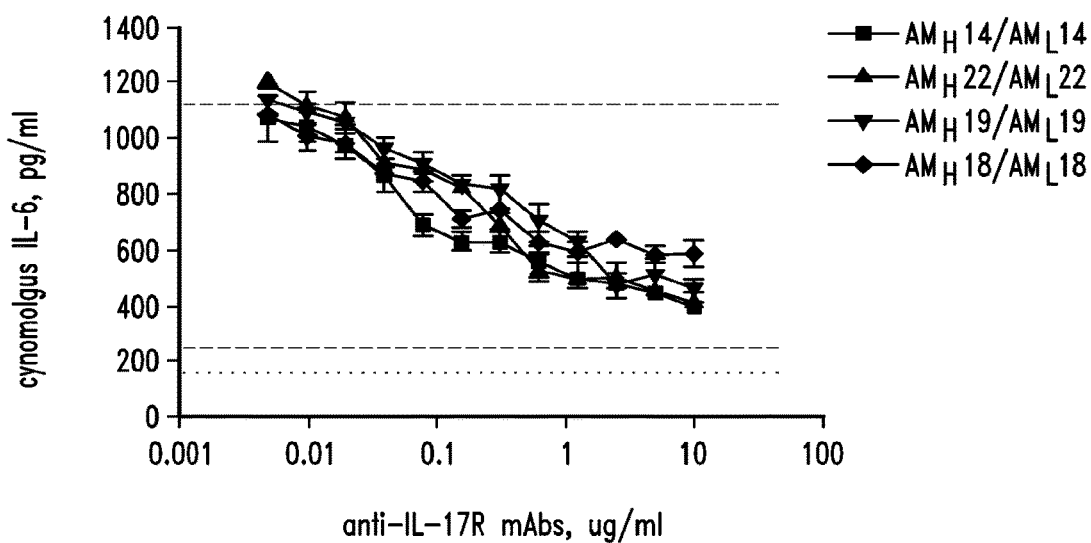
FIG. 12 shows exemplary IL-17RA human mAbs ($AM_H14/AM_L14$, $AM_H22/AM_L22$, $AM_H19/AM_L19$, and $AM_H18/AM_L18$) were able to inhibit cynomolgus IL-17-induced IL-6 production from JTC-12 cells (cynomolgus kidney cell line). The (---) line depicts the positive control value of cynomolgus IL-17 in combination with TNF-alpha. The (-.-.-) line depicts the positive control value of cynomolgus TNF-alpha. The (....) line depicts the media control value.

Exemplary IL-17RA human mAbs were tested in a cynomolgus bioassay utilizing the cynomolgus-derived kidney epithelial cell line JTC-12 stimulated with cynomolgus IL-17A. FIG. 12 shows IL-17RA mAbs having the heavy and light chain sequences (AM$_H$22/AM$_L$22), (AM$_H$19/AM$_L$19), (AM$_H$18/AM$_L$18) and (AM$_H$14/AM$_L$14) in the inhibition of cynomolgus IL-17A-induced IL-6 production from JTC-12 cells. The (----) line depicts the positive control value of cynomolgus IL-17 in combination with TNF-alpha. The (-.-.-) line depicts the positive control value of cynomolgus TNF-alpha. The (....) line depicts the media control value. JTC-12 cells were preincubated for 30 mins with anti-IL-17RA mAbs and then stimulated overnight with cynomolgus IL-17A (5 ng/ml) and human TNF-alpha (5 ng/ml). FIG. 12 shows that each antibody was able to inhibit cynomolgous IL-17A from binding IL-17RA and inhibit IL-17RA activation, as determined by IL-6 production from JTC-12 cells. The IL-17RA antibody (AM$_H$14/AM$_L$14) was able to antagonize cynomolgous IL-17A-induced IL-6 production from JTC-12 cells with an IC50 of approximately 1.2 nM.

Example 11

In vitro binding of IL-17RA mAbs was assayed. The binding affinities of IL-17RA antibodies were measured by surface plasmon resonance using a Biacore 3000® instrument by standard methods known in the art. Antibody candidates were captured on CM4 chips derivatized with goat anti-human IgG (H+L) antibody (Jackson immuno Research, Bar Harbor, ME). A CM4 chip coated with goat anti-human IgG (H+L) antibody but without captured antibody was used as a reference. Soluble huIL-17RA-FLAG-polyHis (SEQ ID NO:431) at a concentration range of 0.46-1000 nM was flowed over the chips for 2 minutes (association phase) followed by a 15-30 minute disassociation phase. FLAG peptide. Asp-Tyr-Lys-Asp-Asp-Asp-Asp-Lys (DYKDDDDK) (SEQ ID NO:447) as described in Hopp et al., Bio/Technology 6:1204, 1988, and U.S. Pat. No. 5,011,912 enables rapid assay and facile purification of expressed recombinant protein. Reagents useful for preparing fusion proteins in which the FLAG peptide is fused to a given polypeptide are commercially available (Sigma, St. Louis, MO).

Experiments were conducted at 25° C. using a 50 uL/min flow rate. Data was fit to a 1:1 Model+Local Rmax using B1Aeval software® (v4.1).

TABLE 10

| Human Antibody | $k_a$ (1/Ms) | $K_D$ (1/s) | $K_A$ (1/M) | $K_D$ (M) |
|---|---|---|---|---|
| (AM$_H$14/AM$_L$14) | $2.60 \times 10^5$ | $6.22 \times 10^{-5}$ | $4.18 \times 10^9$ | $2.39 \times 10^{-10}$ |
| (AM$_H$22/AM$_L$22) | $2.35 \times 10^5$ | $1.17 \times 10^{-4}$ | $2.01 \times 10^9$ | $4.98 \times 10^{-10}$ |
| (AM$_H$19/AM$_L$19) | $1.42 \times 10^5$ | $1.14 \times 10^{-4}$ | $1.25 \times 10^9$ | $8.02 \times 10^{-10}$ |
| (AM$_H$18/AM$_L$18) | $1.02 \times 10^5$ | $1.01 \times 10^{-3}$ | $1.01 \times 10^8$ | $9.88 \times 10^{-9}$ |

TABLE 10 shows the $K_D$ of the human mAb clones was on the order of $10^{-10}$ to $10^{-9}$, with the clone having the heavy and light chain sequences (AM$_H$14/AM$_L$14) having the highest affinity. Each of the human monoclonal antibodies' kinetic data was consistent with the equilibrium data. The antibody with the heavy and light chain variable sequences (AM$_H$14/AM$_L$14; SEQ ID NO:14 and SEQ ID NO:40, respectively) had the highest affinity for IL-17RA, as well as the slowest off-rate.

Example 12

The agonistic potential of IL-17RA human mAb having the heavy and light chain variable sequences (AM$_H$14/AM$_L$14) was assessed in vitro. The IL-17RA mAb (AM$_H$14/AM$_L$14) was tested for its agonist effects on HFF cells. IL-17RA mAb having the heavy and light chain sequences (AM$_H$14/AM$_L$14) was also tested under conditions of cross-linking with goat anti-human F(ab')$^2$, goat anti-human IgG and mouse anti-human IgG prior to incubation with HFF cells. Recombinant IL-17RA mAb AM$_H$14/AM$_L$14 at 0, 0.1, 0.5, 1, 1.5 and 10 µg/ml, alone and pre-cross linked with murine anti-human IgG (Zymed/Invitrogen, San Diego, CA), goat anti-human F(ab')2 (Goat a-h-Fab) and goat anti-human IgG (Goat a-h IgG) were incubated overnight with HFF cells. GRO-alpha was assessed by ELISA. IL-17A alone served as a positive control for GRO-alpha production in this experiment. These data are representative of 2 independent experiments. IL-17RA mAb (AM$_H$14/AM$_L$14) alone had no effect on HFF cells. Pre-crosslinking anti-IL-17RA mAb (AM$_H$14/AM$_L$14) had no effect on GRO-alpha production from HFF cells. These data demonstrate that anti-IL-17RA mAb (AM$_H$14/AM$_L$14) either alone or pre-cross-linked and incubated with HFF cells was unable to induce a ORO-alpha response and therefore is not an agonistic mAb to IL-17RA.

Example 13

Figure 13:
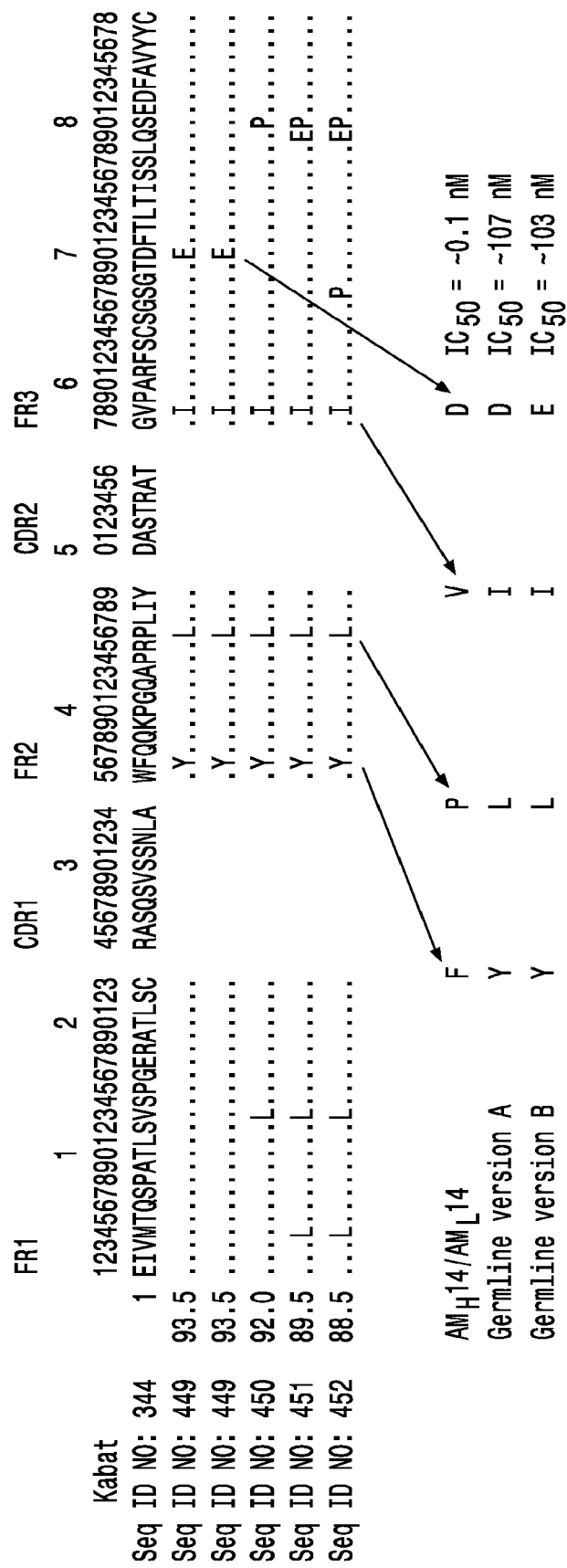
FIG. 13 shows sequence variation in the framework regions of SEQ ID NO:40 ($AM_L14$) in relation to germline residues and the effect on IC50 values.

The effects of the germline (GL) changes to IL-17RA mAb AM$_H$14/AM$_L$14 were tested in the HFF bioassay. FIG. 13 shows sequence variation in the framework regions of SEQ ID NO:40 (AM$_L$14) in relation to germline residues and the effect on IC50 values. SEQ ID NO:40 (AM$_L$14) contains four non-germline residues in the framework, two in FR2 and two in FR3. Standard site-directed mutagenesis methods were used to generate germline versions A and B of AM$_H$14/AM$_L$14. These variants were tested in the IL-17A and IL-17F HFF bioassay; HFF cells were preincubated for 30 mins with various anti-IL-17RA mAbs and then stimulated overnight with IL-17 (5 ng/ml).

Figure 14:
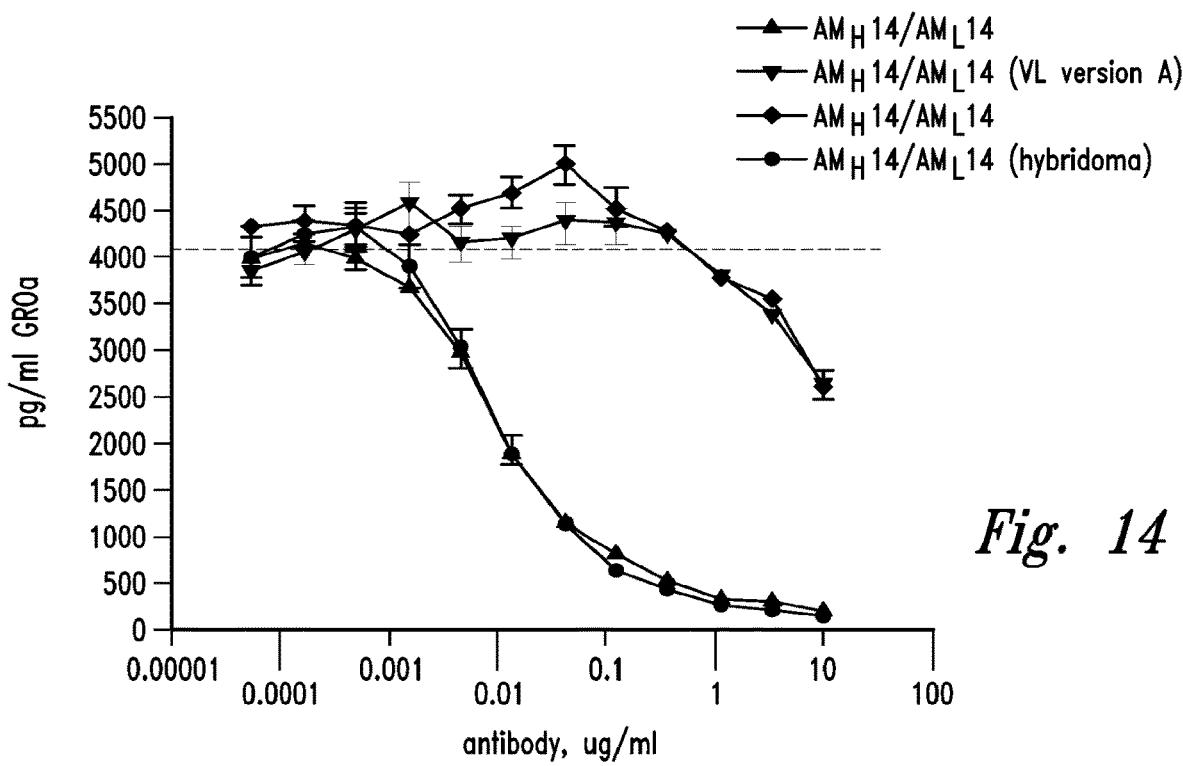
FIG. 14 shows that the two variants having residues returned to germline (see FIG. 13) had reduced IL-17A inhibitory activity in relation to $AM_H14/AM_L14$, indicating that some variation in the framework regions was tolerated but that some residues may influence activity. The (----) line indicates the positive control value of IL-17 stimulation in the absence of antibody (approximately 4062 pg/ml).

FIG. 14 shows that the two variants that had the residues returned to germline (see FIG. 13) had reduced IL-17A inhibitory activity in relation to AM$_H$14/AM$_L$14, indicating that some variation in the framework regions was tolerated but that some residues may influence activity. The (---) line indicates the positive control value of IL-17 stimulation in the absence of antibody (approximately 4062 pg/ml). The media-only control gave a value of approximately 71 pg/ml.

Figure 15:
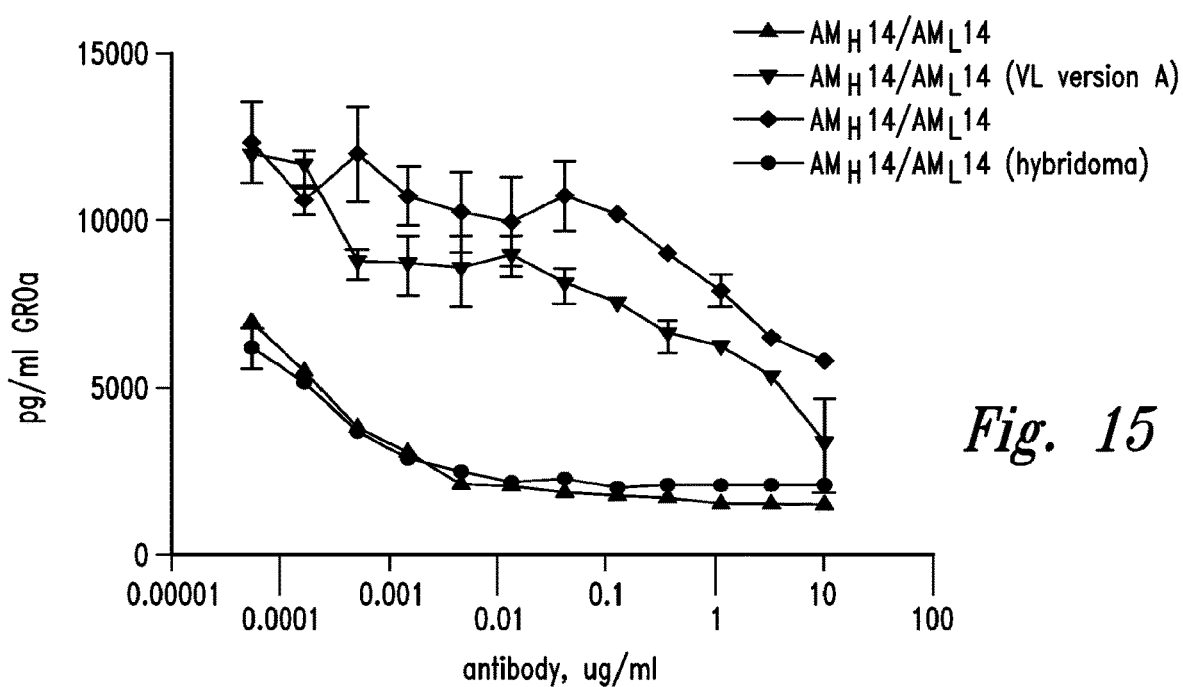
FIG. 15 shows that the two variants having residues returned to germline (see FIG. 13) had reduced IL-17F (in combination with TNF-alpha) inhibitory activity in relation to $AM_H4/AM_L14$.

FIG. 15 shows that the two variants that had the residues returned to germline (see FIG. 13) had reduced IL-17F inhibitory activity in relation to AM$_H$14/AM$_L$14, indicating that some variation in the framework regions was tolerated but that some residues may influence activity. The positive control value of IL-17F in combination with TNF-alpha stimulation in the absence of antibody was approximately 10994 pg/ml, the value for TNF-alpha only was approximately 1534 pg/ml, and the media-only control gave a value of approximately 55 pg/ml.

Example 14

Studies were conducted to determine where the various IL-17RA antigen binding proteins (in the form of human antibodies) bound to human IL-17RA. The ForteBio™ Octet™ System is one of several systems and techniques available for measuring antibody binding. The methods used for screening antibody binding essentially followed the manufacturer's recommendations. For more information see www dot fortebio dot com. In brief, streptavidin sensors (ForteBio™) were presoaked for 10 minutes in PBSAT (1% BSA/PBS+0.05% Tween20® (polyoxyethylene sorbitan monolaurate). Biotinylated $AM_H14/AM_L14$ at 10 ug/mL in PBSAT was loaded onto the sensors for 900 seconds. A new baseline was run for 600 seconds in PBSAT. Wild-type IL-17RA-FLAG-polyHis (SEC ID NO:431) at 10 ug/mL in PBSAT was then bound to the sensors for 900 seconds. A new baseline was established for 600 seconds in PBSAT. 200 nM of the following mAbs $AM_H22/AM_L22$, $AM_H19/AM_L19$, and $AM_H18/AM_L18$ were associated for 900 seconds, followed by dissociation for 900 seconds in PBSAT. The data showed that $AM_H18/AM_L18$ did not compete with $AM_H4/AM_L4$ for binding, showing that $AM_H14/AM_L14$ and $AM_H18/AM_L18$ bind to different neutralizing determinants. $AM_H22/AM_L22$ and $AM_H19/AM_L19$ did not bind in the presence of $AM_H14/AM_L14$, suggesting that all three of these antibodies bind to the same or to a similar neutralizing determinant and therefore are considered to bin together.

Example 15

Cross-competition studies were performed to determine IL-17RA binding characteristics of exemplary IL-17RA antibodies. A modification of the multiplexed binning method described by Jia, el al. was used (see Jia, et al., *J. Immun. Meth.*, 2004, 288:91-98). The method employed the Bio-Plex Workstation and software (BioRad, Hercules, CA), as well as reagents from Luminex® Corp. (Austin, TX). The manufacturers' basic protocols were followed except where noted below (see www.bio-rad.com and www.luminexcorp.com for details). Each bead code of streptavidin-coated Luminex® beads (Luminex®, #L100-L1XX-01, where "XX" specifies the bead code) were incubated in 150 ul of 50 ug/ml biotinylated monovalent mouse-anti-human IgG capture antibody (BD Pharmingen. Becton Dickinson, Franklin Lakes, NJ, product #555785) for 1 hour at room temperature in the dark and then washed 3 times with PBSAT. The mouse-anti-human IgG coating was evaluated and the beads quantified by FACS. Each bead code was separately incubated with 10 ul of anti-IL-17RA antibody for 1 hour at room temperature and then washed. The beads were pooled and then dispensed to a 96-well filter plate (Millipore, Billerica, MA, product #MSBVN1250). 80 ul of 2 ug/ml IL-17RA (SEQ ID NO:431) was added to half the wells and buffer to the other half and incubated at room temperature for 1 hour then washed with PBSAT. 10 ul of an anti-IL-17RA antibody was added to one well with IL-17RA (SEQ ID NO:431) and one well without IL-17RA and incubated at room temperature for 1 hour then washed with PBSAT. An irrelevant human-IgG (Jackson Labs., Bar Harbor, ME, product #009-000-003) was included as a negative control. 50 ul PE-conjugated monovalent mouse-anti-human IgG (BD Pharmingen, Becton Dickinson, Franklin Lakes. NJ, #555787) was added to each well and incubated at room temperature for 1 hour and then washed with PBSAT. The PE-tagged monovalent antibody will detect the presence of the second mAb added to the well, but not the first mAb captured by the monovalent mouse-anti-human IgG antibody. Beads were resuspended in 120 ul PBSAT and at least 100 events/bead code were collected on the Bio-Plex workstation as per the manufacturer's recommended protocol.

Median Fluorescent Intensity (MFI) of the antibody pair without IL-17RA was subtracted from the MFI signal of the corresponding reaction containing IL-17RA to normalize for background noise. The criteria for determining if two antibodies cross-competed with each other and therefore "binned" together was a matter of determining the degree to which the second antibody was detectable. If the normalized MFI was higher than the highest of any of the following three values, then the anti-IL-17RA antibodies were considered to be simultaneously bound to IL-17RA and were considered to be in different bins (i.e., the antibodies did not cross-compete): the normalized MFI is greater than 3 times the MFI value of the antibody paired with itself, or 3 times the MFI value of the antibody paired with a huIgG control, or a MFI of 300. Generally speaking, antibodies assigned to different bins bind different parts of IL-17RA and antibodies assigned to the same bin(s) bind similar parts of IL-17RA.

FIGS. 16A and 16B show the results of multiplexed binning of anti-IL-17RA antibodies. Shaded values indicate antibody pairs that bind to IL-17RA simultaneously, suggesting that these antibodies bind to different neutralizing determinants. Boxed values indicate antibodies paired against themselves and cross-compete. The following monoclonal human antibodies containing the ascribed heavy and light variable domains were tested: A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, G: $AM_H18/AM_L18$, H: $AM_H11/AM_L11$, I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$, P: $AM_H26/AM_L26$, Q: $AM_H21/AM_L21$, and R: $AM_H20/AM_L20$.

FIGS. 16A and 16B also show that antibodies A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, and G: $AM_H18/AM_L18$ competed with one another for binding to human IL-17RA and as a consequence fell into a defined group (Bin 1). In general, antibodies I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$ competed with one another for binding to human IL-17RA and as a consequence fell into a defined group (Bin 3). Generally speaking, the antibodies of Bin 1 did not compete with the antibodies of Bin 3.

Antibody H: $AM_H1/AM_L1$ was unique in its competition pattern and formed Bin 2, but is most similar to Bin 3. Antibody P: $AM_H26/AM_L26$ formed Bin 4 and showed little cross-competition with any of the other antibodies, suggesting a neutralizing determinant unique to this antibody. Antibodies Q: $AM_H21/AM_L21$ and R: $AM_H20/AM_L20$, showed individually unique competition patterns, but with considerable similarities to Bin 3 antibodies, and formed Bins 5 and 6, respectively. This data provides evidence of several species within a subgenus of cross-competing antibodies.

Example 16

As described above, antibodies that bind human IL-17RA and inhibit, or neutralize, the binding of IL-17A and/or IL-17F were created and characterized. To determine the neutralizing determinants on human IL-17RA that these various IL-17RA antibodies bound, a number of chimeric human/mouse IL-17RA proteins were constructed. This method takes advantage of the non-cross reactivity of the various IL-17RA antibodies with mouse IL-17RA. For each chimera, one or two regions of human IL-17RA extracellular domain (SEQ ID NO:431) was/were replaced with the corresponding region(s) of mouse IL-17RA (SEQ ID NO:432). FIG. 17 shows mouse IL-17RA (SEQ ID NO:432) and the 5 domains, A, B, C, D, E, and F that replaced the counterpart domains in the human IL-17RA sequence. Such techniques are known in the art, see for example Stemmer, W. P. C. et al., 1995 Gene 164:49-53.

Six single-region and 8 double-region chimeras were constructed in pTT5 vectors. Chimeric constructs A through F (single region chimeras) were made synthetically by PCR annealing of 65-mer sense and antisense oligonucleotides which span the protein from a Sal1 site 5' of the initiation codon to a Not1 site 3' of the termination codon. The template used in the first round of PCR was a mix of oligos (sense and antisense) spanning the region from the Sal1 site to the Not1 site. PCR was done in 2 steps as follows:

```
95C  3'   ⎫
95C  30"  ⎪
42C  30"  ⎬ 3x
72C  35"  ⎪        product used as
95C  30"  ⎫   ───────────────────────▶
56C  30"  ⎬ 10x   template in 2nd PCR reaction
72C  35"  ⎭
                │
                ▼
           95C  3"   ⎫
           95C  30"  ⎪
           42C  30"  ⎬ 3x
           72C  35"  ⎪        PCR product was
           95C  30"  ⎫        digested with Sal1 and
           56C  30"  ⎬ 25x ─▶ Not1 and cloned into
           72C  35"  ⎪        pTT5 vector for
           72C  5'   ⎭        transient expression.
```

Double chimeric constructs were made by digestion of single chimeras A through D with Sal1 and Sac1 restriction enzymes and a 3-way ligation with Sac1 and Not1 digested chimeras E and F using pTT5 as the expression vector. The chimeras, huIL-17RA-FLAG-polyHis (SEQ ID NO:431), and muIL-17RA-FLAG-polyHis (SEQ ID NO:432) were expressed transiently using 2936-E cells (available from the National Research Council of Canada (NRCC); see NRCC document L-11565 for further information) as host cells in roller bottles. Such transient expression techniques are well known in the art, see for example Durocher, Y. et al., 2002 *Nucleic Acids Res.* January 15;30(2):E9. The supernatants were purified using a HisTrap™ HP column as per the manufacturer's general guidelines (GE Healthcare, Piscataway NJ) and eluted using a standard imidazole gradient (see manufacturer's recommended protocols). Purified protein was desalted into PBS, pH 7.2.

The chimeras were aligned using standard analysis tools, such as ClustalW (EMBL-EBI). The resulting chimeric proteins are shown in FIGS. 18A-18D. With reference to FIGS. 17 and 18A-18D, Chimera A (SEQ ID NO:433) is human IL-17RA extracellular domain with mouse Domain A; Chimera B (SEQ ID NO:434) is human IL-17RA extracellular domain with mouse Domain B; Chimera C (SEQ ID NO:435) is human IL-17RA extracellular domain with mouse Domain C; Chimera D (SEQ ID NO:436) is human IL-17RA extracellular domain with mouse Domain D; Chimera E (SEQ ID NO:437) is human IL-17RA extracellular domain with mouse Domain E; Chimera F (SEQ ID NO:438) is human IL-17RA extracellular domain with mouse Domain F; Chimera G (SEQ ID NO:439) is human IL-17RA extracellular domain with mouse Domains A and E; Chimera H (SEQ ID NO:440) is human IL-17RA extracellular domain with mouse Domains B and E; Chimera I (SEQ ID NO:441) is human IL-17RA extracellular domain with mouse Domains C and E; Chimera J (SEQ ID NO:442) is human IL-17RA extracellular domain with mouse Domains D and E; Chimera K (SEQ ID NO:443) is human IL-17RA extracellular domain with mouse Domains A and F; Chimera L (SEQ ID NO:444) is human IL-17RA extracellular domain with mouse Domains B and F; Chimera M (SEQ ID NO:445) is human IL-17RA extracellular domain with mouse Domains C and F; and Chimera N (SEQ ID NO:446) is human IL-17RA extracellular domain with mouse Domains D and F.

Using methods similar to those described in Example 15, multiplex analysis using the Bio-Plex Workstation and software (BioRad, Hercules, CA) was performed to determine neutralizing determinants on human IL-17RA by analyzing exemplary human IL-17RA mAbs differential binding to chimeric versus wild-type IL-17RA proteins. Twelve bead codes of pentaHis-coated beads (Qiagen, Valencia, CA; see www1.giagen.com) were used to capture histidine-tagged protein. The 12 bead codes allowed the multiplexing of 11 chimeric and the wild type human IL-17RA.

To prepare the beads, 100 ul of wild-type IL-17RA supernatant from transient expression culture and 100 ul of 2.5 ug/ml chimeric protein were bound to penta-His-coated beads overnight at 4° C. or 2 hours at room temperature with vigorous shaking. The beads were washed as per the manufacturer's protocol and the 12 bead set was pooled and aliquoted into 2 or 3 columns of a 96-well filter plate (Millipore, Billerica, MA, product #MSBVN1250) for duplicate or triplicate assay points, respectively. 100 ul anti-IL-17RA antibodies in 4-fold dilutions were added to the wells, incubated for 1 hour at room temperature, and washed. 100 ul of a 1:100 dilution of PE-conjugated anti-human IgG Fc (Jackson Labs., Bar Harbor, ME, product #109-116-170) was added to each well, incubated for 1 hour at room temperature and washed. Beads were resuspended in 1% BSA, shaken for 3 minutes, and read on the Bio-Plex workstation. Antibody binding to IL-17RA chimeric protein was compared to antibody binding to the human IL-17RA wild-type from the same pool. A titration of antibody over approximately a 5 log scale was performed. Median Fluorescence Intensity (MFI) of chimeric proteins was graphed as a percent of maximum wild-type human IL-17RA signal. Mutations (i.e., mouse domains) that increase the EC50 (expressed in nM) for the IL-17RA mAb by 3-fold or greater (as calculated by GraphPad Prism®) were considered to have negatively affected IL-17RA mAb binding. Through these methods, neutralizing determinants for various IL-17RA antibodies were elucidated.

FIG. 19 is a table summarizing the IL-17RA mAbs capacity to bind the various chimeric proteins. Shaded values denote where the IL-17RA mAb did not meet the criteria for binding to that particular chimeric protein ("n.d.," i.e., "not determined" means that the chimera was not assayed). As described above, EC50 values are provided. A zero value indicates that antibody binding was ablated. The underlined value was assigned an EC50 value by the GraphPad Prism® even though the titration curve was essentially flat. TABLE 11 shows the control values in nM for the assay.

TABLE 11

| mAb | mu WT | huWT ctrl | 3x wt ctrl | 2x wt ctrl |
|---|---|---|---|---|
| $AM_H18/AM_L18$ | 0.000 | 0.061 | 0.182 | 0.121 |
| $AM_H1/AM_L1$ | 1.879 | 0.134 | 0.403 | 0.269 |
| $AM_H22/AM_L22$ | 0.000 | 0.043 | 0.128 | 0.085 |
| $AM_H14/AM_L14$ | 3416.000 | 0.027 | 0.082 | 0.055 |
| $AM_H19/AM_L19$ | 770.100 | 0.062 | 0.187 | 0.125 |
| $AM_H23/AM_L23$ | 0.000 | 0.053 | 0.158 | 0.106 |
| $AM_H26/AM_L26$ | 0.000 | 0.281 | 0.843 | 0.562 |
| $AM_H21/AM_L21$ | 0.196 | 0.018 | 0.055 | 0.037 |
| $AM_H20/AM_L20$ | 1.333 | 0.022 | 0.066 | 0.044 |

As can be seen in FIG. 19, at least three neutralizing determinants were identified based on those regions affecting the binding of neutralizing IL-17RA antibodies, namely Domain B spanning amino acids 75-96 of human IL-17RA (SEQ ID NO:431). Domain C spanning amino acids 128-154 of human IL-17RA (SEQ ID NO:431), and Domain D spanning amino acids 176-197 of human IL-17RA (SEQ ID NO:431). Domain B spanning amino acids 75-96 of human IL-17RA (SEQ ID NO:431) negatively affected the binding of neutralizing antibodies $AM_H1/AM_L1$ and $AM_H23/AM_L23$. Domain C spanning amino acids 128-154 of human IL-17RA (SEQ ID NO:431) negatively affected the binding of neutralizing antibodies $AM_H22/AM_L22$ and $AM_H23/AM_L23$. Domain D spanning amino acids 176-197 of human IL-17RA (SEQ ID NO:431) negatively affected the binding of neutralizing antibodies $AM_H1/AM_L1$, $AM_H22/AM_L22$, $AM_H14/AM_L14$, $AM_H19/AM_L19$, $AM_H23/AM_L23$, $AM_H21/AM_L21$, and $AM_H20/AM_L20$. The binding characteristics of the IL-17RA antibodies in relation to where the antibodies bound on human IL-17RA was confirmed by the double chimeras. Thus, Domain B. C, and D are considered neutralizing determinants.

Example 17

As described above, antibodies that bind human IL-17RA and inhibit, or neutralize, the binding of IL-17A and/or IL-17F were created and characterized. To determine the neutralizing determinants on human IL-17RA that these various IL-17RA antibodies bound, a number of mutant IL-17RA proteins were constructed having arginine substitutions at select amino acid residues of human IL-17RA. Arginine scanning is an art-recognized method of evaluating where antibodies, or other proteins, bind to another protein, see for example Nanevicz, T., et al., 1995, J. Biol. Chem., 270:37, 21619-21625 and Zupnick, A., et al., 2006, J. Biol. Chem., 281:29, 20464-20473. In general, the arginine side-chain is positively charged and relatively bulky as compared to other amino acids, which may disrupt antibody binding to a region of the antigen where the mutation is introduced. Arginine scanning is a method that determines if a residue is part of a neutralizing determinant and/or an epitope.

95 amino acids distributed throughout the human IL-17RA extracellular domain were selected for mutation to arginine. The selection was biased towards charged or polar amino acids to maximize the possibility of the residue being on the surface and reduce the likelihood of the mutation resulting in misfolded protein. FIG. 20 depicts the amino acid residues that were replaced with an arginine residue in SEQ ID NO:431. Using standard techniques known in the art, sense and anti-sense oligonucleotides containing the mutated residues were designed based on criteria provided by Stratagene Quickchange® H protocol kit (Stratagene/Agilent, Santa Clara, CA). Mutagenesis of the wild-type (WT) HuIL-17RA-Flag-pHis was performed using a Quickchange® 11 kit (Stratagene). All chimeric constructs were constructed to encode a FLAG-histidine tag (six histidines) on the carboxy terminus of the extracellular domain to facilitate purification via the poly-His tag.

Multiplex analysis using the Bio-Plex Workstation and software (BioRad, Hercules, CA) was performed to determine neutralizing determinants on human IL-17RA by analyzing exemplary human IL-17RA mAbs differential binding to arginine mutants versus wild-type IL-17RA proteins. Twelve bead codes of pentaHis-coated beads (Qiagen, Valencia, CA; see www1.qiagen.com) were used to capture histidine-tagged protein. The 12 bead codes allowed the multiplexing of 11 IL-17RA arginine mutants and wild-type human IL-17RA (SEQ ID NO:431).

To prepare the beads, 100 ul of wild-type IL-17RA and IL-17RA arginine mutant supernatants from transient expression culture were bound to penta-His-coated beads overnight at 4° C. or 2 hours at room temperature with vigorous shaking. The beads were washed as per the manufacturer's protocol and the 12 bead set was pooled and aliquoted into 2 or 3 columns of a 96-well filter plate (Millipore, Billerica, MA, product #MSBVN1250) for duplicate or triplicate assay points, respectively. 100 ul anti-IL-17RA antibodies in 4-fold dilutions were added to the wells, incubated for 1 hour at room temperature, and washed. 100 ul of a 1:100 dilution of PE-conjugated anti-human IgG Fc (Jackson Labs., Bar Harbor, ME, product #109-116-170) was added to each well, incubated for 1 hour at room temperature and washed. Beads were resuspended in 1% BSA, shaken for 3 minutes, and read on the Bio-Plex workstation. Antibody binding to IL-17RA arginine mutant protein was compared to antibody binding to the human IL-17RA wild-type from the same pool. A titration of antibody over approximately a 5 log scale was performed. Median Fluorescence Intensity (MFI) of IL-17RA arginine mutant proteins was graphed as a percent of maximum wild-type human IL-17RA signal. Those mutants for which signal from all the antibodies are below 30% of wild-type IL-17RA were deemed to be either of too low a protein concentration on the bead due to poor expression in the transient culture or possibly misfolded and were excluded from analysis: these were T51R, K53R, S55R, H64R, D75R, E110R, Q118R, T121, E123R, S147R, H148R, E158R, T160R, H163R, K191R, T193R, E213R, H251R, T269R, H279R, and D293R. Mutations (i.e., arginine substitutions) that increase the EC50 for the IL-17RA mAb by 3-fold or greater (as calculated by GraphPad Prism®) were considered to have negatively affected IL-17RA mAb binding. Through these methods, neutralizing determinants and epitopes for various IL-17RA antibodies were elucidated.

Figure 21:
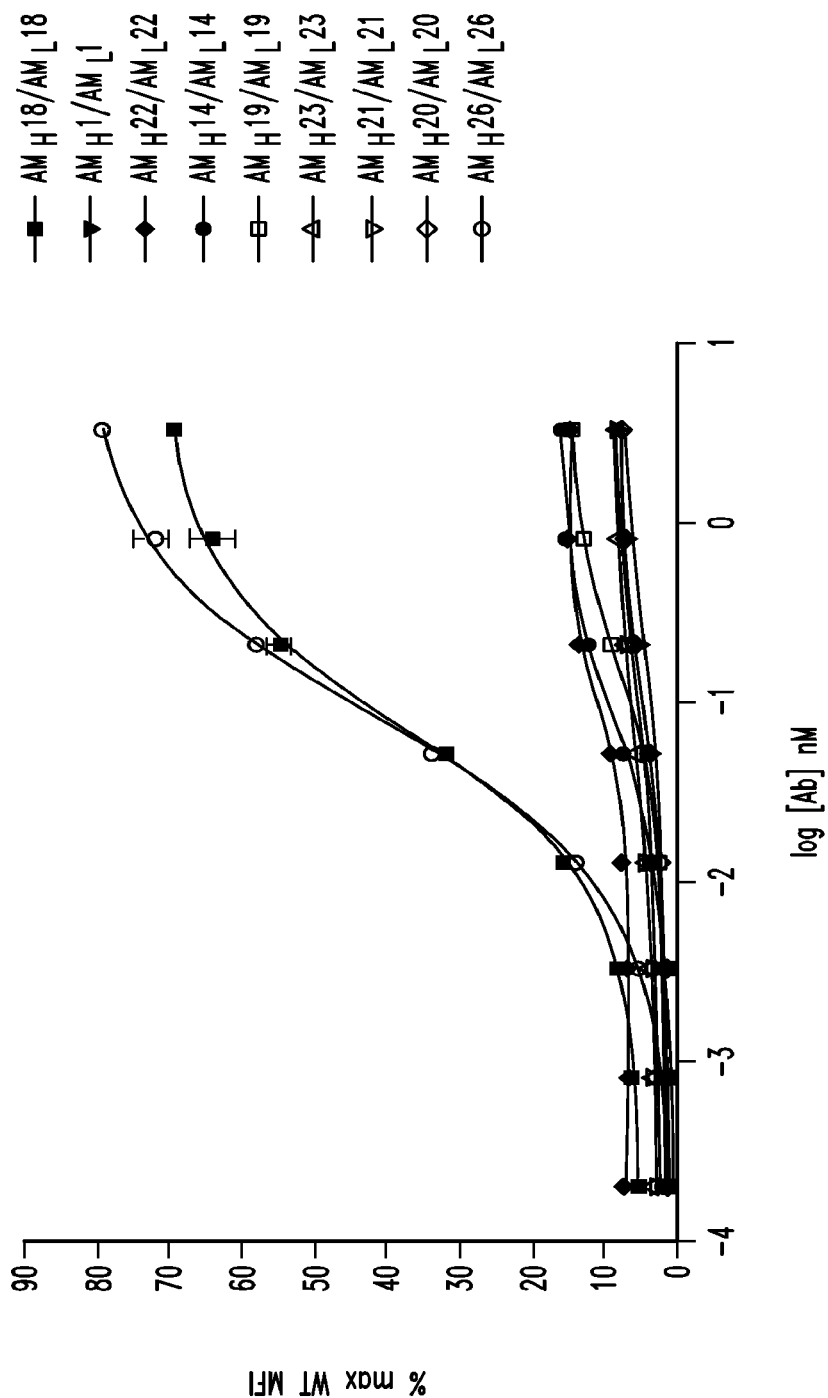
FIG. 21 illustrates titration curves of various IL-17RA mAbs binding to the D152R IL-17RA mutant.

FIG. 21 illustrates titration curves of various IL-17RA mAbs binding to the D152R IL-17RA mutant (i.e., the aspartic acid at position 152 of SEQ ID NO:431 was mutagenized to be an arginine). Antibodies $AM_H1/AM_L1$, $AM_H22/AM_H22$, $AM_L14/AM_L14$, $AM_H19/AM_L0.19$, $AM_H23/AM_L23$, $AM_H21/AM_L21$, and $AM_H20/AM_L20$ lost the capacity to bind the D152R IL-17RA mutant. Antibodies $AM_H18/AM_L18$ and $AM_H26/AM_L26$ were only marginally affected but did not meet the cutoff criteria.

A summary of the arginine scan, binning, and chimera data is presented in FIG. 22. The arginine scan methodology identified several neutralizing determinants: $AM_H18/AM_L18$ bound a domain spanning amino acids 220-284 of human IL-17RA (SEQ ID NO:431); $AM_H1/AM_L1$ bound a domain focused on amino acid residue 152 of human IL-17RA (SEQ ID NO:431); $AM_H22/AM_L22$ bound a domain spanning amino acids 152-198 of human IL-17RA (SEQ ID NO:431); $AM_H14/AM_L14$ bound a domain spanning amino acids 152-297 of human IL-17RA (SEQ ID NO:431); $AM_H19/AM_L19$ bound a domain spanning amino acids 152-186 of human IL-17RA (SEQ ID NO:431); $AM_H23/AM_L23$ bound a domain spanning amino acids 97-297 of human IL-17RA (SEQ ID NO:431); $AM_H26/AM_L26$ bound a domain spanning amino acids 138-270 of human IL-17RA (SEQ ID NO:431); $AM_H21/AM_L21$ bound a domain spanning amino acids 113-198 of human IL-17RA (SEQ ID NO:431); and $AM_H20/AM_L20$ bound a domain spanning amino acids 152-270 of human IL-17RA (SEQ ID NO:431).

All of the residues shown in FIG. 22 have been shown to ablate binding of a neutralizing human monoclonal antibody that specifically binds to human IL-17RA.

What is claimed is:

1. A method of treating scleroderma in a human patient in need thereof, which method comprises administering to the patient an effective amount of human monoclonal antibody, or an antigen-binding fragment thereof, that specifically binds the human IL-17 receptor A, wherein the human monoclonal antibody comprises:

(a) a heavy chain CDR1 comprising the amino acid sequence of SEQ ID NO: 146, a heavy chain CDR2 comprising the amino acid sequence of SEQ ID NO: 147, a heavy chain CDR3 comprising the amino acid sequence of SEQ ID NO: 148, and a light chain CDR1 comprising the amino acid sequence of SEQ ID NO: 224, a light chain CDR2 comprising the amino acid sequence of SEQ ID NO: 225, and a light chain CDR3 comprising the amino acid sequence of SEQ ID NO: 226; or (b) a heavy chain variable domain comprising the amino acid sequence of SEQ ID NO: 14 and a light chain variable domain comprising the amino acid sequence of SEQ ID NO: 40, whereby the human monoclonal antibody specifically binds to human IL-17 receptor A and inhibits the binding of IL-17A to IL-17 receptor A, and the scleroderma is treated in the human patient.

2. The method of claim 1, wherein the human monoclonal antibody or antigen-binding fragment thereof is selected from a single chain antibody, a diabody, a triabody, a tetrabody, a Fab fragment, a F(ab')2 fragment, an IgD antibody, an IgE antibody, an IgM antibody, an IgG1 antibody, an IgG2 antibody, an IgG3 antibody; and an IgG4 antibody.

3. The method of claim 1, wherein the human monoclonal antibody is administered to the human patient in the form of a composition comprising a pharmaceutically acceptable carrier.

4. The method of claim 3, wherein the composition is administered to the patient subcutaneously, intramuscularly, or intravenously.

* * * * *